(12) United States Patent
Salfeld et al.

(10) Patent No.: US 9,035,030 B2
(45) Date of Patent: *May 19, 2015

(54) HUMAN ANTIBODIES THAT BIND THE P40 SUBUNIT OF HUMAN IL-12 AND METHODS FOR USING THE SAME

(75) Inventors: Jochen Salfeld, North Grafton, MA (US); Michael Roguska, Ashland, MA (US); Michael Paskind, Sterling, MA (US); Subhashis Banerjee, Hamden, CT (US); Daniel Tracey, Harvard, MA (US); Michael White, Framingham, MA (US); Zehra Kaymakcalan, Westborough, MA (US); Boris Labkovsky, Marlborough, MA (US); Paul Sakorafas, Newton Highlands, MA (US); Geertruida M. Veldman, Sudbury, MA (US); Amy Venturini, Lexington, MA (US); Angela Widom, Acton, MA (US); Stuart Friedrich, Morpeth (CA); Nicholas W. Warne, Andover, MA (US); Angela Myles, Pepperell, MA (US); John Gawain Elvin, Royston (GB); Alexander Robert Duncan, Cambridge (GB); Elaine Joy Derbyshire, Berks (GB); Sara Carmen, Cambridge (GB); Stephen Smith, Ely (GB); Thor Las Holtet, Ronde (DK); Sarah Leila Du Fou, Hitchen (GB)

(73) Assignee: AbbVie Deutschland GmbH & Co. KG, Wiesbaden (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/401,559

(22) Filed: Feb. 21, 2012

(65) Prior Publication Data

US 2012/0244168 A1   Sep. 27, 2012

Related U.S. Application Data

(60) Continuation of application No. 12/253,103, filed on Oct. 16, 2008, now abandoned, which is a continuation of application No. 10/884,830, filed on Jul. 1, 2004, now Pat. No. 7,504,485, which is a division of application No. 09/534,717, filed on Mar. 24, 2000, now Pat. No. 6,914,128.

(60) Provisional application No. 60/126,603, filed on Mar. 25, 1999.

(51) Int. Cl.
| | |
|---|---|
| C07K 16/24 | (2006.01) |
| C12P 21/08 | (2006.01) |
| A61K 39/395 | (2006.01) |
| A61K 39/00 | (2006.01) |
| C07K 16/18 | (2006.01) |
| C07K 16/00 | (2006.01) |
| C07K 14/54 | (2006.01) |
| A61K 38/20 | (2006.01) |

(52) U.S. Cl.
CPC ............ *C07K 16/244* (2013.01); *A61K 39/3955* (2013.01); *C07K 16/00* (2013.01); *C07K 16/18* (2013.01); *C07K 14/5434* (2013.01); *A61K 39/00* (2013.01); *A61K 38/208* (2013.01); *A61K 2039/505* (2013.01); *C07K 2317/21* (2013.01); *C07K 2317/565* (2013.01); *C07K 2317/73* (2013.01); *Y10S 514/863* (2013.01); *Y10S 514/885* (2013.01); *Y10S 514/886* (2013.01)

(58) Field of Classification Search
None
See application file for complete search history.

(56) References Cited

U.S. PATENT DOCUMENTS

| | | |
|---|---|---|
| 4,816,397 A | 3/1989 | Boss et al. |
| 5,530,101 A | 6/1996 | Queen et al. |
| 5,545,806 A | 8/1996 | Lonberg et al. |
| 5,545,807 A | 8/1996 | Surani et al. |
| 5,569,825 A | 10/1996 | Lonberg et al. |
| 5,625,126 A | 4/1997 | Lonberg et al. |
| 5,633,425 A | 5/1997 | Lonberg et al. |
| 5,643,768 A | 7/1997 | Kawasaki |

(Continued)

FOREIGN PATENT DOCUMENTS

| | | |
|---|---|---|
| CA | 2226575 A1 | 2/1997 |
| EP | 0638644 | 2/1995 |

(Continued)

OTHER PUBLICATIONS

Schoenhaut D.S. et al. Cloning and expression of murine IL-12. Journal of Immunology, 1992, vol. 148, No. 11, p. 3433-3440.*

(Continued)

*Primary Examiner* — Robert Landsman
*Assistant Examiner* — Bruce D Hissong
(74) *Attorney, Agent, or Firm* — McCarter & English LLP; Maria Laccotripe Zacharakis; Briana M. Erickson

(57) ABSTRACT

Human antibodies, preferably recombinant human antibodies, that specifically bind to human interleukin-12 (hIL-12) are disclosed. Preferred antibodies have high affinity for hIL-12 and neutralize hIL-12 activity in vitro and in vivo. An antibody of the invention can be a full-length antibody or an antigen-binding portion thereof. The antibodies, or antibody portions, of the invention are useful for detecting hIL-12 and for inhibiting hIL-12 activity, e.g., in a human subject suffering from a disorder in which hIL-12 activity is detrimental. Nucleic acids, vectors and host cells for expressing the recombinant human antibodies of the invention, and methods of synthesizing the recombinant human antibodies, are also encompassed by the invention.

18 Claims, 22 Drawing Sheets

(56) References Cited

U.S. PATENT DOCUMENTS

| | | |
|---|---|---|
| 5,650,492 A | 7/1997 | Gately et al. |
| 5,652,138 A | 7/1997 | Burton et al. |
| 5,654,407 A | 8/1997 | Boyle et al. |
| 5,656,272 A | 8/1997 | Le et al. |
| 5,658,754 A | 8/1997 | Kawasaki |
| 5,661,016 A | 8/1997 | Lonberg et al. |
| 5,698,195 A | 12/1997 | Le et al. |
| 5,762,923 A | 6/1998 | Gross et al. |
| 5,770,429 A | 6/1998 | Lonberg et al. |
| 5,780,597 A | 7/1998 | Gately et al. |
| 5,789,650 A | 8/1998 | Lonberg et al. |
| 5,792,838 A | 8/1998 | Smith et al. |
| 5,804,440 A | 9/1998 | Burton et al. |
| 5,811,523 A | 9/1998 | Trinchieri et al. |
| 5,814,318 A | 9/1998 | Lonberg et al. |
| 5,853,697 A | 12/1998 | Strober et al. |
| 5,910,486 A | 6/1999 | Curiel et al. |
| 5,919,452 A | 7/1999 | Le et al. |
| 6,054,487 A | 4/2000 | Sekut et al. |
| 6,090,382 A | 7/2000 | Salfeld et al. |
| 6,150,584 A | 11/2000 | Kucherlapati et al. |
| 6,225,117 B1 | 5/2001 | Gately et al. |
| 6,255,458 B1 | 7/2001 | Lonberg et al. |
| 6,258,562 B1 | 7/2001 | Salfeld et al. |
| 6,277,969 B1 | 8/2001 | Le et al. |
| 6,284,471 B1 | 9/2001 | Le et al. |
| 6,300,129 B1 | 10/2001 | Lonberg et al. |
| 6,338,848 B1 | 1/2002 | Leonard et al. |
| 6,342,634 B2 | 1/2002 | Nicholson et al. |
| 6,673,986 B1 | 1/2004 | Kucherlapati et al. |
| 6,713,610 B1 | 3/2004 | Kucherlapati et al. |
| 6,902,734 B2 | 6/2005 | Giles-Komar et al. |
| 6,914,128 B1 | 7/2005 | Salfeld et al. |
| 7,060,268 B2 | 6/2006 | Andya et al. |
| 7,063,964 B2 | 6/2006 | Giles-Komar et al. |
| 7,084,260 B1 | 8/2006 | Lonberg et al. |
| 7,166,285 B2 | 1/2007 | Giles-Komar et al. |
| 7,279,157 B2 | 10/2007 | Giles-Komar et al. |
| 7,504,485 B2 | 3/2009 | Salfeld |
| 7,560,247 B2 | 7/2009 | Giles-Komar et al. |
| 7,776,331 B1 | 8/2010 | Chartash |
| 7,883,704 B2 | 2/2011 | Salfeld |
| 8,178,092 B2 | 5/2012 | Valdes |
| 2002/0161199 A1 | 10/2002 | Ashkenazi et al. |
| 2002/0194631 A1 | 12/2002 | Ehrhardt et al. |
| 2003/0070185 A1 | 4/2003 | Jakobovits et al. |
| 2004/0156835 A1 | 8/2004 | Imoto et al. |
| 2004/0191265 A1 | 9/2004 | Schenerman et al. |
| 2005/0137385 A1 | 6/2005 | Benson et al. |
| 2005/0159364 A1 | 7/2005 | Cooper |
| 2005/0276823 A1 | 12/2005 | Cini et al. |
| 2007/0009526 A1 | 1/2007 | Benson et al. |
| 2007/0020255 A1 | 1/2007 | Ueno et al. |
| 2007/0172475 A1 | 7/2007 | Matheus et al. |
| 2008/0071063 A1 | 3/2008 | Allan et al. |
| 2009/0175857 A1 | 7/2009 | Salfeld |
| 2009/0269302 A1 | 10/2009 | Salfeld |
| 2009/0311241 A9 | 12/2009 | Salfeld et al. |
| 2010/0028363 A1 | 2/2010 | Valdes |
| 2010/0297143 A1 | 11/2010 | Chartash |
| 2011/0123544 A1 | 5/2011 | Salfeld |
| 2012/0201831 A1 | 8/2012 | Salfeld |
| 2012/0213792 A1 | 8/2012 | Salfeld |
| 2012/0225080 A1 | 9/2012 | Hruska |
| 2012/0308514 A1 | 12/2012 | Salfeld |

FOREIGN PATENT DOCUMENTS

| | | |
|---|---|---|
| EP | 0659766 | 6/1995 |
| EP | 0953639 | 11/1999 |
| WO | WO90/05144 | 5/1990 |
| WO | WO 92/01047 | 1/1992 |
| WO | WO 92/09690 | 6/1992 |
| WO | WO 92/20791 | 11/1992 |
| WO | WO93/06213 | 4/1993 |
| WO | WO93/11236 | 6/1993 |
| WO | WO94/02602 | 2/1994 |
| WO | WO 94/04679 | 3/1994 |
| WO | WO94/25585 | 11/1994 |
| WO | WO 95/14780 | 6/1995 |
| WO | WO 95/24918 | 9/1995 |
| WO | WO 96/33735 | 10/1996 |
| WO | WO96/34096 | 10/1996 |
| WO | WO97/13852 | 4/1997 |
| WO | WO 97/15327 | 5/1997 |
| WO | 97/29131 A1 | 8/1997 |
| WO | WO 98/16248 | 4/1998 |
| WO | WO 98/22137 | 5/1998 |
| WO | WO98/24884 | 6/1998 |
| WO | WO98/24893 | 6/1998 |
| WO | WO 98/41232 | 9/1998 |
| WO | WO 98/42378 | 10/1998 |
| WO | WO98/50433 | 11/1998 |
| WO | 98/56418 A1 | 12/1998 |
| WO | WO 99/09055 | 2/1999 |
| WO | WO 99/22766 | 5/1999 |
| WO | WO 99/37682 | 7/1999 |
| WO | WO 99/57151 | 11/1999 |
| WO | WO 00/56772 | 9/2000 |
| WO | WO 02/12500 | 2/2002 |
| WO | WO 02/072636 | 9/2002 |
| WO | WO 02/097048 A2 | 12/2002 |
| WO | WO2004091510 | 10/2004 |
| WO | WO2005062967 | 7/2005 |
| WO | WO 2005/121177 | 12/2005 |
| WO | WO 2006/012500 | 2/2006 |
| WO | WO 2006/069036 | 6/2006 |
| WO | WO2008046033 | 4/2008 |

OTHER PUBLICATIONS

Barbas et al., Selection and Evolution of High-Affinity Human Anti-Viral Antibodies. Trends Biotechnol. 14:230 (1996).
Barbas et al., Semisynthetic combinatorial antibody libraries: A chemical solution to the diversity problem. PNAS 89:4457 (1992).
Beeson et al., Thymus, thymoma, and specific T cells in myasthenia gravis. Ann. NY Acad. Sci. 841:371 (1998).
Bruggemann et al., Production of human antibody repertoires in transgenic mice. Curr. Op. Biotechnol. 8:455 (1997).
Bruggemann et al., Strategies for expressing human antibody repertoires in transgenic mice. Immunol. Today 17:391 (1996).
Bruggmenn et al., A repertoire of monoclonal antibodies with human heavy chains from transgenic mice. PNAS 86:6709 (1989).
Burton et al. Human antibodies from combinatorial libraries. Adv. Immunol. 57:191 (1994).
Choi et al., Transgenic mice containing a human heavy chain immunoglobulin gene fragment cloned in a yeast artificial chromosome. Nature Genetics 4:117 (1993).
Davies et al, Creation of mice expressing human antibody light chains by introduction of a yeast artificial chromosome containing the core region of the human immunoglobulin kappa locus. Bio/Technology 11:911 (1993).
Eren et al., Human monoclonal antibodies specific to hepatitis B virus generated in a human/mouse radiation chimera: the Trimera system. Immunol. 93:154 (1998).
Fishwild et al., High-avidity human IgGk monoclonal antibodies from a novel strain of minilocus transgenic mice. Nature Biotechnology 14:845 (1996).
Green et al., Antigen-specific human monoclonal antibodies from mice engineered with human Ig heavy and light chain YACs. Nature Genetics 7:12 (1994).
Griffiths et al., Isolation of high affinity human antibodies directly from large synthetic repertoires. EMBO J. 13:3245 (1994).
Hanes et al., Ribosome display efficiently selects and evolves high-affinity antibodies in vitro from immune libraries. PNAS 95:14130 (1998).
Harding et al., Class Switching in Human Immunoglobulin Transgenic Mice. Ann. NY Acad. Sci. 764:536 (1995).

(56) References Cited

OTHER PUBLICATIONS

Hoogenboom et al., By-passing Immunisation: Human Antibodies from Synthetic Repertoires of Germline VH Gene Segments Rearranged in Vitro. J. Mol. Biol. 227:381 (1992).
Jakobovits, Production of fully human antibodies by transgenic mice. Curr. Op. Biotechnol. 6:561 (1995).
Jespers et al., Guiding the Selection of Human Antibodies from Phage Display Repertoires to a Single Epitope of an Antigen. Nature Biotechnology 12:899 (1994).
Kang et al. Antibody redesign by chain shuffling from random combinatorial immunoglobulin libraries. PNAS 88:11120 (1991).
Kang et al., Linkage of recognition and replication functions by assembling combinatorial antibody Fab libraries along phage surfaces. PNAS 88:4363 (1991).
Katsube et al., Analysis of kappa light chain contribution to anti-DNA antibody activity of a human VH4-21-encoded monoclonal antibody (NE-1) by antibody-phage display technique. Int. J. Mol. Med. 1:863 (1998).
Lonberg et al., Antigen-specific human antibodies from mice comprising four distinct genetic modifications. Nature 368:856 (1994).
Lonberg et al., Human Antibodies from Transgenic Mice. Int. Rev. Immunol. 13:65 (1995).
MacCallum et al., Antibody-antigen Interactions: Contact Analysis and Binding Site Topography. J. Mol. Biol. 262:732 (1996).
Marks et al., By-Passing Immunization: Building High Affinity Human Antibodies by Chain Shuffling. Bio/Technology 10:779 (1992).
Marks et al., Human Antibody Fragments Specific for Human Blood Group Antigens from a Phage Display Library. Bio/Technology 11:1145 (1993).
Marks et al., Molecular evolution of proteins on filamentous phage. Mimicking the strategy of the immune system. J. Biol. Chem. 267:16007 (1992).
Marks et al.,. By-passing Immunization: Human Antibodies from V-gene Libraries Displayed on Phage. J. Mol. Biol. 222:581 (1991).
Meager et al., Spontaneous neutralising antibodies to interferon-a and interleukin-12 in thymoma-associated autoimmune disease Lancet 350, 1596 (1997).
Mendez et al., Functional transplant of megabase human immunoglobulin loci recapitulates human antibody response in mice. Nature Genetics 15:146 (1997).
Neuberger et al., Mice perform a human repertoire. Nature 386:25 (1997).
Nguyen et al., Production of human monoclonal antibodies in SCID mouse. Microbiol. Immunol. 41:901 (1997).
Persson et al., Generation of diverse high-affinity human monoclonal antibodies by repertoire cloning. PNAS 88:2432 (1991).
Rader et al., Phage display of combinatorial antibody libraries. Curr. Op. Biotechnol. 8:503 (1997).
Salfeld, "Development of a Fully Human Antibody to TNF by Phage Display Technology," IBC Conference Antibody Engineering, Dec. 1996.
Sandhu et al., The use of SCID mice in biotechnology and as a model for human disease. Crit. Rev. Biotechnol. 16:95 (1996).
Schier et al., Isolation of Picomolar Affinity Anti-c-erbB-2 Single-chain Fv by Molecular Evolution of the Complementarity Determining Regions in the Center of the Antibody Binding Site. J. Mol. Biol. 263:551 (1996).
Sheets et al., Efficient construction of a large nonimmune phage antibody library: The production of high-affinity human single-chain antibodies to protein antigens. PNAS 95:6157 (1998).
Taylor et al., Human immunoglobulin transgenes undergo rearrangement, somatic mutation and class switching in mice that lack endogenous IgM. Int. Immunol. 6:579 (1994).
Trinchieri, Interleukin-12: a proinflammatory cytokine with immunoregulatory functions that bridge innate resistance and antigen-specific adaptive immunity. Ann. Rev. Immunol., 13:251 (1995).
Tuaillon et al., Human immunoglobulin heavy-chain minilocus recombination in transgenic mice: Gene-segment use in mu and gamma transcripts. PNAS 90:3720 (1993).
Wagner et al., Antibodies generated from human immunoglobulin miniloci in transgenic mice. Nucl. Acids Res. 22:1389 (1994).
Wagner et al., The diversity of antigen-specific monoclonal antibodies from transgenic mice bearing human immunoglobulin gene miniloci. Eur. J. Immunol. 24:2672 (1994).
Wysocka et al., Interleukin-12 is required for interferon-gamma production and lethality in lipopolysaccharide-induced shock in mice. Eur. J. Immunol. 25:672 (1995).
Zou et al., Dominant expression of a 1.3 Mb human Igk locus replacing mouse light chain production. FASEB J. 10:1227 (1996).
Australian Office Action for Application No. 2006225302, dated Oct. 27, 2008.
Balashov, K.E., et al. "Increased interleukin 12 production in progressive multiple sclerosis: induction by activated CD4+ T cells via CD40 ligand." Proc Natl Acad Sci USA. Jan. 21, 1997; 94(2) :599-603.
Baldock, P. et al. "A Comparison of Microbatch and Vapor Diffusion for Initial Screening of Crystallization Conditions." 1996 J. Crystal Growth 168 (1-4); pp. 170-174 (abstract only).
Barbas, III, C. F. , et al. "Assembly of combinatorial antibody libraries on phage surfaces: the gene III site." Proc Natl Acad Sci USA. Sep. 15, 1991; 88(18):7978-82.
Barrie et al. "The interleukin-12 family of cytokines: Therapeutic targets for inflammatory disease mediation." 2005 Clinical and Applied Immun. Rev. 5(4): 225-240.
Berrebi, D., et al. "Interleukin-12 expression is focally enhanced in the gastric mucosa of pediatric patients with Crohn's disease." Am J Pathol. Mar. 1998; 152(3):667-72.
Bird, RE., et al. "Single-chain antigen-binding proteins." Science. Oct. 21, 1988; 242(4877): 423-6.
Brown, Jr., P.S., et al. "Anti-Tac-H, a humanized antibody to the interleukin 2 receptor, prolongs primate cardiac allograft survival" Proc Natl Acad Sci USA. 1991 88(7):2663-7.
Bucht, A, et al. "Expression of interferon-gamma (IFN-gamma), IL-10, IL-12 and transforming growth factor-beta (TGF-beta) mRNA in synovial fluid cells from patients in the early and late phases of rheumatoid arthritis (RA)." Clin Exp Immunol. Mar. 1996; 103(3):357-67.
Cambridge Antibody Technology Group plc, "Applying technology to target disease," Annual Report (1998).
Cambridge Antibody Technology, "Clinical Trials From CAT," PR Newswire (1999).
Carter, RW., et al. "Production and characterization of monoclonal antibodies to human interleukin-12," Hybridoma. Aug. 1997; 16(4):363-9.
Casset et al. "A peptide mimetic of an anti-CD4 monoclonal antibody by rational design." 2003 Biochem and Biophys Res Comm 307:198-205.
Chames et al., "Improving the Affinity and the Fine Specificity of an Anti-Cortisol Antibody by Parsimonious Mutagenesis and Phage Display," J Immunol, (1998) 161: pp. 5421-5429.
Chizzonite, R et al., "IL-12: Monoclonal antibodies specific to the 40-kDa subunit block receptor binding and biological activity on activated human lymphoblasts," J. Immunol., 1991, vol. 147:1548-1556.
Clackson, T., et al. "Making antibody fragments using phage display libraries." Nature. Aug. 15, 1991; 352(6336):624-8.
Clark, Steven C., "Interleukin 12: Molecular, Biological and Clinical Perspectives," Molecular Biology of Haematopoiesis, vol. 3:3-14 (1993).
Cordoba et al. "Non-enzymatic hinge region fragmentation of antibodies in solution" 2005 J Chromatogr B Analyt Technol Biomed Life Sci 818:115-121.
Dall'Acqua, W., et al. "Antibody engineering." Curr Opin Struct Bioi. Aug. 1998; 8(4):443-50.
D'Andrea, A. et al., "Production of Natural Killer Cell Stimulatory Factor (Interleukin 12) by Peripheral Blood Mononuclear cells," J. Exp. Med., 1992, vol. 176:1387-1398.
Daugherty et al. "Antibody affinity maturation using bacterial surface display." 1998 Protein Eng. 11 (9):825-832.
Deng et al. "Basis for selection of improved carbohydrate-binding single-chain antibodies from synthetic gene libraries" PNAS (1995) 92: 4992-4996.

(56) References Cited

OTHER PUBLICATIONS

Ding, et al. "ABT-874, a fully human monoclonal anti-IL-12/IL-23 antibody for the potential treatment of autoimmune diseases." 2008 Current Opinion in Investigational Drugs 9(5):515-522.
Duchmann, R., et al. "Tolerance towards resident intestinal flora in mice is abrogated in experimental colitis and restored by treatment with interleukin-10 or antibodies to interleukin-12." Eur. J. Immunol. 1996, 26:934-8.
Fais, S., et al. "Interferon expression in Crohn's disease patients: increased interferon-gamma and -alpha mRNA in the intestinal lamina propria mononuclear cells." J Interferon Res. Oct. 1994; 14(5):235-8.
Fauchet et al. "Characterization of Monoclonal Antibodies against Human Interleukin-12 and Their Use in an Elisa for the Measurement of This Cytokine." 1996 Annals of the New York Academy of Sciences, vol. 795, pp. 334-336.
Fehr et al. "Nucleotide and Predicted Peptide Sequence of Feline Interleukin-12 (IL-12)." 1997 DNA sequence 8:77-82.
Fuchs, P., et al. "Targeting recombinant antibodies to the surface of *Escherichia coli*: fusion to a peptidoglycan associated lipoprotein." Biotechnology (NY). Dec. 1991; 9(12):1369-72.
Fuss, I.J., et al. "Disparate CD4+ lamina propria (LP) lymphokine secretion profiles in inflammatory bowel disease. Crohn's disease LP cells manifest increased secretion of IFN-gamma, whereas ulcerative colitis LP cells manifest increased secretion of IL-5." J Immunol. Aug. 1, 1996; 157(3):1261-70.
Garrard, L.J., et al. "Fab assembly and enrichment in a monovalent phage display system," Biotechnology(NY), Dec. 1991; vol. 12:1373-7.
Gately, M.K., et al. "The interleukin-12/interleukin-12-receptor system: role in normal and pathologic immune responses." Annu Rev Immunol. 1998; 16:495-521.
Gram, H., et al. "In vitro selection and affinity maturation of antibodies from a naive combinatorial immunoglobulin library." Proc Natl Acad Sci USA. Apr. 15, 1992; 89(8):3576-80.
Griffiths, A. D., et al. "Human anti-self antibodies with high specificity from phage display libraries." EMBO J. Feb. 1993; 12(2):725-34.
Hamid, Q., et al. "In vivo expression of IL-12 and IL-13 in atopic dermatitis." J Allergy Clin Immunol. Jul. 1996; 98(1):225-31.
Hanes, J., et al. "In vitro selection and evolution of functional proteins by using ribosome display." Proc Natl Acad Sci USA. May 13, 1997; 94(10):4937-42.
Hawkins, RE., et al. "Selection of phage antibodies by binding affinity. Mimicking affinity maturation." J Mol Biol. Aug. 5, 1992; 226(3):889-96.
Hay, B. N., et al. "Bacteriophage cloning and *Escherichia coli* expression of a human IgM Fab." Hum Antibodies Hybridomas. Apr. 1992; 3(2):81-5.
He, M., et al. "Antibody-ribosome-mRNA (ARM) complexes as efficient selection particles for in vitro display and evolution of antibody combining sites." Nucleic Acids Res. Dec. 15, 1997; 25(24):5132-4.
Heinzel et al. "Interleukin 12 is Produced In Vivo during Endotoxemia and Stimulates Synthesis of Gamma Interferon." 1994 Infection and Immunity 62(10): 4244-4249.
Hoogenboom, H. R, et al. "Multi-subunit proteins on the surface of filamentous phage: methodologies for displaying antibody (Fab) heavy and light chains." Nucleic Acids Res. Aug. 11, 1991; 19(15):4133-7.
Hoogenboom, Hennie R et al., "Antibody phage display technology and its applications," Immunotechnology, vol. 4:1-20 (1998).
Hoogenboom, Hennie R, "Designing and optimizing library selection strategies for generating high-affinity antibodies," Trends Biotechnol., vol. 15(2):62-70 (1997).
http://www.bdbiosciences.com "Purified mouse anti-human IL-12, p40/p70 monoclonal antibody, clone C8.6." 2005 BD Pharmingen Technical Data Sheet for product #554659. 2005.
http://www.biolegend.com "LEAF Purified anti-human IL-12/IL-23, p40 (monomer, dimer, heterodimer), clone 11.5." May 1, 2007 Technical Data Sheet for product #501812.
http://www.clinicaltrials.gov "A Safety and Efficacy Study of CNTO 1275 in Patients with Multiple Sclerosis" 2009 ClinicalTrials.gov Identifier: NCT00207727; (Jul. 14, 2009).
http://www.clinicaltrials.gov "A Study of the Safety and Efficacy of CNTO 1275 in Subjects with Moderate to Severe Psoriasis." 2009 ClinicalTrials.gov Identifier: NCT00307437; (Jul. 14, 2009) (4 pages).
http://www.clinicaltrials.gov "A Study of the Safety and Efficacy of CNTO 1275 in Patients with Active Psoriatic Arthritis." 2009 ClinicalTrials.gov Identifier: NCT00267956; (Jul. 14, 2009).
http://www.clinicaltrials.gov "A Study of the Safety and Efficacy of CNTO 1275 in Subjects with Severe Plaque-Type Psoriasis." 2009 ClinicalTrials.gov Identifier: NCT00320216; (Jul. 14, 2009).
http://www.clinicaltrials.gov "A Study of the Safety and Efficacy of CNTO 1275 in Patients with Severe Plaque-Type Psoriasis" 2009 ClinicalTrials.gov Identifier: NCT00267969; (Jul. 14, 2009).
http://www.clinicaltrials.gov "Efficacy and Safety of ABT-874 in Subjects With Moderate to Severe Chronic Plaque Psoriasis." 2009 ClinicalTrials.gov Identifier: NCT00292396; (Jul. 14, 2009).
http://www.clinicaltrials.gov "Monoclonal Antibody Treatment of Crohn's Disease" 2009 ClinicalTrials.gov Identifier: NCT00007163; (Jul. 14, 2009).
http://www.clinicaltrials.gov "Safety and Effectiveness of Two Doses of ABT-874 as Compared to Placebo in Subjects with Multiple Sclerosis." (MS) 2009 ClinicalTrials.gov Identifier: NCT00086671; (Jul. 14, 2009).
Huse, W.D., et al. "Generation of a large combinatorial library of the immunoglobulin repertoire in phage lambda." Science. Dec. 8, 1989; 246(4935):1275-81.
Huston, J.S., et al. "Protein engineering of antibody binding sites: recovery of specific activity in an anti-digoxin single-chain Fv analogue produced in Escherichia coiL" Proc Natl Acad Sci USA. Aug. 1988; 85(16):5879-83.
International Search Report of the International Searching Authority dated Aug. 8, 2000, issued in connection with International Patent Appln. No. PCT/US08/00564.
International Search Report for Application of the International Searching Authority dated Mar. 25, 2010 issued in connection with International Patent Appln. No. PCT/US09/65714.
International Search Report of the International Searching Authority dated Aug. 8, 2000, issued in connection with International Patent Appln. No. PCT/USOO/07946 (4 pages).
International Search Report of the International Searching Authority dated Jun. 18, 2008, issued in connection with International Patent Appln. No. PCT/US07/26212 (1 page).
International Search Report of the International Searching Authority dated Dec. 19, 2009, issued in connection with International Patent Appln. No. PCT/US09/36765 (2 pages).
International Search. Report of the International Searching Authority dated Jun. 5, 2008, issued in connection with International Patent Appln. No. PCT/US08/04006 (2 pages).
Irving, R.A., et al. "Affinity maturation of recombinant antibodies using *E. coli* mutator cells." Immunotechnology. Jun. 1996; 2(2):127-43.
Jackson JR, et al. In vitro antibody maturation. Improvement of a high affinity, neutralizing antibody against IL-1 beta. J Immunol. Apr. 1, 1995 ;154(7):3310-9.
Junghans, R.P., et al. "Anti-Tac-H, a humanized antibody to the interleukin 2 receptor with new features for immunotherapy in malignant and immune disorders." Cancer Res. Mar. 1, 1990 ; 50(5):1495-502.
Kabat, E.A., et al. "Attempts to locate complementarity-determining residues in the variable positions of light and heavy chains." Ann NY Acad Sci. Dec. 31, 1971; 190:382-93.
Kabat, E.A., et al. Accession No. PB91-192898, Sequences of Proteins of Immunological Interest, Fifth Edition, U.S. Department of Health and Human Services, NIH Publication No. 91/3242, 1991.
Kasper et al., "A phase I trial of an interleukin-12/23 monoclonal antibody in relapsing multiple sclerosis" 2006 Current Medical Research and Opinion, 22(9):1671-1678.

(56) References Cited

OTHER PUBLICATIONS

Kauffman, et al. "A Phase I Study Evaluating the Safety, Pharmacokinetics, and Clinical Response of a Human IL-12 p40 Antibody in Subjects with Plaque Psoriasis" 2004 J. Invest. Dermatology, vol. 123:1037-1044.
Kettleborough, C.A., et al. "Humanization of a mouse monoclonal antibody by CDR-grafting: the importance of framework residues on loop conformation." Protein Eng. 1991, 4 :773-83.
Kimball, et al "Safety and Efficacy of ABT-874, a Fully Human Interleukin 12/23 Monoclonal Antibody, in the Treatment of Moderate to Severe Chronic Plaque Psoriasis" 2008 ARCH Dermatol, 144(2):200-207.
Kobayashi, M., et al. "Identification and purification of natural killer cel l stimulatory factor (NKSF), a cytokine with multiple biologic effects on human lymphocytes." J Exp Med. Sep. 1, 1989; 170(3):827-45.
Kosako et al., "Isolation and characterization of neutralizing single-chain antibodies against *Xenopus* mitogen-activated protein kinase kinase from phage display libraries" Biochemistry (1996) 35:13212-21.
Leonard et al. "Prevention of Experimental Autoimmune Encephalomyelitis by Antibodies Against Interleukin 12" 1995 J. Exp. Med.181:381-386.
Ling, P., et al. "Human IL-12 p40 homodimer binds to the IL-12 receptor but does not mediate biologic activity." J Immunol. Jan. 1, 1995; 154(1 ):116-27.
Liu et al. "Analysis of the Interrelationship between IL-12, TNF-alpha, and IFN-gamma Production during Murine Listeriosis" 1995 Cellular Immunology 163(2):260-267.
Longbrake, E.E., et al. Why did IL-12/IL23 antibody therapy fail in multiple sclerosis. Expert Rev. Neurother., 2009, vol. 9, No. 3, p. 319-321 (3 pages).
Mannon et al., "Anti-Interleukin-12 Antibody for Active Crohn's Disease" 2004 New England J. Med. 351 :2069-2079.
McCafferty, J., et al. "Phage antibodies: filamentous phage displaying antibody variable domains." Nature. Dec. 6, 1990; 348(6301):552-4.
McPherson "A comparison of salts for the crystallization of macromolecules" 2001 Protein Science, vol. 10:418-422.
Medical News Today, Press release. Abbott's ABT 874 Shows Positive Results for Maintenance of Response in Phase II Psoriasis Study. Oct. 2, 2007 Retrieved from internet Dec. 17, 2009 http://www.medicalnewstoday.com/printerfriendlynews.php?news.php?newsid=84202.
Monteleone, G. , et al. "Interleukin 12 is expressed and actively released by Crohn's disease intestinal lamina propria mononuclear cells." Gastroenterology. Apr. 1997; 112(4): 1169-78.
Morita,Y., et al. "Expression of interleukin-12 in synovial tissue from patients with rheumatoid arthritis." Arthritis Rheum. Feb. 1998; 41 (2):306-14.
Neri et al. Targeting by affinity-matured recombinant antibody fragments of an angiogenesis associated fibronectin isoform. 1997 Nature Biotechnology 15(12) 1271-1275.
Neurath, M. F., et al. "Antibodies to interleukin 12 abrogate established experimental colitis in mice." J Exp Med. Nov. 1, 1995; 182(5):1281-90.
Oppmann, B. et al. , "Novel p19 Protein Engages IL-12p40 to form a cytokine, IL-23, with biological activities similar as well as distinct from IL-12," Immunity, 2000, vol. 13:715-725.
Oswald et al. Interleukin-12 Synthesis Is a Required Step in Terhalose Dimycolate-Induced Activation of Mouse Peritoneal Macrophages 1997 Infection and Immunity 65(4): 1364-1369.
Panaccione et al. Briakinumab (Anti-interleukin 12/23p40, ABT874) for Treatment of Crohn's Disease (CD) 2010 abstract of submission to American College of Gastroenterology Annual Scientific Meeting.
Paper 128 of Patent Interference 105,592 McK, Technology Center 1600, *Centocor, Inc.*, vs. *Abbott GmbH & Co.*, KG entered Jul. 1, 2008.

Paper 20 of Patent Interference 105,592 McK, Technology Center 1600, *Centocor, Inc.* , vs. *Abbott GmbH & Co.*, KG entered Feb. 5, 2008.
Parronchi, P., et al. "Type 1 T-helper cell predominance and interleukin-12 expression in the gut of patients with Crohn's disease." Am J Pathol. Mar. 1997; 150(3):823-32.
Paul 1993 Fundamental Immunology 3rd Ed., 1993 292-295.
Pini, A., et al. "Design and use of a phage display library. Human antibodies with subnanomolar affinity against a marker of angiogenesis eluted from a two-dimensional geL" J Biol Chem Aug. 21, 1998; 273(34):21769-76.
Pini, A., et al. "Hierarchical affinity maturation of a phage library derived antibody for the selective removal of cytomegalovirus from plasma." J Immunol Methods. Aug. 7, 1997; 206(1-2): 171-82.
Podlaski, F.J., et al. "Molecular characterization of interleukin 12." Arch Biochem Biophys. Apr. 1992; 294(1):230-7.
Riechmann, Lutz et al., "Phage Display and Selection of a Site-Directed Randomized Single-Chain Antibody Fv Fragment for Its Affinity Improvement," Biochemistry, vol. 32:8848-8855 (1993).
Ryan, C, et al. The use of ustekinumab in autoimmune disease. Expert Opin. Biol. Ther., 2010, vol. 10, No. 4, p. 587-604 (18 pages).
Scherl, E.J., et al. Review of the safety and efficacy of ustekinumab. Ther. Adv. Gastroenterol., 2010, vol. 3, No. 5, p. 321-328 (8 pages).
Schwaller et al. Interleukin-12 Expression in Human Lymphomas and Nonneoplastic Lympohoid Disorders 1995 Blood 85(8): 2182-2188.
Seder, R.A., et al. "Interleukin 12 acts directly on CD4+ T cells to enhance priming for interferon gamma production and diminishes interleukin 4 inhibition of such priming." Proc Natl Acad Sci USA. Nov. 1, 1993; 90(21 ):10188-92.
Segal, B.M., et al. Repeated subcutaneous injections of IL23/23 p40 neutralising antibody, ustekinumab, in patients with relapsing-remitting multiple sclerosis: a phase II, double-blind, placebo-controlled, randomised, dose-ranging study. Lancet Neurol., 2008, vol. 7, p. 796-804 (9 pages).
Sharon, J. "Structural correlates of high antibody affinity: three engineered amino acid substitutions can increase the affinity of an anti-p-azophenylarsonate antibody 200-fold." Proc Natl Acad Sci USA. Jun. 1990; 87(12):4814-7.
Short et al. Contribution of Antibody Heavy Chain CDR1 to Digoxin Binding Analyzed by Random Mutagenesis of Phage-displayed Fab 26-10, 1995, J. Biol. Chem. 270(48):28541-28550.
Smith et al. Specific cleavage of immunoglobulin G by copper ions 1996 Int J Peptide Protein Res 48:48-55.
Supplemental European Search Report for European Application No. EP08742311, Feb. 26, 2010.
Tao, W. et al., "P19ARF Stabilizes p53 by Blocking Nucleo-cytoplasmic shuttling of Mdm2," Proc. Natl. Acad. Sci. USA., 1999, vol. 96:6937-6941.
Taylor, L. D., et al. "A transgenic mouse that expresses a diversity of human sequence heavy and light chain immunoglobulins." Nucleic Acids Res. Dec. 11, 1992; 20(23):6287-95.
Toichi et al., An anti-IL-12p40 antibody down-regulates type 1 cytokines, chemokines, and IL-12/IL-23 in psoriasis. 2006. J Immunol. 177:4917-4926.
Tomlinson, Ian M. et al., "The Imprint of Somatic Hypermutation on the Repertoire of Human Germline V Genes," J. Mol. Biol., vol. 256:813-817 (1996).
Trinchieri, Giorgio, "Interleukin-12 and its role in the generation of TH1 celis," Immunology Today, vol. 14(7):335-338 (1993).
Turka, L.A., et al. "Interleukin 12: a potential link between nerve cells and the immune response in inflammatory disorders." Mol Med. Sep. 1995; 1 (6):690-9.
United States Patent and Trademark Office, "Patent Interference No. 1 05,592," Centocor Motion 1 (2007).
United States Patent and Trademark Office, "Patent Interference No. 1 05,592," Declaration (2007).
Valiante, Nicholas M. et al., "Role of the Production of Natural Killer Cell Stimulatory Factor (NKSF/IL-12) in the Ability of B Cell Lines to Stimulate T and NK Cell Proliferation," Cellular Immunology, vol. 145:187-198 (1992).

(56) References Cited

OTHER PUBLICATIONS

Vaughan et al., Human Antibodies with Sub-nanomolar Affinities Isolated from a Large Non-immunized Phage Display Library 1996 Nature Biotechnology, 14:309-314.
Vollmer et al. A Phase 2, 24-Week, Randomized, Placebo-Controlled, Double-Blind Study Examining the Efficacy and Safety of an Anti-Interleukin-12 and -23 Monoclonal Antibody in Patients With Relapsing-Remitting or Secondary-Progressive Multiple Sclerosis. 2010, manuscript submission to Multiple Sclerosis Dec. 6, 2010 [Epub ahead of print].
Wilkinson et al. Characterization of anti-mouse IL-12 monoclonal antibodies and measurement of mouse IL-12 by ELISA 1996. J. Immun. Methods 189(1): 15-24.
Williamson et al. Neutralizing IL-12 During Induction of Murine Acute Graft-Versus-Host Disease Polarizes the Cytokine Profile Toward a Th2-Type Alloimmune Response and Confers Long Term Protection From Disease 1997 J. Immun.159:1208-1215.
Windhagen, A., et al. "Expression of costimulatory molecules B7-1 (CD80), B7-2 (CD86), and interleukin 12 cytokine in multiple sclerosis lesions." J Exp Med. Dec. 1, 1996; 182(6}:1985-996.
Winter, G., et al. "Making antibodies by phage display technology." Annu Rev Immunol. 1994; 12:433-55.
Wolf, S.F. et al., "Cloning of cDNA for Natural Killer Cell Stimulatory Factor, A Heterodimeric Cytokine with Multiple Biologic Effects on T and Natural Killer Cells," J. Immunol. 1991, vol. 146 :3074-3081.
Wu et al., Simultaneous targeting of multiple disease mediators by a dual-variable-domain immunoglobulin 2007 Nature Biotechnology, 25(11):1290-1297.
Yago, T., et al. IL-23 induces human osteoclastogenesis via IL-17 in vitro, and anti-IL-23 antibody attenuates collagen-induced arthritis in rats. Arthritis Res. Ther, 2007, vol. 9, R96 (12 pages).
Yang et al. Crystalline monoclonal antibodies for subcutaneous delivery 2003 PNAS vol. 100(12):6934-6939.
Yawalkar et al. Expression of Interleukin-12 is Increased in Psoriatic Skin 1998 Journal of Investigative Dermatology, vol. 111, pp. 1053-1057.
Arkin et al., Probing the importance of second sphere residues in an esterolytic antibody by phage display. J. Mol. Biol. 284(4): 1083-1094 (1998).
Baca et al., Phage display of a catalytic antibody to optimize affinity for transition-state analog binding. Proc. Natl. Acad. Sci. USA 94(19):10063-10068 (1997).
Bendig, MM, Humanization of rodent monoclonal antibodies by CDR grafting. *Methods: A Companion to Methods in Immunology*, 8:83-93 (1995).
Benhar et al., Identification of residues that stabilize the single-chain Fv of monoclonal antibodies B3. J. Biol. Chem. 270(40): 23373-23380 (1995).
Borrebaeck, "Antibody Engineering," 1995, Oxford University Press, 2nd Edition (Part Ia, pp. 1-68).
Borrebaeck, "Antibody Engineering," 1995, Oxford University Press, 2nd Edition (Part Ib, pp. 69-139).
Borrebaeck, "Antibody Engineering," 1995, Oxford University Press, 2nd Edition (Part II, pp. 140-292).
Borrebaeck, "Antibody Engineering," 1995, Oxford University Press, 2nd Edition (Part III, pp. 293-390).
Dennison et al., Nonneutralizing HIV-1 gp41 envelope cluster II human monoclonal antibodies show polyreactivity for binding to phospholipids and protein autoantigens. J. Virol. 85(3): 1340-1347 (2011).
Krueger G., A human Interleukin-12/23 monoclonal antibody for the treatment of Psoriasis, NEJM, 356(6): 580-592 (2007).
Lesser Medical Encyclopedia: 6 vols, Academy of the Medical Sciences USSR, ed. by V.I. Pokrovsky, Moscow: soviet Encyclopedia, p. 138 (1991).
Malgarini and Pimpinella, Briakinumab versus Methotrexate for Psoriasis. NEJM, 366:379-380 (2012).
Memorandum and Order on Cross-Motions for Summary Judgment, Document No. 333, Case 4:09-cv-11340-FDS, filed Mar. 9, 2012.
Memorandum and Order on Motion for Judgment as a Matter of Law, Document No. 540, Case 4:09-cv-11340-FDS, filed Mar. 8, 2013.
Mérienne, K. et al., The Functional Architecture of an Acetylcholine Receptor-mimicking Antibody. J. Biol. Chem. 272(38): 23775-23783 (1997).
Nicholson et al., Antibody repertoires of four- and five-feature translocus mice carrying human immunoglobulin heavy chain and kappa and lambda light chain yeast artificial chromosomes. J. Immunol. 163(12): 6898-6906 (Dec. 15, 1999).
Parhami-Seren, B. and Margolies, MN, Contribution of Heavy Chain junctional Amino Acid Diversity to Antibody Affinity Among p-Azophenylarsonate-Specific Antibodies. J. Immunol.157: 2066-2072 (1996).
RayBio® Human IL-12 (p40) ELISA kit, User Manual, cat#:ELH-IL12p40-001, 2004.
Rich et al., A global benchmark study using affinity based biosensors, Anal. Biochem. 386:194-216 (2009).
Rovai et al., The murine neutrophilchemoattractant chemokines LIX, KC, and MIP-2 have distinct induction kinetics, tissue distributions, and tissue-specific sensitivities to glucocorticoid regulation in endotoxemia. J. Leukoc. Biol. 64(4): 494-502 (1998).
Schier et al., Efficient in vitro affinity maturation of phage antibodies using BIAcore guided selections. Hum. Antibodies Hybridomas. 7(3): 97-105 (1996).
Thompson et al., Affinity maturation of a high-affinity human monoclonal antibody against the third hypervariable loop of human immunodeficiency virus: use of phage display to improve affinity and broaden strain reactivity. J. Mol. Biol. 256(1): 77-88 (1996).
Yelton et al., Affinity maturation of the BR96 anti-carcinoma antibody by codon-based mutagenesis. J. Immunol. 155(4): 1994-2004 (1995).
Yoshikawa et al., Elevation of IL-12 p40 and its antibody in myasthenia gravis with thymoma. J. Neuroimmunol. 175, Jun. p. 169-175 (2006).
Zhang-Hoover et al., CD40/CD40 ligand interactions are critical for elicitation of autoimmune-mediated fibrosis in the lung. J. Immunol. 166(5): 3556-3563 (2001).
Barbas et al., "Human autoantibody recognition of DNA." PNAS USA (1995) 92:2529-2533.
Barbas et al., "Recognition of DNA by synthetic antibodies." J. Am. Chem. Soc. (1994) 116:2161-2162.
Beiboer et al., "Guided selection of a pan carcinoma specific antibody reveals similar binding characteristics yet structural divergence between the original murine antibody and its human equivalent." J. Mol. Biol. (2000) 296:833-849.
Berzofsky et al., "Chapter 8: Immunogenicity and Antigen Structure," Fundamental Immunology 3rd Edition, (1993), William E. Paul, Ed., pp. 292-295.
Canadian Federal Court, Docket T-1310-09, Citation: 2014 FC 55, Reasons for Judgment and Judgment, Jan. 17, 2014.
Decision revoking the European Patent (Art. 101(3)(b)EPC), European Patent No. EP-B-2 168 984, European Patent Office, Oct. 10, 2014.
Minutes of the Oral Proceedings Before the Opposition Division, European Patent No. EP-B-2 168 984, European Patent Office, Oct. 10, 2014.
Ditzel et al., "Determinants of polyreactivity in a large panel of recombinant human antibodies from HIV-1 infection." J. Immunol. (1996) 157:739-749.
Foote et al., "Antibody framework residues affecting the conformation of the hypervariable loops." J. Mol. Biol., (1992) 224(2):487-499.
Foote et al., "Kinetic and affinity limits on antibodies produced during immune responses." PNAS USA (1995) 92:1254-1256.
Klimka et al., "Human anti-CD30 recombinant antibodies by guided phage antibody selection using cell panning." British J. of Cancer (2000) 83:252-260.
Lam et al., "Antioxidants for prevention of methionine oxidation in recombinant monoclonal antibody HER2." J Pharm Sci. Nov. 1997; 86(11):1250-5.
Ma et al., "Human endothelial cells effectively costimulate cytokine production by, but not differentiation of, naïve CD4+ T cells." J. Immunol., (1998) 161(5):2158-2167.

(56) References Cited

OTHER PUBLICATIONS

United States Court of Appeals for the Federal Circuit, Case 2013-1338, Document 1346, Appeals from the United States District Court for the District of Massachusetts in Nos. 09-CV-11340-FDS, 10-CV-40003-FDS, and 10-CV-40004-FDS, decided Jul. 1, 2014.

Winter et al., "Humanized antibodies." Immunol. Today, (1993) 14(6):243-246.

Yang et al., "CDR walking mutagenesis for the affinity maturation of a potent human anti-HIV-1 antibody into the picomolar range." J. Mol. Biol., (1995) 254(3):392-403.

Altshuler, E.P. et al., "Generation of Recombinant Antibodies and Means for Increasing Their Affinity", *Biochemistry (Moscow)*, vol. 75, No. 13, pp. 1584-1605 (2010).

Carmen, S. et al., "Concepts in antibody phage display", *Briefings in Functional Genomics and Proteomics*, vol. 1, No. 2, pp. 189-203 (2002).

Harding FA et al., "The immunogenicity of humanized and fully human antibodies: residual immunogenicity resides in the CDR regions." *MAbs*. 2:256-65. Epub May 1, 2010.

Kim, Sang Jick, et al., "Antibody Engineering for the Development of Therapeutic Antibodies", *Mol. Cells*, vol. 20, No. 1, pp. 17-29 (2005).

Rudikoff, et al., "Single amino acid substitution altering antigen-binding specificity", *Proc. Natl. Acad. Sci.*, vol. 79, pp. 1979-1983 (1982).

United States District Court, District of Massachusetts, Civil Action 4:09-cv-11340-FDS. Verdict Form, Document No. 492, filed on Sep. 25, 2012.

United States Court of Appeals for the Federal Circuit, Case 13/1338, Document 36, Appeals from the United States District Court for the District of Massachusetts in consolidated No. 4:09-cv-11340-FDS, filed Aug. 19, 2013.

Vaughan TJ, Human antibodies by design. *Nat Biotechnol*. Jun;16(6):535-9. 1998.

\* cited by examiner

FIG. 1A
Heavy Chain Variable Region Sequences

| SEQ ID NO.: | Kabat number | 1-30 | CDR H1 (31-35) | 36-49 | CDR H2 (50-56) |
|---|---|---|---|---|---|
| | | QVQLVQSGGGVVQPGRSLRLSCAASGFTFS | SYGMH | WVRQAPGKGLEWVA | FIRYDGSN |
| 33 | JOE9wt VH | ............................ | ..... | .............. | ........ |
| 35 | Cos-3/JH3 VH | .....E........................ | ..... | .............. | ........ |
| 37 | 70-1 VH | .............................. | ..... | .............. | ........ |
| 39 | 78-34 VH | .............G................ | ..... | .............. | ........ |
| 41 | 79-1 VH | .............................. | ..... | .............. | ........ |
| 43 | 101-11 VH | .............................. | ..... | .............. | ........ |
| 45 | 26-1 VH | .............................. | ..... | .............. | ........ |
| 47 | 136-15 VH | .....E........................ | ..... | .............. | ........ |
| 49 | 136-15 VH germline | .............................. | ..... | .............. | ........ |
| 51 | 149-5 VH | .............................. | ..... | .............. | ........ |
| 53 | 149-6 VH | .............................. | ..... | .............. | ........ |
| 55 | 103-4 VH | .............................. | ..... | .............. | ........ |
| 57 | 103-8 VH | .............................. | ..... | .............. | ........ |
| 59 | 103-14 VH | .............................. | ..... | .............. | ........ |
| 61 | G6 VH | .....E........................ | ..... | .............. | ........ |
| 63 | Y139 VH | .............................. | ..... | .............. | ........ |
| 65 | A03 VH | .....E........................ | ..... | .............. | ........ |
| 67 | A03 VH germline | .............................. | ..... | .............. | ........ |
| 23 | Y61 VH | .............................. | ....E | .............. | ........ |
| 69 | Y61 VH germline | .............................. | ..... | .............. | ........ |
| 71 | Y61-H31E VH | .............................. | ....E | .............. | ........ |
| 73 | Y61 L50Y VH | .............................. | ..... | .............. | ........ |
| 75 | Y61-L94Y VH | .............................. | ..... | .............. | ........ |
| 31 | J695 | .....E........................ | ..... | .............. | ........ |

FIG. 1B
Heavy Chain Variable Region Sequences

CDR H2 positions 57-65: KYYADSVKG
Positions 66-94: RFTISRDNSKNTLYLQMKSLRAEDTAVYYCTT
CDR H3 positions 95-113: SGSYDY WGQGTMVTVSS (reference JOE9wt VH)

| SEQ ID NO.: | Kabat number | 57-65 (CDR H2) | 66-94 | 95-102 (CDR H3) | 103-113 |
|---|---|---|---|---|---|
| 33 | JOE9wt VH | KYYADSVKG | RFTISRDNSKNTLYLQMKSLRAEDTAVYYCTT | SGSYDY | WGQGTMVTVSS |
| 35 | Cos-3/JH3 VH | . . . . . . . . . | . . . . . . . . . . . . . . . . . . . . . . . . . . . .AK | . . . . . . | . . . . . . . . . . . |
| 37 | 70-1 VH | . . . . . . . . . | . . . . . . . . . . . . . . . . . . . . . . . . N . . . . . . | H . . H . N | . . . . . . . . . . . |
| 39 | 78-34 VH | . . . . . . . . . | . . . . . . . . . . . . . . . . . . . . . . . . . . . . . . . | . . . . . . | . . . . . . . . . . . |
| 41 | 79-1 VH | . . . . . . . . . | . . . . . . . . . . . . . . . . . . . . . . . . . . . . . . . | H . . H . N | . . . . . . . . . . . |
| 43 | 101-11 VH | . . . . . . . . . | . . . . . . . . . . . . . . . . . . . . . . . . . . . . K . | H . . H . N | . . . . . . . . . . . |
| 45 | 26-1 VH | . . . . . . . . . | . . . . . . . . . . . . . . . . . . . . . . . . . . . . K . | H . . H . N | . . . . . . . . . . . |
| 47 | 136-15 VH | . . . . . . . . . | . . . . . . . . . . . . . . . . . N . . . . . . . . . . . . . | H . . H . N | . . . . . . . . . . . |
| 49 | 136-15 VH germline | . . . . . . . . . | . . . . . . . . . . . . . . . . . N . . . . . . . . . . . . . | . . . . . . | . . . . . . . . . . . |
| 51 | 149-5 VH | . . . . . . . . . | . . . . . . . . . . . . . . . . . . . . . . . . . . . . K . | H . . H . N | . . . . . . . . . . . |
| 53 | 149-6 VH | . . . . . . . . . | . . . . . . . . . . . . . . . . . . . . . . . . . . . . K . | H . . H . N | . . . . . . . . . . . |
| 55 | 103-4 VH | . . . . . . . . . | . . . . . . . . . . . . . . . . . N . . . . . . . . . . K . | H . . H . N | . . . . . . . . . . . |
| 57 | 103-8 VH | . . . . . . . . . | . . . . . . . . . . . . . . . . . . . . . . . . . . . . K . | H . . H . N | . . . . . . . . . . . |
| 59 | 103-14 VH | . . . . . . . . . | . . . . . . . . . . . . . . . . . . . . . . . . . . . . K . | H . . H . N | . . . . . . . . . . . |
| 61 | G6 VH | . . . . . . . . . | . . . . . . . . . . . . . . . . . . . . . . . . . . . . K . | H . . H . N | . . . . . . . . . . . |
| 63 | Y139 VH | . . . . . . . . . | . . . . . . . . . . . . . . . . . N . . . . . . . . . . K . | H . . H . N | . . . . . . . . . . . |
| 65 | A03 VH | . . . . . . . . . | . . . . . . . . . . . . . . . . . . . . . . . . . . . . K . | H . . H . N | . . . . . . . . . . . |
| 67 | A03 VH germline | . . . . . . . . . | . . . . . . . . . . . . . . . . . . . . . . . . . . . . . . . | . . . . . . | . . . . . . . . . . . |
| 23 | Y61 VH | . . . . . . . . . | . . . . . . . . . . . . . . . . . N . . . . . . . . . . K . | H . . H . N | . . . . . . . . . . . |
| 69 | Y61 VH germline | . . . . . . . . . | . . . . . . . . . . . . . . . . . N . . . . . . . . . . . . . | . . . . . . | . . . . . . . . . . . |
| 71 | Y61-H31E VH | . . . . . . . . . | . . . . . . . . . . . . . . . . . N . . . . . . . . . . K . | H . . H . N | . . . . . . . . . . . |
| 73 | Y61-L50Y VH | . . . . . . . . . | . . . . . . . . . . . . . . . . . N . . . . . . . . . . K . | H . . H . N | . . . . . . . . . . . |
| 75 | Y61-L94Y VH | . . . . . . . . . | . . . . . . . . . . . . . . . . . N . . . . . . . . . . K . | H . . H . N | . . . . . . . . . . . |
| 31 | J695 | . . . . . . . . . | . . . . . . . . . . . . . . . . . N . . . . . . . . . . K . | H . . H . N | . . . . . . . . . . . |

FIG. 1C
Light Chain Variable Region Sequences

| SEQ ID NO.: | Kabat number | 1-23 SYVLTQPPSVSGTPGQRVTISC | CDR L1 24-34 SGGRSNIGSNTVK | 35-49 WYQQLPTAPKLLIY | CDR L2 50-56 GNDQRPS |
|---|---|---|---|---|---|
| 34 | JOE9 VL wt | SYVLTQPPSVSGTPGQRVTISC | SGGRSNIGSNTVK | WYQQLPTAPKLLIY | GNDQRPS |
| 36 | Dp18 Lv1042/Jλ1 | QS.................... | T.SS......AGYD.H | ............... | ..SN... |
| 38 | 70-1 VL | ............A......... | ............. | ............... | ....... |
| 40 | 78-34 VL | ...................... | ............. | ............... | ....... |
| 42 | 79-1 VL | ...................... | ............. | ............... | ....... |
| 44 | 101-11 VL | ...................... | ..S.......... | ............... | ....... |
| 46 | 26-1 VL | ...................... | ..S.......... | ............... | ....... |
| 48 | 136-15 VL | QS..........A......... | ............. | ............... | ....... |
| 50 | 136-15 VL germline | QS.................... | ............. | ............... | ....... |
| 52 | 149-5 VL | ...................... | .........V... | ............... | ....... |
| 54 | 149-6 VL | ...................... | .........V... | ............... | ....... |
| 56 | 103-4 VL | ...................... | ............. | ............... | ....... |
| 58 | 103-8 VL | ...................... | ..S.......... | ............... | ....... |
| 60 | 103-14 VL | ...................... | ..S.......... | ............... | ....... |
| 62 | G6 VL | ...................... | ............. | ............... | ....... |
| 64 | Y139 VL | QS..........A......... | ..S.......... | ............... | ....... |
| 66 | A03 VL | ...................... | ............. | ............... | ....... |
| 68 | A03 VL germline | QS..........A......... | ............. | ............... | ....... |
| 24 | Y61 VL | QS..........A......... | ..S.......... | ............... | ....... |
| 70 | Y61 VL germline | QS..........A......... | ..S.......... | ............... | ....... |
| 72 | Y61-H31E VL | QS..........A......... | ..S.......... | ............... | ....... |
| 74 | Y61 L50Y VL | QS..........A......... | ..S.......... | ............... | Y...... |
| 76 | Y61-L94Y VL | QS..........A......... | ..S.......... | ............... | ....... |
| 32 | J695 VL | QS..........A......... | ..S.......... | ............... | Y...... |

FIG. 1D
Light Chain Variable Region Sequences

| SEQ ID NO.: | Kabat number | 57-88 GVPDRFSGSKSGTSASLAITGVQAEDEADYYC | CDR L3 89-97 QSYDSSLRGSRV | 98-107 FGTGTKVTVLG |
|---|---|---|---|---|
| 34 | JOE9 VL wt | GVPDRFSGSKSGTSASLAITGVQAEDEADYYC | QSYDSSLRGSRV | FGTGTKVTVLG |
| 36 | Dp18 Lv1042/Jλ1 | ............................... | ..........S. | ........... |
| 38 | 70-1 VL | ............................... | ....RGFT.... | ........... |
| 40 | 78-34 VL | .....................L......... | ......W..... | ........... |
| 42 | 79-1 VL | ............................... | ....RGFT.... | ........... |
| 44 | 101-11 VL | ............................... | ......W..... | ........... |
| 46 | 26-1 VL | .....................L......... | ............ | ........... |
| 48 | 136-15 VL | ............................... | .T..KGFT..S. | ........... |
| 50 | 136-15 VL germline | ............................... | .T..KGFT..S. | ........... |
| 52 | 149-5 VL | ............................... | ......W.T... | ........... |
| 54 | 149-6 VL | ............................... | ....RGFT.... | ........... |
| 56 | 103-4 VL | ............................... | ....RGFT.A.. | ........... |
| 58 | 103-8 VL | ............................... | .T..KGFT..S. | ........... |
| 60 | 103-14 VL | ............................... | .EKGFT...M.. | ........... |
| 62 | G6 VL | ............................... | ..RGTHPLTI.. | ........... |
| 64 | Y139 VL | ............................... | ..RGSHPALI.. | ........... |
| 66 | A03 VL | ............................... | ..RGTHPLTM.. | ........... |
| 68 | A03 VL germline | .....................L......... | ..RGTHPLTM.. | ........... |
| 24 | Y61 VL | .....................L......... | ..RGTHPALL.. | ........... |
| 70 | Y61 VL germline | .....................L......... | ..RGTHPALL.. | ........... |
| 72 | Y61-H31E VL | .....................L......... | ..RGTHPALL.. | ........... |
| 74 | Y61-L50Y VL | ............................... | ..RGTHPALL.. | ........... |
| 76 | Y61-L94Y VL | .....................L......... | ..RYTHPALL.. | ........... |
| 32 | J695 VL | .....................L......... | ..RYTHPALL.. | ........... |

FIG. 2A

Y61 Heavy Chain CDR H1 Mutagenesis

| SEQ ID NO: | | 27 | 28 | 29 | 30 | 31 | 32 | 33 | 34 | 35 | $k_{off}$ (× 10$^5$) |
|---|---|---|---|---|---|---|---|---|---|---|---|
| 21 | Y61 | F | T | F | S | S | Y | G | M | H | |
| 288 | | . | . | . | E | . | . | . | . | . | 22.8 |
| 289 | | . | . | . | S | . | . | . | . | . | 16.8 |
| 290 | | . | . | . | Y | . | . | . | . | . | 31.9 |
| 291 | | . | . | . | H | . | . | . | . | . | 29.6 |
| 292 | | . | . | . | K | . | . | . | . | . | 22.5 |
| 293 | | . | . | . | R | . | . | . | . | . | 24.5 |
| 294 | | . | . | . | N | . | . | . | . | . | 30.1 |
| 295 | | . | . | . | T | . | . | . | . | . | 32.0 |
| 296 | | . | . | . | G | . | . | . | . | . | 23.3 |
| 297 | | . | . | . | V | . | . | . | . | . | 39.9 |
| 298 | | . | . | . | I | . | . | . | . | . | 20.7 |
| 299 | | . | . | . | W | . | . | . | . | . | 21.6 |
| 300 | | . | . | . | . | E | . | . | . | . | 21.9 |
| 301 | | . | . | . | . | C | . | . | . | . | 12.0 |
| 302 | | . | . | . | . | S | . | . | . | . | 24.9 |
| 303 | | . | . | . | . | Y | . | . | . | . | 39.8 |
| 304 | | . | . | . | . | H | . | . | . | . | 30.9 |
| 305 | | . | . | . | . | R | . | . | . | . | 66.4 |
| 306 | | . | . | . | . | N | . | . | . | . | 19.1 |
| 307 | | . | . | . | . | Q | . | . | . | . | 15.2 |
| 308 | | . | . | . | . | T | . | . | . | . | 71.6 |
| 309 | | . | . | . | . | A | . | . | . | . | 20.5 |
| 310 | | . | . | . | . | I | . | . | . | . | 33.4 |
| 311 | | . | . | . | . | . | E | . | . | . | 229.0 |
| 312 | | . | . | . | . | . | C | . | . | . | 383.0 |
| 313 | | . | . | . | . | . | S | . | . | . | 157.5 |
| 314 | | . | . | . | . | . | Y | . | . | . | 33.7 |
| 315 | | . | . | . | . | . | H | . | . | . | 46.1 |
| 316 | | . | . | . | . | . | R | . | . | . | 448.5 |
| 317 | | . | . | . | . | . | N | . | . | . | 297.0 |
| 318 | | . | . | . | . | . | T | . | . | . | 148.0 |
| 319 | | . | . | . | . | . | A | . | . | . | 165.5 |
| 320 | | . | . | . | . | . | V | . | . | . | 133.5 |
| 321 | | . | . | . | . | . | L | . | . | . | 226.0 |
| 322 | | . | . | . | . | . | I | . | . | . | 160.5 |
| 323 | | . | . | . | . | . | . | D | . | . | 152.0 |
| 324 | | . | . | . | . | . | . | E | . | . | 189.0 |
| 325 | | . | . | . | . | . | . | C | . | . | 286.5 |
| 326 | | . | . | . | . | . | . | S | . | . | 39.9 |
| 327 | | . | . | . | . | . | . | Y | . | . | 250.5 |
| 328 | | . | . | . | . | . | . | N | . | . | 30.8 |
| 329 | | . | . | . | . | . | . | G | . | . | 17.8 |
| 330 | | . | . | . | . | . | . | A | . | . | 27.3 |
| 331 | | . | . | . | . | . | . | V | . | . | 191.0 |
| 332 | | . | . | . | . | . | . | M | . | . | 21.5 |
| 333 | | . | . | . | . | . | . | I | . | . | 250.0 |
| 334 | | . | . | . | . | . | . | P | . | . | 159.5 |

Y61 Mutagenesis: H30

Y61 Mutagenesis: H31

Y61 Mutagenesis: H32

Y61 Mutagenesis: H33

FIG. 2B

Y61 Heavy Chain CDR H2 Mutagenesis

| SEQ ID NO: | | CDR H2 | | | | | | | | | | | | | | | | $k_{off}$ (x $10^5$) |
|---|---|---|---|---|---|---|---|---|---|---|---|---|---|---|---|---|---|---|
| | | 50 | 51 | 52 | 52A | 53 | 54 | 55 | 56 | 57 | 58 | 59 | 60 | 61 | 62 | 63 | 64 | 65 | |
| 19 | Y61 | F | I | R | Y | D | G | S | N | K | Y | Y | A | D | S | V | K | G | |
| 335 | | E | . | . | . | . | . | . | . | . | . | . | . | . | . | . | . | . | 34.7 |
| 336 | | C | . | . | . | . | . | . | . | . | . | . | . | . | . | . | . | . | 28.5 |
| 337 | | Y | . | . | . | . | . | . | . | . | . | . | . | . | . | . | . | . | 23.0 |
| 338 | | H | . | . | . | . | . | . | . | . | . | . | . | . | . | . | . | . | 30.9 |
| 339 | | K | . | . | . | . | . | . | . | . | . | . | . | . | . | . | . | . | 61.2 |
| 340 | | N | . | . | . | . | . | . | . | . | . | . | . | . | . | . | . | . | 34.4 |
| 341 | | Q | . | . | . | . | . | . | . | . | . | . | . | . | . | . | . | . | 42.0 |
| 342 | | T | . | . | . | . | . | . | . | . | . | . | . | . | . | . | . | . | 20.5 |
| 343 | | L | . | . | . | . | . | . | . | . | . | . | . | . | . | . | . | . | 44.0 |
| 344 | | F | . | . | . | . | . | . | . | . | . | . | . | . | . | . | . | . | 20.4 |
| 345 | | . | . | E | . | . | . | . | . | . | . | . | . | . | . | . | . | . | 31.8 |
| 346 | | . | . | S | . | . | . | . | . | . | . | . | . | . | . | . | . | . | 29.2 |
| 347 | | . | . | Y | . | . | . | . | . | . | . | . | . | . | . | . | . | . | 29.8 |
| 348 | | . | . | H | . | . | . | . | . | . | . | . | . | . | . | . | . | . | 40.7 |
| 349 | | . | . | K | . | . | . | . | . | . | . | . | . | . | . | . | . | . | 26.2 |
| 350 | | . | . | R | . | . | . | . | . | . | . | . | . | . | . | . | . | . | 20.6 |
| 351 | | . | . | Q | . | . | . | . | . | . | . | . | . | . | . | . | . | . | 28.5 |
| 352 | | . | . | T | . | . | . | . | . | . | . | . | . | . | . | . | . | . | 37.4 |
| 353 | | . | . | G | . | . | . | . | . | . | . | . | . | . | . | . | . | . | 32.1 |
| 354 | | . | . | A | . | . | . | . | . | . | . | . | . | . | . | . | . | . | 17.1 |
| 355 | | . | . | V | . | . | . | . | . | . | . | . | . | . | . | . | . | . | 31.7 |
| 356 | | . | . | L | . | . | . | . | . | . | . | . | . | . | . | . | . | . | 34.7 |
| 357 | | . | . | W | . | . | . | . | . | . | . | . | . | . | . | . | . | . | 35.1 |
| 358 | | . | . | . | . | D | . | . | . | . | . | . | . | . | . | . | . | . | 15.1 |
| 359 | | . | . | . | . | E | . | . | . | . | . | . | . | . | . | . | . | . | 39.9 |
| 360 | | . | . | . | . | S | . | . | . | . | . | . | . | . | . | . | . | . | 36.8 |
| 361 | | . | . | . | . | Y | . | . | . | . | . | . | . | . | . | . | . | . | 61.1 |
| 362 | | . | . | . | . | K | . | . | . | . | . | . | . | . | . | . | . | . | 158.0 |
| 363 | | . | . | . | . | R | . | . | . | . | . | . | . | . | . | . | . | . | 166.5 |
| 364 | | . | . | . | . | N | . | . | . | . | . | . | . | . | . | . | . | . | 72.7 |
| 365 | | . | . | . | . | Q | . | . | . | . | . | . | . | . | . | . | . | . | 79.2 |
| 366 | | . | . | . | . | T | . | . | . | . | . | . | . | . | . | . | . | . | 50.0 |
| 367 | | . | . | . | . | A | . | . | . | . | . | . | . | . | . | . | . | . | 40.4 |
| 368 | | . | . | . | . | V | . | . | . | . | . | . | . | . | . | . | . | . | 44.0 |
| 369 | | . | . | . | . | L | . | . | . | . | . | . | . | . | . | . | . | . | 109.5 |
| 370 | | . | . | . | . | I | . | . | . | . | . | . | . | . | . | . | . | . | 94.4 |
| 371 | | . | . | . | . | F | . | . | . | . | . | . | . | . | . | . | . | . | 168.5 |
| 372 | | . | . | . | . | . | D | . | . | . | . | . | . | . | . | . | . | . | 45.5 |
| 373 | | . | . | . | . | . | E | . | . | . | . | . | . | . | . | . | . | . | 35.1 |
| 374 | | . | . | . | . | . | S | . | . | . | . | . | . | . | . | . | . | . | 37.3 |
| 375 | | . | . | . | . | . | Y | . | . | . | . | . | . | . | . | . | . | . | 64.6 |
| 376 | | . | . | . | . | . | K | . | . | . | . | . | . | . | . | . | . | . | 40.7 |
| 377 | | . | . | . | . | . | R | . | . | . | . | . | . | . | . | . | . | . | 2.5 |
| 378 | | . | . | . | . | . | N | . | . | . | . | . | . | . | . | . | . | . | 44.7 |
| 379 | | . | . | . | . | . | Q | . | . | . | . | . | . | . | . | . | . | . | 31.6 |
| 380 | | . | . | . | . | . | T | . | . | . | . | . | . | . | . | . | . | . | 64.4 |
| 381 | | . | . | . | . | . | G | . | . | . | . | . | . | . | . | . | . | . | 17.8 |
| 382 | | . | . | . | . | . | V | . | . | . | . | . | . | . | . | . | . | . | 43.5 |

Y61 Mutagenesis: H50

Y61 Mutagenesis: H52

Y61 Mutagenesis: H53

Y61 Mutagenesis: H54

FIG. 2C

Y61 Heavy Chain CDR H2 Mutagenesis

| SEQ ID NO: | | CDR H2 | | | | | | | | | | | | | | | | | $k_{off}$ (x $10^5$) |
|---|---|---|---|---|---|---|---|---|---|---|---|---|---|---|---|---|---|---|---|
| | | 50 | 51 | 52 | 52A | 53 | 54 | 55 | 56 | 57 | 58 | 59 | 60 | 61 | 62 | 63 | 64 | 65 | |
| 19 | Y61 | F | I | R | Y | D | G | S | N | K | Y | Y | A | D | S | V | K | G | |
| 383 | | . | . | . | . | . | F | . | . | . | . | . | . | . | . | . | . | . | 66.3 |
| 384 | | . | . | . | . | . | . | . | S | . | . | . | . | . | . | . | . | . | 62.4 |
| 385 | | . | . | . | . | . | . | . | Y | . | . | . | . | . | . | . | . | . | 39.0 |
| 386 | | . | . | . | . | . | . | . | H | . | . | . | . | . | . | . | . | . | 42.0 |
| 387 | | . | . | . | . | . | . | . | N | . | . | . | . | . | . | . | . | . | 38.5 |
| 388 | | . | . | . | . | . | . | . | T | . | . | . | . | . | . | . | . | . | 23.5 |
| 389 | | . | . | . | . | . | . | . | G | . | . | . | . | . | . | . | . | . | 27.2 |
| 390 | | . | . | . | . | . | . | . | M | . | . | . | . | . | . | . | . | . | 38.3 |
| 391 | | . | . | . | . | . | . | . | L | . | . | . | . | . | . | . | . | . | 26.4 |
| 392 | | . | . | . | . | . | . | . | I | . | . | . | . | . | . | . | . | . | 16.9 |
| 393 | | . | . | . | . | . | . | . | P | . | . | . | . | . | . | . | . | . | 29.9 |
| 394 | | . | . | . | . | . | . | . | F | . | . | . | . | . | . | . | . | . | 34.5 |
| 395 | | . | . | . | . | . | . | . | . | . | E | . | . | . | . | . | . | . | 41.5 |
| 396 | | . | . | . | . | . | . | . | . | . | S | . | . | . | . | . | . | . | 94.1 |
| 397 | | . | . | . | . | . | . | . | . | . | Y | . | . | . | . | . | . | . | 31.0 |
| 398 | | . | . | . | . | . | . | . | . | . | N | . | . | . | . | . | . | . | 83.1 |
| 399 | | . | . | . | . | . | . | . | . | . | V | . | . | . | . | . | . | . | 52.4 |
| 400 | | . | . | . | . | . | . | . | . | . | L | . | . | . | . | . | . | . | 73.0 |
| 401 | | . | . | . | . | . | . | . | . | . | I | . | . | . | . | . | . | . | 65.7 |
| 402 | | . | . | . | . | . | . | . | . | . | P | . | . | . | . | . | . | . | 62.8 |
| 403 | | . | . | . | . | . | . | . | . | . | F | . | . | . | . | . | . | . | 79.4 |

Y61 Mutagenesis: H56

Y61 Mutagenesis: H58

FIG. 2D

Y61 Heavy Chain CDR H3 Mutagenesis

| SEQ ID NO: | | \multicolumn{6}{c}{CDR H3} | $k_{off}$ (x $10^5$) |
|---|---|---|---|---|---|---|---|---|
| | | 95 | 96 | 97 | 98 | 101 | 102 | |
| 17 | Y61 | H | G | S | H | D | N | |
| 404 | | E | . | . | . | . | . | 231.5 |
| 405 | | S | . | . | . | . | . | 193.0 |
| 406 | | H | . | . | . | . | . | 28.7 |
| 407 | | K | . | . | . | . | . | 227.5 |
| 408 | | Q | . | . | . | . | . | 85.9 |
| 409 | | T | . | . | . | . | . | 202.0 |
| 410 | | A | . | . | . | . | . | 150.0 |
| 411 | | L | . | . | . | . | . | 147.5 |
| 412 | | P | . | . | . | . | . | 471.0 |
| 413 | | F | . | . | . | . | . | 514.0 |
| 414 | | . | D | . | . | . | . | 223.5 |
| 415 | | . | C | . | . | . | . | 24.2 |
| 416 | | . | H | . | . | . | . | 23.7 |
| 417 | | . | R | . | . | . | . | 96.2 |
| 418 | | . | T | . | . | . | . | 186.0 |
| 419 | | . | G | . | . | . | . | 39.7 |
| 420 | | . | V | . | . | . | . | 38.2 |
| 421 | | . | M | . | . | . | . | 204.5 |
| 422 | | . | L | . | . | . | . | 261.0 |
| 423 | | . | I | . | . | . | . | 207.5 |
| 424 | | . | P | . | . | . | . | 129.0 |
| 425 | | . | W | . | . | . | . | 197.0 |
| 426 | | . | . | D | . | . | . | 202.0 |
| 427 | | . | . | S | . | . | . | 37.5 |
| 428 | | . | . | Y | . | . | . | 273.0 |
| 429 | | . | . | H | . | . | . | 190.5 |
| 430 | | . | . | R | . | . | . | 224.0 |
| 431 | | . | . | N | . | . | . | 221.5 |
| 432 | | . | . | T | . | . | . | 58.8 |
| 433 | | . | . | G | . | . | . | 229.0 |
| 434 | | . | . | A | . | . | . | 143.0 |
| 435 | | . | . | I | . | . | . | 208.0 |
| 436 | | . | . | P | . | . | . | 300.0 |
| 437 | | . | . | W | . | . | . | 239.0 |
| 438 | | . | . | F | . | . | . | 180.5 |
| 439 | | . | . | . | H | . | . | 25.5 |
| 440 | | . | . | . | R | . | . | 34.0 |
| 441 | | . | . | . | T | . | . | 22.7 |
| 442 | | . | . | . | A | . | . | 67.3 |
| 443 | | . | . | . | V | . | . | 29.3 |
| 444 | | . | . | . | L | . | . | 59.8 |
| 445 | | . | . | . | I | . | . | 34.3 |
| 446 | | . | . | . | F | . | . | 68.8 |
| 447 | | . | . | . | . | D | . | 14.4 |
| 448 | | . | . | . | . | S | . | 44.9 |
| 449 | | . | . | . | . | Y | . | 465.0 |
| 450 | | . | . | . | . | H | . | 327.0 |
| 451 | | . | . | . | . | R | . | 110.0 |

Y61 Mutagenesis: H95

Y61 Mutagenesis: H96

Y61 Mutagenesis: H97

Y61 Mutagenesis: H98

FIG. 2E
Y61 Heavy Chain CDR H3 Mutagenesis

| SEQ ID NO: | | CDR H3 | | | | | | $K_{off}$ (x $10^5$) |
|---|---|---|---|---|---|---|---|---|
| | | 95 | 96 | 97 | 98 | 101 | 102 | |
| 17 | Y61 | H | G | S | H | D | N | |
| 452 | | . | . | . | . | N | . | 223.0 |
| 453 | | . | . | . | . | G | . | 375.0 |
| 454 | | . | . | . | . | A | . | 106.5 |
| 455 | | . | . | . | . | V | . | 163.0 |
| 456 | | . | . | . | . | I | . | 162.5 |
| 457 | | . | . | . | . | . | S | 32.5 |
| 458 | | . | . | . | . | . | H | 18.0 |
| 459 | | . | . | . | . | . | K | 40.5 |
| 460 | | . | . | . | . | . | R | 57.5 |
| 461 | | . | . | . | . | . | N | 40.3 |
| 462 | | . | . | . | . | . | T | 33.3 |
| 463 | | . | . | . | . | . | G | 69.2 |
| 464 | | . | . | . | . | . | A | 38.2 |
| 465 | | . | . | . | . | . | L | 95.6 |
| 466 | | . | . | . | . | . | I | 99.6 |
| 467 | | . | . | . | . | . | P | 181.5 |
| 468 | | . | . | . | . | . | W | 23.5 |
| 469 | | . | . | . | . | . | F | 31.8 |

Y61 Mutagenesis: H101

Y61 Mutagenesis: H102

FIG. 2F
Y61 Light Chain CDR L1 Mutagenesis

| SEQ ID NO: | | \multicolumn{13}{c|}{CDR L1} | $-k_{off}$ (x $10^5$) |
|---|---|---|---|---|---|---|---|---|---|---|---|---|---|---|---|
| | | 24 | 25 | 26 | 27 | 27A | 27B | 28 | 29 | 30 | 31 | 32 | 33 | 34 | |
| 22 | Y61 | S | G | G | R | S | N | I | G | S | N | T | V | K | |
| 470 | | . | . | . | . | . | . | . | . | D | . | . | . | . | 22.0 |
| 471 | | . | . | . | . | . | . | . | . | C | . | . | . | . | 18.6 |
| 472 | | . | . | . | . | . | . | . | . | S | . | . | . | . | 21.1 |
| 473 | | . | . | . | . | . | . | . | . | Y | . | . | . | . | 48.3 |
| 474 | | . | . | . | . | . | . | . | . | K | . | . | . | . | 34.6 |
| 475 | | . | . | . | . | . | . | . | . | R | . | . | . | . | 18.2 |
| 476 | | . | . | . | . | . | . | . | . | N | . | . | . | . | 16.6 |
| 477 | | . | . | . | . | . | . | . | . | T | . | . | . | . | 22.6 |
| 478 | | . | . | . | . | . | . | . | . | P | . | . | . | . | 25.0 |
| 479 | | . | . | . | . | . | . | . | . | . | D | . | . | . | 58.0 |
| 480 | | . | . | . | . | . | . | . | . | . | E | . | . | . | 38.4 |
| 481 | | . | . | . | . | . | . | . | . | . | S | . | . | . | 39.2 |
| 482 | | . | . | . | . | . | . | . | . | . | Y | . | . | . | 35.7 |
| 483 | | . | . | . | . | . | . | . | . | . | H | . | . | . | 31.5 |
| 484 | | . | . | . | . | . | . | . | . | . | K | . | . | . | 33.1 |
| 485 | | . | . | . | . | . | . | . | . | . | N | . | . | . | 22.9 |
| 486 | | . | . | . | . | . | . | . | . | . | Q | . | . | . | 29.2 |
| 487 | | . | . | . | . | . | . | . | . | . | T | . | . | . | 30.9 |
| 488 | | . | . | . | . | . | . | . | . | . | G | . | . | . | 36.6 |
| 489 | | . | . | . | . | . | . | . | . | . | M | . | . | . | 17.4 |
| 490 | | . | . | . | . | . | . | . | . | . | I | . | . | . | 9.7 |
| 491 | | . | . | . | . | . | . | . | . | . | . | D | . | . | 25.2 |
| 492 | | . | . | . | . | . | . | . | . | . | . | C | . | . | 381.5 |
| 493 | | . | . | . | . | . | . | . | . | . | . | S | . | . | 191.0 |
| 494 | | . | . | . | . | . | . | . | . | . | . | Y | . | . | 21.3 |
| 495 | | . | . | . | . | . | . | . | . | . | . | H | . | . | 26.0 |
| 496 | | . | . | . | . | . | . | . | . | . | . | K | . | . | 31.8 |
| 497 | | . | . | . | . | . | . | . | . | . | . | R | . | . | 690.0 |
| 498 | | . | . | . | . | . | . | . | . | . | . | N | . | . | 196.5 |
| 499 | | . | . | . | . | . | . | . | . | . | . | Q | . | . | 247.0 |
| 500 | | . | . | . | . | . | . | . | . | . | . | T | . | . | 24.1 |
| 501 | | . | . | . | . | . | . | . | . | . | . | A | . | . | 190.5 |
| 502 | | . | . | . | . | . | . | . | . | . | . | V | . | . | 164.5 |
| 503 | | . | . | . | . | . | . | . | . | . | . | L | . | . | 215.5 |
| 504 | | . | . | . | . | . | . | . | . | . | . | I | . | . | 154.0 |
| 505 | | . | . | . | . | . | . | . | . | . | . | P | . | . | 42.4 |

Y61 Mutagenesis: L30

Y61 Mutagenesis: L31

Y61 Mutagenesis: L32

FIG. 2G
Y61 Light Chain CDRL2 Mutagenesis

| SEQ ID NO: | | CDR L2 | | | | | | | $k_{off}$ ($\times 10^5$) |
|---|---|---|---|---|---|---|---|---|---|
| | | 50 | 51 | 52 | 53 | 54 | 55 | 56 | |
| 20 | Y61 | G | N | D | Q | R | P | S | |
| 506 | | D | . | . | . | . | . | . | 34.8 |
| 507 | | E | . | . | . | . | . | . | 61.7 |
| 508 | | C | . | . | . | . | . | . | 46.7 |
| 509 | | S | . | . | . | . | . | . | 28.6 |
| 510 | | Y | . | . | . | . | . | . | 17.4 |
| 511 | | H | . | . | . | . | . | . | 76.1 |
| 512 | | K | . | . | . | . | . | . | 242.5 |
| 513 | | R | . | . | . | . | . | . | 44.4 |
| 514 | | N | . | . | . | . | . | . | 30.5 |
| 515 | | Q | . | . | . | . | . | . | 34.8 |
| 516 | | T | . | . | . | . | . | . | 27.2 |
| 517 | | G | . | . | . | . | . | . | 21.5 |
| 518 | | A | . | . | . | . | . | . | 37.2 |
| 519 | | V | . | . | . | . | . | . | 38.5 |
| 520 | | M | . | . | . | . | . | . | 95.3 |
| 521 | | L | . | . | . | . | . | . | 61.6 |
| 522 | | I | . | . | . | . | . | . | 120.5 |
| 523 | | P | . | . | . | . | . | . | 41.0 |
| 524 | | W | . | . | . | . | . | . | 38.2 |
| 525 | | F | . | . | . | . | . | . | 3,476.7 |
| 526 | | . | . | . | S | . | . | . | 86.6 |
| 527 | | . | . | . | Y | . | . | . | 73.3 |
| 528 | | . | . | . | R | . | . | . | 61.4 |
| 529 | | . | . | . | Q | . | . | . | 29.7 |
| 530 | | . | . | . | T | . | . | . | 83.4 |
| 531 | | . | . | . | A | . | . | . | 55.4 |
| 532 | | . | . | . | I | . | . | . | 85.5 |
| 533 | | . | . | . | P | . | . | . | 97.4 |

Y61 Mutagenesis: L50

Y61 Mutagenesis: L53

FIG. 2H
Y61 Light Chain CDR L3 Mutagenesis

| SEQ ID NO: | | CDR L3 | | | | | | | | | | | | $k_{off}$ $(\times 10^5)$ |
|---|---|---|---|---|---|---|---|---|---|---|---|---|---|---|
| | | 89 | 90 | 91 | 92 | 93 | 94 | 95 | 95A | 95B | 95C | 96 | 97 | |
| 18 | Y61 | Q | S | Y | D | R | G | T | H | P | A | L | L | |
| 534 | | . | . | . | D | . | . | . | . | . | . | . | . | 25.9 |
| 535 | | . | . | . | C | . | . | . | . | . | . | . | . | 45.3 |
| 536 | | . | . | . | S | . | . | . | . | . | . | . | . | 30.7 |
| 537 | | . | . | . | Y | . | . | . | . | . | . | . | . | 51.1 |
| 538 | | . | . | . | N | . | . | . | . | . | . | . | . | 34.7 |
| 539 | | . | . | . | Q | . | . | . | . | . | . | . | . | 42.7 |
| 540 | | . | . | . | T | . | . | . | . | . | . | . | . | 40.8 |
| 541 | | . | . | . | G | . | . | . | . | . | . | . | . | 34.9 |
| 542 | | . | . | . | A | . | . | . | . | . | . | . | . | 35.7 |
| 543 | | . | . | . | L | . | . | . | . | . | . | . | . | 72.8 |
| 544 | | . | . | . | I | . | . | . | . | . | . | . | . | 61.8 |
| 545 | | . | . | . | W | . | . | . | . | . | . | . | . | 72.0 |
| 546 | | . | . | . | F | . | . | . | . | . | . | . | . | 44.9 |
| 547 | | . | . | . | . | D | . | . | . | . | . | . | . | 34.3 |
| 548 | | . | . | . | . | C | . | . | . | . | . | . | . | 32.0 |
| 549 | | . | . | . | . | S | . | . | . | . | . | . | . | 34.1 |
| 550 | | . | . | . | . | Y | . | . | . | . | . | . | . | 33.5 |
| 551 | | . | . | . | . | R | . | . | . | . | . | . | . | 19.9 |
| 552 | | . | . | . | . | N | . | . | . | . | . | . | . | 31.6 |
| 553 | | . | . | . | . | Q | . | . | . | . | . | . | . | 30.0 |
| 554 | | . | . | . | . | T | . | . | . | . | . | . | . | 31.6 |
| 555 | | . | . | . | . | G | . | . | . | . | . | . | . | 39.2 |
| 556 | | . | . | . | . | A | . | . | . | . | . | . | . | 31.0 |
| 557 | | . | . | . | . | V | . | . | . | . | . | . | . | 26.9 |
| 558 | | . | . | . | . | M | . | . | . | . | . | . | . | 27.5 |
| 559 | | . | . | . | . | L | . | . | . | . | . | . | . | 30.0 |
| 560 | | . | . | . | . | I | . | . | . | . | . | . | . | 29.5 |
| 561 | | . | . | . | . | P | . | . | . | . | . | . | . | 34.9 |
| 562 | | . | . | . | . | W | . | . | . | . | . | . | . | 34.9 |
| 563 | | . | . | . | . | . | D | . | . | . | . | . | . | 25.3 |
| 564 | | . | . | . | . | . | C | . | . | . | . | . | . | 52.0 |
| 565 | | . | . | . | . | . | S | . | . | . | . | . | . | 28.7 |
| 566 | | . | . | . | . | . | Y | . | . | . | . | . | . | 13.1 |
| 567 | | . | . | . | . | . | H | . | . | . | . | . | . | 18.7 |
| 568 | | . | . | . | . | . | R | . | . | . | . | . | . | 23.1 |
| 569 | | . | . | . | . | . | N | . | . | . | . | . | . | 13.7 |
| 570 | | . | . | . | . | . | Q | . | . | . | . | . | . | 25.0 |
| 571 | | . | . | . | . | . | T | . | . | . | . | . | . | 30.5 |
| 572 | | . | . | . | . | . | G | . | . | . | . | . | . | 25.6 |
| 573 | | . | . | . | . | . | A | . | . | . | . | . | . | 52.6 |
| 574 | | . | . | . | . | . | V | . | . | . | . | . | . | 35.1 |
| 575 | | . | . | . | . | . | L | . | . | . | . | . | . | 24.4 |
| 576 | | . | . | . | . | . | I | . | . | . | . | . | . | 27.6 |
| 577 | | . | . | . | . | . | P | . | . | . | . | . | . | 33.2 |
| 578 | | . | . | . | . | . | W | . | . | . | . | . | . | 29.3 |
| 579 | | . | . | . | . | . | F | . | . | . | . | . | . | 23.6 |

Y61 Mutagenesis: L92

Y61 Mutagenesis: L93

Y61 Mutagenesis: L94

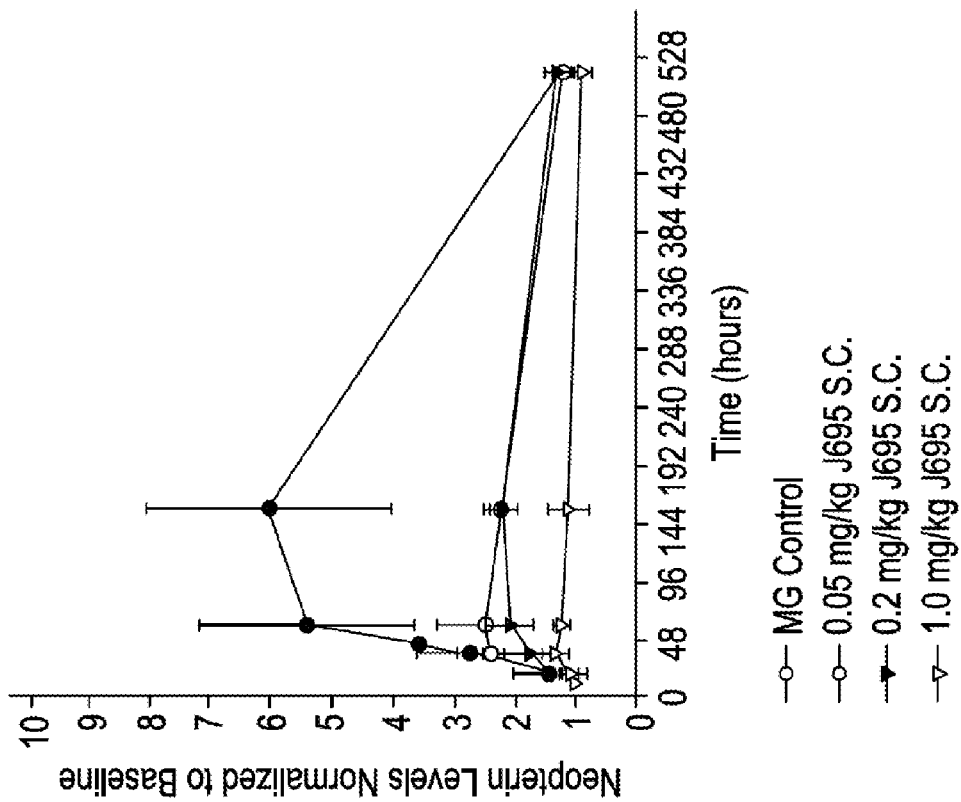
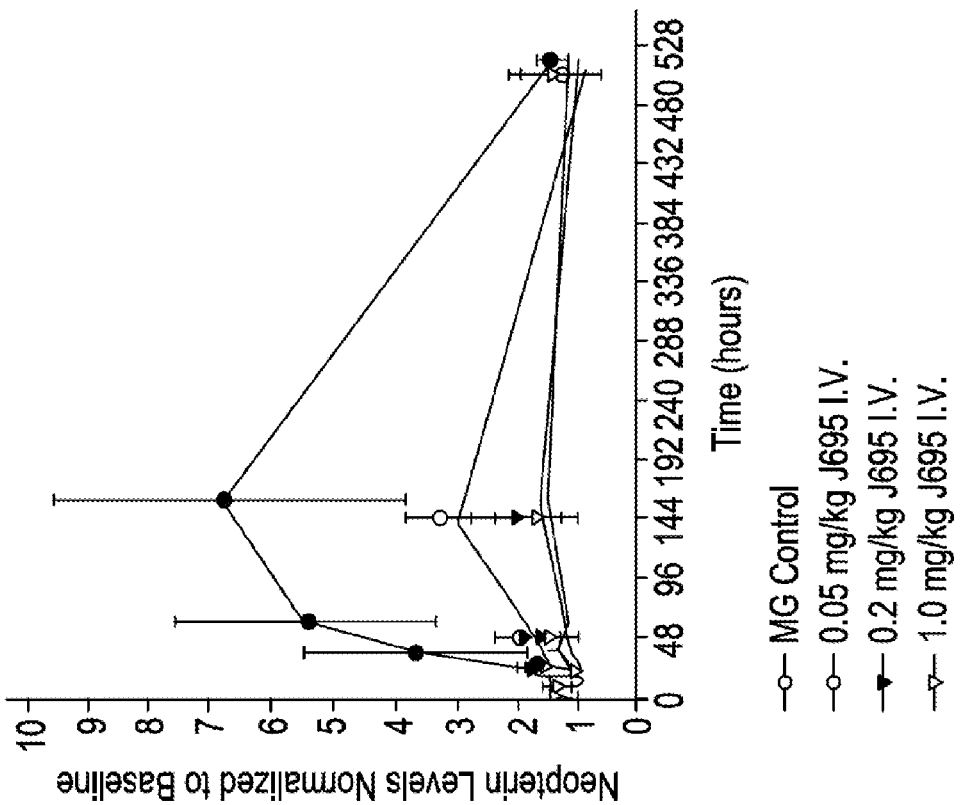

SEQUENCE LISTING

```
<160> NUMBER OF SEQ ID NOS: 675

<210> SEQ ID NO 1
<211> LENGTH: 6
<212> TYPE: PRT
<213> ORGANISM: Homo sapiens
<220> FEATURE:
<223> OTHER INFORMATION: Xaa at position 1 could be either His or Ser
<220> FEATURE:
<223> OTHER INFORMATION: Xaa at position 4 could be either Tyr or His
```

```
<220> FEATURE:
<223> OTHER INFORMATION: Xaa at position 6 could be either Tyr, Asn or
      Thr

<400> SEQUENCE: 1

Xaa Gly Ser Xaa Asp Xaa
 1               5

<210> SEQ ID NO 2
<211> LENGTH: 12
<212> TYPE: PRT
<213> ORGANISM: Homo sapiens
<220> FEATURE:
<223> OTHER INFORMATION: Xaa at position 2 could be either Ser or Thr
<220> FEATURE:
<223> OTHER INFORMATION: Xaa at position 4 could be either Asp or Glu
<220> FEATURE:
<223> OTHER INFORMATION: Xaa at position 5 could be either Ser, Arg or
      Lys
<220> FEATURE:
<223> OTHER INFORMATION: Xaa at position 6 could be either Ser, Gly or
      Tyr
<220> FEATURE:
<223> OTHER INFORMATION: Xaa at position 7 could be either Leu, Phe, Thr
      or Ser
<220> FEATURE:
<223> OTHER INFORMATION: Xaa at position 8 could be either Arg, Ser,
      Thr, Trp or His
<220> FEATURE:
<223> OTHER INFORMATION: Xaa at position 9 could be either Gly or Pro
<220> FEATURE:
<223> OTHER INFORMATION: Xaa at position 10 could be either Ser, Thr,
      Ala or Leu
<220> FEATURE:
<223> OTHER INFORMATION: Xaa at position 11 could be either Arg, Ser,
      Met, Thr or Leu
<220> FEATURE:
<223> OTHER INFORMATION: Xaa at position 12 could be either Val, Ile,
      Thr, Met or Leu

<400> SEQUENCE: 2

Gln Xaa Tyr Xaa Xaa Xaa Xaa Xaa Xaa Xaa Xaa Xaa
 1               5                  10

<210> SEQ ID NO 3
<211> LENGTH: 17
<212> TYPE: PRT
<213> ORGANISM: Homo sapiens

<400> SEQUENCE: 3

Phe Ile Arg Tyr Asp Gly Ser Asn Lys Tyr Tyr Ala Asp Ser Val Lys
 1               5                  10                  15

Gly

<210> SEQ ID NO 4
<211> LENGTH: 7
<212> TYPE: PRT
<213> ORGANISM: Homo sapiens
<220> FEATURE:
<223> OTHER INFORMATION: Xaa at position 1 could be either Gly or Tyr
<220> FEATURE:
<223> OTHER INFORMATION: Xaa at position 3 could be either Asp or Ser
<220> FEATURE:
<223> OTHER INFORMATION: Xaa at position 4 could be either Gln or Asn

<400> SEQUENCE: 4

Xaa Asn Xaa Xaa Arg Pro Ser
 1               5

<210> SEQ ID NO 5
```

```
<211> LENGTH: 9
<212> TYPE: PRT
<213> ORGANISM: Homo sapiens
<220> FEATURE:
<223> OTHER INFORMATION: Xaa represents either Ser or Glu

<400> SEQUENCE: 5

Phe Thr Phe Ser Xaa Tyr Gly Met His
  1               5

<210> SEQ ID NO 6
<211> LENGTH: 13
<212> TYPE: PRT
<213> ORGANISM: Homo sapiens
<220> FEATURE:
<223> OTHER INFORMATION: Xaa at position 1 could be either Ser or Thr
<220> FEATURE:
<223> OTHER INFORMATION: Xaa at position 3 could be either Ser or Gly
<220> FEATURE:
<223> OTHER INFORMATION: Xaa at position 4 could be either Arg or Ser
<220> FEATURE:
<223> OTHER INFORMATION: Xaa at position 8 could be either Gly or Val
<220> FEATURE:
<223> OTHER INFORMATION: Xaa at position 9 could be either Ser or Ala
<220> FEATURE:
<223> OTHER INFORMATION: Xaa at position 10 could be either Asn, Gly or
      Tyr
<220> FEATURE:
<223> OTHER INFORMATION: Xaa at position 11 could be either Thr or Asp
<220> FEATURE:
<223> OTHER INFORMATION: Xaa at position 13 could be either Lys or His

<400> SEQUENCE: 6

Xaa Gly Xaa Xaa Ser Asn Ile Xaa Xaa Xaa Xaa Val Xaa
  1               5                  10

<210> SEQ ID NO 7
<211> LENGTH: 115
<212> TYPE: PRT
<213> ORGANISM: Homo sapiens
<220> FEATURE:
<223> OTHER INFORMATION: Xaa at position 6 could be either Gln or Glu
<220> FEATURE:
<223> OTHER INFORMATION: Xaa at position 16 could be either Arg or Gly
<220> FEATURE:
<223> OTHER INFORMATION: Xaa at position 31 could be either Ser or Glu
<220> FEATURE:
<223> OTHER INFORMATION: Xaa at position 84 could be either Lys or Asn
<220> FEATURE:
<223> OTHER INFORMATION: Xaa at position 97 could be either Thr, Ala or
      Lys
<220> FEATURE:
<223> OTHER INFORMATION: Xaa at position 98 could be either Thr or Lys
<220> FEATURE:
<223> OTHER INFORMATION: Xaa at position 99 could be either Ser or His
<220> FEATURE:
<223> OTHER INFORMATION: Xaa at position 102 could be either Tyr or His
<220> FEATURE:
<223> OTHER INFORMATION: Xaa at position 104 could be either Tyr, Asn or
      Thr

<400> SEQUENCE: 7

Gln Val Gln Leu Val Xaa Ser Gly Gly Gly Val Val Gln Pro Gly Xaa
  1               5                  10                  15

Ser Leu Arg Leu Ser Cys Ala Ala Ser Gly Phe Thr Phe Ser Xaa Tyr
                 20                  25                  30

Gly Met His Trp Val Arg Gln Ala Pro Gly Lys Gly Leu Glu Trp Val
             35                  40                  45

Ala Phe Ile Arg Tyr Asp Gly Ser Asn Lys Tyr Tyr Ala Asp Ser Asx
 50                  55                  60
```

```
Lys Gly Arg Phe Thr Ile Ser Arg Asp Asn Ser Lys Asn Thr Leu Tyr
 65                  70                  75                  80

Leu Gln Met Xaa Ser Leu Arg Ala Glu Asp Thr Ala Val Tyr Tyr Cys
                 85                  90                  95

Xaa Xaa Xaa Gly Ser Xaa Asp Xaa Trp Gly Gln Gly Thr Met Val Thr
            100                 105                 110

Val Ser Ser
        115

<210> SEQ ID NO 8
<211> LENGTH: 112
<212> TYPE: PRT
<213> ORGANISM: Homo sapiens
<220> FEATURE:
<223> OTHER INFORMATION: Xaa at position 1 could be either Ser or Gln
<220> FEATURE:
<223> OTHER INFORMATION: Xaa at position 2 could be either Tyr or Ser
<220> FEATURE:
<223> OTHER INFORMATION: Xaa at position 13 could be either Thr or Ala
<220> FEATURE:
<223> OTHER INFORMATION: Xaa at position 23 and 91  could be either Ser
      or Thr
<220> FEATURE:
<223> OTHER INFORMATION: Xaa at position 25 could be either Gly or Ser
<220> FEATURE:
<223> OTHER INFORMATION: Xaa at position 26 could be either Arg or Ser
<220> FEATURE:
<223> OTHER INFORMATION: Xaa at position 30 could be either Gly or Val
<220> FEATURE:
<223> OTHER INFORMATION: Xaa at position 31 could be either Ser or Ala
<220> FEATURE:
<223> OTHER INFORMATION: Xaa at position 35 could be either Lys or His
<220> FEATURE:
<223> OTHER INFORMATION: Xaa at position 51 could be either Gly or Lys
<220> FEATURE:
<223> OTHER INFORMATION: Xaa at position 54 could be either Gln or Asn
<220> FEATURE:
<223> OTHER INFORMATION: Xaa at position 79 could be either Val or Leu
<220> FEATURE:
<223> OTHER INFORMATION: Xaa at position 93 could be either Asp or Glu
<220> FEATURE:
<223> OTHER INFORMATION: Xaa at position 94 could be either Ser, Arg or
      Lys
<220> FEATURE:
<223> OTHER INFORMATION: Xaa at position 95 could be either Ser, Gly or
      Tyr
<220> FEATURE:
<223> OTHER INFORMATION: Xaa at position 96 could be either Leu, Phe,
      Thr or Ser
<220> FEATURE:
<223> OTHER INFORMATION: Xaa at position 97 could be either Arg, Ser,
      Thr, Trp or His
<220> FEATURE:
<223> OTHER INFORMATION: Xaa at position 98 could be either Gly or Pro
<220> FEATURE:
<223> OTHER INFORMATION: Xaa at position 99 could be either Ser, Thr,
      Ala or Leu
<220> FEATURE:
<223> OTHER INFORMATION: Xaa at position 100 could be either Arg, Ser,
      Met, Thr or Leu
<220> FEATURE:
<223> OTHER INFORMATION: Xaa at position 101 could be either Val, Ile,
      Thr, Met or Leu
<220> FEATURE:
<223> OTHER INFORMATION: Xaa at position 32 could be either Asn, Gly or
      Tyr
<220> FEATURE:
<223> OTHER INFORMATION: Xaa at position 33 could be either Thr or Asp
<220> FEATURE:
<223> OTHER INFORMATION: Xaa at position 53 could be either Asp or Ser

<400> SEQUENCE: 8

Xaa Xaa Val Leu Thr Gln Pro Pro Ser Val Ser Gly Xaa Pro Gly Gln
  1               5                  10                  15
```

```
Arg Val Thr Ile Ser Cys Xaa Gly Xaa Xaa Ser Asn Ile Xaa Xaa Xaa
             20                  25                  30

Xaa Val Xaa Trp Tyr Gln Gln Leu Pro Gly Thr Ala Pro Lys Leu Leu
         35                  40                  45

Ile Tyr Xaa Asn Xaa Xaa Arg Pro Ser Gly Val Pro Asp Arg Phe Ser
     50                  55                  60

Gly Ser Lys Ser Gly Thr Ser Ala Ser Leu Ala Ile Thr Gly Xaa Gln
 65                  70                  75                  80

Ala Glu Asp Glu Ala Asp Tyr Tyr Cys Gln Xaa Tyr Xaa Xaa Xaa Xaa
                 85                  90                  95

Xaa Xaa Xaa Xaa Xaa Phe Gly Thr Gly Thr Lys Val Thr Val Leu Gly
             100                 105                 110
```

<210> SEQ ID NO 9
<211> LENGTH: 6
<212> TYPE: PRT
<213> ORGANISM: Homo sapiens
<220> FEATURE:
<223> OTHER INFORMATION: Xaa at position 2 could be either Gly, Val, Cys
      or His
<220> FEATURE:
<223> OTHER INFORMATION: Xaa at position 3 could be either Ser or Thr
<220> FEATURE:
<223> OTHER INFORMATION: Xaa at position 4 could be either His, Thr,
      Val, Arg,
<223> OTHER INFORMATION: or Ile
<220> FEATURE:
<223> OTHER INFORMATION: Xaa at position 5 could be either Asp or Ser
<220> FEATURE:
<223> OTHER INFORMATION: Xaa at position 6 could be either Asn, Lys,
      Ala, Thr, Ser, Phe, Trp, or His

<400> SEQUENCE: 9

```
His Xaa Xaa Xaa Xaa Xaa
 1               5
```

<210> SEQ ID NO 10
<211> LENGTH: 12
<212> TYPE: PRT
<213> ORGANISM: Homo sapiens
<220> FEATURE:
<223> OTHER INFORMATION: Xaa at position 4 could be either Asp or Ser
<220> FEATURE:
<223> OTHER INFORMATION: Xaa at position 5 represents any amino acid
<220> FEATURE:
<223> OTHER INFORMATION: Xaa at position 6 could be either Gly, Asp,
      Gln, Leu, Phe, Arg, His, Asn or Tyr

<400> SEQUENCE: 10

```
Gln Ser Tyr Xaa Xaa Xaa Thr His Pro Ala Leu Leu
 1               5                  10
```

<210> SEQ ID NO 11
<211> LENGTH: 17
<212> TYPE: PRT
<213> ORGANISM: Homo sapiens
<220> FEATURE:
<223> OTHER INFORMATION: Xaa at position 1 could be either Phe, Thr or
      Tyr
<220> FEATURE:
<223> OTHER INFORMATION: Xaa at position 3 could be either Arg or Ala
<220> FEATURE:
<223> OTHER INFORMATION: Xaa at position 5 could be either Asp, Ser, Glu
      or Ala
<220> FEATURE:
<223> OTHER INFORMATION: Xaa at position 6 could be either Gly or Arg
<220> FEATURE:
<223> OTHER INFORMATION: Xaa at position 8 represents any amino acid

```
<220> FEATURE:
<223> OTHER INFORMATION: Xaa at position 10 could be either Tyr or Glu

<400> SEQUENCE: 11

Xaa Ile Xaa Tyr Xaa Xaa Ser Xaa Lys Xaa Tyr Ala Asp Ser Val Lys
 1               5                  10                  15

Gly

<210> SEQ ID NO 12
<211> LENGTH: 7
<212> TYPE: PRT
<213> ORGANISM: Homo sapiens
<220> FEATURE:
<223> OTHER INFORMATION: Xaa at position 1 could be either Gly, Tyr,
      Ser, Thr, Asn or Gln

<400> SEQUENCE: 12

Xaa Asn Asp Gln Arg Pro Ser
 1               5

<210> SEQ ID NO 13
<211> LENGTH: 9
<212> TYPE: PRT
<213> ORGANISM: Homo sapiens
<220> FEATURE:
<223> OTHER INFORMATION: Xaa at position 4 and 5 represents any amino
      acid
<220> FEATURE:
<223> OTHER INFORMATION: Xaa at position 6 could be either Tyr or His
<220> FEATURE:
<223> OTHER INFORMATION: Xaa at position 7 could be either Gly, Met,
      Ala, Asn or Ser

<400> SEQUENCE: 13

Phe Thr Phe Xaa Xaa Xaa Xaa Met His
 1               5

<210> SEQ ID NO 14
<211> LENGTH: 13
<212> TYPE: PRT
<213> ORGANISM: Homo sapiens
<220> FEATURE:
<223> OTHER INFORMATION: Xaa at position 9 could be either Ser, Cys,
      Arg, Asn, Asp or Thr
<220> FEATURE:
<223> OTHER INFORMATION: Xaa at position 10 could be either Asn, Met or
      Ile
<220> FEATURE:
<223> OTHER INFORMATION: Xaa at position 11 could be either Thr, Tyr,
      Asp, His, Lys or Pro

<400> SEQUENCE: 14

Ser Gly Gly Arg Ser Asn Ile Gly Xaa Xaa Xaa Val Lys
 1               5                  10

<210> SEQ ID NO 15
<211> LENGTH: 114
<212> TYPE: PRT
<213> ORGANISM: Homo sapiens
<220> FEATURE:
<223> OTHER INFORMATION: Xaa at position 30 could be Ser or Glu
<220> FEATURE:
<223> OTHER INFORMATION: Xaa at position 83 could be Lys or Asn
<220> FEATURE:
<223> OTHER INFORMATION: Xaa at position 5 could be either Gln or Glu

<400> SEQUENCE: 15

Gln Val Gln Val Xaa Ser Gly Gly Gly Val Val Gln Pro Gly Arg Ser
 1               5                  10                  15
```

```
Leu Arg Leu Ser Cys Ala Ala Ser Gly Phe Thr Phe Ser Xaa Tyr Gly
            20                  25                  30

Met His Trp Val Arg Gln Ala Pro Gly Lys Gly Leu Glu Trp Val Ala
            35                  40                  45

Phe Ile Arg Tyr Asp Gly Ser Asn Lys Tyr Tyr Ala Asp Ser Val Lys
50                  55                  60

Gly Arg Phe Thr Ile Ser Arg Asp Asn Ser Lys Asn Thr Leu Tyr Leu
65                  70                  75                  80

Gln Met Xaa Ser Leu Arg Ala Glu Asp Thr Ala Val Tyr Tyr Cys Lys
            85                  90                  95

Thr His Gly Ser His Asp Asn Trp Gly Gln Gly Thr Met Val Thr Val
            100                 105                 110

Ser Ser

<210> SEQ ID NO 16
<211> LENGTH: 112
<212> TYPE: PRT
<213> ORGANISM: Homo sapiens
<220> FEATURE:
<223> OTHER INFORMATION: Xaa at position 1  could be either Ser or Gln
<220> FEATURE:
<223> OTHER INFORMATION: Xaa at position 2 could be Tyr or Ser
<220> FEATURE:
<223> OTHER INFORMATION: Xaa at position 13 could be either Thr or Ala
<220> FEATURE:
<223> OTHER INFORMATION: Xaa at position 25 could be either Gly or Ser
<220> FEATURE:
<223> OTHER INFORMATION: Xaa at position 51 and 95  could be either Gly
      or Tyr
<220> FEATURE:
<223> OTHER INFORMATION: Xaa at position 79 could be either Val or Leu

<400> SEQUENCE: 16

Xaa Xaa Val Leu Thr Gln Pro Pro Ser Val Ser Gly Xaa Pro Gly Gln
1               5                   10                  15

Arg Val Thr Ile Ser Cys Ser Gly Xaa Arg Ser Asn Ile Gly Ser Asn
            20                  25                  30

Thr Val Lys Trp Tyr Gln Gln Leu Pro Gly Thr Ala Pro Lys Leu Leu
            35                  40                  45

Ile Tyr Xaa Asn Asp Gln Arg Pro Ser Gly Val Pro Asp Arg Phe Ser
50                  55                  60

Gly Ser Lys Ser Gly Thr Ser Ala Ser Leu Ala Ile Thr Gly Xaa Gln
65                  70                  75                  80

Ala Glu Asp Glu Ala Asp Tyr Tyr Cys Gln Ser Tyr Asp Arg Xaa Thr
            85                  90                  95

His Pro Ala Leu Leu Phe Gly Thr Gly Thr Lys Val Thr Val Leu Gly
            100                 105                 110

<210> SEQ ID NO 17
<211> LENGTH: 6
<212> TYPE: PRT
<213> ORGANISM: Homo sapiens

<400> SEQUENCE: 17

His Gly Ser His Asp Asn
1               5

<210> SEQ ID NO 18
<211> LENGTH: 12
<212> TYPE: PRT
<213> ORGANISM: Homo sapiens
```

<400> SEQUENCE: 18

Gln Ser Tyr Asp Arg Gly Thr His Pro Ala Leu Leu
1               5                   10

<210> SEQ ID NO 19
<211> LENGTH: 17
<212> TYPE: PRT
<213> ORGANISM: Homo sapiens

<400> SEQUENCE: 19

Phe Ile Arg Tyr Asp Gly Ser Asn Lys Tyr Tyr Ala Asp Ser Val Lys
1               5                   10                  15

Gly

<210> SEQ ID NO 20
<211> LENGTH: 7
<212> TYPE: PRT
<213> ORGANISM: Homo sapiens

<400> SEQUENCE: 20

Gly Asn Asp Gln Arg Pro Ser
1               5

<210> SEQ ID NO 21
<211> LENGTH: 9
<212> TYPE: PRT
<213> ORGANISM: Homo sapiens

<400> SEQUENCE: 21

Phe Thr Phe Ser Ser Tyr Gly Met His
1               5

<210> SEQ ID NO 22
<211> LENGTH: 13
<212> TYPE: PRT
<213> ORGANISM: Homo sapiens

<400> SEQUENCE: 22

Ser Gly Gly Arg Ser Asn Ile Gly Ser Asn Thr Val Lys
1               5                   10

<210> SEQ ID NO 23
<211> LENGTH: 115
<212> TYPE: PRT
<213> ORGANISM: Homo sapiens

<400> SEQUENCE: 23

Gln Val Gln Leu Val Gln Ser Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Phe Ile Arg Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Lys Ser Leu Arg Ala Glu Asp Thr Ala Val Tyr Tyr Cys
                85                  90                  95

Lys Thr His Gly Ser His Asp Asn Trp Gly Gln Gly Thr Met Val Thr

```
                       100                 105                 110

Val Ser Ser
        115

<210> SEQ ID NO 24
<211> LENGTH: 112
<212> TYPE: PRT
<213> ORGANISM: Homo sapiens

<400> SEQUENCE: 24

Ser Tyr Val Leu Thr Gln Pro Pro Ser Val Ser Gly Thr Pro Gly Gln
  1               5                  10                  15

Arg Val Thr Ile Ser Cys Ser Gly Gly Arg Ser Trp Ile Gly Ser Asn
                 20                  25                  30

Thr Val Lys Trp Tyr Gln Gln Leu Pro Gly Thr Ala Pro Lys Leu Leu
             35                  40                  45

Ile Tyr Gly Asn Asp Gln Arg Pro Ser Gly Val Pro Asp Arg Phe Ser
 50                  55                  60

Gly Ser Lys Ser Gly Thr Ser Ala Ser Leu Ala Ile Thr Gly Val Gln
 65                  70                  75                  80

Ala Glu Asp Glu Ala Asp Tyr Tyr Cys Gln Ser Tyr Asp Arg Gly Thr
                 85                  90                  95

His Pro Ala Leu Leu Phe Gly Thr Gly Thr Lys Val Thr Val Leu Gly
            100                 105                 110

<210> SEQ ID NO 25
<211> LENGTH: 6
<212> TYPE: PRT
<213> ORGANISM: Homo sapiens

<400> SEQUENCE: 25

His Gly Ser His Asp Asn
  1               5

<210> SEQ ID NO 26
<211> LENGTH: 12
<212> TYPE: PRT
<213> ORGANISM: Homo sapiens

<400> SEQUENCE: 26

Gln Ser Tyr Asp Arg Tyr Thr His Pro Ala Leu Leu
  1               5                  10

<210> SEQ ID NO 27
<211> LENGTH: 17
<212> TYPE: PRT
<213> ORGANISM: Homo sapiens

<400> SEQUENCE: 27

Phe Ile Arg Tyr Asp Gly Ser Asn Lys Tyr Tyr Ala Asp Ser Val Lys
  1               5                  10                  15

Gly

<210> SEQ ID NO 28
<211> LENGTH: 7
<212> TYPE: PRT
<213> ORGANISM: Homo sapiens

<400> SEQUENCE: 28

Tyr Asn Asp Gln Arg Pro Ser
  1               5
```

<210> SEQ ID NO 29
<211> LENGTH: 9
<212> TYPE: PRT
<213> ORGANISM: Homo sapiens

<400> SEQUENCE: 29

Phe Thr Phe Ser Ser Tyr Gly Met His
1               5

<210> SEQ ID NO 30
<211> LENGTH: 13
<212> TYPE: PRT
<213> ORGANISM: Homo sapiens

<400> SEQUENCE: 30

Ser Gly Ser Arg Ser Asn Ile Gly Ser Asn Thr Val Lys
1               5                   10

<210> SEQ ID NO 31
<211> LENGTH: 115
<212> TYPE: PRT
<213> ORGANISM: Homo sapiens

<400> SEQUENCE: 31

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Phe Ile Arg Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Lys Thr His Gly Ser His Asp Asn Trp Gly Gln Gly Thr Met Val Thr
            100                 105                 110

Val Ser Ser
        115

<210> SEQ ID NO 32
<211> LENGTH: 112
<212> TYPE: PRT
<213> ORGANISM: Homo sapiens

<400> SEQUENCE: 32

Gln Ser Val Leu Thr Gln Pro Pro Ser Val Ser Gly Ala Pro Gly Gln
1               5                   10                  15

Arg Val Thr Ile Ser Cys Ser Gly Ser Arg Ser Asn Ile Gly Ser Asn
            20                  25                  30

Thr Val Lys Trp Tyr Gln Gln Leu Pro Gly Thr Ala Pro Lys Leu Leu
        35                  40                  45

Ile Tyr Tyr Asn Asp Gln Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ala Glu Asp Glu Ala Asp Tyr Tyr Cys Gln Ser Tyr Asp Arg Tyr Thr

```
                    85                  90                  95

His Pro Ala Leu Leu Phe Gly Thr Gly Thr Lys Val Thr Val Leu Gly
            100                 105                 110

<210> SEQ ID NO 33
<211> LENGTH: 115
<212> TYPE: PRT
<213> ORGANISM: Homo sapiens

<400> SEQUENCE: 33

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Phe Ile Arg Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Lys Ser Leu Arg Ala Glu Asp Thr Ala Val Tyr Tyr Cys
                85                  90                  95

Thr Thr Ser Gly Ser Tyr Asp Tyr Trp Gly Gln Gly Thr Met Val Thr
            100                 105                 110

Val Ser Ser
        115

<210> SEQ ID NO 34
<211> LENGTH: 112
<212> TYPE: PRT
<213> ORGANISM: Homo sapiens

<400> SEQUENCE: 34

Ser Tyr Val Leu Thr Gln Pro Pro Ser Val Ser Gly Thr Pro Gly Gln
1               5                   10                  15

Arg Val Thr Ile Ser Cys Ser Gly Gly Arg Ser Asn Ile Gly Ser Asn
            20                  25                  30

Thr Val Lys Trp Tyr Gln Gln Leu Pro Gly Thr Ala Pro Lys Leu Leu
        35                  40                  45

Ile Tyr Gly Asn Asp Gln Arg Pro Ser Gly Val Pro Asp Arg Phe Ser
    50                  55                  60

Gly Ser Lys Ser Gly Thr Ser Ala Ser Leu Ala Ile Thr Gly Val Gln
65                  70                  75                  80

Ala Glu Asp Glu Ala Asp Tyr Tyr Cys Gln Ser Tyr Asp Ser Ser Leu
                85                  90                  95

Arg Gly Ser Arg Val Phe Gly Thr Gly Thr Lys Val Thr Val Leu Gly
            100                 105                 110

<210> SEQ ID NO 35
<211> LENGTH: 115
<212> TYPE: PRT
<213> ORGANISM: Homo sapiens

<400> SEQUENCE: 35

Gln Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Ser Tyr
            20                  25                  30
```

```
Gly Met His Trp Val Arg Gln Ala Pro Gly Lys Gly Leu Glu Trp Val
        35                  40                  45

Ala Phe Ile Arg Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Gly Ser Tyr Asp Tyr Trp Gly Gln Gly Thr Met Val Thr
            100                 105                 110

Val Ser Ser
    115

<210> SEQ ID NO 36
<211> LENGTH: 112
<212> TYPE: PRT
<213> ORGANISM: Homo sapiens
<220> FEATURE:
<223> OTHER INFORMATION: Xaa at position 32 represents either Gly or Tyr

<400> SEQUENCE: 36

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Xaa
            20                  25                  30

Asp Val His Trp Tyr Gln Gln Leu Pro Gly Thr Ala Pro Lys Leu Leu
        35                  40                  45

Ile Tyr Gly Asn Ser Asn Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ala Glu Asp Glu Ala Asp Tyr Tyr Cys Gln Ser Tyr Asp Ser Ser Leu
                85                  90                  95

Ser Gly Ser Arg Val Phe Gly Thr Gly Thr Lys Val Thr Val Leu Gly
            100                 105                 110

<210> SEQ ID NO 37
<211> LENGTH: 115
<212> TYPE: PRT
<213> ORGANISM: Homo sapiens

<400> SEQUENCE: 37

Gln Val Gln Leu Val Gln Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Phe Ile Arg Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Lys Ser Leu Arg Ala Glu Asp Thr Ala Val Tyr Tyr Cys
                85                  90                  95

Thr Thr His Gly Ser His Asp Asn Trp Gly Gln Gly Thr Met Val Thr
            100                 105                 110
```

Val Ser Ser
        115

<210> SEQ ID NO 38
<211> LENGTH: 112
<212> TYPE: PRT
<213> ORGANISM: Homo sapiens

<400> SEQUENCE: 38

Ser Tyr Val Leu Thr Gln Pro Pro Ser Val Ser Gly Thr Pro Gly Gln
 1               5                  10                  15

Arg Val Thr Ile Ser Cys Ser Gly Gly Arg Ser Asn Ile Gly Ser Asn
                20                  25                  30

Thr Val Lys Trp Tyr Gln Gln Leu Pro Gly Thr Ala Pro Lys Leu Leu
            35                  40                  45

Ile Tyr Gly Asn Asp Gln Arg Pro Ser Gly Val Pro Asp Arg Phe Ser
        50                  55                  60

Gly Ser Lys Ser Gly Thr Ser Ala Ser Leu Ala Ile Thr Gly Val Gln
65                  70                  75                  80

Ala Glu Asp Glu Ala Asp Tyr Tyr Cys Gln Ser Tyr Asp Ser Ser Leu
                85                  90                  95

Arg Gly Ser Arg Val Phe Gly Thr Gly Thr Lys Val Thr Val Leu Gly
               100                 105                 110

<210> SEQ ID NO 39
<211> LENGTH: 115
<212> TYPE: PRT
<213> ORGANISM: Homo sapiens

<400> SEQUENCE: 39

Gln Val Gln Leu Val Gln Ser Gly Gly Val Val Gln Pro Gly Arg
 1               5                  10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Phe Ile Arg Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Lys Ser Leu Arg Ala Glu Asp Thr Ala Val Tyr Tyr Cys
                85                  90                  95

Thr Thr Ser Gly Ser Tyr Asp Tyr Trp Gly Gln Gly Thr Met Val Thr
               100                 105                 110

Val Ser Ser
        115

<210> SEQ ID NO 40
<211> LENGTH: 112
<212> TYPE: PRT
<213> ORGANISM: Homo sapiens

<400> SEQUENCE: 40

Ser Tyr Val Leu Thr Gln Pro Pro Ser Val Ser Gly Thr Pro Gly Gln
 1               5                  10                  15

Arg Val Thr Ile Ser Cys Ser Gly Gly Arg Ser Asn Ile Gly Ser Asn
                20                  25                  30

Thr Val Lys Trp Tyr Gln Gln Leu Pro Gly Thr Ala Pro Lys Leu Leu

```
              35                  40                  45
Ile Tyr Gly Asn Asp Gln Arg Pro Ser Gly Val Pro Asp Arg Phe Ser
         50                  55                  60

Gly Ser Lys Ser Gly Thr Ser Ala Ser Leu Ala Ile Thr Gly Val Gln
 65                  70                  75                  80

Ala Glu Asp Glu Ala Asp Tyr Tyr Cys Gln Ser Tyr Asp Arg Gly Phe
                 85                  90                  95

Thr Gly Ser Arg Val Phe Gly Thr Gly Thr Lys Val Thr Val Leu Gly
            100                 105                 110

<210> SEQ ID NO 41
<211> LENGTH: 115
<212> TYPE: PRT
<213> ORGANISM: Homo sapiens

<400> SEQUENCE: 41

Gln Val Gln Leu Val Gln Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
             35                  40                  45

Ala Phe Ile Arg Tyr Asp Gly Ser Asn Lys Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Lys Ser Leu Arg Ala Glu Asp Thr Ala Val Tyr Tyr Cys
                 85                  90                  95

Thr Thr Ser Gly Ser Tyr Asp Tyr Trp Gly Gln Gly Thr Met Val Thr
            100                 105                 110

Val Ser Ser
       115

<210> SEQ ID NO 42
<211> LENGTH: 112
<212> TYPE: PRT
<213> ORGANISM: Homo sapiens

<400> SEQUENCE: 42

Ser Tyr Val Leu Thr Gln Pro Pro Ser Val Ser Gly Thr Pro Gly Gln
 1               5                  10                  15

Arg Val Thr Ile Ser Cys Ser Gly Gly Arg Ser Asn Ile Gly Ser Asn
                20                  25                  30

Thr Val Lys Trp Tyr Gln Gln Leu Pro Gly Thr Ala Pro Lys Leu Leu
             35                  40                  45

Ile Tyr Gly Asn Asp Gln Arg Pro Ser Gly Val Pro Asp Arg Phe Ser
         50                  55                  60

Gly Ser Lys Ser Gly Thr Ser Ala Ser Leu Ala Ile Thr Gly Val Gln
 65                  70                  75                  80

Ala Glu Asp Glu Ala Asp Tyr Tyr Cys Gln Ser Tyr Asp Ser Ser Leu
                 85                  90                  95

Trp Gly Ser Arg Val Phe Gly Thr Gly Thr Lys Val Thr Val Leu Gly
            100                 105                 110

<210> SEQ ID NO 43
<211> LENGTH: 115
<212> TYPE: PRT
```

<213> ORGANISM: Homo sapiens

<400> SEQUENCE: 43

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Phe Ile Arg Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Lys Ser Leu Arg Ala Glu Asp Thr Ala Val Tyr Tyr Cys
                85                  90                  95

Thr Thr His Gly Ser His Asp Asn Trp Gly Gln Gly Thr Met Val Thr
            100                 105                 110

Val Ser Ser
        115

<210> SEQ ID NO 44
<211> LENGTH: 112
<212> TYPE: PRT
<213> ORGANISM: Homo sapiens

<400> SEQUENCE: 44

Ser Tyr Val Leu Thr Gln Pro Pro Ser Val Ser Gly Thr Pro Gly Gln
1               5                   10                  15

Arg Val Thr Ile Ser Cys Ser Gly Gly Arg Ser Asn Ile Gly Ser Asn
            20                  25                  30

Thr Val Lys Trp Tyr Gln Gln Leu Pro Gly Thr Ala Pro Lys Leu Leu
        35                  40                  45

Ile Tyr Gly Asn Asp Gln Arg Pro Ser Gly Val Pro Asp Arg Phe Ser
    50                  55                  60

Gly Ser Lys Ser Gly Thr Ser Ala Ser Leu Ala Ile Thr Gly Val Gln
65                  70                  75                  80

Ala Glu Asp Glu Ala Asp Tyr Tyr Cys Gln Ser Tyr Asp Arg Gly Phe
                85                  90                  95

Thr Gly Ser Arg Val Phe Gly Thr Gly Thr Lys Val Thr Val Leu Gly
            100                 105                 110

<210> SEQ ID NO 45
<211> LENGTH: 115
<212> TYPE: PRT
<213> ORGANISM: Homo sapiens

<400> SEQUENCE: 45

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Phe Ile Arg Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Lys Ser Leu Arg Ala Glu Asp Thr Ala Val Tyr Tyr Cys
                85                  90                  95

Thr Thr His Gly Ser His Asp Asn Trp Gly Gln Gly Thr Met Val Thr
            100                 105                 110

Val Ser Ser
        115

<210> SEQ ID NO 46
<211> LENGTH: 112
<212> TYPE: PRT
<213> ORGANISM: Homo sapiens

<400> SEQUENCE: 46

Ser Tyr Val Leu Thr Gln Pro Pro Ser Val Ser Gly Thr Pro Gly Gln
1               5                   10                  15

Arg Val Thr Ile Ser Cys Ser Gly Arg Ser Asn Ile Gly Ser Asn
            20                  25                  30

Thr Val Lys Trp Tyr Gln Gln Leu Pro Gly Thr Ala Pro Lys Leu Leu
            35                  40                  45

Ile Tyr Gly Asn Asp Gln Arg Pro Ser Gly Val Pro Asp Arg Phe Ser
        50                  55                  60

Gly Ser Lys Ser Gly Thr Ser Ala Ser Leu Ala Ile Thr Gly Val Gln
65                  70                  75                  80

Ala Glu Asp Glu Ala Asp Tyr Tyr Cys Gln Ser Tyr Asp Ser Ser Leu
                85                  90                  95

Trp Gly Ser Arg Val Phe Gly Thr Gly Thr Lys Val Thr Val Leu Gly
            100                 105                 110

<210> SEQ ID NO 47
<211> LENGTH: 115
<212> TYPE: PRT
<213> ORGANISM: Homo sapiens

<400> SEQUENCE: 47

Gln Val Gln Leu Val Gln Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
            35                  40                  45

Ala Phe Ile Arg Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Lys Ser Leu Arg Ala Glu Asp Thr Ala Val Tyr Tyr Cys
                85                  90                  95

Lys Thr His Gly Ser His Asp Asn Trp Gly Gln Gly Thr Met Val Thr
            100                 105                 110

Val Ser Ser
        115

<210> SEQ ID NO 48
<211> LENGTH: 112
<212> TYPE: PRT
<213> ORGANISM: Homo sapiens

<400> SEQUENCE: 48

```
Ser Tyr Val Leu Thr Gln Pro Pro Ser Val Ser Gly Thr Pro Gly Gln
  1               5                  10                  15

Arg Val Thr Ile Ser Cys Ser Gly Ser Arg Ser Asn Ile Gly Ser Asn
             20                  25                  30

Thr Val Lys Trp Tyr Gln Gln Leu Pro Gly Thr Ala Pro Lys Leu Leu
         35                  40                  45

Ile Tyr Gly Asn Asp Gln Arg Pro Ser Gly Val Pro Asp Arg Phe Ser
     50                  55                  60

Gly Ser Lys Ser Gly Thr Ser Ala Ser Leu Ala Ile Thr Gly Val Gln
 65                  70                  75                  80

Ala Glu Asp Glu Ala Asp Tyr Tyr Cys Gln Thr Tyr Asp Lys Gly Phe
                 85                  90                  95

Thr Gly Ser Ser Val Phe Gly Thr Gly Thr Lys Val Thr Val Leu Gly
            100                 105                 110
```

<210> SEQ ID NO 49
<211> LENGTH: 115
<212> TYPE: PRT
<213> ORGANISM: Homo sapiens

<400> SEQUENCE: 49

```
Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Ser Ser Tyr
             20                  25                  30

Gly Met His Trp Val Arg Gln Ala Pro Gly Lys Gly Leu Glu Trp Val
         35                  40                  45

Ala Phe Ile Arg Tyr Asp Gly Ser Asn Lys Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Lys Thr His Gly Ser His Asp Asn Trp Gly Gln Gly Thr Met Val Thr
            100                 105                 110

Val Ser Ser
        115
```

<210> SEQ ID NO 50
<211> LENGTH: 112
<212> TYPE: PRT
<213> ORGANISM: Homo sapiens

<400> SEQUENCE: 50

```
Gln Ser Val Leu Thr Gln Pro Pro Ser Val Ser Gly Ala Pro Gly Gln
  1               5                  10                  15

Arg Val Thr Ile Ser Cys Ser Gly Ser Arg Ser Asn Ile Gly Ser Asn
             20                  25                  30

Thr Val Lys Trp Tyr Gln Gln Leu Pro Gly Thr Ala Pro Lys Leu Leu
         35                  40                  45

Ile Tyr Gly Asn Asp Gln Arg Pro Ser Gly Val Pro Asp Arg Phe Ser
     50                  55                  60

Gly Ser Lys Ser Gly Thr Ser Ala Ser Leu Ala Ile Thr Gly Leu Gln
 65                  70                  75                  80

Ala Glu Asp Glu Ala Asp Tyr Tyr Cys Gln Thr Tyr Asp Lys Gly Phe
                 85                  90                  95
```

```
Thr Gly Ser Ser Val Phe Gly Thr Gly Thr Lys Val Thr Val Leu Gly
            100                 105                 110
```

```
<210> SEQ ID NO 51
<211> LENGTH: 115
<212> TYPE: PRT
<213> ORGANISM: Homo sapiens

<400> SEQUENCE: 51
```

```
Gln Val Gln Leu Val Gln Ser Gly Gly Val Val Gln Pro Gly Arg
 1               5                  10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Phe Ile Arg Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
 65                 70                  75                  80

Leu Gln Met Lys Ser Leu Arg Ala Glu Asp Thr Ala Val Tyr Tyr Cys
                85                  90                  95

Thr Thr His Gly Ser His Asp Thr Trp Gly Gln Gly Thr Met Val Thr
            100                 105                 110

Val Ser Ser
        115
```

```
<210> SEQ ID NO 52
<211> LENGTH: 112
<212> TYPE: PRT
<213> ORGANISM: Homo sapiens

<400> SEQUENCE: 52
```

```
Ser Tyr Val Leu Thr Gln Pro Pro Ser Val Ser Gly Thr Pro Gly Gln
 1               5                  10                  15

Arg Val Thr Ile Ser Cys Ser Gly Gly Arg Ser Asn Ile Gly Ser Asn
                20                  25                  30

Thr Val Lys Trp Tyr Gln Gln Leu Pro Gly Thr Ala Pro Lys Leu Leu
            35                  40                  45

Ile Tyr Gly Asn Asp Gln Arg Pro Ser Gly Val Pro Asp Arg Phe Ser
        50                  55                  60

Gly Ser Lys Ser Gly Thr Ser Ala Ser Leu Ala Ile Thr Gly Val Gln
 65                 70                  75                  80

Ala Glu Asp Glu Ala Asp Tyr Tyr Cys Gln Ser Tyr Asp Ser Ser Leu
                85                  90                  95

Trp Gly Thr Arg Val Phe Gly Thr Gly Thr Lys Val Thr Val Leu Gly
            100                 105                 110
```

```
<210> SEQ ID NO 53
<211> LENGTH: 115
<212> TYPE: PRT
<213> ORGANISM: Homo sapiens

<400> SEQUENCE: 53
```

```
Gln Val Gln Leu Val Gln Ser Gly Gly Val Val Gln Pro Gly Arg
 1               5                  10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
```

```
                35                  40                  45
Ala Phe Ile Arg Tyr Asp Gly Ser Asn Lys Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Lys Ser Leu Arg Ala Glu Asp Thr Ala Val Tyr Tyr Cys
                 85                  90                  95

Thr Thr His Gly Ser His Asp Asn Trp Gly Gln Gly Thr Met Val Thr
            100                 105                 110

Val Ser Ser
        115

<210> SEQ ID NO 54
<211> LENGTH: 112
<212> TYPE: PRT
<213> ORGANISM: Homo sapiens

<400> SEQUENCE: 54

Ser Tyr Val Leu Thr Gln Pro Pro Ser Val Ser Gly Thr Pro Gly Gln
 1               5                  10                  15

Arg Val Thr Ile Ser Cys Ser Gly Gly Arg Ser Asn Ile Val Ser Asn
                20                  25                  30

Thr Val Lys Trp Tyr Gln Gln Leu Pro Gly Thr Ala Pro Lys Leu Leu
            35                  40                  45

Ile Tyr Gly Asn Asp Gln Arg Pro Ser Gly Val Pro Asp Arg Phe Ser
         50                  55                  60

Gly Ser Lys Ser Gly Thr Ser Ala Ser Leu Ala Ile Thr Gly Val Gln
 65                  70                  75                  80

Ala Glu Asp Glu Ala Asp Tyr Tyr Cys Gln Ser Tyr Asp Arg Gly Phe
                 85                  90                  95

Thr Gly Ser Arg Val Phe Gly Thr Gly Thr Lys Val Thr Val Leu Gly
            100                 105                 110

<210> SEQ ID NO 55
<211> LENGTH: 115
<212> TYPE: PRT
<213> ORGANISM: Homo sapiens

<400> SEQUENCE: 55

Gln Val Gln Leu Val Gln Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Phe Ile Arg Tyr Asp Gly Ser Asn Lys Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Lys Ser Leu Arg Ala Glu Asp Thr Ala Val Tyr Tyr Cys
                 85                  90                  95

Thr Thr His Gly Ser His Asp Asn Trp Gly Gln Gly Thr Met Val Thr
            100                 105                 110

Val Ser Ser
        115
```

-continued

```
<210> SEQ ID NO 56
<211> LENGTH: 112
<212> TYPE: PRT
<213> ORGANISM: Homo sapiens

<400> SEQUENCE: 56

Ser Tyr Val Leu Thr Gln Pro Pro Ser Val Ser Gly Thr Pro Gly Gln
  1               5                  10                  15

Arg Val Thr Ile Ser Cys Ser Gly Gly Arg Ser Asn Ile Val Ser Asn
             20                  25                  30

Thr Val Lys Trp Tyr Gln Gln Leu Pro Gly Thr Ala Pro Lys Leu Leu
         35                  40                  45

Ile Tyr Gly Asn Asp Gln Arg Pro Ser Gly Val Pro Asp Arg Phe Ser
     50                  55                  60

Gly Ser Lys Ser Gly Thr Ser Ala Ser Leu Ala Ile Thr Gly Val Gln
 65                  70                  75                  80

Ala Glu Asp Glu Ala Asp Tyr Tyr Cys Gln Ser Tyr Asp Arg Gly Phe
                 85                  90                  95

Thr Gly Ala Arg Val Phe Gly Thr Gly Thr Lys Val Thr Val Leu Gly
            100                 105                 110

<210> SEQ ID NO 57
<211> LENGTH: 115
<212> TYPE: PRT
<213> ORGANISM: Homo sapiens

<400> SEQUENCE: 57

Gln Val Gln Leu Val Gln Ser Gly Gly Gly Val Val Gln Pro Gly Arg
  1               5                  10                  15

Ser Leu Arg Leu Ser Cys Ala Ala Ser Gly Phe Thr Phe Ser Ser Tyr
             20                  25                  30

Gly Met His Trp Val Arg Gln Ala Pro Gly Lys Gly Leu Glu Trp Val
         35                  40                  45

Ala Phe Ile Arg Tyr Asp Gly Ser Asn Lys Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Lys Ser Leu Arg Ala Glu Asp Thr Ala Val Tyr Tyr Cys
                 85                  90                  95

Lys Thr His Gly Ser His Asp Asn Trp Gly Gln Gly Thr Met Val Thr
            100                 105                 110

Val Ser Ser
        115

<210> SEQ ID NO 58
<211> LENGTH: 112
<212> TYPE: PRT
<213> ORGANISM: Homo sapiens

<400> SEQUENCE: 58

Ser Tyr Val Leu Thr Gln Pro Pro Ser Val Ser Gly Thr Pro Gly Gln
  1               5                  10                  15

Arg Val Thr Ile Ser Cys Ser Gly Gly Arg Ser Asn Ile Gly Ser Asn
             20                  25                  30

Thr Val Lys Trp Tyr Gln Gln Leu Pro Gly Thr Ala Pro Lys Leu Leu
         35                  40                  45

Ile Tyr Gly Asn Asp Gln Arg Pro Ser Gly Val Pro Asp Arg Phe Ser
     50                  55                  60
```

```
Gly Ser Lys Ser Gly Thr Ser Ala Ser Leu Ala Ile Thr Gly Val Gln
 65                  70                  75                  80

Ala Glu Asp Glu Ala Asp Tyr Tyr Cys Gln Thr Tyr Asp Lys Gly Phe
                 85                  90                  95

Thr Gly Ser Ser Val Phe Gly Thr Gly Thr Lys Val Thr Val Leu Gly
            100                 105                 110
```

<210> SEQ ID NO 59
<211> LENGTH: 115
<212> TYPE: PRT
<213> ORGANISM: Homo sapiens

<400> SEQUENCE: 59

```
Gln Val Gln Leu Val Gln Ser Gly Gly Val Val Gln Pro Gly Arg
  1               5                  10                  15

Ser Leu Arg Leu Ser Cys Ala Ala Ser Gly Phe Thr Phe Ser Ser Tyr
             20                  25                  30

Gly Met His Trp Val Arg Gln Ala Pro Gly Lys Gly Leu Glu Trp Val
         35                  40                  45

Ala Phe Ile Arg Tyr Asp Gly Ser Asn Lys Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Lys Ser Leu Arg Ala Glu Asp Thr Ala Val Tyr Tyr Cys
                 85                  90                  95

Lys Thr His Gly Ser His Asp Asn Trp Gly Gln Gly Thr Met Val Thr
            100                 105                 110

Val Ser Ser
        115
```

<210> SEQ ID NO 60
<211> LENGTH: 112
<212> TYPE: PRT
<213> ORGANISM: Homo sapiens

<400> SEQUENCE: 60

```
Ser Tyr Val Leu Thr Gln Pro Pro Ser Val Ser Gly Thr Pro Gly Gln
  1               5                  10                  15

Arg Val Thr Ile Ser Cys Ser Gly Gly Arg Ser Asn Ile Gly Ser Asn
             20                  25                  30

Thr Val Lys Trp Tyr Gln Gln Leu Pro Gly Thr Ala Pro Lys Leu Leu
         35                  40                  45

Ile Tyr Gly Asn Asp Gln Arg Pro Ser Gly Val Pro Asp Arg Phe Ser
     50                  55                  60

Gly Ser Lys Ser Gly Thr Ser Ala Ser Leu Ala Ile Thr Gly Val Gln
 65                  70                  75                  80

Ala Glu Asp Glu Ala Asp Tyr Tyr Cys Gln Ser Tyr Glu Arg Gly Phe
                 85                  90                  95

Thr Gly Ser Met Val Phe Gly Thr Gly Thr Lys Val Thr Val Leu Gly
            100                 105                 110
```

<210> SEQ ID NO 61
<211> LENGTH: 115
<212> TYPE: PRT
<213> ORGANISM: Homo sapiens

<400> SEQUENCE: 61

```
Gln Val Gln Leu Val Gln Ser Gly Gly Gly Val Val Gln Pro Gly Arg
  1               5                  10                  15

Ser Leu Arg Leu Ser Cys Ala Ala Ser Gly Phe Thr Phe Ser Ser Tyr
             20                  25                  30

Gly Met His Trp Val Arg Gln Ala Pro Gly Lys Gly Leu Glu Trp Val
         35                  40                  45

Ala Phe Ile Arg Tyr Asp Gly Ser Asn Lys Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Lys Ser Leu Arg Ala Glu Asp Thr Ala Val Tyr Tyr Cys
             85                  90                  95

Lys Thr His Gly Ser His Asp Asn Trp Gly Gln Gly Thr Met Val Thr
            100                 105                 110

Val Ser Ser
        115

<210> SEQ ID NO 62
<211> LENGTH: 112
<212> TYPE: PRT
<213> ORGANISM: Homo sapiens

<400> SEQUENCE: 62

Ser Tyr Val Leu Thr Gln Pro Pro Ser Val Ser Gly Thr Pro Gly Gln
  1               5                  10                  15

Arg Val Thr Ile Ser Cys Ser Gly Gly Arg Ser Asn Ile Gly Ser Asn
             20                  25                  30

Thr Val Lys Trp Tyr Gln Gln Leu Pro Gly Thr Ala Pro Lys Leu Leu
         35                  40                  45

Ile Tyr Gly Asn Asp Gln Arg Pro Ser Gly Val Pro Asp Arg Phe Ser
     50                  55                  60

Gly Ser Lys Ser Gly Thr Ser Ala Ser Leu Ala Ile Thr Gly Val Gln
 65                  70                  75                  80

Ala Glu Asp Glu Ala Asp Tyr Tyr Cys Gln Ser Tyr Asp Arg Gly Thr
             85                  90                  95

His Pro Leu Thr Ile Phe Gly Thr Gly Thr Lys Val Thr Val Leu Gly
            100                 105                 110

<210> SEQ ID NO 63
<211> LENGTH: 115
<212> TYPE: PRT
<213> ORGANISM: Homo sapiens

<400> SEQUENCE: 63

Gln Val Gln Leu Val Gln Ser Gly Gly Gly Val Val Gln Pro Gly Arg
  1               5                  10                  15

Ser Leu Arg Leu Ser Cys Ala Ala Ser Gly Phe Thr Phe Ser Ser Tyr
             20                  25                  30

Gly Met His Trp Val Arg Gln Ala Pro Gly Lys Gly Leu Glu Trp Val
         35                  40                  45

Ala Phe Ile Arg Tyr Asp Gly Ser Asn Lys Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Lys Ser Leu Arg Ala Glu Asp Thr Ala Val Tyr Tyr Cys
             85                  90                  95
```

```
Lys Thr His Gly Ser His Asp Asn Trp Gly Gln Gly Thr Met Val Thr
            100                 105                 110

Val Ser Ser
        115

<210> SEQ ID NO 64
<211> LENGTH: 112
<212> TYPE: PRT
<213> ORGANISM: Homo sapiens

<400> SEQUENCE: 64

Ser Tyr Val Leu Thr Gln Pro Pro Ser Val Gly Thr Pro Gly Gln
  1               5                  10                  15

Arg Val Thr Ile Ser Cys Ser Gly Gly Arg Ser Asn Ile Gly Ser Asn
             20                  25                  30

Thr Val Lys Trp Tyr Gln Gln Leu Pro Gly Thr Ala Pro Lys Leu Leu
         35                  40                  45

Ile Tyr Gly Asn Asp Gln Arg Pro Ser Gly Val Pro Asp Arg Phe Ser
     50                  55                  60

Gly Ser Lys Ser Gly Thr Ser Ala Ser Leu Ala Ile Thr Gly Val Gln
 65                  70                  75                  80

Ala Glu Asp Glu Ala Asp Tyr Tyr Cys Gln Ser Tyr Asp Arg Gly Ser
                 85                  90                  95

His Pro Ala Leu Thr Phe Gly Gly Thr Lys Val Thr Val Leu Gly
            100                 105                 110

<210> SEQ ID NO 65
<211> LENGTH: 115
<212> TYPE: PRT
<213> ORGANISM: Homo sapiens

<400> SEQUENCE: 65

Gln Val Gln Leu Val Gln Ser Gly Gly Gly Val Val Gln Pro Gly Arg
  1               5                  10                  15

Ser Leu Arg Leu Ser Cys Ala Ala Ser Gly Phe Thr Phe Ser Ser Tyr
             20                  25                  30

Gly Met His Trp Val Arg Gln Ala Pro Gly Lys Gly Leu Glu Trp Val
         35                  40                  45

Ala Phe Ile Arg Tyr Asp Gly Ser Asn Lys Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Lys Ser Leu Arg Ala Glu Asp Thr Ala Val Tyr Tyr Cys
                 85                  90                  95

Lys Thr His Gly Ser His Asp Asn Trp Gly Gln Gly Thr Met Val Thr
            100                 105                 110

Val Ser Ser
        115

<210> SEQ ID NO 66
<211> LENGTH: 112
<212> TYPE: PRT
<213> ORGANISM: Homo sapiens

<400> SEQUENCE: 66

Ser Tyr Val Leu Thr Gln Pro Pro Ser Val Gly Thr Pro Gly Gln
  1               5                  10                  15

Arg Val Thr Ile Ser Cys Ser Gly Gly Arg Ser Asn Ile Gly Ser Asn
```

```
            20                  25                  30
Thr Val Lys Trp Tyr Gln Gln Leu Pro Gly Thr Ala Pro Lys Leu Leu
             35                  40                  45

Ile Tyr Gly Asn Asp Gln Arg Pro Ser Gly Val Pro Asp Arg Phe Ser
         50                  55                  60

Gly Ser Lys Ser Gly Thr Ser Ala Ser Leu Ala Ile Thr Gly Val Gln
 65                  70                  75                  80

Ala Glu Asp Glu Ala Asp Tyr Tyr Cys Gln Ser Tyr Asp Arg Gly Thr
                 85                  90                  95

His Pro Leu Thr Met Phe Gly Thr Gly Thr Lys Val Thr Val Leu Gly
            100                 105                 110

<210> SEQ ID NO 67
<211> LENGTH: 115
<212> TYPE: PRT
<213> ORGANISM: Homo sapiens

<400> SEQUENCE: 67

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
             20                  25                  30

Gly Met His Trp Val Arg Gln Ala Pro Gly Lys Gly Leu Glu Trp Val
         35                  40                  45

Ala Phe Ile Arg Tyr Asp Gly Ser Asn Lys Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Lys Thr His Gly Ser His Asp Asn Trp Gly Gln Gly Thr Met Val Thr
            100                 105                 110

Val Ser Ser
        115

<210> SEQ ID NO 68
<211> LENGTH: 112
<212> TYPE: PRT
<213> ORGANISM: Homo sapiens

<400> SEQUENCE: 68

Gln Ser Val Leu Thr Gln Pro Pro Ser Val Ser Gly Ala Pro Gly Gln
 1               5                  10                  15

Arg Val Thr Ile Ser Cys Ser Gly Ser Arg Ser Asn Ile Gly Ser Asn
             20                  25                  30

Thr Val Lys Trp Tyr Gln Gln Leu Pro Gly Thr Ala Pro Lys Leu Leu
         35                  40                  45

Ile Tyr Gly Asn Asp Gln Arg Pro Ser Gly Val Pro Asp Arg Phe Ser
     50                  55                  60

Gly Ser Lys Ser Gly Thr Ser Ala Ser Leu Ala Ile Thr Gly Leu Gln
 65                  70                  75                  80

Ala Glu Asp Glu Ala Asp Tyr Tyr Cys Gln Ser Tyr Asp Arg Gly Thr
                 85                  90                  95

His Pro Leu Thr Met Phe Gly Thr Gly Thr Lys Val Thr Val Leu Gly
            100                 105                 110
```

<210> SEQ ID NO 69
<211> LENGTH: 115
<212> TYPE: PRT
<213> ORGANISM: Homo sapiens

<400> SEQUENCE: 69

```
Gln Val Gln Leu Val Glu Ser Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Phe Ile Arg Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Lys Thr His Gly Ser His Asp Asn Trp Gly Gln Gly Thr Met Val Thr
               100                 105                 110

Val Ser Ser
       115
```

<210> SEQ ID NO 70
<211> LENGTH: 112
<212> TYPE: PRT
<213> ORGANISM: Homo sapiens

<400> SEQUENCE: 70

```
Gln Ser Val Leu Thr Gln Pro Pro Ser Val Ser Gly Ala Pro Gly Gln
 1               5                  10                  15

Arg Val Thr Ile Ser Cys Ser Gly Ser Arg Ser Asn Ile Gly Ser Asn
            20                  25                  30

Thr Val Lys Trp Tyr Gln Gln Leu Pro Gly Thr Ala Pro Lys Leu Leu
        35                  40                  45

Ile Tyr Gly Asn Asp Gln Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ala Glu Asp Glu Ala Asp Tyr Tyr Cys Gln Ser Tyr Asp Arg Gly Thr
                85                  90                  95

His Pro Ala Leu Leu Phe Gly Thr Gly Thr Lys Val Thr Val Leu Gly
               100                 105                 110
```

<210> SEQ ID NO 71
<211> LENGTH: 115
<212> TYPE: PRT
<213> ORGANISM: Homo sapiens

<400> SEQUENCE: 71

```
Gln Val Gln Leu Val Gln Ser Gly Gly Val Val Gln Pro Gly Arg
 1               5                  10                  15

Ser Leu Arg Leu Ser Cys Ala Ala Ser Gly Phe Thr Phe Ser Glu Tyr
            20                  25                  30

Gly Met His Trp Val Arg Gln Ala Pro Gly Lys Gly Leu Glu Trp Val
        35                  40                  45

Ala Phe Ile Arg Tyr Asp Gly Ser Asn Lys Tyr Tyr Ala Asp Ser Val
    50                  55                  60
```

-continued

Lys Gly Arg Phe Thr Ile Ser Arg Asp Asn Ser Lys Asn Thr Leu Tyr
 65                  70                  75                  80

Leu Gln Met Lys Ser Leu Arg Ala Glu Asp Thr Ala Val Tyr Tyr Cys
             85                  90                  95

Lys Thr His Gly Ser His Asp Asn Trp Gly Gln Gly Thr Met Val Thr
         100                 105                 110

Val Ser Ser
        115

<210> SEQ ID NO 72
<211> LENGTH: 112
<212> TYPE: PRT
<213> ORGANISM: Homo sapiens

<400> SEQUENCE: 72

Gln Ser Val Leu Thr Gln Pro Pro Ser Val Ser Gly Ala Pro Gly Gln
  1               5                  10                  15

Arg Val Thr Ile Ser Cys Ser Gly Ser Arg Ser Asn Ile Gly Ser Asn
             20                  25                  30

Thr Val Lys Trp Tyr Gln Gln Leu Pro Gly Thr Ala Pro Lys Leu Leu
         35                  40                  45

Ile Tyr Gly Asn Asp Gln Arg Pro Ser Gly Val Pro Asp Arg Phe Ser
 50                  55                  60

Gly Ser Lys Ser Gly Thr Ser Ala Ser Leu Ala Ile Thr Gly Leu Gln
 65                  70                  75                  80

Ala Glu Asp Glu Ala Asp Tyr Tyr Cys Gln Ser Tyr Asp Arg Gly Thr
             85                  90                  95

His Pro Ala Leu Leu Phe Gly Thr Gly Thr Lys Val Thr Val Leu Gly
         100                 105                 110

<210> SEQ ID NO 73
<211> LENGTH: 115
<212> TYPE: PRT
<213> ORGANISM: Homo sapiens

<400> SEQUENCE: 73

Gln Val Gln Leu Val Gln Ser Gly Gly Gly Val Val Gln Pro Gly Arg
  1               5                  10                  15

Ser Leu Arg Leu Ser Cys Ala Ala Ser Gly Phe Thr Phe Ser Ser Tyr
             20                  25                  30

Gly Met His Trp Val Arg Gln Ala Pro Gly Lys Gly Leu Glu Trp Val
         35                  40                  45

Ala Phe Ile Arg Tyr Asp Gly Ser Asn Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Lys Ser Leu Arg Ala Glu Asp Thr Ala Val Tyr Tyr Cys
             85                  90                  95

Lys Thr His Gly Ser His Asp Asn Trp Gly Gln Gly Thr Met Val Thr
         100                 105                 110

Val Ser Ser
        115

<210> SEQ ID NO 74
<211> LENGTH: 112
<212> TYPE: PRT
<213> ORGANISM: Homo sapiens

```
<400> SEQUENCE: 74

Gln Ser Val Leu Thr Gln Pro Pro Ser Val Gly Ala Pro Gly Gln
 1               5                  10                  15

Arg Val Thr Ile Ser Cys Ser Gly Ser Arg Ser Asn Ile Gly Ser Asn
            20                  25                  30

Thr Val Lys Trp Tyr Gln Gln Leu Pro Gly Thr Ala Pro Lys Leu Leu
        35                  40                  45

Ile Tyr Tyr Asn Asp Gln Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ala Glu Asp Glu Ala Asp Tyr Tyr Cys Gln Ser Tyr Asp Arg Gly Thr
                85                  90                  95

His Pro Ala Leu Leu Phe Gly Thr Gly Thr Lys Val Thr Val Leu Gly
            100                 105                 110

<210> SEQ ID NO 75
<211> LENGTH: 115
<212> TYPE: PRT
<213> ORGANISM: Homo sapiens

<400> SEQUENCE: 75

Gln Val Gln Leu Val Gln Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Phe Ile Arg Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Lys Ser Leu Arg Ala Glu Asp Thr Ala Val Tyr Tyr Cys
                85                  90                  95

Lys Thr His Gly Ser His Asp Asn Trp Gly Gln Gly Thr Met Val Thr
            100                 105                 110

Val Ser Ser
        115

<210> SEQ ID NO 76
<211> LENGTH: 112
<212> TYPE: PRT
<213> ORGANISM: Homo sapiens

<400> SEQUENCE: 76

Gln Ser Val Leu Thr Gln Pro Pro Ser Val Gly Ala Pro Gly Gln
 1               5                  10                  15

Arg Val Thr Ile Ser Cys Ser Gly Ser Arg Ser Asn Ile Gly Ser Asn
            20                  25                  30

Thr Val Lys Trp Tyr Gln Gln Leu Pro Gly Thr Ala Pro Lys Leu Leu
        35                  40                  45

Ile Tyr Gly Asn Asp Gln Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80
```

Ala Glu Asp Glu Ala Asp Tyr Tyr Cys Gln Ser Tyr Asp Arg Tyr Thr
            85                  90                  95

His Pro Ala Leu Leu Phe Gly Thr Gly Thr Lys Val Thr Val Leu Gly
            100                 105                 110

<210> SEQ ID NO 77
<211> LENGTH: 6
<212> TYPE: PRT
<213> ORGANISM: Homo sapiens

<400> SEQUENCE: 77

Ser Gly Ser Tyr Asp Tyr
1               5

<210> SEQ ID NO 78
<211> LENGTH: 6
<212> TYPE: PRT
<213> ORGANISM: Homo sapiens

<400> SEQUENCE: 78

His Gly Ser His Asp Asn
1               5

<210> SEQ ID NO 79
<211> LENGTH: 6
<212> TYPE: PRT
<213> ORGANISM: Homo sapiens

<400> SEQUENCE: 79

His Gly Ser Tyr Asp Tyr
1               5

<210> SEQ ID NO 80
<211> LENGTH: 6
<212> TYPE: PRT
<213> ORGANISM: Homo sapiens

<400> SEQUENCE: 80

Arg Arg Arg Ser Asn Tyr
1               5

<210> SEQ ID NO 81
<211> LENGTH: 6
<212> TYPE: PRT
<213> ORGANISM: Homo sapiens

<400> SEQUENCE: 81

Ser Gly Ser Ile Asp Tyr
1               5

<210> SEQ ID NO 82
<211> LENGTH: 6
<212> TYPE: PRT
<213> ORGANISM: Homo sapiens

<400> SEQUENCE: 82

His Gly Ser His Asp Asp
1               5

<210> SEQ ID NO 83
<211> LENGTH: 6
<212> TYPE: PRT
<213> ORGANISM: Homo sapiens

<400> SEQUENCE: 83

His Gly Ser His Asp Asn
 1               5

<210> SEQ ID NO 84
<211> LENGTH: 12
<212> TYPE: PRT
<213> ORGANISM: Homo sapiens

<400> SEQUENCE: 84

Thr Thr His Gly Ser His Asp Asn Trp Gly Gln Gly
 1               5                  10

<210> SEQ ID NO 85
<211> LENGTH: 12
<212> TYPE: PRT
<213> ORGANISM: Homo sapiens

<400> SEQUENCE: 85

Ala Lys His Gly Ser His Asp Asn Trp Gly Gln Gly
 1               5                  10

<210> SEQ ID NO 86
<211> LENGTH: 12
<212> TYPE: PRT
<213> ORGANISM: Homo sapiens

<400> SEQUENCE: 86

Thr Thr His Gly Ser His Asp Asn Trp Ser Gln Gly
 1               5                  10

<210> SEQ ID NO 87
<211> LENGTH: 12
<212> TYPE: PRT
<213> ORGANISM: Homo sapiens

<400> SEQUENCE: 87

Thr Thr His Gly Ser His Asp Thr Trp Gly Gln Gly
 1               5                  10

<210> SEQ ID NO 88
<211> LENGTH: 12
<212> TYPE: PRT
<213> ORGANISM: Homo sapiens

<400> SEQUENCE: 88

Lys Thr His Gly Ser His Asp Asn Trp Gly Gln Gly
 1               5                  10

<210> SEQ ID NO 89
<211> LENGTH: 12
<212> TYPE: PRT
<213> ORGANISM: Homo sapiens

<400> SEQUENCE: 89

Lys Thr His Gly Ser His Asp Asn Trp Gly His Gly
 1               5                  10

<210> SEQ ID NO 90
<211> LENGTH: 12
<212> TYPE: PRT
<213> ORGANISM: Homo sapiens

<400> SEQUENCE: 90

Thr Thr His Gly Ser His Asp Asn Trp Ser Gln Gly

```
                   1               5                  10
```

<210> SEQ ID NO 91
<211> LENGTH: 12
<212> TYPE: PRT
<213> ORGANISM: Homo sapiens

<400> SEQUENCE: 91

```
Thr Thr His Arg Ser His Asn Asn Trp Gly Gln Gly
  1               5                  10
```

<210> SEQ ID NO 92
<211> LENGTH: 8
<212> TYPE: PRT
<213> ORGANISM: Homo sapiens

<400> SEQUENCE: 92

```
Thr Thr His Gly Ser His Asp Asn
  1               5
```

<210> SEQ ID NO 93
<211> LENGTH: 8
<212> TYPE: PRT
<213> ORGANISM: Homo sapiens

<400> SEQUENCE: 93

```
Thr Thr His Gly Ser His Asp Thr
  1               5
```

<210> SEQ ID NO 94
<211> LENGTH: 8
<212> TYPE: PRT
<213> ORGANISM: Homo sapiens

<400> SEQUENCE: 94

```
Thr Lys His Gly Ser His Asp Asn
  1               5
```

<210> SEQ ID NO 95
<211> LENGTH: 8
<212> TYPE: PRT
<213> ORGANISM: Homo sapiens

<400> SEQUENCE: 95

```
Thr Thr Gln Gly Arg His Asp Asn
  1               5
```

<210> SEQ ID NO 96
<211> LENGTH: 8
<212> TYPE: PRT
<213> ORGANISM: Homo sapiens

<400> SEQUENCE: 96

```
Lys Thr Arg Gly Arg His Asp Asn
  1               5
```

<210> SEQ ID NO 97
<211> LENGTH: 8
<212> TYPE: PRT
<213> ORGANISM: Homo sapiens

<400> SEQUENCE: 97

```
Thr Thr His Gly Ser His Asp Lys
  1               5
```

```
<210> SEQ ID NO 98
<211> LENGTH: 8
<212> TYPE: PRT
<213> ORGANISM: Homo sapiens

<400> SEQUENCE: 98

Thr Thr His Gly Ser His Asp Asp
 1               5

<210> SEQ ID NO 99
<211> LENGTH: 8
<212> TYPE: PRT
<213> ORGANISM: Homo sapiens

<400> SEQUENCE: 99

Lys Thr His Gly Ser His Asp Asn
 1               5

<210> SEQ ID NO 100
<211> LENGTH: 8
<212> TYPE: PRT
<213> ORGANISM: Homo sapiens

<400> SEQUENCE: 100

Lys Thr His Gly Ser His Asp Asn
 1               5

<210> SEQ ID NO 101
<211> LENGTH: 8
<212> TYPE: PRT
<213> ORGANISM: Homo sapiens

<400> SEQUENCE: 101

Thr Thr His Gly Ser His Asp Asn
 1               5

<210> SEQ ID NO 102
<211> LENGTH: 8
<212> TYPE: PRT
<213> ORGANISM: Homo sapiens

<400> SEQUENCE: 102

Thr Thr Ser Gly Ser Tyr Asp Tyr
 1               5

<210> SEQ ID NO 103
<211> LENGTH: 8
<212> TYPE: PRT
<213> ORGANISM: Homo sapiens

<400> SEQUENCE: 103

Thr Thr His Gly Ser His Asp Asn
 1               5

<210> SEQ ID NO 104
<211> LENGTH: 8
<212> TYPE: PRT
<213> ORGANISM: Homo sapiens

<400> SEQUENCE: 104

Thr Thr His Gly Ser Gln Asp Asn
 1               5

<210> SEQ ID NO 105
```

```
<211> LENGTH: 8
<212> TYPE: PRT
<213> ORGANISM: Homo sapiens

<400> SEQUENCE: 105

Ala Thr His Gly Ser Gln Asp Asn
 1               5

<210> SEQ ID NO 106
<211> LENGTH: 6
<212> TYPE: PRT
<213> ORGANISM: Homo sapiens

<400> SEQUENCE: 106

His Gly Ser Gln Asp Thr
 1               5

<210> SEQ ID NO 107
<211> LENGTH: 6
<212> TYPE: PRT
<213> ORGANISM: Homo sapiens

<400> SEQUENCE: 107

Ser Gly Ser Tyr Asp Tyr
 1               5

<210> SEQ ID NO 108
<211> LENGTH: 6
<212> TYPE: PRT
<213> ORGANISM: Homo sapiens

<400> SEQUENCE: 108

His Gly Ser Gln Asp Asn
 1               5

<210> SEQ ID NO 109
<211> LENGTH: 9
<212> TYPE: PRT
<213> ORGANISM: Homo sapiens

<400> SEQUENCE: 109

Cys Lys Thr His Gly Ser His Asp Asn
 1               5

<210> SEQ ID NO 110
<211> LENGTH: 12
<212> TYPE: PRT
<213> ORGANISM: Homo sapiens

<400> SEQUENCE: 110

Gln Ser Tyr Asp Ser Ser Leu Arg Gly Ser Arg Val
 1               5                  10

<210> SEQ ID NO 111
<211> LENGTH: 12
<212> TYPE: PRT
<213> ORGANISM: Homo sapiens

<400> SEQUENCE: 111

Gln Ser Tyr Asp Arg Gly Phe Thr Gly Ser Arg Val
 1               5                  10

<210> SEQ ID NO 112
<211> LENGTH: 12
<212> TYPE: PRT
```

<213> ORGANISM: Homo sapiens

<400> SEQUENCE: 112

Gln Ser Tyr Asp Ser Ser Leu Arg Gly Ser Arg Val
1               5                   10

<210> SEQ ID NO 113
<211> LENGTH: 12
<212> TYPE: PRT
<213> ORGANISM: Homo sapiens

<400> SEQUENCE: 113

Gln Ser Tyr Asp Ser Ser Leu Thr Gly Ser Arg Val
1               5                   10

<210> SEQ ID NO 114
<211> LENGTH: 12
<212> TYPE: PRT
<213> ORGANISM: Homo sapiens

<400> SEQUENCE: 114

Gln Ser Tyr Asp Ser Ser Leu Trp Gly Ser Arg Val
1               5                   10

<210> SEQ ID NO 115
<211> LENGTH: 12
<212> TYPE: PRT
<213> ORGANISM: Homo sapiens

<400> SEQUENCE: 115

Gln Thr Tyr Asp Ile Ser Glu Ser Gly Ser Arg Val
1               5                   10

<210> SEQ ID NO 116
<211> LENGTH: 12
<212> TYPE: PRT
<213> ORGANISM: Homo sapiens

<400> SEQUENCE: 116

Gln Ser Tyr Asp Arg Gly Phe Thr Gly Ser Arg Val
1               5                   10

<210> SEQ ID NO 117
<211> LENGTH: 12
<212> TYPE: PRT
<213> ORGANISM: Homo sapiens

<400> SEQUENCE: 117

Gln Thr Tyr Asp Arg Gly Phe Thr Gly Ser Arg Val
1               5                   10

<210> SEQ ID NO 118
<211> LENGTH: 12
<212> TYPE: PRT
<213> ORGANISM: Homo sapiens

<400> SEQUENCE: 118

Gln Thr Tyr Asp Lys Gly Phe Thr Gly Ser Ser Val
1               5                   10

<210> SEQ ID NO 119
<211> LENGTH: 12
<212> TYPE: PRT
<213> ORGANISM: Homo sapiens

```
<400> SEQUENCE: 119

Gln Ser Tyr Asp Arg Arg Phe Thr Gly Ser Arg Val
 1               5                  10

<210> SEQ ID NO 120
<211> LENGTH: 12
<212> TYPE: PRT
<213> ORGANISM: Homo sapiens

<400> SEQUENCE: 120

Gln Ser Tyr Asp Trp Asn Phe Thr Gly Ser Arg Val
 1               5                  10

<210> SEQ ID NO 121
<211> LENGTH: 12
<212> TYPE: PRT
<213> ORGANISM: Homo sapiens

<400> SEQUENCE: 121

Gln Ser Tyr Asp Arg Gly Phe Thr Gly Ser Arg Val
 1               5                  10

<210> SEQ ID NO 122
<211> LENGTH: 12
<212> TYPE: PRT
<213> ORGANISM: Homo sapiens

<400> SEQUENCE: 122

Gln Ser Tyr Asp Asn Gly Phe Thr Gly Ser Arg Val
 1               5                  10

<210> SEQ ID NO 123
<211> LENGTH: 12
<212> TYPE: PRT
<213> ORGANISM: Homo sapiens

<400> SEQUENCE: 123

Gln Ser Tyr Asp Asn Ala Val Thr Ala Ser Lys Val
 1               5                  10

<210> SEQ ID NO 124
<211> LENGTH: 12
<212> TYPE: PRT
<213> ORGANISM: Homo sapiens

<400> SEQUENCE: 124

Gln Ser Tyr Asp Arg Gly Phe Thr Gly Ser Arg Val
 1               5                  10

<210> SEQ ID NO 125
<211> LENGTH: 12
<212> TYPE: PRT
<213> ORGANISM: Homo sapiens

<400> SEQUENCE: 125

Gln Ser Tyr Asp Ser Ser Leu Trp Gly Thr Arg Val
 1               5                  10

<210> SEQ ID NO 126
<211> LENGTH: 12
<212> TYPE: PRT
<213> ORGANISM: Homo sapiens

<400> SEQUENCE: 126
```

```
Gln Ser Tyr Asp Arg Asp Phe Thr Gly Ser Arg Val
 1               5                  10
```

<210> SEQ ID NO 127
<211> LENGTH: 12
<212> TYPE: PRT
<213> ORGANISM: Homo sapiens

<400> SEQUENCE: 127

```
Gln Ser Tyr Glu Arg Gly Phe Thr Gly Ser Met Val
 1               5                  10
```

<210> SEQ ID NO 128
<211> LENGTH: 12
<212> TYPE: PRT
<213> ORGANISM: Homo sapiens

<400> SEQUENCE: 128

```
Gln Ser Tyr Asp Asn Gly Phe Thr Gly Ala Arg Val
 1               5                  10
```

<210> SEQ ID NO 129
<211> LENGTH: 12
<212> TYPE: PRT
<213> ORGANISM: Homo sapiens

<400> SEQUENCE: 129

```
Gln Ser Tyr Asp Arg Arg Phe Thr Gly Ser Arg Val
 1               5                  10
```

<210> SEQ ID NO 130
<211> LENGTH: 12
<212> TYPE: PRT
<213> ORGANISM: Homo sapiens

<400> SEQUENCE: 130

```
Gln Thr Tyr Asp Lys Gly Phe Thr Gly Ser Ser Val
 1               5                  10
```

<210> SEQ ID NO 131
<211> LENGTH: 12
<212> TYPE: PRT
<213> ORGANISM: Homo sapiens

<400> SEQUENCE: 131

```
Gln Ser Tyr Asp Arg Asp Phe Thr Gly Thr Arg Val
 1               5                  10
```

<210> SEQ ID NO 132
<211> LENGTH: 12
<212> TYPE: PRT
<213> ORGANISM: Homo sapiens

<400> SEQUENCE: 132

```
Gln Ser Tyr Asp Arg Gly Phe Tyr Gly Ser Met Val
 1               5                  10
```

<210> SEQ ID NO 133
<211> LENGTH: 12
<212> TYPE: PRT
<213> ORGANISM: Homo sapiens

<400> SEQUENCE: 133

```
Gln Thr Tyr Asp Lys Gly Phe Thr Gly Ser Ser Val
 1               5                  10
```

```
<210> SEQ ID NO 134
<211> LENGTH: 12
<212> TYPE: PRT
<213> ORGANISM: Homo sapiens

<400> SEQUENCE: 134

Gln Ser Tyr Asp Arg Gly Phe Thr Gly Ala Arg Val
 1               5                  10

<210> SEQ ID NO 135
<211> LENGTH: 12
<212> TYPE: PRT
<213> ORGANISM: Homo sapiens

<400> SEQUENCE: 135

Gln Ser Tyr Glu Arg Gly Phe Thr Gly Ala Arg Val
 1               5                  10

<210> SEQ ID NO 136
<211> LENGTH: 13
<212> TYPE: PRT
<213> ORGANISM: Homo sapiens

<400> SEQUENCE: 136

Gln Ser Tyr Asp Arg Gly Phe Thr Gly Ser Arg Val Phe
 1               5                  10

<210> SEQ ID NO 137
<211> LENGTH: 13
<212> TYPE: PRT
<213> ORGANISM: Homo sapiens

<400> SEQUENCE: 137

Gln Ser Tyr Asp Arg Gly Phe Thr Gly Phe Lys Val Phe
 1               5                  10

<210> SEQ ID NO 138
<211> LENGTH: 13
<212> TYPE: PRT
<213> ORGANISM: Homo sapiens

<400> SEQUENCE: 138

Gln Ser Tyr Asp Arg Gly Phe Val Ser Ala Tyr Val Phe
 1               5                  10

<210> SEQ ID NO 139
<211> LENGTH: 13
<212> TYPE: PRT
<213> ORGANISM: Homo sapiens

<400> SEQUENCE: 139

Gln Ser Tyr Asp Arg Gly Leu Thr Val Thr Lys Val Phe
 1               5                  10

<210> SEQ ID NO 140
<211> LENGTH: 13
<212> TYPE: PRT
<213> ORGANISM: Homo sapiens

<400> SEQUENCE: 140

Gln Ser Tyr Asp Arg Gly Tyr Thr Ala Ser Arg Val Phe
 1               5                  10
```

```
<210> SEQ ID NO 141
<211> LENGTH: 13
<212> TYPE: PRT
<213> ORGANISM: Homo sapiens

<400> SEQUENCE: 141

Gln Ser Tyr Asp Arg Gly Phe Thr Gly Ser Lys Val Phe
 1               5                  10

<210> SEQ ID NO 142
<211> LENGTH: 13
<212> TYPE: PRT
<213> ORGANISM: Homo sapiens

<400> SEQUENCE: 142

Gln Ser Tyr Asp Arg Gly Leu Thr Gly Phe Arg Val Phe
 1               5                  10

<210> SEQ ID NO 143
<211> LENGTH: 13
<212> TYPE: PRT
<213> ORGANISM: Homo sapiens

<400> SEQUENCE: 143

Gln Ser Tyr Asp Arg Gly Phe Thr Gly Tyr Lys Val Phe
 1               5                  10

<210> SEQ ID NO 144
<211> LENGTH: 13
<212> TYPE: PRT
<213> ORGANISM: Homo sapiens

<400> SEQUENCE: 144

Gln Ser Tyr Asp Arg Gly Leu Thr Gly Tyr Arg Leu Phe
 1               5                  10

<210> SEQ ID NO 145
<211> LENGTH: 13
<212> TYPE: PRT
<213> ORGANISM: Homo sapiens

<400> SEQUENCE: 145

Gln Ser Tyr Asp Arg Gly Phe Thr Asp Tyr Lys Val Phe
 1               5                  10

<210> SEQ ID NO 146
<211> LENGTH: 13
<212> TYPE: PRT
<213> ORGANISM: Homo sapiens

<400> SEQUENCE: 146

Gln Ser Tyr Asp Arg Gly Phe Thr Gly Pro Arg Leu Phe
 1               5                  10

<210> SEQ ID NO 147
<211> LENGTH: 13
<212> TYPE: PRT
<213> ORGANISM: Homo sapiens

<400> SEQUENCE: 147

Gln Ser Tyr Asp Arg Gly Leu Thr Gly Ser Arg Val Phe
 1               5                  10

<210> SEQ ID NO 148
<211> LENGTH: 13
```

```
<212> TYPE: PRT
<213> ORGANISM: Homo sapiens

<400> SEQUENCE: 148

Gln Ser Tyr Asp Arg Gly Phe Thr Gly Ala Arg Val Trp
1               5                   10

<210> SEQ ID NO 149
<211> LENGTH: 13
<212> TYPE: PRT
<213> ORGANISM: Homo sapiens

<400> SEQUENCE: 149

Gln Ser Tyr Asp Arg Gly Phe Thr Gly Tyr Arg Val Phe
1               5                   10

<210> SEQ ID NO 150
<211> LENGTH: 13
<212> TYPE: PRT
<213> ORGANISM: Homo sapiens

<400> SEQUENCE: 150

Gln Ser Tyr Asp Arg Gly Phe Thr Gly Pro Arg Val Phe
1               5                   10

<210> SEQ ID NO 151
<211> LENGTH: 13
<212> TYPE: PRT
<213> ORGANISM: Homo sapiens

<400> SEQUENCE: 151

Gln Ser Tyr Asp Arg Gly Met Thr Ser Ser Arg Val Phe
1               5                   10

<210> SEQ ID NO 152
<211> LENGTH: 13
<212> TYPE: PRT
<213> ORGANISM: Homo sapiens

<400> SEQUENCE: 152

Gln Ser Tyr Asp Arg Asp Ser Thr Gly Ser Arg Val Phe
1               5                   10

<210> SEQ ID NO 153
<211> LENGTH: 13
<212> TYPE: PRT
<213> ORGANISM: Homo sapiens

<400> SEQUENCE: 153

Gln Ser Tyr Asp Ser Ser Leu Arg Gly Ser Arg Val Phe
1               5                   10

<210> SEQ ID NO 154
<211> LENGTH: 13
<212> TYPE: PRT
<213> ORGANISM: Homo sapiens

<400> SEQUENCE: 154

His Ser Tyr Asp Ser Asp Phe Thr Gly Ser Arg Val Phe
1               5                   10

<210> SEQ ID NO 155
<211> LENGTH: 13
<212> TYPE: PRT
<213> ORGANISM: Homo sapiens
```

<400> SEQUENCE: 155

His Ser Ser Glu Ser Gly Phe Thr Gly Ser Arg Val Phe
 1               5                  10

<210> SEQ ID NO 156
<211> LENGTH: 13
<212> TYPE: PRT
<213> ORGANISM: Homo sapiens

<400> SEQUENCE: 156

His Ser Tyr Asp Asn Arg Phe Thr Gly Ser Arg Val Phe
 1               5                  10

<210> SEQ ID NO 157
<211> LENGTH: 13
<212> TYPE: PRT
<213> ORGANISM: Homo sapiens

<400> SEQUENCE: 157

His Ser Tyr Asp Ser Arg Phe Thr Gly Ser Arg Val Phe
 1               5                  10

<210> SEQ ID NO 158
<211> LENGTH: 13
<212> TYPE: PRT
<213> ORGANISM: Homo sapiens

<400> SEQUENCE: 158

Gln Ser Tyr Asp Ser Glu Phe Thr Gly Ser Arg Val Phe
 1               5                  10

<210> SEQ ID NO 159
<211> LENGTH: 13
<212> TYPE: PRT
<213> ORGANISM: Homo sapiens

<400> SEQUENCE: 159

Gln Ser Tyr Asp Thr Gly Phe Thr Gly Ser Arg Val Phe
 1               5                  10

<210> SEQ ID NO 160
<211> LENGTH: 13
<212> TYPE: PRT
<213> ORGANISM: Homo sapiens

<400> SEQUENCE: 160

His Ser Tyr Asp Ser Gly Phe Thr Gly Ser Arg Val Phe
 1               5                  10

<210> SEQ ID NO 161
<211> LENGTH: 13
<212> TYPE: PRT
<213> ORGANISM: Homo sapiens

<400> SEQUENCE: 161

Gln Ser Tyr Asp Thr Gly Phe Thr Gly Ser Arg Val Phe
 1               5                  10

<210> SEQ ID NO 162
<211> LENGTH: 13
<212> TYPE: PRT
<213> ORGANISM: Homo sapiens

<400> SEQUENCE: 162

His Ser Tyr Asp Thr Lys Phe Thr Gly Ser Arg Val Phe
 1               5                  10

<210> SEQ ID NO 163
<211> LENGTH: 13
<212> TYPE: PRT
<213> ORGANISM: Homo sapiens

<400> SEQUENCE: 163

His Ser Ser Asp Ser Gly Phe Thr Gly Ser Arg Val Phe
 1               5                  10

<210> SEQ ID NO 164
<211> LENGTH: 13
<212> TYPE: PRT
<213> ORGANISM: Homo sapiens

<400> SEQUENCE: 164

Gln Ser Tyr Asp Ser Asp Phe Thr Gly Ser Arg Val Phe
 1               5                  10

<210> SEQ ID NO 165
<211> LENGTH: 13
<212> TYPE: PRT
<213> ORGANISM: Homo sapiens

<400> SEQUENCE: 165

His Ser Tyr Glu Ser Gly Phe Thr Gly Ser Arg Val Phe
 1               5                  10

<210> SEQ ID NO 166
<211> LENGTH: 13
<212> TYPE: PRT
<213> ORGANISM: Homo sapiens

<400> SEQUENCE: 166

Gln Ser Tyr Asp Ala Pro Trp Ser Gly Ser Arg Val Phe
 1               5                  10

<210> SEQ ID NO 167
<211> LENGTH: 13
<212> TYPE: PRT
<213> ORGANISM: Homo sapiens

<400> SEQUENCE: 167

Gln Ser Tyr Asp Ser Asp Phe Thr Gly Ser Lys Val Phe
 1               5                  10

<210> SEQ ID NO 168
<211> LENGTH: 13
<212> TYPE: PRT
<213> ORGANISM: Homo sapiens

<400> SEQUENCE: 168

His Thr Asn Asp Ser Gly Phe Thr Gly Ser Arg Val Phe
 1               5                  10

<210> SEQ ID NO 169
<211> LENGTH: 13
<212> TYPE: PRT
<213> ORGANISM: Homo sapiens

<400> SEQUENCE: 169

His Ser Tyr Asp Thr Arg Phe Thr Gly Ser Arg Val Phe

```
              1               5                  10
```

<210> SEQ ID NO 170
<211> LENGTH: 13
<212> TYPE: PRT
<213> ORGANISM: Homo sapiens

<400> SEQUENCE: 170

```
Gln Ser Tyr Asp Met Arg Phe Thr Gly Ser Arg Val Phe
  1               5                  10
```

<210> SEQ ID NO 171
<211> LENGTH: 13
<212> TYPE: PRT
<213> ORGANISM: Homo sapiens

<400> SEQUENCE: 171

```
His Ser Ser Asp Ser Asp Ser Thr Gly Ser Arg Val Phe
  1               5                  10
```

<210> SEQ ID NO 172
<211> LENGTH: 13
<212> TYPE: PRT
<213> ORGANISM: Homo sapiens

<400> SEQUENCE: 172

```
Gln Ser Tyr Asn Thr Asp Phe Thr Gly Ser Arg Val Phe
  1               5                  10
```

<210> SEQ ID NO 173
<211> LENGTH: 13
<212> TYPE: PRT
<213> ORGANISM: Homo sapiens

<400> SEQUENCE: 173

```
Gln Ser Tyr Asp Ser Gly Phe Thr Gly Ser Arg Val Phe
  1               5                  10
```

<210> SEQ ID NO 174
<211> LENGTH: 13
<212> TYPE: PRT
<213> ORGANISM: Homo sapiens

<400> SEQUENCE: 174

```
His Ser Tyr Asp Met Gly Phe Thr Gly Ser Arg Val Phe
  1               5                  10
```

<210> SEQ ID NO 175
<211> LENGTH: 13
<212> TYPE: PRT
<213> ORGANISM: Homo sapiens

<400> SEQUENCE: 175

```
His Ser Tyr Asp Asn Gly Phe Thr Gly Ser Arg Val Phe
  1               5                  10
```

<210> SEQ ID NO 176
<211> LENGTH: 13
<212> TYPE: PRT
<213> ORGANISM: Homo sapiens

<400> SEQUENCE: 176

```
His Ser His Asp Arg Asp Phe Thr Gly Ser Arg Val Phe
  1               5                  10
```

<210> SEQ ID NO 177
<211> LENGTH: 12
<212> TYPE: PRT
<213> ORGANISM: Homo sapiens

<400> SEQUENCE: 177

Gln Ser Tyr Asp Ser Ser Leu Arg Gly Ser Arg Val
 1               5                  10

<210> SEQ ID NO 178
<211> LENGTH: 13
<212> TYPE: PRT
<213> ORGANISM: Homo sapiens

<400> SEQUENCE: 178

Gln Ser Tyr Asp Arg Gly Ile His Gly Ser Arg Val Phe
 1               5                  10

<210> SEQ ID NO 179
<211> LENGTH: 13
<212> TYPE: PRT
<213> ORGANISM: Homo sapiens

<400> SEQUENCE: 179

Gln Ser Tyr Asp Ser Gly Phe Pro Gly Ser Arg Val Phe
 1               5                  10

<210> SEQ ID NO 180
<211> LENGTH: 13
<212> TYPE: PRT
<213> ORGANISM: Homo sapiens

<400> SEQUENCE: 180

Gln Ser Tyr Asp Ile Gly Ser Thr Gly Ser Arg Val Phe
 1               5                  10

<210> SEQ ID NO 181
<211> LENGTH: 13
<212> TYPE: PRT
<213> ORGANISM: Homo sapiens

<400> SEQUENCE: 181

Gln Ser Tyr Asp Ser Gly Leu Thr Gly Ser Arg Val Phe
 1               5                  10

<210> SEQ ID NO 182
<211> LENGTH: 13
<212> TYPE: PRT
<213> ORGANISM: Homo sapiens

<400> SEQUENCE: 182

Gln Ser Tyr Asp Ile Gly Met Thr Gly Ser Arg Val Phe
 1               5                  10

<210> SEQ ID NO 183
<211> LENGTH: 13
<212> TYPE: PRT
<213> ORGANISM: Homo sapiens

<400> SEQUENCE: 183

Gln Ser Tyr Asp Ile Gly Leu Thr Gly Ser Arg Val Phe
 1               5                  10

<210> SEQ ID NO 184

```
<211> LENGTH: 13
<212> TYPE: PRT
<213> ORGANISM: Homo sapiens

<400> SEQUENCE: 184

Gln Ser Tyr Asp Ser Gly Val Thr Gly Ser Arg Val Phe
 1               5                  10

<210> SEQ ID NO 185
<211> LENGTH: 13
<212> TYPE: PRT
<213> ORGANISM: Homo sapiens

<400> SEQUENCE: 185

Gln Ser Tyr Asp Arg Gly Leu Thr Ala Ser Arg Val Phe
 1               5                  10

<210> SEQ ID NO 186
<211> LENGTH: 13
<212> TYPE: PRT
<213> ORGANISM: Homo sapiens

<400> SEQUENCE: 186

Gln Ser Tyr Asp Thr Gly Leu Thr Gly Ser Arg Val Phe
 1               5                  10

<210> SEQ ID NO 187
<211> LENGTH: 13
<212> TYPE: PRT
<213> ORGANISM: Homo sapiens

<400> SEQUENCE: 187

Gln Ser Tyr Asp Thr Ala Leu Thr Gly Ser Arg Val Phe
 1               5                  10

<210> SEQ ID NO 188
<211> LENGTH: 13
<212> TYPE: PRT
<213> ORGANISM: Homo sapiens

<400> SEQUENCE: 188

Gln Ser Tyr Asp Ile Arg Phe Thr Gly Ser Arg Val Phe
 1               5                  10

<210> SEQ ID NO 189
<211> LENGTH: 13
<212> TYPE: PRT
<213> ORGANISM: Homo sapiens

<400> SEQUENCE: 189

Gln Ser Tyr Asp Ile Arg Ser Thr Gly Ser Arg Val Phe
 1               5                  10

<210> SEQ ID NO 190
<211> LENGTH: 13
<212> TYPE: PRT
<213> ORGANISM: Homo sapiens

<400> SEQUENCE: 190

Gln Ser Tyr Asp Asn Arg Leu Thr Gly Ser Arg Val Phe
 1               5                  10

<210> SEQ ID NO 191
<211> LENGTH: 13
<212> TYPE: PRT
```

<213> ORGANISM: Homo sapiens

<400> SEQUENCE: 191

Gln Ser Tyr Glu Thr Ser Phe Thr Gly Ser Arg Val Phe
 1               5                   10

<210> SEQ ID NO 192
<211> LENGTH: 13
<212> TYPE: PRT
<213> ORGANISM: Homo sapiens

<400> SEQUENCE: 192

Gln Ser Tyr Asp Ser Ser Ser Thr Gly Ser Arg Val Phe
 1               5                   10

<210> SEQ ID NO 193
<211> LENGTH: 13
<212> TYPE: PRT
<213> ORGANISM: Homo sapiens

<400> SEQUENCE: 193

Gln Ser Tyr Asp Ser Gly Phe Thr Ala Ser Arg Val Phe
 1               5                   10

<210> SEQ ID NO 194
<211> LENGTH: 13
<212> TYPE: PRT
<213> ORGANISM: Homo sapiens

<400> SEQUENCE: 194

Gln Thr Tyr Asp Lys Gly Phe Thr Gly Ser Ser Val Phe
 1               5                   10

<210> SEQ ID NO 195
<211> LENGTH: 13
<212> TYPE: PRT
<213> ORGANISM: Homo sapiens

<400> SEQUENCE: 195

Gln Ser Tyr Asp Asn Gly Phe Thr Gly Ser Arg Val Phe
 1               5                   10

<210> SEQ ID NO 196
<211> LENGTH: 13
<212> TYPE: PRT
<213> ORGANISM: Homo sapiens

<400> SEQUENCE: 196

Gln Ser Tyr Asp Thr Gly Phe Thr Lys Ser Arg Val Phe
 1               5                   10

<210> SEQ ID NO 197
<211> LENGTH: 13
<212> TYPE: PRT
<213> ORGANISM: Homo sapiens

<400> SEQUENCE: 197

Gln Ser Tyr Asp Ser Asp Val Thr Gly Ser Arg Val Phe
 1               5                   10

<210> SEQ ID NO 198
<211> LENGTH: 13
<212> TYPE: PRT
<213> ORGANISM: Homo sapiens -continued

```
<400> SEQUENCE: 198

Gln Ser Tyr Asp Ala Gly Phe Thr Gly Ser Arg Val Phe
1               5                   10

<210> SEQ ID NO 199
<211> LENGTH: 12
<212> TYPE: PRT
<213> ORGANISM: Homo sapiens

<400> SEQUENCE: 199

Gln Ser Tyr Asp Arg Gly Thr His Pro Ser Met Leu
1               5                   10

<210> SEQ ID NO 200
<211> LENGTH: 12
<212> TYPE: PRT
<213> ORGANISM: Homo sapiens

<400> SEQUENCE: 200

Gln Ser Tyr Asp Arg Gly Thr Thr Pro Arg Pro Met
1               5                   10

<210> SEQ ID NO 201
<211> LENGTH: 12
<212> TYPE: PRT
<213> ORGANISM: Homo sapiens

<400> SEQUENCE: 201

Gln Ser Tyr Asp Arg Gly Arg Asn Pro Ala Leu Thr
1               5                   10

<210> SEQ ID NO 202
<211> LENGTH: 12
<212> TYPE: PRT
<213> ORGANISM: Homo sapiens

<400> SEQUENCE: 202

Gln Ser Tyr Asp Arg Gly Thr His Pro Trp Leu His
1               5                   10

<210> SEQ ID NO 203
<211> LENGTH: 12
<212> TYPE: PRT
<213> ORGANISM: Homo sapiens

<400> SEQUENCE: 203

Gln Ser Tyr Asp Arg Gly Asn Ser Pro Ala Thr Val
1               5                   10

<210> SEQ ID NO 204
<211> LENGTH: 12
<212> TYPE: PRT
<213> ORGANISM: Homo sapiens

<400> SEQUENCE: 204

Gln Ser Tyr Asp Arg Gly Thr Phe Pro Ser Pro Gln
1               5                   10

<210> SEQ ID NO 205
<211> LENGTH: 12
<212> TYPE: PRT
<213> ORGANISM: Homo sapiens

<400> SEQUENCE: 205
```

Gln Ser Tyr Asp Arg Gly Leu Asn Pro Ser Ala Thr
1               5                   10

<210> SEQ ID NO 206
<211> LENGTH: 12
<212> TYPE: PRT
<213> ORGANISM: Homo sapiens

<400> SEQUENCE: 206

Gln Ser Tyr Asp Arg Gly Lys Ser Asn Lys Met Leu
1               5                   10

<210> SEQ ID NO 207
<211> LENGTH: 12
<212> TYPE: PRT
<213> ORGANISM: Homo sapiens

<400> SEQUENCE: 207

Gln Ser Tyr Asp Arg Gly His Thr Ala His Leu Tyr
1               5                   10

<210> SEQ ID NO 208
<211> LENGTH: 12
<212> TYPE: PRT
<213> ORGANISM: Homo sapiens

<400> SEQUENCE: 208

Gln Ser Tyr Asp Arg Gly Gln Thr Pro Ser Ile Thr
1               5                   10

<210> SEQ ID NO 209
<211> LENGTH: 12
<212> TYPE: PRT
<213> ORGANISM: Homo sapiens

<400> SEQUENCE: 209

Gln Ser Tyr Asp Arg Gly Tyr Pro Arg Asn Ile Leu
1               5                   10

<210> SEQ ID NO 210
<211> LENGTH: 12
<212> TYPE: PRT
<213> ORGANISM: Homo sapiens

<400> SEQUENCE: 210

Gln Ser Tyr Asp Arg Gly Ile Thr Pro Gly Leu Ala
1               5                   10

<210> SEQ ID NO 211
<211> LENGTH: 12
<212> TYPE: PRT
<213> ORGANISM: Homo sapiens

<400> SEQUENCE: 211

Gln Ser Tyr Asp Arg Gly Gln Pro His Ala Val Leu
1               5                   10

<210> SEQ ID NO 212
<211> LENGTH: 12
<212> TYPE: PRT
<213> ORGANISM: Homo sapiens

<400> SEQUENCE: 212

Gln Ser Tyr Asp Arg Gly Asn Ser Pro Ile Pro Thr
1               5                   10

<210> SEQ ID NO 213
<211> LENGTH: 12
<212> TYPE: PRT
<213> ORGANISM: Homo sapiens

<400> SEQUENCE: 213

Gln Ser Tyr Asp Arg Gly Thr Pro Asn Asn Ser Phe
 1               5                  10

<210> SEQ ID NO 214
<211> LENGTH: 12
<212> TYPE: PRT
<213> ORGANISM: Homo sapiens

<400> SEQUENCE: 214

Gln Ser Tyr Asp Ser Gly Val Asp Pro Gly Pro Tyr
 1               5                  10

<210> SEQ ID NO 215
<211> LENGTH: 12
<212> TYPE: PRT
<213> ORGANISM: Homo sapiens

<400> SEQUENCE: 215

Gln Ser Tyr Asp Arg Gly Arg Pro Arg His Ala Leu
 1               5                  10

<210> SEQ ID NO 216
<211> LENGTH: 12
<212> TYPE: PRT
<213> ORGANISM: Homo sapiens

<400> SEQUENCE: 216

Gln Ser Tyr Asp Arg Gly Pro Tyr His Pro Ile Arg
 1               5                  10

<210> SEQ ID NO 217
<211> LENGTH: 12
<212> TYPE: PRT
<213> ORGANISM: Homo sapiens

<400> SEQUENCE: 217

Gln Ser Tyr Asp Arg Gly Pro His Thr Gln Pro Thr
 1               5                  10

<210> SEQ ID NO 218
<211> LENGTH: 12
<212> TYPE: PRT
<213> ORGANISM: Homo sapiens

<400> SEQUENCE: 218

Gln Ser Tyr Asp Arg Gly His Asn Asn Phe Ser Pro
 1               5                  10

<210> SEQ ID NO 219
<211> LENGTH: 12
<212> TYPE: PRT
<213> ORGANISM: Homo sapiens

<400> SEQUENCE: 219

Gln Ser Tyr Asp Arg Gly Pro Thr His Leu Pro His
 1               5                  10

```
<210> SEQ ID NO 220
<211> LENGTH: 12
<212> TYPE: PRT
<213> ORGANISM: Homo sapiens

<400> SEQUENCE: 220

Gln Ser Tyr Asp Arg Gly Thr Pro Ser Tyr Pro Thr
 1               5                  10

<210> SEQ ID NO 221
<211> LENGTH: 12
<212> TYPE: PRT
<213> ORGANISM: Homo sapiens

<400> SEQUENCE: 221

Gln Ser Tyr Asp Ser Gly Thr Ser Asn Leu Leu Pro
 1               5                  10

<210> SEQ ID NO 222
<211> LENGTH: 12
<212> TYPE: PRT
<213> ORGANISM: Homo sapiens

<400> SEQUENCE: 222

Gln Ser Tyr Asp Arg Gly Asp Ser Asn His Asp Leu
 1               5                  10

<210> SEQ ID NO 223
<211> LENGTH: 12
<212> TYPE: PRT
<213> ORGANISM: Homo sapiens

<400> SEQUENCE: 223

Gln Ser Tyr Asp Arg Gly Leu Pro Arg Leu Thr His
 1               5                  10

<210> SEQ ID NO 224
<211> LENGTH: 12
<212> TYPE: PRT
<213> ORGANISM: Homo sapiens

<400> SEQUENCE: 224

Gln Ser Tyr Asp Arg Gly Ile Pro Thr Ser Tyr Leu
 1               5                  10

<210> SEQ ID NO 225
<211> LENGTH: 12
<212> TYPE: PRT
<213> ORGANISM: Homo sapiens

<400> SEQUENCE: 225

Gln Ser Tyr Asp Arg Gly Leu Arg Val Gln Ala Pro
 1               5                  10

<210> SEQ ID NO 226
<211> LENGTH: 12
<212> TYPE: PRT
<213> ORGANISM: Homo sapiens

<400> SEQUENCE: 226

Gln Ser Tyr Asp Arg Gly Leu Ser Asp Ser Pro Leu
 1               5                  10

<210> SEQ ID NO 227
<211> LENGTH: 12
```

```
<212> TYPE: PRT
<213> ORGANISM: Homo sapiens

<400> SEQUENCE: 227

Gln Ser Tyr Asp Ser Gly Ser Leu Arg Arg Ile Leu
 1               5                  10

<210> SEQ ID NO 228
<211> LENGTH: 12
<212> TYPE: PRT
<213> ORGANISM: Homo sapiens

<400> SEQUENCE: 228

Gln Ser Tyr Asp Arg Gly Pro Ala Arg Thr Ser Pro
 1               5                  10

<210> SEQ ID NO 229
<211> LENGTH: 12
<212> TYPE: PRT
<213> ORGANISM: Homo sapiens

<400> SEQUENCE: 229

Gln Ser Tyr Asp Arg Gly Arg Ala Ala His Pro Gln
 1               5                  10

<210> SEQ ID NO 230
<211> LENGTH: 12
<212> TYPE: PRT
<213> ORGANISM: Homo sapiens

<400> SEQUENCE: 230

Gln Ser Tyr Asp Arg Gly Thr Gln Pro Ala Asx Ile
 1               5                  10

<210> SEQ ID NO 231
<211> LENGTH: 12
<212> TYPE: PRT
<213> ORGANISM: Homo sapiens

<400> SEQUENCE: 231

Gln Ser Tyr Asp Arg Gly Thr His Pro Thr Met Ile
 1               5                  10

<210> SEQ ID NO 232
<211> LENGTH: 12
<212> TYPE: PRT
<213> ORGANISM: Homo sapiens

<400> SEQUENCE: 232

Gln Ser Tyr Asp Arg Gly Arg Ile Pro Ala Asx Thr
 1               5                  10

<210> SEQ ID NO 233
<211> LENGTH: 12
<212> TYPE: PRT
<213> ORGANISM: Homo sapiens

<400> SEQUENCE: 233

Gln Ser Tyr Asp Arg Gly Thr His Pro Val Pro Ala
 1               5                  10

<210> SEQ ID NO 234
<211> LENGTH: 12
<212> TYPE: PRT
<213> ORGANISM: Homo sapiens
```

<400> SEQUENCE: 234

Gln Ser Tyr Asp Arg Gly Ser Asx Pro Ile Pro Ala
1               5                   10

<210> SEQ ID NO 235
<211> LENGTH: 12
<212> TYPE: PRT
<213> ORGANISM: Homo sapiens

<400> SEQUENCE: 235

Gln Ser Tyr Asp Arg Gly Thr His Pro Val Pro Ala
1               5                   10

<210> SEQ ID NO 236
<211> LENGTH: 12
<212> TYPE: PRT
<213> ORGANISM: Homo sapiens

<400> SEQUENCE: 236

Gln Ser Tyr Asp Arg Gly Thr His Pro Thr Met Tyr
1               5                   10

<210> SEQ ID NO 237
<211> LENGTH: 12
<212> TYPE: PRT
<213> ORGANISM: Homo sapiens

<400> SEQUENCE: 237

Gln Ser Tyr Asp Arg Gly His His Tyr Thr Thr Phe
1               5                   10

<210> SEQ ID NO 238
<211> LENGTH: 12
<212> TYPE: PRT
<213> ORGANISM: Homo sapiens

<400> SEQUENCE: 238

Gln Ser Tyr Asp Arg Gly Ser His Pro Ala Ala Glu
1               5                   10

<210> SEQ ID NO 239
<211> LENGTH: 12
<212> TYPE: PRT
<213> ORGANISM: Homo sapiens

<400> SEQUENCE: 239

Gln Ser Tyr Asp Arg Gly Thr Ile Pro Ser Ile Glu
1               5                   10

<210> SEQ ID NO 240
<211> LENGTH: 12
<212> TYPE: PRT
<213> ORGANISM: Homo sapiens

<400> SEQUENCE: 240

Gln Ser Tyr Asp Arg Gly Ser Ser Pro Ala Ile Met
1               5                   10

<210> SEQ ID NO 241
<211> LENGTH: 12
<212> TYPE: PRT
<213> ORGANISM: Homo sapiens

<400> SEQUENCE: 241

Gln Ser Tyr Asp Arg Gly Ile Trp Pro Asn Leu Asn
1               5                   10

<210> SEQ ID NO 242
<211> LENGTH: 12
<212> TYPE: PRT
<213> ORGANISM: Homo sapiens

<400> SEQUENCE: 242

Gln Ser Tyr Asp Arg Gly Thr His Pro Asn Leu Asn
1               5                   10

<210> SEQ ID NO 243
<211> LENGTH: 12
<212> TYPE: PRT
<213> ORGANISM: Homo sapiens

<400> SEQUENCE: 243

Gln Ser Tyr Asp Arg Gly Thr His Pro Ser Ile Ser
1               5                   10

<210> SEQ ID NO 244
<211> LENGTH: 12
<212> TYPE: PRT
<213> ORGANISM: Homo sapiens

<400> SEQUENCE: 244

Gln Ser Tyr Asp Arg Gly Ser Ala Pro Met Ile Asn
1               5                   10

<210> SEQ ID NO 245
<211> LENGTH: 12
<212> TYPE: PRT
<213> ORGANISM: Homo sapiens

<400> SEQUENCE: 245

Gln Ser Tyr Asp Arg Gly His His Pro Ala Met Ser
1               5                   10

<210> SEQ ID NO 246
<211> LENGTH: 12
<212> TYPE: PRT
<213> ORGANISM: Homo sapiens

<400> SEQUENCE: 246

Gln Ser Tyr Asp Arg Gly Thr His Pro Ser Ile Thr
1               5                   10

<210> SEQ ID NO 247
<211> LENGTH: 12
<212> TYPE: PRT
<213> ORGANISM: Homo sapiens

<400> SEQUENCE: 247

Gln Ser Tyr Asp Arg Gly Thr Asp Pro Ala Ile Val
1               5                   10

<210> SEQ ID NO 248
<211> LENGTH: 12
<212> TYPE: PRT
<213> ORGANISM: Homo sapiens

<400> SEQUENCE: 248

Gln Ser Tyr Asp Arg Gly Thr His Pro Ala Leu Leu

```
            1               5                  10
```

<210> SEQ ID NO 249
<211> LENGTH: 12
<212> TYPE: PRT
<213> ORGANISM: Homo sapiens

<400> SEQUENCE: 249

```
Gln Ser Tyr Asp Arg Gly Ser His Pro Ala Leu Thr
  1               5                  10
```

<210> SEQ ID NO 250
<211> LENGTH: 12
<212> TYPE: PRT
<213> ORGANISM: Homo sapiens

<400> SEQUENCE: 250

```
Gln Ser Tyr Asp Arg Gly Thr Thr Pro Ala Pro Glu
  1               5                  10
```

<210> SEQ ID NO 251
<211> LENGTH: 12
<212> TYPE: PRT
<213> ORGANISM: Homo sapiens

<400> SEQUENCE: 251

```
Gln Ser Tyr Asp Arg Gly Ser His Pro Thr Leu Ile
  1               5                  10
```

<210> SEQ ID NO 252
<211> LENGTH: 12
<212> TYPE: PRT
<213> ORGANISM: Homo sapiens

<400> SEQUENCE: 252

```
Gln Ser Tyr Asp Arg Gly Thr His Pro Ser Met Leu
  1               5                  10
```

<210> SEQ ID NO 253
<211> LENGTH: 12
<212> TYPE: PRT
<213> ORGANISM: Homo sapiens

<400> SEQUENCE: 253

```
Gln Ser Tyr Asp Arg Gly Thr Thr Pro Arg Pro Met
  1               5                  10
```

<210> SEQ ID NO 254
<211> LENGTH: 12
<212> TYPE: PRT
<213> ORGANISM: Homo sapiens

<400> SEQUENCE: 254

```
Gln Ser Tyr Asp Arg Gly Arg Leu Pro Ala Gln Thr
  1               5                  10
```

<210> SEQ ID NO 255
<211> LENGTH: 12
<212> TYPE: PRT
<213> ORGANISM: Homo sapiens

<400> SEQUENCE: 255

```
Gln Ser Tyr Asp Arg Gly Thr His Pro Leu Thr Ile
  1               5                  10
```

<210> SEQ ID NO 256
<211> LENGTH: 12
<212> TYPE: PRT
<213> ORGANISM: Homo sapiens

<400> SEQUENCE: 256

Gln Ser Tyr Asp Arg Gly Gln Thr Pro Ser Ile Thr
 1               5                  10

<210> SEQ ID NO 257
<211> LENGTH: 12
<212> TYPE: PRT
<213> ORGANISM: Homo sapiens

<400> SEQUENCE: 257

Gln Ser Tyr Asp Arg Gly Thr His Phe Gln Met Tyr
 1               5                  10

<210> SEQ ID NO 258
<211> LENGTH: 12
<212> TYPE: PRT
<213> ORGANISM: Homo sapiens

<400> SEQUENCE: 258

Gln Ser Tyr Asp Arg Gly Arg Asn Pro Ala Leu Thr
 1               5                  10

<210> SEQ ID NO 259
<211> LENGTH: 12
<212> TYPE: PRT
<213> ORGANISM: Homo sapiens

<400> SEQUENCE: 259

Gln Ser Tyr Asp Arg Gly Thr His Pro Leu Thr Met
 1               5                  10

<210> SEQ ID NO 260
<211> LENGTH: 12
<212> TYPE: PRT
<213> ORGANISM: Homo sapiens

<400> SEQUENCE: 260

Gln Ser Tyr Asp Arg Gly Thr His Pro Leu Thr Met
 1               5                  10

<210> SEQ ID NO 261
<211> LENGTH: 12
<212> TYPE: PRT
<213> ORGANISM: Homo sapiens

<400> SEQUENCE: 261

Gln Ser Tyr Asp Ser Gly Tyr Thr Gly Ser Arg Val
 1               5                  10

<210> SEQ ID NO 262
<211> LENGTH: 12
<212> TYPE: PRT
<213> ORGANISM: Homo sapiens

<400> SEQUENCE: 262

Gln Ser Tyr Asp Ser Gly Phe Thr Gly Ser Arg Val
 1               5                  10

<210> SEQ ID NO 263

```
<211> LENGTH: 12
<212> TYPE: PRT
<213> ORGANISM: Homo sapiens

<400> SEQUENCE: 263

Gln Ser Tyr Asp Ser Arg Phe Thr Gly Ser Arg Val
 1               5                  10

<210> SEQ ID NO 264
<211> LENGTH: 12
<212> TYPE: PRT
<213> ORGANISM: Homo sapiens

<400> SEQUENCE: 264

Gln Ser Tyr Pro Asp Gly Thr Pro Ala Ser Arg Val
 1               5                  10

<210> SEQ ID NO 265
<211> LENGTH: 12
<212> TYPE: PRT
<213> ORGANISM: Homo sapiens

<400> SEQUENCE: 265

Gln Ser Tyr Ser Thr His Met Pro Ile Ser Arg Val
 1               5                  10

<210> SEQ ID NO 266
<211> LENGTH: 12
<212> TYPE: PRT
<213> ORGANISM: Homo sapiens

<400> SEQUENCE: 266

Gln Ser Tyr Asp Ser Gly Ser Thr Gly Ser Arg Val
 1               5                  10

<210> SEQ ID NO 267
<211> LENGTH: 12
<212> TYPE: PRT
<213> ORGANISM: Homo sapiens

<400> SEQUENCE: 267

Gln Ser Tyr Pro Asn Ser Tyr Pro Ile Ser Arg Val
 1               5                  10

<210> SEQ ID NO 268
<211> LENGTH: 10
<212> TYPE: PRT
<213> ORGANISM: Homo sapiens

<400> SEQUENCE: 268

Gln Ser Tyr Ile Arg Ala Pro Gln Gln Val
 1               5                  10

<210> SEQ ID NO 269
<211> LENGTH: 12
<212> TYPE: PRT
<213> ORGANISM: Homo sapiens

<400> SEQUENCE: 269

Gln Ser Tyr Leu Lys Ser Arg Ala Phe Ser Arg Val
 1               5                  10

<210> SEQ ID NO 270
<211> LENGTH: 12
<212> TYPE: PRT
```

<213> ORGANISM: Homo sapiens

<400> SEQUENCE: 270

Gln Ser Tyr Asp Ser Arg Phe Thr Gly Ser Arg Val
1               5                   10

<210> SEQ ID NO 271
<211> LENGTH: 12
<212> TYPE: PRT
<213> ORGANISM: Homo sapiens

<400> SEQUENCE: 271

Gln Ser Tyr Asp Arg Gly Phe Thr Gly Ser Met Val
1               5                   10

<210> SEQ ID NO 272
<211> LENGTH: 12
<212> TYPE: PRT
<213> ORGANISM: Homo sapiens

<400> SEQUENCE: 272

Gln Ser Tyr Asp Arg Gly Phe Thr Gly Ser Met Val
1               5                   10

<210> SEQ ID NO 273
<211> LENGTH: 12
<212> TYPE: PRT
<213> ORGANISM: Homo sapiens

<400> SEQUENCE: 273

Gln Ser Tyr Asp Arg Gly Phe Thr Gly Phe Asp Gly
1               5                   10

<210> SEQ ID NO 274
<211> LENGTH: 12
<212> TYPE: PRT
<213> ORGANISM: Homo sapiens

<400> SEQUENCE: 274

Gln Ser Tyr Asp Arg Gly Thr Ala Pro Ala Leu Ser
1               5                   10

<210> SEQ ID NO 275
<211> LENGTH: 12
<212> TYPE: PRT
<213> ORGANISM: Homo sapiens

<400> SEQUENCE: 275

Gln Ser Tyr Asp Arg Gly Ser Tyr Pro Ala Leu Arg
1               5                   10

<210> SEQ ID NO 276
<211> LENGTH: 12
<212> TYPE: PRT
<213> ORGANISM: Homo sapiens

<400> SEQUENCE: 276

Gln Ser Tyr Asp Arg Gly Asn Trp Pro Asn Ser Asn
1               5                   10

<210> SEQ ID NO 277
<211> LENGTH: 12
<212> TYPE: PRT
<213> ORGANISM: Homo sapiens

<400> SEQUENCE: 277

Gln Ser Tyr Asp Arg Gly Thr Ala Pro Ser Leu Leu
 1               5                  10

<210> SEQ ID NO 278
<211> LENGTH: 12
<212> TYPE: PRT
<213> ORGANISM: Homo sapiens

<400> SEQUENCE: 278

Gln Ser Tyr Asp Arg Gly Phe Thr Gly Ser Met Val
 1               5                  10

<210> SEQ ID NO 279
<211> LENGTH: 12
<212> TYPE: PRT
<213> ORGANISM: Homo sapiens

<400> SEQUENCE: 279

Gln Ser Tyr Asp Arg Gly Thr Thr Pro Arg Ile Arg
 1               5                  10

<210> SEQ ID NO 280
<211> LENGTH: 12
<212> TYPE: PRT
<213> ORGANISM: Homo sapiens

<400> SEQUENCE: 280

Gln Ser Tyr Asp Arg Gly Phe Thr Gly Ser Met Val
 1               5                  10

<210> SEQ ID NO 281
<211> LENGTH: 12
<212> TYPE: PRT
<213> ORGANISM: Homo sapiens

<400> SEQUENCE: 281

Gln Ser Tyr Asp Arg Gly Phe Thr Gly Ser Met Val
 1               5                  10

<210> SEQ ID NO 282
<211> LENGTH: 12
<212> TYPE: PRT
<213> ORGANISM: Homo sapiens

<400> SEQUENCE: 282

Gln Ser Tyr Asp Arg Gly Met Ile Pro Ala Leu Thr
 1               5                  10

<210> SEQ ID NO 283
<211> LENGTH: 12
<212> TYPE: PRT
<213> ORGANISM: Homo sapiens

<400> SEQUENCE: 283

Gln Ser Tyr Asp Arg Asn Thr His Pro Ala Leu Leu
 1               5                  10

<210> SEQ ID NO 284
<211> LENGTH: 12
<212> TYPE: PRT
<213> ORGANISM: Homo sapiens

<400> SEQUENCE: 284

Gln Ser Tyr Asp Arg Phe Thr His Pro Ala Leu Leu
 1               5                  10

<210> SEQ ID NO 285
<211> LENGTH: 12
<212> TYPE: PRT
<213> ORGANISM: Homo sapiens

<400> SEQUENCE: 285

Gln Ser Tyr Asp Arg Tyr Thr His Pro Ala Leu Leu
 1               5                  10

<210> SEQ ID NO 286
<211> LENGTH: 12
<212> TYPE: PRT
<213> ORGANISM: Homo sapiens

<400> SEQUENCE: 286

Gln Ser Tyr Asp Arg Gly Thr His Pro Ala Leu Leu
 1               5                  10

<210> SEQ ID NO 287
<211> LENGTH: 12
<212> TYPE: PRT
<213> ORGANISM: Homo sapiens

<400> SEQUENCE: 287

Gln Ser Tyr Asp Arg Tyr Thr His Pro Ala Leu Leu
 1               5                  10

<210> SEQ ID NO 288
<211> LENGTH: 9
<212> TYPE: PRT
<213> ORGANISM: Homo sapiens

<400> SEQUENCE: 288

Phe Thr Phe Glu Ser Tyr Gly Met His
 1               5

<210> SEQ ID NO 289
<211> LENGTH: 9
<212> TYPE: PRT
<213> ORGANISM: Homo sapiens

<400> SEQUENCE: 289

Phe Thr Phe Ser Ser Tyr Gly Met His
 1               5

<210> SEQ ID NO 290
<211> LENGTH: 9
<212> TYPE: PRT
<213> ORGANISM: Homo sapiens

<400> SEQUENCE: 290

Phe Thr Phe Tyr Ser Tyr Gly Met His
 1               5

<210> SEQ ID NO 291
<211> LENGTH: 9
<212> TYPE: PRT
<213> ORGANISM: Homo sapiens

<400> SEQUENCE: 291

Phe Thr Phe His Ser Tyr Gly Met His
 1               5

<210> SEQ ID NO 292
<211> LENGTH: 9
<212> TYPE: PRT
<213> ORGANISM: Homo sapiens

<400> SEQUENCE: 292

Phe Thr Phe Lys Ser Tyr Gly Met His
 1               5

<210> SEQ ID NO 293
<211> LENGTH: 9
<212> TYPE: PRT
<213> ORGANISM: Homo sapiens

<400> SEQUENCE: 293

Phe Thr Phe Arg Ser Tyr Gly Met His
 1               5

<210> SEQ ID NO 294
<211> LENGTH: 9
<212> TYPE: PRT
<213> ORGANISM: Homo sapiens

<400> SEQUENCE: 294

Phe Thr Phe Asn Ser Tyr Gly Met His
 1               5

<210> SEQ ID NO 295
<211> LENGTH: 9
<212> TYPE: PRT
<213> ORGANISM: Homo sapiens

<400> SEQUENCE: 295

Phe Thr Phe Thr Ser Tyr Gly Met His
 1               5

<210> SEQ ID NO 296
<211> LENGTH: 9
<212> TYPE: PRT
<213> ORGANISM: Homo sapiens

<400> SEQUENCE: 296

Phe Thr Phe Gly Ser Tyr Gly Met His
 1               5

<210> SEQ ID NO 297
<211> LENGTH: 9
<212> TYPE: PRT
<213> ORGANISM: Homo sapiens

<400> SEQUENCE: 297

Phe Thr Phe Val Ser Tyr Gly Met His
 1               5

<210> SEQ ID NO 298
<211> LENGTH: 9
<212> TYPE: PRT
<213> ORGANISM: Homo sapiens

<400> SEQUENCE: 298

Phe Thr Phe Ile Ser Tyr Gly Met His
 1               5

```
<210> SEQ ID NO 299
<211> LENGTH: 9
<212> TYPE: PRT
<213> ORGANISM: Homo sapiens

<400> SEQUENCE: 299

Phe Thr Phe Trp Ser Tyr Gly Met His
 1               5

<210> SEQ ID NO 300
<211> LENGTH: 9
<212> TYPE: PRT
<213> ORGANISM: Homo sapiens

<400> SEQUENCE: 300

Phe Thr Phe Ser Glu Tyr Gly Met His
 1               5

<210> SEQ ID NO 301
<211> LENGTH: 9
<212> TYPE: PRT
<213> ORGANISM: Homo sapiens

<400> SEQUENCE: 301

Phe Thr Phe Ser Cys Tyr Gly Met His
 1               5

<210> SEQ ID NO 302
<211> LENGTH: 9
<212> TYPE: PRT
<213> ORGANISM: Homo sapiens

<400> SEQUENCE: 302

Phe Thr Phe Ser Ser Tyr Gly Met His
 1               5

<210> SEQ ID NO 303
<211> LENGTH: 9
<212> TYPE: PRT
<213> ORGANISM: Homo sapiens

<400> SEQUENCE: 303

Phe Thr Phe Ser Tyr Tyr Gly Met His
 1               5

<210> SEQ ID NO 304
<211> LENGTH: 9
<212> TYPE: PRT
<213> ORGANISM: Homo sapiens

<400> SEQUENCE: 304

Phe Thr Phe Ser His Tyr Gly Met His
 1               5

<210> SEQ ID NO 305
<211> LENGTH: 9
<212> TYPE: PRT
<213> ORGANISM: Homo sapiens

<400> SEQUENCE: 305

Phe Thr Phe Ser Arg Tyr Gly Met His
 1               5

<210> SEQ ID NO 306
<211> LENGTH: 9
```

```
<212> TYPE: PRT
<213> ORGANISM: Homo sapiens

<400> SEQUENCE: 306

Phe Thr Phe Ser Asn Tyr Gly Met His
 1               5

<210> SEQ ID NO 307
<211> LENGTH: 9
<212> TYPE: PRT
<213> ORGANISM: Homo sapiens

<400> SEQUENCE: 307

Phe Thr Phe Ser Gln Tyr Gly Met His
 1               5

<210> SEQ ID NO 308
<211> LENGTH: 9
<212> TYPE: PRT
<213> ORGANISM: Homo sapiens

<400> SEQUENCE: 308

Phe Thr Phe Ser Thr Tyr Gly Met His
 1               5

<210> SEQ ID NO 309
<211> LENGTH: 9
<212> TYPE: PRT
<213> ORGANISM: Homo sapiens

<400> SEQUENCE: 309

Phe Thr Phe Ser Ala Tyr Gly Met His
 1               5

<210> SEQ ID NO 310
<211> LENGTH: 9
<212> TYPE: PRT
<213> ORGANISM: Homo sapiens

<400> SEQUENCE: 310

Phe Thr Phe Ser Ile Tyr Gly Met His
 1               5

<210> SEQ ID NO 311
<211> LENGTH: 9
<212> TYPE: PRT
<213> ORGANISM: Homo sapiens

<400> SEQUENCE: 311

Phe Thr Phe Ser Ser Glu Gly Met His
 1               5

<210> SEQ ID NO 312
<211> LENGTH: 9
<212> TYPE: PRT
<213> ORGANISM: Homo sapiens

<400> SEQUENCE: 312

Phe Thr Phe Ser Ser Cys Gly Met His
 1               5

<210> SEQ ID NO 313
<211> LENGTH: 9
<212> TYPE: PRT
<213> ORGANISM: Homo sapiens
```

<400> SEQUENCE: 313

Phe Thr Phe Ser Ser Ser Gly Met His
 1               5

<210> SEQ ID NO 314
<211> LENGTH: 9
<212> TYPE: PRT
<213> ORGANISM: Homo sapiens

<400> SEQUENCE: 314

Phe Thr Phe Ser Ser Tyr Gly Met His
 1               5

<210> SEQ ID NO 315
<211> LENGTH: 9
<212> TYPE: PRT
<213> ORGANISM: Homo sapiens

<400> SEQUENCE: 315

Phe Thr Phe Ser Ser His Gly Met His
 1               5

<210> SEQ ID NO 316
<211> LENGTH: 9
<212> TYPE: PRT
<213> ORGANISM: Homo sapiens

<400> SEQUENCE: 316

Phe Thr Phe Ser Ser Arg Gly Met His
 1               5

<210> SEQ ID NO 317
<211> LENGTH: 9
<212> TYPE: PRT
<213> ORGANISM: Homo sapiens

<400> SEQUENCE: 317

Phe Thr Phe Ser Ser Asn Gly Met His
 1               5

<210> SEQ ID NO 318
<211> LENGTH: 9
<212> TYPE: PRT
<213> ORGANISM: Homo sapiens

<400> SEQUENCE: 318

Phe Thr Phe Ser Ser Thr Gly Met His
 1               5

<210> SEQ ID NO 319
<211> LENGTH: 9
<212> TYPE: PRT
<213> ORGANISM: Homo sapiens

<400> SEQUENCE: 319

Phe Thr Phe Ser Ser Ala Gly Met His
 1               5

<210> SEQ ID NO 320
<211> LENGTH: 9
<212> TYPE: PRT
<213> ORGANISM: Homo sapiens

<400> SEQUENCE: 320

Phe Thr Phe Ser Ser Val Gly Met His
 1               5

<210> SEQ ID NO 321
<211> LENGTH: 9
<212> TYPE: PRT
<213> ORGANISM: Homo sapiens

<400> SEQUENCE: 321

Phe Thr Phe Ser Ser Leu Gly Met His
 1               5

<210> SEQ ID NO 322
<211> LENGTH: 9
<212> TYPE: PRT
<213> ORGANISM: Homo sapiens

<400> SEQUENCE: 322

Phe Thr Phe Ser Ser Ile Gly Met His
 1               5

<210> SEQ ID NO 323
<211> LENGTH: 9
<212> TYPE: PRT
<213> ORGANISM: Homo sapiens

<400> SEQUENCE: 323

Phe Thr Phe Ser Ser Tyr Asp Met His
 1               5

<210> SEQ ID NO 324
<211> LENGTH: 9
<212> TYPE: PRT
<213> ORGANISM: Homo sapiens

<400> SEQUENCE: 324

Phe Thr Phe Ser Ser Tyr Glu Met His
 1               5

<210> SEQ ID NO 325
<211> LENGTH: 9
<212> TYPE: PRT
<213> ORGANISM: Homo sapiens

<400> SEQUENCE: 325

Phe Thr Phe Ser Ser Tyr Cys Met His
 1               5

<210> SEQ ID NO 326
<211> LENGTH: 9
<212> TYPE: PRT
<213> ORGANISM: Homo sapiens

<400> SEQUENCE: 326

Phe Thr Phe Ser Ser Tyr Ser Met His
 1               5

<210> SEQ ID NO 327
<211> LENGTH: 9
<212> TYPE: PRT
<213> ORGANISM: Homo sapiens

<400> SEQUENCE: 327

Phe Thr Phe Ser Ser Tyr Tyr Met His

```
    1               5
```

<210> SEQ ID NO 328
<211> LENGTH: 9
<212> TYPE: PRT
<213> ORGANISM: Homo sapiens

<400> SEQUENCE: 328

```
Phe Thr Phe Ser Ser Tyr Asn Met His
    1               5
```

<210> SEQ ID NO 329
<211> LENGTH: 9
<212> TYPE: PRT
<213> ORGANISM: Homo sapiens

<400> SEQUENCE: 329

```
Phe Thr Phe Ser Ser Tyr Gly Met His
    1               5
```

<210> SEQ ID NO 330
<211> LENGTH: 9
<212> TYPE: PRT
<213> ORGANISM: Homo sapiens

<400> SEQUENCE: 330

```
Phe Thr Phe Ser Ser Tyr Ala Met His
    1               5
```

<210> SEQ ID NO 331
<211> LENGTH: 9
<212> TYPE: PRT
<213> ORGANISM: Homo sapiens

<400> SEQUENCE: 331

```
Phe Thr Phe Ser Ser Tyr Val Met His
    1               5
```

<210> SEQ ID NO 332
<211> LENGTH: 9
<212> TYPE: PRT
<213> ORGANISM: Homo sapiens

<400> SEQUENCE: 332

```
Phe Thr Phe Ser Ser Tyr Met Met His
    1               5
```

<210> SEQ ID NO 333
<211> LENGTH: 9
<212> TYPE: PRT
<213> ORGANISM: Homo sapiens

<400> SEQUENCE: 333

```
Phe Thr Phe Ser Ser Tyr Ile Met His
    1               5
```

<210> SEQ ID NO 334
<211> LENGTH: 9
<212> TYPE: PRT
<213> ORGANISM: Homo sapiens

<400> SEQUENCE: 334

```
Phe Thr Phe Ser Ser Tyr Pro Met His
    1               5
```

```
<210> SEQ ID NO 335
<211> LENGTH: 17
<212> TYPE: PRT
<213> ORGANISM: Homo sapiens

<400> SEQUENCE: 335

Glu Ile Arg Tyr Asp Gly Ser Asn Lys Tyr Tyr Ala Asp Ser Val Lys
 1               5                  10                  15

Gly

<210> SEQ ID NO 336
<211> LENGTH: 17
<212> TYPE: PRT
<213> ORGANISM: Homo sapiens

<400> SEQUENCE: 336

Cys Ile Arg Tyr Asp Gly Ser Asn Lys Tyr Tyr Ala Asp Ser Val Lys
 1               5                  10                  15

Gly

<210> SEQ ID NO 337
<211> LENGTH: 17
<212> TYPE: PRT
<213> ORGANISM: Homo sapiens

<400> SEQUENCE: 337

Tyr Ile Arg Tyr Asp Gly Ser Asn Lys Tyr Tyr Ala Asp Ser Val Lys
 1               5                  10                  15

Gly

<210> SEQ ID NO 338
<211> LENGTH: 17
<212> TYPE: PRT
<213> ORGANISM: Homo sapiens

<400> SEQUENCE: 338

His Ile Arg Tyr Asp Gly Ser Asn Lys Tyr Tyr Ala Asp Ser Val Lys
 1               5                  10                  15

Gly

<210> SEQ ID NO 339
<211> LENGTH: 17
<212> TYPE: PRT
<213> ORGANISM: Homo sapiens

<400> SEQUENCE: 339

Lys Ile Arg Tyr Asp Gly Ser Asn Lys Tyr Tyr Ala Asp Ser Val Lys
 1               5                  10                  15

Gly

<210> SEQ ID NO 340
<211> LENGTH: 17
<212> TYPE: PRT
<213> ORGANISM: Homo sapiens

<400> SEQUENCE: 340

Asn Ile Arg Tyr Asp Gly Ser Asn Lys Tyr Tyr Ala Asp Ser Val Lys
 1               5                  10                  15

Gly
```

-continued

<210> SEQ ID NO 341
<211> LENGTH: 17
<212> TYPE: PRT
<213> ORGANISM: Homo sapiens

<400> SEQUENCE: 341

Gln Ile Arg Tyr Asp Gly Ser Asn Lys Tyr Tyr Ala Asp Ser Val Lys
 1               5                  10                  15
Gly

<210> SEQ ID NO 342
<211> LENGTH: 17
<212> TYPE: PRT
<213> ORGANISM: Homo sapiens

<400> SEQUENCE: 342

Thr Ile Arg Tyr Asp Gly Ser Asn Lys Tyr Tyr Ala Asp Ser Val Lys
 1               5                  10                  15
Gly

<210> SEQ ID NO 343
<211> LENGTH: 17
<212> TYPE: PRT
<213> ORGANISM: Homo sapiens

<400> SEQUENCE: 343

Leu Ile Arg Tyr Asp Gly Ser Asn Lys Tyr Tyr Ala Asp Ser Val Lys
 1               5                  10                  15
Gly

<210> SEQ ID NO 344
<211> LENGTH: 17
<212> TYPE: PRT
<213> ORGANISM: Homo sapiens

<400> SEQUENCE: 344

Phe Ile Arg Tyr Asp Gly Ser Asn Lys Tyr Tyr Ala Asp Ser Val Lys
 1               5                  10                  15
Gly

<210> SEQ ID NO 345
<211> LENGTH: 17
<212> TYPE: PRT
<213> ORGANISM: Homo sapiens

<400> SEQUENCE: 345

Phe Ile Glu Tyr Asp Gly Ser Asn Lys Tyr Tyr Ala Asp Ser Val Lys
 1               5                  10                  15
Gly

<210> SEQ ID NO 346
<211> LENGTH: 17
<212> TYPE: PRT
<213> ORGANISM: Homo sapiens

<400> SEQUENCE: 346

Phe Ile Ser Tyr Asp Gly Ser Asn Lys Tyr Tyr Ala Asp Ser Val Lys
 1               5                  10                  15
Gly

<210> SEQ ID NO 347

```
<211> LENGTH: 17
<212> TYPE: PRT
<213> ORGANISM: Homo sapiens

<400> SEQUENCE: 347

Phe Ile Tyr Tyr Asp Gly Ser Asn Lys Tyr Tyr Ala Asp Ser Val Lys
 1               5                  10                  15

Gly

<210> SEQ ID NO 348
<211> LENGTH: 17
<212> TYPE: PRT
<213> ORGANISM: Homo sapiens

<400> SEQUENCE: 348

Phe Ile His Tyr Asp Gly Ser Asn Lys Tyr Tyr Ala Asp Ser Val Lys
 1               5                  10                  15

Gly

<210> SEQ ID NO 349
<211> LENGTH: 17
<212> TYPE: PRT
<213> ORGANISM: Homo sapiens

<400> SEQUENCE: 349

Phe Ile Lys Tyr Asp Gly Ser Asn Lys Tyr Tyr Ala Asp Ser Val Lys
 1               5                  10                  15

Gly

<210> SEQ ID NO 350
<211> LENGTH: 17
<212> TYPE: PRT
<213> ORGANISM: Homo sapiens

<400> SEQUENCE: 350

Phe Ile Arg Tyr Asp Gly Ser Asn Lys Tyr Tyr Ala Asp Ser Val Lys
 1               5                  10                  15

Gly

<210> SEQ ID NO 351
<211> LENGTH: 17
<212> TYPE: PRT
<213> ORGANISM: Homo sapiens

<400> SEQUENCE: 351

Phe Ile Gln Tyr Asp Gly Ser Asn Lys Tyr Tyr Ala Asp Ser Val Lys
 1               5                  10                  15

Gly

<210> SEQ ID NO 352
<211> LENGTH: 17
<212> TYPE: PRT
<213> ORGANISM: Homo sapiens

<400> SEQUENCE: 352

Phe Ile Thr Tyr Asp Gly Ser Asn Lys Tyr Tyr Ala Asp Ser Val Lys
 1               5                  10                  15

Gly

<210> SEQ ID NO 353
<211> LENGTH: 17
```

<212> TYPE: PRT
<213> ORGANISM: Homo sapiens

<400> SEQUENCE: 353

Phe Ile Gly Tyr Asp Gly Ser Asn Lys Tyr Tyr Ala Asp Ser Val Lys
 1               5                  10                  15

Gly

<210> SEQ ID NO 354
<211> LENGTH: 17
<212> TYPE: PRT
<213> ORGANISM: Homo sapiens

<400> SEQUENCE: 354

Phe Ile Ala Tyr Asp Gly Ser Asn Lys Tyr Tyr Ala Asp Ser Val Lys
 1               5                  10                  15

Gly

<210> SEQ ID NO 355
<211> LENGTH: 17
<212> TYPE: PRT
<213> ORGANISM: Homo sapiens

<400> SEQUENCE: 355

Phe Ile Val Tyr Asp Gly Ser Asn Lys Tyr Tyr Ala Asp Ser Val Lys
 1               5                  10                  15

Gly

<210> SEQ ID NO 356
<211> LENGTH: 17
<212> TYPE: PRT
<213> ORGANISM: Homo sapiens

<400> SEQUENCE: 356

Phe Ile Leu Tyr Asp Gly Ser Asn Lys Tyr Tyr Ala Asp Ser Val Lys
 1               5                  10                  15

Gly

<210> SEQ ID NO 357
<211> LENGTH: 17
<212> TYPE: PRT
<213> ORGANISM: Homo sapiens

<400> SEQUENCE: 357

Phe Ile Trp Tyr Asp Gly Ser Asn Lys Tyr Tyr Ala Asp Ser Val Lys
 1               5                  10                  15

Gly

<210> SEQ ID NO 358
<211> LENGTH: 17
<212> TYPE: PRT
<213> ORGANISM: Homo sapiens

<400> SEQUENCE: 358

Phe Ile Arg Tyr Asp Gly Ser Asn Lys Tyr Tyr Ala Asp Ser Val Lys
 1               5                  10                  15

Gly

<210> SEQ ID NO 359
<211> LENGTH: 17
<212> TYPE: PRT

<213> ORGANISM: Homo sapiens

<400> SEQUENCE: 359

Phe Ile Arg Tyr Glu Gly Ser Asn Lys Tyr Tyr Ala Asp Ser Val Lys
1               5                   10                  15

Gly

<210> SEQ ID NO 360
<211> LENGTH: 17
<212> TYPE: PRT
<213> ORGANISM: Homo sapiens

<400> SEQUENCE: 360

Phe Ile Arg Tyr Ser Gly Ser Asn Lys Tyr Tyr Ala Asp Ser Val Lys
1               5                   10                  15

Gly

<210> SEQ ID NO 361
<211> LENGTH: 17
<212> TYPE: PRT
<213> ORGANISM: Homo sapiens

<400> SEQUENCE: 361

Phe Ile Arg Tyr Tyr Gly Ser Asn Lys Tyr Tyr Ala Asp Ser Val Lys
1               5                   10                  15

Gly

<210> SEQ ID NO 362
<211> LENGTH: 17
<212> TYPE: PRT
<213> ORGANISM: Homo sapiens

<400> SEQUENCE: 362

Phe Ile Arg Tyr Lys Gly Ser Asn Lys Tyr Tyr Ala Asp Ser Val Lys
1               5                   10                  15

Gly

<210> SEQ ID NO 363
<211> LENGTH: 17
<212> TYPE: PRT
<213> ORGANISM: Homo sapiens

<400> SEQUENCE: 363

Phe Ile Arg Tyr Arg Gly Ser Asn Lys Tyr Tyr Ala Asp Ser Val Lys
1               5                   10                  15

Gly

<210> SEQ ID NO 364
<211> LENGTH: 17
<212> TYPE: PRT
<213> ORGANISM: Homo sapiens

<400> SEQUENCE: 364

Phe Ile Arg Tyr Asn Gly Ser Asn Lys Tyr Tyr Ala Asp Ser Val Lys
1               5                   10                  15

Gly

<210> SEQ ID NO 365
<211> LENGTH: 17
<212> TYPE: PRT
<213> ORGANISM: Homo sapiens

<400> SEQUENCE: 365

Phe Ile Arg Tyr Gln Gly Ser Asn Lys Tyr Tyr Ala Asp Ser Val Lys
1               5                   10                  15
Gly

<210> SEQ ID NO 366
<211> LENGTH: 17
<212> TYPE: PRT
<213> ORGANISM: Homo sapiens

<400> SEQUENCE: 366

Phe Ile Arg Tyr Thr Gly Ser Asn Lys Tyr Tyr Ala Asp Ser Val Lys
1               5                   10                  15
Gly

<210> SEQ ID NO 367
<211> LENGTH: 17
<212> TYPE: PRT
<213> ORGANISM: Homo sapiens

<400> SEQUENCE: 367

Phe Ile Arg Tyr Ala Gly Ser Asn Lys Tyr Tyr Ala Asp Ser Val Lys
1               5                   10                  15
Gly

<210> SEQ ID NO 368
<211> LENGTH: 17
<212> TYPE: PRT
<213> ORGANISM: Homo sapiens

<400> SEQUENCE: 368

Phe Ile Arg Tyr Val Gly Ser Asn Lys Tyr Tyr Ala Asp Ser Val Lys
1               5                   10                  15
Gly

<210> SEQ ID NO 369
<211> LENGTH: 17
<212> TYPE: PRT
<213> ORGANISM: Homo sapiens

<400> SEQUENCE: 369

Phe Ile Arg Tyr Leu Gly Ser Asn Lys Tyr Tyr Ala Asp Ser Val Lys
1               5                   10                  15
Gly

<210> SEQ ID NO 370
<211> LENGTH: 17
<212> TYPE: PRT
<213> ORGANISM: Homo sapiens

<400> SEQUENCE: 370

Phe Ile Arg Tyr Ile Gly Ser Asn Lys Tyr Tyr Ala Asp Ser Val Lys
1               5                   10                  15
Gly

<210> SEQ ID NO 371
<211> LENGTH: 17
<212> TYPE: PRT
<213> ORGANISM: Homo sapiens

<400> SEQUENCE: 371

Phe Ile Arg Tyr Phe Gly Ser Asn Lys Tyr Tyr Ala Asp Ser Val Lys
1               5                   10                  15
Gly

<210> SEQ ID NO 372
<211> LENGTH: 17
<212> TYPE: PRT
<213> ORGANISM: Homo sapiens

<400> SEQUENCE: 372

Phe Ile Arg Tyr Asp Asp Ser Asn Lys Tyr Tyr Ala Asp Ser Val Lys
1               5                   10                  15
Gly

<210> SEQ ID NO 373
<211> LENGTH: 17
<212> TYPE: PRT
<213> ORGANISM: Homo sapiens

<400> SEQUENCE: 373

Phe Ile Arg Tyr Asp Glu Ser Asn Lys Tyr Tyr Ala Asp Ser Val Lys
1               5                   10                  15
Gly

<210> SEQ ID NO 374
<211> LENGTH: 17
<212> TYPE: PRT
<213> ORGANISM: Homo sapiens

<400> SEQUENCE: 374

Phe Ile Arg Tyr Asp Ser Ser Asn Lys Tyr Tyr Ala Asp Ser Val Lys
1               5                   10                  15
Gly

<210> SEQ ID NO 375
<211> LENGTH: 17
<212> TYPE: PRT
<213> ORGANISM: Homo sapiens

<400> SEQUENCE: 375

Phe Ile Arg Tyr Asp Tyr Ser Asn Lys Tyr Tyr Ala Asp Ser Val Lys
1               5                   10                  15
Gly

<210> SEQ ID NO 376
<211> LENGTH: 17
<212> TYPE: PRT
<213> ORGANISM: Homo sapiens

<400> SEQUENCE: 376

Phe Ile Arg Tyr Asp Lys Ser Asn Lys Tyr Tyr Ala Asp Ser Val Lys
1               5                   10                  15
Gly

<210> SEQ ID NO 377
<211> LENGTH: 17
<212> TYPE: PRT
<213> ORGANISM: Homo sapiens

<400> SEQUENCE: 377

Phe Ile Arg Tyr Asp Arg Ser Asn Lys Tyr Tyr Ala Asp Ser Val Lys
 1               5                  10                  15
Gly

<210> SEQ ID NO 378
<211> LENGTH: 17
<212> TYPE: PRT
<213> ORGANISM: Homo sapiens

<400> SEQUENCE: 378

Phe Ile Arg Tyr Asp Asn Ser Asn Lys Tyr Tyr Ala Asp Ser Val Lys
 1               5                  10                  15
Gly

<210> SEQ ID NO 379
<211> LENGTH: 17
<212> TYPE: PRT
<213> ORGANISM: Homo sapiens

<400> SEQUENCE: 379

Phe Ile Arg Tyr Asp Gln Ser Asn Lys Tyr Tyr Ala Asp Ser Val Lys
 1               5                  10                  15
Gly

<210> SEQ ID NO 380
<211> LENGTH: 17
<212> TYPE: PRT
<213> ORGANISM: Homo sapiens

<400> SEQUENCE: 380

Phe Ile Arg Tyr Asp Thr Ser Asn Lys Tyr Tyr Ala Asp Ser Val Lys
 1               5                  10                  15
Gly

<210> SEQ ID NO 381
<211> LENGTH: 17
<212> TYPE: PRT
<213> ORGANISM: Homo sapiens

<400> SEQUENCE: 381

Phe Ile Arg Tyr Asp Gly Ser Asn Lys Tyr Tyr Ala Asp Ser Val Lys
 1               5                  10                  15
Gly

<210> SEQ ID NO 382
<211> LENGTH: 17
<212> TYPE: PRT
<213> ORGANISM: Homo sapiens

<400> SEQUENCE: 382

Phe Ile Arg Tyr Asp Val Ser Asn Lys Tyr Tyr Ala Asp Ser Val Lys
 1               5                  10                  15
Gly

<210> SEQ ID NO 383
<211> LENGTH: 17
<212> TYPE: PRT
<213> ORGANISM: Homo sapiens

<400> SEQUENCE: 383

```
Phe Ile Arg Tyr Asp Phe Ser Asn Lys Tyr Tyr Ala Asp Ser Val Lys
 1               5                  10                  15
Gly

<210> SEQ ID NO 384
<211> LENGTH: 17
<212> TYPE: PRT
<213> ORGANISM: Homo sapiens

<400> SEQUENCE: 384

Phe Ile Arg Tyr Asp Gly Ser Ser Lys Tyr Tyr Ala Asp Ser Val Lys
 1               5                  10                  15
Gly

<210> SEQ ID NO 385
<211> LENGTH: 17
<212> TYPE: PRT
<213> ORGANISM: Homo sapiens

<400> SEQUENCE: 385

Phe Ile Arg Tyr Asp Gly Ser Tyr Lys Tyr Tyr Ala Asp Ser Val Lys
 1               5                  10                  15
Gly

<210> SEQ ID NO 386
<211> LENGTH: 17
<212> TYPE: PRT
<213> ORGANISM: Homo sapiens

<400> SEQUENCE: 386

Phe Ile Arg Tyr Asp Gly Ser His Lys Tyr Tyr Ala Asp Ser Val Lys
 1               5                  10                  15
Gly

<210> SEQ ID NO 387
<211> LENGTH: 17
<212> TYPE: PRT
<213> ORGANISM: Homo sapiens

<400> SEQUENCE: 387

Phe Ile Arg Tyr Asp Gly Ser Asn Lys Tyr Tyr Ala Asp Ser Val Lys
 1               5                  10                  15
Gly

<210> SEQ ID NO 388
<211> LENGTH: 17
<212> TYPE: PRT
<213> ORGANISM: Homo sapiens

<400> SEQUENCE: 388

Phe Ile Arg Tyr Asp Gly Ser Thr Lys Tyr Tyr Ala Asp Ser Val Lys
 1               5                  10                  15
Gly

<210> SEQ ID NO 389
<211> LENGTH: 17
<212> TYPE: PRT
<213> ORGANISM: Homo sapiens

<400> SEQUENCE: 389

Phe Ile Arg Tyr Asp Gly Ser Gly Lys Tyr Tyr Ala Asp Ser Val Lys
```

```
                        1               5                   10                  15

Gly

<210> SEQ ID NO 390
<211> LENGTH: 17
<212> TYPE: PRT
<213> ORGANISM: Homo sapiens

<400> SEQUENCE: 390

Phe Ile Arg Tyr Asp Gly Ser Met Lys Tyr Tyr Ala Asp Ser Val Lys
 1               5                   10                  15

Gly

<210> SEQ ID NO 391
<211> LENGTH: 17
<212> TYPE: PRT
<213> ORGANISM: Homo sapiens

<400> SEQUENCE: 391

Phe Ile Arg Tyr Asp Gly Ser Leu Lys Tyr Tyr Ala Asp Ser Val Lys
 1               5                   10                  15

Gly

<210> SEQ ID NO 392
<211> LENGTH: 17
<212> TYPE: PRT
<213> ORGANISM: Homo sapiens

<400> SEQUENCE: 392

Phe Ile Arg Tyr Asp Gly Ser Ile Lys Tyr Tyr Ala Asp Ser Val Lys
 1               5                   10                  15

Gly

<210> SEQ ID NO 393
<211> LENGTH: 17
<212> TYPE: PRT
<213> ORGANISM: Homo sapiens

<400> SEQUENCE: 393

Phe Ile Arg Tyr Asp Gly Ser Pro Lys Tyr Tyr Ala Asp Ser Val Lys
 1               5                   10                  15

Gly

<210> SEQ ID NO 394
<211> LENGTH: 17
<212> TYPE: PRT
<213> ORGANISM: Homo sapiens

<400> SEQUENCE: 394

Phe Ile Arg Tyr Asp Gly Ser Phe Lys Tyr Tyr Ala Asp Ser Val Lys
 1               5                   10                  15

Gly

<210> SEQ ID NO 395
<211> LENGTH: 17
<212> TYPE: PRT
<213> ORGANISM: Homo sapiens

<400> SEQUENCE: 395

Phe Ile Arg Tyr Asp Gly Ser Asn Lys Glu Tyr Ala Asp Ser Val Lys
 1               5                   10                  15
```

Gly

<210> SEQ ID NO 396
<211> LENGTH: 17
<212> TYPE: PRT
<213> ORGANISM: Homo sapiens

<400> SEQUENCE: 396

Phe Ile Arg Tyr Asp Gly Ser Asn Lys Ser Tyr Ala Asp Ser Val Lys
 1               5                  10                  15

Gly

<210> SEQ ID NO 397
<211> LENGTH: 17
<212> TYPE: PRT
<213> ORGANISM: Homo sapiens

<400> SEQUENCE: 397

Phe Ile Arg Tyr Asp Gly Ser Asn Lys Tyr Tyr Ala Asp Ser Val Lys
 1               5                  10                  15

Gly

<210> SEQ ID NO 398
<211> LENGTH: 17
<212> TYPE: PRT
<213> ORGANISM: Homo sapiens

<400> SEQUENCE: 398

Phe Ile Arg Tyr Asp Gly Ser Asn Lys Asn Tyr Ala Asp Ser Val Lys
 1               5                  10                  15

Gly

<210> SEQ ID NO 399
<211> LENGTH: 17
<212> TYPE: PRT
<213> ORGANISM: Homo sapiens

<400> SEQUENCE: 399

Phe Ile Arg Tyr Asp Gly Ser Asn Lys Val Tyr Ala Asp Ser Val Lys
 1               5                  10                  15

Gly

<210> SEQ ID NO 400
<211> LENGTH: 17
<212> TYPE: PRT
<213> ORGANISM: Homo sapiens

<400> SEQUENCE: 400

Phe Ile Arg Tyr Asp Gly Ser Asn Lys Leu Tyr Ala Asp Ser Val Lys
 1               5                  10                  15

Gly

<210> SEQ ID NO 401
<211> LENGTH: 17
<212> TYPE: PRT
<213> ORGANISM: Homo sapiens

<400> SEQUENCE: 401

Phe Ile Arg Tyr Asp Gly Ser Asn Lys Ile Tyr Ala Asp Ser Val Lys
 1               5                  10                  15

Gly

<210> SEQ ID NO 402
<211> LENGTH: 17
<212> TYPE: PRT
<213> ORGANISM: Homo sapiens

<400> SEQUENCE: 402

Phe Ile Arg Tyr Asp Gly Ser Asn Lys Pro Tyr Ala Asp Ser Val Lys
1               5                   10                  15

Gly

<210> SEQ ID NO 403
<211> LENGTH: 17
<212> TYPE: PRT
<213> ORGANISM: Homo sapiens

<400> SEQUENCE: 403

Phe Ile Arg Tyr Asp Gly Ser Asn Lys Phe Tyr Ala Asp Ser Val Lys
1               5                   10                  15

Gly

<210> SEQ ID NO 404
<211> LENGTH: 6
<212> TYPE: PRT
<213> ORGANISM: Homo sapiens

<400> SEQUENCE: 404

Glu Gly Ser His Asp Asn
1               5

<210> SEQ ID NO 405
<211> LENGTH: 6
<212> TYPE: PRT
<213> ORGANISM: Homo sapiens

<400> SEQUENCE: 405

Ser Gly Ser His Asp Asn
1               5

<210> SEQ ID NO 406
<211> LENGTH: 6
<212> TYPE: PRT
<213> ORGANISM: Homo sapiens

<400> SEQUENCE: 406

His Gly Ser His Asp Asn
1               5

<210> SEQ ID NO 407
<211> LENGTH: 6
<212> TYPE: PRT
<213> ORGANISM: Homo sapiens

<400> SEQUENCE: 407

Lys Gly Ser His Asp Asn
1               5

<210> SEQ ID NO 408
<211> LENGTH: 6
<212> TYPE: PRT
<213> ORGANISM: Homo sapiens

<400> SEQUENCE: 408

Gln Gly Ser His Asp Asn
1               5

<210> SEQ ID NO 409
<211> LENGTH: 6
<212> TYPE: PRT
<213> ORGANISM: Homo sapiens

<400> SEQUENCE: 409

Thr Gly Ser His Asp Asn
1               5

<210> SEQ ID NO 410
<211> LENGTH: 6
<212> TYPE: PRT
<213> ORGANISM: Homo sapiens

<400> SEQUENCE: 410

Ala Gly Ser His Asp Asn
1               5

<210> SEQ ID NO 411
<211> LENGTH: 6
<212> TYPE: PRT
<213> ORGANISM: Homo sapiens

<400> SEQUENCE: 411

Leu Gly Ser His Asp Asn
1               5

<210> SEQ ID NO 412
<211> LENGTH: 6
<212> TYPE: PRT
<213> ORGANISM: Homo sapiens

<400> SEQUENCE: 412

Pro Gly Ser His Asp Asn
1               5

<210> SEQ ID NO 413
<211> LENGTH: 6
<212> TYPE: PRT
<213> ORGANISM: Homo sapiens

<400> SEQUENCE: 413

Phe Gly Ser His Asp Asn
1               5

<210> SEQ ID NO 414
<211> LENGTH: 6
<212> TYPE: PRT
<213> ORGANISM: Homo sapiens

<400> SEQUENCE: 414

His Asp Ser His Asp Asn
1               5

<210> SEQ ID NO 415
<211> LENGTH: 6
<212> TYPE: PRT
<213> ORGANISM: Homo sapiens

<400> SEQUENCE: 415

His Cys Ser His Asp Asn

-continued

```
          1               5

<210> SEQ ID NO 416
<211> LENGTH: 6
<212> TYPE: PRT
<213> ORGANISM: Homo sapiens

<400> SEQUENCE: 416

His His Ser His Asp Asn
  1               5

<210> SEQ ID NO 417
<211> LENGTH: 6
<212> TYPE: PRT
<213> ORGANISM: Homo sapiens

<400> SEQUENCE: 417

His Arg Ser His Asp Asn
  1               5

<210> SEQ ID NO 418
<211> LENGTH: 6
<212> TYPE: PRT
<213> ORGANISM: Homo sapiens

<400> SEQUENCE: 418

His Thr Ser His Asp Asn
  1               5

<210> SEQ ID NO 419
<211> LENGTH: 6
<212> TYPE: PRT
<213> ORGANISM: Homo sapiens

<400> SEQUENCE: 419

His Gly Ser His Asp Asn
  1               5

<210> SEQ ID NO 420
<211> LENGTH: 6
<212> TYPE: PRT
<213> ORGANISM: Homo sapiens

<400> SEQUENCE: 420

His Val Ser His Asp Asn
  1               5

<210> SEQ ID NO 421
<211> LENGTH: 6
<212> TYPE: PRT
<213> ORGANISM: Homo sapiens

<400> SEQUENCE: 421

His Met Ser His Asp Asn
  1               5

<210> SEQ ID NO 422
<211> LENGTH: 6
<212> TYPE: PRT
<213> ORGANISM: Homo sapiens

<400> SEQUENCE: 422

His Leu Ser His Asp Asn
  1               5
```

```
<210> SEQ ID NO 423
<211> LENGTH: 6
<212> TYPE: PRT
<213> ORGANISM: Homo sapiens

<400> SEQUENCE: 423

His Ile Ser His Asp Asn
 1               5

<210> SEQ ID NO 424
<211> LENGTH: 6
<212> TYPE: PRT
<213> ORGANISM: Homo sapiens

<400> SEQUENCE: 424

His Pro Ser His Asp Asn
 1               5

<210> SEQ ID NO 425
<211> LENGTH: 6
<212> TYPE: PRT
<213> ORGANISM: Homo sapiens

<400> SEQUENCE: 425

His Trp Ser His Asp Asn
 1               5

<210> SEQ ID NO 426
<211> LENGTH: 6
<212> TYPE: PRT
<213> ORGANISM: Homo sapiens

<400> SEQUENCE: 426

His Gly Asp His Asp Asn
 1               5

<210> SEQ ID NO 427
<211> LENGTH: 6
<212> TYPE: PRT
<213> ORGANISM: Homo sapiens

<400> SEQUENCE: 427

His Gly Ser His Asp Asn
 1               5

<210> SEQ ID NO 428
<211> LENGTH: 6
<212> TYPE: PRT
<213> ORGANISM: Homo sapiens

<400> SEQUENCE: 428

His Gly Tyr His Asp Asn
 1               5

<210> SEQ ID NO 429
<211> LENGTH: 6
<212> TYPE: PRT
<213> ORGANISM: Homo sapiens

<400> SEQUENCE: 429

His Gly His His Asp Asn
 1               5

<210> SEQ ID NO 430
```

```
<211> LENGTH: 6
<212> TYPE: PRT
<213> ORGANISM: Homo sapiens

<400> SEQUENCE: 430

His Gly Arg His Asp Asn
  1               5

<210> SEQ ID NO 431
<211> LENGTH: 6
<212> TYPE: PRT
<213> ORGANISM: Homo sapiens

<400> SEQUENCE: 431

His Gly Asn His Asp Asn
  1               5

<210> SEQ ID NO 432
<211> LENGTH: 6
<212> TYPE: PRT
<213> ORGANISM: Homo sapiens

<400> SEQUENCE: 432

His Gly Thr His Asp Asn
  1               5

<210> SEQ ID NO 433
<211> LENGTH: 6
<212> TYPE: PRT
<213> ORGANISM: Homo sapiens

<400> SEQUENCE: 433

His Gly Gly His Asp Asn
  1               5

<210> SEQ ID NO 434
<211> LENGTH: 6
<212> TYPE: PRT
<213> ORGANISM: Homo sapiens

<400> SEQUENCE: 434

His Gly Ala His Asp Asn
  1               5

<210> SEQ ID NO 435
<211> LENGTH: 6
<212> TYPE: PRT
<213> ORGANISM: Homo sapiens

<400> SEQUENCE: 435

His Gly Ile His Asp Asn
  1               5

<210> SEQ ID NO 436
<211> LENGTH: 6
<212> TYPE: PRT
<213> ORGANISM: Homo sapiens

<400> SEQUENCE: 436

His Gly Pro His Asp Asn
  1               5

<210> SEQ ID NO 437
<211> LENGTH: 6
<212> TYPE: PRT
```

```
<213> ORGANISM: Homo sapiens

<400> SEQUENCE: 437

His Gly Trp His Asp Asn
1               5

<210> SEQ ID NO 438
<211> LENGTH: 6
<212> TYPE: PRT
<213> ORGANISM: Homo sapiens

<400> SEQUENCE: 438

His Gly Phe His Asp Asn
1               5

<210> SEQ ID NO 439
<211> LENGTH: 6
<212> TYPE: PRT
<213> ORGANISM: Homo sapiens

<400> SEQUENCE: 439

His Gly Ser His Asp Asn
1               5

<210> SEQ ID NO 440
<211> LENGTH: 6
<212> TYPE: PRT
<213> ORGANISM: Homo sapiens

<400> SEQUENCE: 440

His Gly Ser Arg Asp Asn
1               5

<210> SEQ ID NO 441
<211> LENGTH: 6
<212> TYPE: PRT
<213> ORGANISM: Homo sapiens

<400> SEQUENCE: 441

His Gly Ser Thr Asp Asn
1               5

<210> SEQ ID NO 442
<211> LENGTH: 6
<212> TYPE: PRT
<213> ORGANISM: Homo sapiens

<400> SEQUENCE: 442

His Gly Ser Ala Asp Asn
1               5

<210> SEQ ID NO 443
<211> LENGTH: 6
<212> TYPE: PRT
<213> ORGANISM: Homo sapiens

<400> SEQUENCE: 443

His Gly Ser Val Asp Asn
1               5

<210> SEQ ID NO 444
<211> LENGTH: 6
<212> TYPE: PRT
<213> ORGANISM: Homo sapiens
```

```
<400> SEQUENCE: 444

His Gly Ser Leu Asp Asn
 1               5

<210> SEQ ID NO 445
<211> LENGTH: 6
<212> TYPE: PRT
<213> ORGANISM: Homo sapiens

<400> SEQUENCE: 445

His Gly Ser Ile Asp Asn
 1               5

<210> SEQ ID NO 446
<211> LENGTH: 6
<212> TYPE: PRT
<213> ORGANISM: Homo sapiens

<400> SEQUENCE: 446

His Gly Ser Phe Asp Asn
 1               5

<210> SEQ ID NO 447
<211> LENGTH: 6
<212> TYPE: PRT
<213> ORGANISM: Homo sapiens

<400> SEQUENCE: 447

His Gly Ser His Asp Asn
 1               5

<210> SEQ ID NO 448
<211> LENGTH: 6
<212> TYPE: PRT
<213> ORGANISM: Homo sapiens

<400> SEQUENCE: 448

His Gly Ser His Ser Asn
 1               5

<210> SEQ ID NO 449
<211> LENGTH: 6
<212> TYPE: PRT
<213> ORGANISM: Homo sapiens

<400> SEQUENCE: 449

His Gly Ser His Tyr Asn
 1               5

<210> SEQ ID NO 450
<211> LENGTH: 6
<212> TYPE: PRT
<213> ORGANISM: Homo sapiens

<400> SEQUENCE: 450

His Gly Ser His His Asn
 1               5

<210> SEQ ID NO 451
<211> LENGTH: 6
<212> TYPE: PRT
<213> ORGANISM: Homo sapiens

<400> SEQUENCE: 451
```

His Gly Ser His Arg Asn
1               5

<210> SEQ ID NO 452
<211> LENGTH: 6
<212> TYPE: PRT
<213> ORGANISM: Homo sapiens

<400> SEQUENCE: 452

His Gly Ser His Asn Asn
1               5

<210> SEQ ID NO 453
<211> LENGTH: 6
<212> TYPE: PRT
<213> ORGANISM: Homo sapiens

<400> SEQUENCE: 453

His Gly Ser His Gly Asn
1               5

<210> SEQ ID NO 454
<211> LENGTH: 6
<212> TYPE: PRT
<213> ORGANISM: Homo sapiens

<400> SEQUENCE: 454

His Gly Ser His Ala Asn
1               5

<210> SEQ ID NO 455
<211> LENGTH: 6
<212> TYPE: PRT
<213> ORGANISM: Homo sapiens

<400> SEQUENCE: 455

His Gly Ser His Val Asn
1               5

<210> SEQ ID NO 456
<211> LENGTH: 6
<212> TYPE: PRT
<213> ORGANISM: Homo sapiens

<400> SEQUENCE: 456

His Gly Ser His Ile Asn
1               5

<210> SEQ ID NO 457
<211> LENGTH: 6
<212> TYPE: PRT
<213> ORGANISM: Homo sapiens

<400> SEQUENCE: 457

His Gly Ser His Asp Ser
1               5

<210> SEQ ID NO 458
<211> LENGTH: 6
<212> TYPE: PRT
<213> ORGANISM: Homo sapiens

<400> SEQUENCE: 458

His Gly Ser His Asp His
1               5

<210> SEQ ID NO 459
<211> LENGTH: 6
<212> TYPE: PRT
<213> ORGANISM: Homo sapiens

<400> SEQUENCE: 459

His Gly Ser His Asp Lys
1               5

<210> SEQ ID NO 460
<211> LENGTH: 6
<212> TYPE: PRT
<213> ORGANISM: Homo sapiens

<400> SEQUENCE: 460

His Gly Ser His Asp Arg
1               5

<210> SEQ ID NO 461
<211> LENGTH: 6
<212> TYPE: PRT
<213> ORGANISM: Homo sapiens

<400> SEQUENCE: 461

His Gly Ser His Asp Asn
1               5

<210> SEQ ID NO 462
<211> LENGTH: 6
<212> TYPE: PRT
<213> ORGANISM: Homo sapiens

<400> SEQUENCE: 462

His Gly Ser His Asp Thr
1               5

<210> SEQ ID NO 463
<211> LENGTH: 6
<212> TYPE: PRT
<213> ORGANISM: Homo sapiens

<400> SEQUENCE: 463

His Gly Ser His Asp Gly
1               5

<210> SEQ ID NO 464
<211> LENGTH: 6
<212> TYPE: PRT
<213> ORGANISM: Homo sapiens

<400> SEQUENCE: 464

His Gly Ser His Asp Ala
1               5

<210> SEQ ID NO 465
<211> LENGTH: 6
<212> TYPE: PRT
<213> ORGANISM: Homo sapiens

<400> SEQUENCE: 465

His Gly Ser His Asp Leu
1               5

<210> SEQ ID NO 466
<211> LENGTH: 6
<212> TYPE: PRT
<213> ORGANISM: Homo sapiens

<400> SEQUENCE: 466

His Gly Ser His Asp Ile
1               5

<210> SEQ ID NO 467
<211> LENGTH: 6
<212> TYPE: PRT
<213> ORGANISM: Homo sapiens

<400> SEQUENCE: 467

His Gly Ser His Asp Pro
1               5

<210> SEQ ID NO 468
<211> LENGTH: 6
<212> TYPE: PRT
<213> ORGANISM: Homo sapiens

<400> SEQUENCE: 468

His Gly Ser His Asp Trp
1               5

<210> SEQ ID NO 469
<211> LENGTH: 6
<212> TYPE: PRT
<213> ORGANISM: Homo sapiens

<400> SEQUENCE: 469

His Gly Ser His Asp Phe
1               5

<210> SEQ ID NO 470
<211> LENGTH: 13
<212> TYPE: PRT
<213> ORGANISM: Homo sapiens

<400> SEQUENCE: 470

Ser Gly Gly Arg Ser Asn Ile Gly Asp Asn Thr Val Lys
1               5                   10

<210> SEQ ID NO 471
<211> LENGTH: 13
<212> TYPE: PRT
<213> ORGANISM: Homo sapiens

<400> SEQUENCE: 471

Ser Gly Gly Arg Ser Asn Ile Gly Cys Asn Thr Val Lys
1               5                   10

<210> SEQ ID NO 472
<211> LENGTH: 13
<212> TYPE: PRT
<213> ORGANISM: Homo sapiens

<400> SEQUENCE: 472

Ser Gly Gly Arg Ser Asn Ile Gly Ser Asn Thr Val Lys
1               5                   10

<210> SEQ ID NO 473
<211> LENGTH: 13

<210> SEQ ID NO 473
<211> LENGTH: 13
<212> TYPE: PRT
<213> ORGANISM: Homo sapiens

<400> SEQUENCE: 473

Ser Gly Gly Arg Ser Asn Ile Gly Tyr Asn Thr Val Lys
 1               5                  10

<210> SEQ ID NO 474
<211> LENGTH: 13
<212> TYPE: PRT
<213> ORGANISM: Homo sapiens

<400> SEQUENCE: 474

Ser Gly Gly Arg Ser Asn Ile Gly Lys Asn Thr Val Lys
 1               5                  10

<210> SEQ ID NO 475
<211> LENGTH: 13
<212> TYPE: PRT
<213> ORGANISM: Homo sapiens

<400> SEQUENCE: 475

Ser Gly Gly Arg Ser Asn Ile Gly Arg Asn Thr Val Lys
 1               5                  10

<210> SEQ ID NO 476
<211> LENGTH: 13
<212> TYPE: PRT
<213> ORGANISM: Homo sapiens

<400> SEQUENCE: 476

Ser Gly Gly Arg Ser Asn Ile Gly Asn Asn Thr Val Lys
 1               5                  10

<210> SEQ ID NO 477
<211> LENGTH: 13
<212> TYPE: PRT
<213> ORGANISM: Homo sapiens

<400> SEQUENCE: 477

Ser Gly Gly Arg Ser Asn Ile Gly Thr Asn Thr Val Lys
 1               5                  10

<210> SEQ ID NO 478
<211> LENGTH: 13
<212> TYPE: PRT
<213> ORGANISM: Homo sapiens

<400> SEQUENCE: 478

Ser Gly Gly Arg Ser Asn Ile Gly Pro Asn Thr Val Lys
 1               5                  10

<210> SEQ ID NO 479
<211> LENGTH: 13
<212> TYPE: PRT
<213> ORGANISM: Homo sapiens

<400> SEQUENCE: 479

Ser Gly Gly Arg Ser Asn Ile Gly Ser Asp Thr Val Lys
 1               5                  10

<210> SEQ ID NO 480
<211> LENGTH: 13
<212> TYPE: PRT
<213> ORGANISM: Homo sapiens

<400> SEQUENCE: 480

Ser Gly Gly Arg Ser Asn Ile Gly Ser Glu Thr Val Lys
 1               5                   10

<210> SEQ ID NO 481
<211> LENGTH: 13
<212> TYPE: PRT
<213> ORGANISM: Homo sapiens

<400> SEQUENCE: 481

Ser Gly Gly Arg Ser Asn Ile Gly Ser Ser Thr Val Lys
 1               5                   10

<210> SEQ ID NO 482
<211> LENGTH: 13
<212> TYPE: PRT
<213> ORGANISM: Homo sapiens

<400> SEQUENCE: 482

Ser Gly Gly Arg Ser Asn Ile Gly Ser Tyr Thr Val Lys
 1               5                   10

<210> SEQ ID NO 483
<211> LENGTH: 13
<212> TYPE: PRT
<213> ORGANISM: Homo sapiens

<400> SEQUENCE: 483

Ser Gly Gly Arg Ser Asn Ile Gly Ser His Thr Val Lys
 1               5                   10

<210> SEQ ID NO 484
<211> LENGTH: 13
<212> TYPE: PRT
<213> ORGANISM: Homo sapiens

<400> SEQUENCE: 484

Ser Gly Gly Arg Ser Asn Ile Gly Ser Lys Thr Val Lys
 1               5                   10

<210> SEQ ID NO 485
<211> LENGTH: 13
<212> TYPE: PRT
<213> ORGANISM: Homo sapiens

<400> SEQUENCE: 485

Ser Gly Gly Arg Ser Asn Ile Gly Ser Asn Thr Val Lys
 1               5                   10

<210> SEQ ID NO 486
<211> LENGTH: 13
<212> TYPE: PRT
<213> ORGANISM: Homo sapiens

<400> SEQUENCE: 486

Ser Gly Gly Arg Ser Asn Ile Gly Ser Gln Thr Val Lys
 1               5                   10

<210> SEQ ID NO 487
<211> LENGTH: 13
<212> TYPE: PRT
<213> ORGANISM: Homo sapiens

<400> SEQUENCE: 487

Ser Gly Gly Arg Ser Asn Ile Gly Ser Thr Thr Val Lys
1               5                   10

<210> SEQ ID NO 488
<211> LENGTH: 13
<212> TYPE: PRT
<213> ORGANISM: Homo sapiens

<400> SEQUENCE: 488

Ser Gly Gly Arg Ser Asn Ile Gly Ser Gly Thr Val Lys
1               5                   10

<210> SEQ ID NO 489
<211> LENGTH: 13
<212> TYPE: PRT
<213> ORGANISM: Homo sapiens

<400> SEQUENCE: 489

Ser Gly Gly Arg Ser Asn Ile Gly Ser Met Thr Val Lys
1               5                   10

<210> SEQ ID NO 490
<211> LENGTH: 13
<212> TYPE: PRT
<213> ORGANISM: Homo sapiens

<400> SEQUENCE: 490

Ser Gly Gly Arg Ser Asn Ile Gly Ser Ile Thr Val Lys
1               5                   10

<210> SEQ ID NO 491
<211> LENGTH: 13
<212> TYPE: PRT
<213> ORGANISM: Homo sapiens

<400> SEQUENCE: 491

Ser Gly Gly Arg Ser Asn Ile Gly Ser Asn Asp Val Lys
1               5                   10

<210> SEQ ID NO 492
<211> LENGTH: 13
<212> TYPE: PRT
<213> ORGANISM: Homo sapiens

<400> SEQUENCE: 492

Ser Gly Gly Arg Ser Asn Ile Gly Ser Asn Cys Val Lys
1               5                   10

<210> SEQ ID NO 493
<211> LENGTH: 13
<212> TYPE: PRT
<213> ORGANISM: Homo sapiens

<400> SEQUENCE: 493

Ser Gly Gly Arg Ser Asn Ile Gly Ser Asn Ser Val Lys
1               5                   10

<210> SEQ ID NO 494
<211> LENGTH: 13
<212> TYPE: PRT
<213> ORGANISM: Homo sapiens

<400> SEQUENCE: 494

Ser Gly Gly Arg Ser Asn Ile Gly Ser Asn Tyr Val Lys

```
         1               5                   10
```

<210> SEQ ID NO 495
<211> LENGTH: 13
<212> TYPE: PRT
<213> ORGANISM: Homo sapiens

<400> SEQUENCE: 495

Ser Gly Gly Arg Ser Asn Ile Gly Ser Asn His Val Lys
 1               5                   10

<210> SEQ ID NO 496
<211> LENGTH: 13
<212> TYPE: PRT
<213> ORGANISM: Homo sapiens

<400> SEQUENCE: 496

Ser Gly Gly Arg Ser Asn Ile Gly Ser Asn Lys Val Lys
 1               5                   10

<210> SEQ ID NO 497
<211> LENGTH: 13
<212> TYPE: PRT
<213> ORGANISM: Homo sapiens

<400> SEQUENCE: 497

Ser Gly Gly Arg Ser Asn Ile Gly Ser Asn Arg Val Lys
 1               5                   10

<210> SEQ ID NO 498
<211> LENGTH: 13
<212> TYPE: PRT
<213> ORGANISM: Homo sapiens

<400> SEQUENCE: 498

Ser Gly Gly Arg Ser Asn Ile Gly Ser Asn Asn Val Lys
 1               5                   10

<210> SEQ ID NO 499
<211> LENGTH: 13
<212> TYPE: PRT
<213> ORGANISM: Homo sapiens

<400> SEQUENCE: 499

Ser Gly Gly Arg Ser Asn Ile Gly Ser Asn Gln Val Lys
 1               5                   10

<210> SEQ ID NO 500
<211> LENGTH: 13
<212> TYPE: PRT
<213> ORGANISM: Homo sapiens

<400> SEQUENCE: 500

Ser Gly Gly Arg Ser Asn Ile Gly Ser Asn Thr Val Lys
 1               5                   10

<210> SEQ ID NO 501
<211> LENGTH: 13
<212> TYPE: PRT
<213> ORGANISM: Homo sapiens

<400> SEQUENCE: 501

Ser Gly Gly Arg Ser Asn Ile Gly Ser Asn Ala Val Lys
 1               5                   10

<210> SEQ ID NO 502
<211> LENGTH: 13
<212> TYPE: PRT
<213> ORGANISM: Homo sapiens

<400> SEQUENCE: 502

Ser Gly Gly Arg Ser Asn Ile Gly Ser Asn Val Val Lys
1               5                   10

<210> SEQ ID NO 503
<211> LENGTH: 13
<212> TYPE: PRT
<213> ORGANISM: Homo sapiens

<400> SEQUENCE: 503

Ser Gly Gly Arg Ser Asn Ile Gly Ser Asn Leu Val Lys
1               5                   10

<210> SEQ ID NO 504
<211> LENGTH: 13
<212> TYPE: PRT
<213> ORGANISM: Homo sapiens

<400> SEQUENCE: 504

Ser Gly Gly Arg Ser Asn Ile Gly Ser Asn Ile Val Lys
1               5                   10

<210> SEQ ID NO 505
<211> LENGTH: 13
<212> TYPE: PRT
<213> ORGANISM: Homo sapiens

<400> SEQUENCE: 505

Ser Gly Gly Arg Ser Asn Ile Gly Ser Asn Pro Val Lys
1               5                   10

<210> SEQ ID NO 506
<211> LENGTH: 7
<212> TYPE: PRT
<213> ORGANISM: Homo sapiens

<400> SEQUENCE: 506

Asp Asn Asp Gln Arg Pro Ser
1               5

<210> SEQ ID NO 507
<211> LENGTH: 7
<212> TYPE: PRT
<213> ORGANISM: Homo sapiens

<400> SEQUENCE: 507

Glu Asn Asp Gln Arg Pro Ser
1               5

<210> SEQ ID NO 508
<211> LENGTH: 7
<212> TYPE: PRT
<213> ORGANISM: Homo sapiens

<400> SEQUENCE: 508

Cys Asn Asp Gln Arg Pro Ser
1               5

<210> SEQ ID NO 509

```
<211> LENGTH: 7
<212> TYPE: PRT
<213> ORGANISM: Homo sapiens

<400> SEQUENCE: 509

Ser Asn Asp Gln Arg Pro Ser
 1               5

<210> SEQ ID NO 510
<211> LENGTH: 7
<212> TYPE: PRT
<213> ORGANISM: Homo sapiens

<400> SEQUENCE: 510

Tyr Asn Asp Gln Arg Pro Ser
 1               5

<210> SEQ ID NO 511
<211> LENGTH: 7
<212> TYPE: PRT
<213> ORGANISM: Homo sapiens

<400> SEQUENCE: 511

His Asn Asp Gln Arg Pro Ser
 1               5

<210> SEQ ID NO 512
<211> LENGTH: 7
<212> TYPE: PRT
<213> ORGANISM: Homo sapiens

<400> SEQUENCE: 512

Lys Asn Asp Gln Arg Pro Ser
 1               5

<210> SEQ ID NO 513
<211> LENGTH: 7
<212> TYPE: PRT
<213> ORGANISM: Homo sapiens

<400> SEQUENCE: 513

Arg Asn Asp Gln Arg Pro Ser
 1               5

<210> SEQ ID NO 514
<211> LENGTH: 7
<212> TYPE: PRT
<213> ORGANISM: Homo sapiens

<400> SEQUENCE: 514

Asn Asn Asp Gln Arg Pro Ser
 1               5

<210> SEQ ID NO 515
<211> LENGTH: 7
<212> TYPE: PRT
<213> ORGANISM: Homo sapiens

<400> SEQUENCE: 515

Gln Asn Asp Gln Arg Pro Ser
 1               5

<210> SEQ ID NO 516
<211> LENGTH: 7
<212> TYPE: PRT
```

```
<213> ORGANISM: Homo sapiens

<400> SEQUENCE: 516

Thr Asn Asp Gln Arg Pro Ser
 1               5

<210> SEQ ID NO 517
<211> LENGTH: 7
<212> TYPE: PRT
<213> ORGANISM: Homo sapiens

<400> SEQUENCE: 517

Gly Asn Asp Gln Arg Pro Ser
 1               5

<210> SEQ ID NO 518
<211> LENGTH: 7
<212> TYPE: PRT
<213> ORGANISM: Homo sapiens

<400> SEQUENCE: 518

Ala Asn Asp Gln Arg Pro Ser
 1               5

<210> SEQ ID NO 519
<211> LENGTH: 7
<212> TYPE: PRT
<213> ORGANISM: Homo sapiens

<400> SEQUENCE: 519

Val Asn Asp Gln Arg Pro Ser
 1               5

<210> SEQ ID NO 520
<211> LENGTH: 7
<212> TYPE: PRT
<213> ORGANISM: Homo sapiens

<400> SEQUENCE: 520

Met Asn Asp Gln Arg Pro Ser
 1               5

<210> SEQ ID NO 521
<211> LENGTH: 7
<212> TYPE: PRT
<213> ORGANISM: Homo sapiens

<400> SEQUENCE: 521

Leu Asn Asp Gln Arg Pro Ser
 1               5

<210> SEQ ID NO 522
<211> LENGTH: 7
<212> TYPE: PRT
<213> ORGANISM: Homo sapiens

<400> SEQUENCE: 522

Ile Asn Asp Gln Arg Pro Ser
 1               5

<210> SEQ ID NO 523
<211> LENGTH: 7
<212> TYPE: PRT
<213> ORGANISM: Homo sapiens
```

<400> SEQUENCE: 523

Pro Asn Asp Gln Arg Pro Ser
1               5

<210> SEQ ID NO 524
<211> LENGTH: 7
<212> TYPE: PRT
<213> ORGANISM: Homo sapiens

<400> SEQUENCE: 524

Trp Asn Asp Gln Arg Pro Ser
1               5

<210> SEQ ID NO 525
<211> LENGTH: 7
<212> TYPE: PRT
<213> ORGANISM: Homo sapiens

<400> SEQUENCE: 525

Phe Asn Asp Gln Arg Pro Ser
1               5

<210> SEQ ID NO 526
<211> LENGTH: 7
<212> TYPE: PRT
<213> ORGANISM: Homo sapiens

<400> SEQUENCE: 526

Gly Asn Asp Ser Arg Pro Ser
1               5

<210> SEQ ID NO 527
<211> LENGTH: 7
<212> TYPE: PRT
<213> ORGANISM: Homo sapiens

<400> SEQUENCE: 527

Gly Asn Asp Tyr Arg Pro Ser
1               5

<210> SEQ ID NO 528
<211> LENGTH: 7
<212> TYPE: PRT
<213> ORGANISM: Homo sapiens

<400> SEQUENCE: 528

Gly Asn Asp Arg Arg Pro Ser
1               5

<210> SEQ ID NO 529
<211> LENGTH: 7
<212> TYPE: PRT
<213> ORGANISM: Homo sapiens

<400> SEQUENCE: 529

Gly Asn Asp Gln Arg Pro Ser
1               5

<210> SEQ ID NO 530
<211> LENGTH: 7
<212> TYPE: PRT
<213> ORGANISM: Homo sapiens

<400> SEQUENCE: 530

Gly Asn Asp Thr Arg Pro Ser
1               5

<210> SEQ ID NO 531
<211> LENGTH: 7
<212> TYPE: PRT
<213> ORGANISM: Homo sapiens

<400> SEQUENCE: 531

Gly Asn Asp Ala Arg Pro Ser
1               5

<210> SEQ ID NO 532
<211> LENGTH: 7
<212> TYPE: PRT
<213> ORGANISM: Homo sapiens

<400> SEQUENCE: 532

Gly Asn Asp Ile Arg Pro Ser
1               5

<210> SEQ ID NO 533
<211> LENGTH: 7
<212> TYPE: PRT
<213> ORGANISM: Homo sapiens

<400> SEQUENCE: 533

Gly Asn Asp Pro Arg Pro Ser
1               5

<210> SEQ ID NO 534
<211> LENGTH: 12
<212> TYPE: PRT
<213> ORGANISM: Homo sapiens

<400> SEQUENCE: 534

Gln Ser Tyr Asp Arg Gly Thr His Pro Ala Leu Leu
1               5                   10

<210> SEQ ID NO 535
<211> LENGTH: 12
<212> TYPE: PRT
<213> ORGANISM: Homo sapiens

<400> SEQUENCE: 535

Gln Ser Tyr Cys Arg Gly Thr His Pro Ala Leu Leu
1               5                   10

<210> SEQ ID NO 536
<211> LENGTH: 12
<212> TYPE: PRT
<213> ORGANISM: Homo sapiens

<400> SEQUENCE: 536

Gln Ser Tyr Ser Arg Gly Thr His Pro Ala Leu Leu
1               5                   10

<210> SEQ ID NO 537
<211> LENGTH: 12
<212> TYPE: PRT
<213> ORGANISM: Homo sapiens

<400> SEQUENCE: 537

Gln Ser Tyr Tyr Arg Gly Thr His Pro Ala Leu Leu
1               5                   10

<210> SEQ ID NO 538
<211> LENGTH: 12
<212> TYPE: PRT
<213> ORGANISM: Homo sapiens

<400> SEQUENCE: 538

Gln Ser Tyr Asn Arg Gly Thr His Pro Ala Leu Leu
 1               5                  10

<210> SEQ ID NO 539
<211> LENGTH: 12
<212> TYPE: PRT
<213> ORGANISM: Homo sapiens

<400> SEQUENCE: 539

Gln Ser Tyr Gln Arg Gly Thr His Pro Ala Leu Leu
 1               5                  10

<210> SEQ ID NO 540
<211> LENGTH: 12
<212> TYPE: PRT
<213> ORGANISM: Homo sapiens

<400> SEQUENCE: 540

Gln Ser Tyr Thr Arg Gly Thr His Pro Ala Leu Leu
 1               5                  10

<210> SEQ ID NO 541
<211> LENGTH: 12
<212> TYPE: PRT
<213> ORGANISM: Homo sapiens

<400> SEQUENCE: 541

Gln Ser Tyr Gly Arg Gly Thr His Pro Ala Leu Leu
 1               5                  10

<210> SEQ ID NO 542
<211> LENGTH: 12
<212> TYPE: PRT
<213> ORGANISM: Homo sapiens

<400> SEQUENCE: 542

Gln Ser Tyr Ala Arg Gly Thr His Pro Ala Leu Leu
 1               5                  10

<210> SEQ ID NO 543
<211> LENGTH: 12
<212> TYPE: PRT
<213> ORGANISM: Homo sapiens

<400> SEQUENCE: 543

Gln Ser Tyr Leu Arg Gly Thr His Pro Ala Leu Leu
 1               5                  10

<210> SEQ ID NO 544
<211> LENGTH: 12
<212> TYPE: PRT
<213> ORGANISM: Homo sapiens

<400> SEQUENCE: 544

Gln Ser Tyr Ile Arg Gly Thr His Pro Ala Leu Leu
 1               5                  10

```
<210> SEQ ID NO 545
<211> LENGTH: 12
<212> TYPE: PRT
<213> ORGANISM: Homo sapiens

<400> SEQUENCE: 545

Gln Ser Tyr Trp Arg Gly Thr His Pro Ala Leu Leu
1               5                   10

<210> SEQ ID NO 546
<211> LENGTH: 12
<212> TYPE: PRT
<213> ORGANISM: Homo sapiens

<400> SEQUENCE: 546

Gln Ser Tyr Phe Arg Gly Thr His Pro Ala Leu Leu
1               5                   10

<210> SEQ ID NO 547
<211> LENGTH: 12
<212> TYPE: PRT
<213> ORGANISM: Homo sapiens

<400> SEQUENCE: 547

Gln Ser Tyr Asp Asp Gly Thr His Pro Ala Leu Leu
1               5                   10

<210> SEQ ID NO 548
<211> LENGTH: 12
<212> TYPE: PRT
<213> ORGANISM: Homo sapiens

<400> SEQUENCE: 548

Gln Ser Tyr Asp Cys Gly Thr His Pro Ala Leu Leu
1               5                   10

<210> SEQ ID NO 549
<211> LENGTH: 12
<212> TYPE: PRT
<213> ORGANISM: Homo sapiens

<400> SEQUENCE: 549

Gln Ser Tyr Asp Ser Gly Thr His Pro Ala Leu Leu
1               5                   10

<210> SEQ ID NO 550
<211> LENGTH: 12
<212> TYPE: PRT
<213> ORGANISM: Homo sapiens

<400> SEQUENCE: 550

Gln Ser Tyr Asp Tyr Gly Thr His Pro Ala Leu Leu
1               5                   10

<210> SEQ ID NO 551
<211> LENGTH: 12
<212> TYPE: PRT
<213> ORGANISM: Homo sapiens

<400> SEQUENCE: 551

Gln Ser Tyr Asp Arg Gly Thr His Pro Ala Leu Leu
1               5                   10

<210> SEQ ID NO 552
<211> LENGTH: 12
```

```
<212> TYPE: PRT
<213> ORGANISM: Homo sapiens

<400> SEQUENCE: 552

Gln Ser Tyr Asp Asn Gly Thr His Pro Ala Leu Leu
 1               5                  10

<210> SEQ ID NO 553
<211> LENGTH: 12
<212> TYPE: PRT
<213> ORGANISM: Homo sapiens

<400> SEQUENCE: 553

Gln Ser Tyr Asp Gln Gly Thr His Pro Ala Leu Leu
 1               5                  10

<210> SEQ ID NO 554
<211> LENGTH: 12
<212> TYPE: PRT
<213> ORGANISM: Homo sapiens

<400> SEQUENCE: 554

Gln Ser Tyr Asp Thr Gly Thr His Pro Ala Leu Leu
 1               5                  10

<210> SEQ ID NO 555
<211> LENGTH: 12
<212> TYPE: PRT
<213> ORGANISM: Homo sapiens

<400> SEQUENCE: 555

Gln Ser Tyr Asp Gly Gly Thr His Pro Ala Leu Leu
 1               5                  10

<210> SEQ ID NO 556
<211> LENGTH: 12
<212> TYPE: PRT
<213> ORGANISM: Homo sapiens

<400> SEQUENCE: 556

Gln Ser Tyr Asp Ala Gly Thr His Pro Ala Leu Leu
 1               5                  10

<210> SEQ ID NO 557
<211> LENGTH: 12
<212> TYPE: PRT
<213> ORGANISM: Homo sapiens

<400> SEQUENCE: 557

Gln Ser Tyr Asp Val Gly Thr His Pro Ala Leu Leu
 1               5                  10

<210> SEQ ID NO 558
<211> LENGTH: 12
<212> TYPE: PRT
<213> ORGANISM: Homo sapiens

<400> SEQUENCE: 558

Gln Ser Tyr Asp Met Gly Thr His Pro Ala Leu Leu
 1               5                  10

<210> SEQ ID NO 559
<211> LENGTH: 12
<212> TYPE: PRT
<213> ORGANISM: Homo sapiens
```

<400> SEQUENCE: 559

Gln Ser Tyr Asp Leu Gly Thr His Pro Ala Leu Leu
1               5                   10

<210> SEQ ID NO 560
<211> LENGTH: 12
<212> TYPE: PRT
<213> ORGANISM: Homo sapiens

<400> SEQUENCE: 560

Gln Ser Tyr Asp Ile Gly Thr His Pro Ala Leu Leu
1               5                   10

<210> SEQ ID NO 561
<211> LENGTH: 12
<212> TYPE: PRT
<213> ORGANISM: Homo sapiens

<400> SEQUENCE: 561

Gln Ser Tyr Asp Pro Gly Thr His Pro Ala Leu Leu
1               5                   10

<210> SEQ ID NO 562
<211> LENGTH: 12
<212> TYPE: PRT
<213> ORGANISM: Homo sapiens

<400> SEQUENCE: 562

Gln Ser Tyr Asp Trp Gly Thr His Pro Ala Leu Leu
1               5                   10

<210> SEQ ID NO 563
<211> LENGTH: 12
<212> TYPE: PRT
<213> ORGANISM: Homo sapiens

<400> SEQUENCE: 563

Gln Ser Tyr Asp Arg Asp Thr His Pro Ala Leu Leu
1               5                   10

<210> SEQ ID NO 564
<211> LENGTH: 12
<212> TYPE: PRT
<213> ORGANISM: Homo sapiens

<400> SEQUENCE: 564

Gln Ser Tyr Asp Arg Cys Thr His Pro Ala Leu Leu
1               5                   10

<210> SEQ ID NO 565
<211> LENGTH: 12
<212> TYPE: PRT
<213> ORGANISM: Homo sapiens

<400> SEQUENCE: 565

Gln Ser Tyr Asp Arg Ser Thr His Pro Ala Leu Leu
1               5                   10

<210> SEQ ID NO 566
<211> LENGTH: 12
<212> TYPE: PRT
<213> ORGANISM: Homo sapiens

<400> SEQUENCE: 566

Gln Ser Tyr Asp Arg Tyr Thr His Pro Ala Leu Leu
1               5                   10

<210> SEQ ID NO 567
<211> LENGTH: 12
<212> TYPE: PRT
<213> ORGANISM: Homo sapiens

<400> SEQUENCE: 567

Gln Ser Tyr Asp Arg His Thr His Pro Ala Leu Leu
1               5                   10

<210> SEQ ID NO 568
<211> LENGTH: 12
<212> TYPE: PRT
<213> ORGANISM: Homo sapiens

<400> SEQUENCE: 568

Gln Ser Tyr Asp Arg Arg Thr His Pro Ala Leu Leu
1               5                   10

<210> SEQ ID NO 569
<211> LENGTH: 12
<212> TYPE: PRT
<213> ORGANISM: Homo sapiens

<400> SEQUENCE: 569

Gln Ser Tyr Asp Arg Asn Thr His Pro Ala Leu Leu
1               5                   10

<210> SEQ ID NO 570
<211> LENGTH: 12
<212> TYPE: PRT
<213> ORGANISM: Homo sapiens

<400> SEQUENCE: 570

Gln Ser Tyr Asp Arg Gln Thr His Pro Ala Leu Leu
1               5                   10

<210> SEQ ID NO 571
<211> LENGTH: 12
<212> TYPE: PRT
<213> ORGANISM: Homo sapiens

<400> SEQUENCE: 571

Gln Ser Tyr Asp Arg Thr Thr His Pro Ala Leu Leu
1               5                   10

<210> SEQ ID NO 572
<211> LENGTH: 12
<212> TYPE: PRT
<213> ORGANISM: Homo sapiens

<400> SEQUENCE: 572

Gln Ser Tyr Asp Arg Gly Thr His Pro Ala Leu Leu
1               5                   10

<210> SEQ ID NO 573
<211> LENGTH: 12
<212> TYPE: PRT
<213> ORGANISM: Homo sapiens

<400> SEQUENCE: 573

Gln Ser Tyr Asp Arg Ala Thr His Pro Ala Leu Leu

```
                    1               5                    10
```

\<210\> SEQ ID NO 574
\<211\> LENGTH: 12
\<212\> TYPE: PRT
\<213\> ORGANISM: Homo sapiens

\<400\> SEQUENCE: 574

```
Gln Ser Tyr Asp Arg Val Thr His Pro Ala Leu Leu
  1               5                  10
```

\<210\> SEQ ID NO 575
\<211\> LENGTH: 12
\<212\> TYPE: PRT
\<213\> ORGANISM: Homo sapiens

\<400\> SEQUENCE: 575

```
Gln Ser Tyr Asp Arg Leu Thr His Pro Ala Leu Leu
  1               5                  10
```

\<210\> SEQ ID NO 576
\<211\> LENGTH: 12
\<212\> TYPE: PRT
\<213\> ORGANISM: Homo sapiens

\<400\> SEQUENCE: 576

```
Gln Ser Tyr Asp Arg Ile Thr His Pro Ala Leu Leu
  1               5                  10
```

\<210\> SEQ ID NO 577
\<211\> LENGTH: 12
\<212\> TYPE: PRT
\<213\> ORGANISM: Homo sapiens

\<400\> SEQUENCE: 577

```
Gln Ser Tyr Asp Arg Pro Thr His Pro Ala Leu Leu
  1               5                  10
```

\<210\> SEQ ID NO 578
\<211\> LENGTH: 12
\<212\> TYPE: PRT
\<213\> ORGANISM: Homo sapiens

\<400\> SEQUENCE: 578

```
Gln Ser Tyr Asp Arg Trp Thr His Pro Ala Leu Leu
  1               5                  10
```

\<210\> SEQ ID NO 579
\<211\> LENGTH: 12
\<212\> TYPE: PRT
\<213\> ORGANISM: Homo sapiens

\<400\> SEQUENCE: 579

```
Gln Ser Tyr Asp Arg Phe Thr His Pro Ala Leu Leu
  1               5                  10
```

\<210\> SEQ ID NO 580
\<211\> LENGTH: 48
\<212\> TYPE: DNA
\<213\> ORGANISM: synthetic construct
\<220\> FEATURE:
\<223\> OTHER INFORMATION: nucleotides at positions 16 to 34 can be
      substituted with any nucleotide such that the
      randomized nucleotides represent 12% of the
      sequence

```
<400> SEQUENCE: 580
tgtcccttgg ccccagtagt catagctccc actggtcgta cagtaata          48

<210> SEQ ID NO 581
<211> LENGTH: 35
<212> TYPE: DNA
<213> ORGANISM: synthetic construct

<400> SEQUENCE: 581
gacacctcga tcagcggata acaatttcac acagg                        35

<210> SEQ ID NO 582
<211> LENGTH: 15
<212> TYPE: DNA
<213> ORGANISM: synthetic construct

<400> SEQUENCE: 582
tggggccaag ggaca                                              15

<210> SEQ ID NO 583
<211> LENGTH: 45
<212> TYPE: DNA
<213> ORGANISM: synthetic construct

<400> SEQUENCE: 583
attcgtccta taccgttcta ctttgtcgtc tttccagacg ttagt             45

<210> SEQ ID NO 584
<211> LENGTH: 18
<212> TYPE: DNA
<213> ORGANISM: synthetic construct

<400> SEQUENCE: 584
attcgtccta taccgttc                                           18

<210> SEQ ID NO 585
<211> LENGTH: 66
<212> TYPE: DNA
<213> ORGANISM: synthetic construct
<220> FEATURE:
<223> OTHER INFORMATION: nucleotides from position 28 to 42 can be
      substituted with any nucleotide such that the
      randomized nucleotides represent 12% of the
      sequence

<400> SEQUENCE: 585
ggtcccagtt ccgaagaccc tcgaacccct caggctgctg tcatatgact ggcagtaata    60
gtcagc                                                        66

<210> SEQ ID NO 586
<211> LENGTH: 15
<212> TYPE: DNA
<213> ORGANISM: synthetic construct

<400> SEQUENCE: 586
tggggccaag ggaca                                              15

<210> SEQ ID NO 587
<211> LENGTH: 24
<212> TYPE: DNA
<213> ORGANISM: synthetic construct

<400> SEQUENCE: 587
```

```
tgaagagacg gtgaccattg tccc                                              24
```

<210> SEQ ID NO 588
<211> LENGTH: 16
<212> TYPE: DNA
<213> ORGANISM: synthetic construct

<400> SEQUENCE: 588

```
gacacctcga tcagcg                                                       16
```

<210> SEQ ID NO 589
<211> LENGTH: 48
<212> TYPE: DNA
<213> ORGANISM: synthetic construct

<400> SEQUENCE: 589

```
gagtcattct cgacttgcgg ccgcacctag gacggtcagc ttggtccc                    48
```

<210> SEQ ID NO 590
<211> LENGTH: 12
<212> TYPE: PRT
<213> ORGANISM: Homo sapiens

<400> SEQUENCE: 590

Gln Ser Tyr Asp Arg Gly Phe Thr Gly Ser Met Val
 1               5                  10

<210> SEQ ID NO 591
<211> LENGTH: 12
<212> TYPE: PRT
<213> ORGANISM: Homo sapiens
<220> FEATURE:
<223> OTHER INFORMATION: Xaa is encoded by a randomized codon of
      sequence NNS with N being any nucleotide and S being either
      deoxycytosine or deoxyguanidine

<400> SEQUENCE: 591

Xaa Xaa Xaa Xaa Xaa Xaa Phe Thr Gly Ser Met Val
 1               5                  10

<210> SEQ ID NO 592
<211> LENGTH: 12
<212> TYPE: PRT
<213> ORGANISM: Homo sapiens
<220> FEATURE:
<223> OTHER INFORMATION: Xaa is encoded by a randomized codon of
      sequence NNS with N being any nucleotide and S being either
      deoxycytosine or deoxyguanidine

<400> SEQUENCE: 592

Gln Ser Tyr Xaa Xaa Xaa Xaa Xaa Xaa Ser Met Val
 1               5                  10

<210> SEQ ID NO 593
<211> LENGTH: 12
<212> TYPE: PRT
<213> ORGANISM: Homo sapiens
<220> FEATURE:
<223> OTHER INFORMATION: Xaa is encoded by a randomized codon of
      sequence NNS with N being any nucleotide and S being either
      deoxycytosine or deoxyguanidine

<400> SEQUENCE: 593

Gln Ser Tyr Asp Arg Gly Xaa Xaa Xaa Xaa Xaa Xaa
 1               5                  10

```
<210> SEQ ID NO 594
<211> LENGTH: 100
<212> TYPE: PRT
<213> ORGANISM: Homo sapiens

<400> SEQUENCE: 594

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Asp His
            20                  25                  30

Tyr Met Asp Trp Val Arg Gln Ala Pro Gly Lys Gly Leu Glu Trp Val
        35                  40                  45

Gly Arg Thr Arg Asn Lys Ala Asn Ser Tyr Thr Thr Glu Tyr Ala Ala
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg
            100

<210> SEQ ID NO 595
<211> LENGTH: 100
<212> TYPE: PRT
<213> ORGANISM: Homo sapiens

<400> SEQUENCE: 595

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Asp His
            20                  25                  30

Tyr Met Ser Trp Val Arg Gln Ala Gln Gly Lys Gly Leu Glu Leu Val
        35                  40                  45

Gly Leu Ile Arg Asn Lys Ala Asn Ser Tyr Thr Thr Glu Tyr Ala Ala
    50                  55                  60

Ser Val Lys Gly Arg Leu Thr Ile Ser Arg Glu Asp Ser Lys Asn Thr
65                  70                  75                  80

Leu Tyr Leu Gln Met Ser Ser Leu Lys Thr Glu Asp Leu Ala Val Tyr
                85                  90                  95

Tyr Cys Ala Arg
            100

<210> SEQ ID NO 596
<211> LENGTH: 100
<212> TYPE: PRT
<213> ORGANISM: Homo sapiens

<400> SEQUENCE: 596

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Asp His
            20                  25                  30

Tyr Met Ser Trp Val Arg Gln Ala Gln Gly Lys Gly Leu Glu Leu Val
        35                  40                  45

Gly Leu Ile Arg Asn Lys Ala Asn Ser Tyr Thr Thr Glu Tyr Ala Ala
    50                  55                  60

Ser Val Lys Gly Arg Leu Thr Ile Ser Arg Glu Asp Ser Lys Asn Thr
65                  70                  75                  80
```

```
Met Tyr Leu Gln Met Ser Asn Leu Lys Thr Glu Asp Leu Ala Val Tyr
                85                  90                  95

Tyr Cys Ala Arg
            100

<210> SEQ ID NO 597
<211> LENGTH: 100
<212> TYPE: PRT
<213> ORGANISM: Homo sapiens

<400> SEQUENCE: 597

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Asp His
                20                  25                  30

Tyr Met Ser Trp Val Arg Gln Ala Gln Gly Lys Gly Leu Glu Leu Val
                35                  40                  45

Gly Leu Ile Arg Asn Lys Ala Asn Ser Tyr Thr Thr Glu Tyr Ala Ala
     50                  55                  60

Ser Val Lys Gly Arg Leu Thr Ile Ser Arg Glu Asp Ser Lys Asn Thr
 65                  70                  75                  80

Leu Tyr Leu Gln Met Ser Ser Leu Lys Thr Glu Asp Leu Ala Val Tyr
                85                  90                  95

Tyr Cys Ala Arg
            100

<210> SEQ ID NO 598
<211> LENGTH: 98
<212> TYPE: PRT
<213> ORGANISM: Homo sapiens

<400> SEQUENCE: 598

Glu Val Gln Leu Val Glu Ser Gly Gly Gly Leu Val Gln Pro Gly Arg
  1               5                  10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Gly Leu Glu Trp Val
                35                  40                  45

Ser Gly Ile Ser Trp Asn Ser Gly Ser Ile Gly Tyr Ala Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
                85                  90                  95

Ala Lys

<210> SEQ ID NO 599
<211> LENGTH: 98
<212> TYPE: PRT
<213> ORGANISM: Homo sapiens

<400> SEQUENCE: 599

Glu Val Gln Leu Val Glu Ser Gly Gly Gly Val Val Arg Pro Gly Gly
  1               5                  10                  15

Ser Leu Arg Leu Ser Cys Ala Ala Ser Gly Phe Thr Phe Asp Asp Tyr
                20                  25                  30

Gly Met Ser Trp Val Arg Gln Ala Pro Gly Lys Gly Leu Glu Trp Val
```

```
                 35                  40                  45
Ser Gly Ile Asn Trp Asn Gly Gly Ser Thr Gly Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr His Cys
                 85                  90                  95

Ala Arg

<210> SEQ ID NO 600
<211> LENGTH: 98
<212> TYPE: PRT
<213> ORGANISM: Homo sapiens

<400> SEQUENCE: 600

Glu Val Gln Leu Val Glu Ser Gly Gly Val Val Gln Pro Gly Gly
  1               5                  10                  15

Ser Leu Arg Leu Ser Cys Ala Ala Ser Gly Phe Thr Phe Asp Asp Tyr
                 20                  25                  30

Thr Met His Trp Val Arg Gln Ala Pro Gly Lys Gly Leu Glu Trp Val
                 35                  40                  45

Ser Leu Ile Ser Trp Asp Gly Gly Ser Thr Tyr Tyr Ala Asp Ser Val
 50                  55                  60

Lys Gly Arg Phe Thr Ile Ser Arg Asp Asn Ser Lys Asn Ser Leu Tyr
 65                  70                  75                  80

Leu Gln Met Asn Ser Leu Arg Thr Glu Asp Thr Ala Leu Tyr Tyr Cys
                 85                  90                  95

Ala Lys

<210> SEQ ID NO 601
<211> LENGTH: 98
<212> TYPE: PRT
<213> ORGANISM: Homo sapiens

<400> SEQUENCE: 601

Gln Val Gln Leu Val Glu Ser Gly Gly Gly Leu Val Lys Pro Gly Gly
  1               5                  10                  15

Ser Leu Arg Leu Ser Cys Ala Ala Ser Gly Phe Thr Phe Ser Asp Tyr
                 20                  25                  30

Tyr Met Ser Trp Ile Arg Gln Ala Pro Gly Lys Gly Leu Glu Trp Val
                 35                  40                  45

Ser Tyr Ile Ser Ser Ser Gly Ser Thr Ile Tyr Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg

<210> SEQ ID NO 602
<211> LENGTH: 98
<212> TYPE: PRT
<213> ORGANISM: Homo sapiens

<400> SEQUENCE: 602

Gln Val Gln Leu Leu Glu Ser Gly Gly Gly Leu Val Lys Pro Gly Gly
  1               5                  10                  15
```

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Ser Tyr Thr Asn Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 603
<211> LENGTH: 100
<212> TYPE: PRT
<213> ORGANISM: Homo sapiens

<400> SEQUENCE: 603

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Gly Ser
            20                  25                  30

Ala Met His Trp Val Arg Gln Ala Ser Gly Lys Gly Leu Glu Trp Val
        35                  40                  45

Gly Arg Ile Arg Ser Lys Ala Asn Ser Tyr Ala Thr Ala Tyr Ala Ala
    50                  55                  60

Ser Val Lys Gly Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Thr Arg
            100

<210> SEQ ID NO 604
<211> LENGTH: 100
<212> TYPE: PRT
<213> ORGANISM: Homo sapiens

<400> SEQUENCE: 604

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr
            100

<210> SEQ ID NO 605
<211> LENGTH: 100

```
<212> TYPE: PRT
<213> ORGANISM: Homo sapiens

<400> SEQUENCE: 605

Glu Val Gln Leu Val Glu Ser Gly Gly Gly Leu Val Lys Pro Gly Gly
  1               5                  10                  15

Ser Leu Arg Leu Ser Cys Ala Ala Ser Gly Phe Thr Phe Ser Asn Ala
             20                  25                  30

Trp Met Ser Trp Val Arg Gln Ala Pro Gly Lys Gly Leu Glu Trp Val
         35                  40                  45

Gly Arg Ile Glu Ser Lys Thr Asp Gly Gly Thr Thr Asp Tyr Ala Ala
     50                  55                  60

Pro Val Lys Gly Arg Phe Thr Ile Ser Arg Asp Asp Ser Lys Asn Thr
 65                  70                  75                  80

Leu Tyr Leu Gln Met Asn Ser Leu Lys Thr Glu Asp Thr Ala Val Tyr
                 85                  90                  95

Tyr Cys Thr Thr
            100

<210> SEQ ID NO 606
<211> LENGTH: 100
<212> TYPE: PRT
<213> ORGANISM: Homo sapiens

<400> SEQUENCE: 606

Glu Val Gln Leu Val Glu Ser Gly Gly Gly Leu Val Lys Pro Gly Gly
  1               5                  10                  15

Ser Leu Arg Leu Ser Cys Ala Ala Ser Gly Phe Thr Phe Ser Asn Ala
             20                  25                  30

Trp Met Ser Trp Val Arg Gln Ala Pro Gly Lys Gly Leu Glu Trp Val
         35                  40                  45

Gly Arg Ile Lys Ser Lys Thr Asp Gly Gly Thr Thr Asp Tyr Ala Ala
     50                  55                  60

Pro Val Lys Gly Arg Phe Thr Ile Ser Arg Asp Asp Ser Lys Asn Thr
 65                  70                  75                  80

Leu Tyr Leu Gln Met Asn Ser Leu Lys Thr Glu Asp Thr Ala Val Tyr
                 85                  90                  95

Tyr Cys Thr Thr
            100

<210> SEQ ID NO 607
<211> LENGTH: 100
<212> TYPE: PRT
<213> ORGANISM: Homo sapiens

<400> SEQUENCE: 607

Glu Val Gln Leu Val Glu Ser Gly Gly Gly Leu Val Lys Pro Gly Gly
  1               5                  10                  15

Ser Leu Arg Leu Ser Cys Ala Ala Ser Gly Phe Thr Phe Ser Asn Ala
             20                  25                  30

Trp Met Ser Trp Val Arg Gln Ala Pro Gly Lys Gly Leu Glu Trp Val
         35                  40                  45

Gly Arg Ile Lys Ser Lys Thr Asp Gly Gly Thr Thr Asn Tyr Ala Ala
     50                  55                  60

Pro Val Lys Gly Arg Phe Thr Ile Ser Arg Asp Asp Ser Lys Asn Thr
 65                  70                  75                  80

Leu Tyr Leu Gln Met Asn Ser Leu Lys Thr Glu Asp Thr Ala Val Tyr
```

```
                85                  90                  95

Tyr Cys Thr Thr
            100

<210> SEQ ID NO 608
<211> LENGTH: 100
<212> TYPE: PRT
<213> ORGANISM: Homo sapiens

<400> SEQUENCE: 608

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asn Ala
            20                  25                  30

Trp Met Asn Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr
            100

<210> SEQ ID NO 609
<211> LENGTH: 100
<212> TYPE: PRT
<213> ORGANISM: Homo sapiens

<400> SEQUENCE: 609

Glu Val Gln Leu Val Glu Ser Gly Gly Ala Leu Val Lys Pro Gly Gly
 1               5                  10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr
            100

<210> SEQ ID NO 610
<211> LENGTH: 98
<212> TYPE: PRT
<213> ORGANISM: Homo sapiens

<400> SEQUENCE: 610

Glu Val Gln Leu Val Glu Ser Gly Gly Gly Leu Val Gln Pro Gly Gly
 1               5                  10                  15

Ser Leu Arg Leu Ser Cys Pro Ala Ser Gly Phe Thr Phe Ser Asn His
            20                  25                  30

Tyr Met Ser Trp Val Arg Gln Ala Pro Gly Lys Gly Leu Glu Trp Val
        35                  40                  45
```

```
Ser Tyr Ile Ser Gly Asp Ser Gly Tyr Thr Asn Tyr Ala Asp Ser Val
        50                  55                  60

Lys Gly Arg Phe Thr Ile Ser Arg Asp Asn Ala Asn Asn Ser Pro Tyr
 65                  70                  75                  80

Leu Gln Met Asn Ser Leu Arg Ala Glu Asp Thr Ala Val Tyr Tyr Cys
                 85                  90                  95

Val Lys

<210> SEQ ID NO 611
<211> LENGTH: 98
<212> TYPE: PRT
<213> ORGANISM: Homo sapiens

<400> SEQUENCE: 611

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Asn His
                 20                  25                  30

Tyr Thr Ser Trp Val Arg Gln Ala Pro Gly Lys Gly Leu Glu Trp Val
             35                  40                  45

Ser Tyr Ser Ser Gly Asn Ser Gly Tyr Thr Asn Tyr Ala Asp Ser Val
        50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Val Lys

<210> SEQ ID NO 612
<211> LENGTH: 98
<212> TYPE: PRT
<213> ORGANISM: Homo sapiens

<400> SEQUENCE: 612

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Asn Ser
                 20                  25                  30

Asp Met Asn Trp Val His Gln Ala Pro Gly Lys Gly Leu Glu Trp Val
             35                  40                  45

Ser Gly Val Ser Trp Asn Gly Ser Arg Thr His Tyr Ala Asp Ser Val
        50                  55                  60

Lys Gly Arg Phe Ile Ile Ser Arg Asp Asn Ser Arg Asn Thr Leu Tyr
 65                  70                  75                  80

Leu Gln Thr Asn Ser Leu Arg Ala Glu Asp Thr Ala Val Tyr Tyr Cys
                 85                  90                  95

Val Arg

<210> SEQ ID NO 613
<211> LENGTH: 98
<212> TYPE: PRT
<213> ORGANISM: Homo sapiens

<400> SEQUENCE: 613

Glu Val Gln Leu Val Glu Ser Gly Gly Gly Leu Val Gln Pro Gly Gly
 1               5                  10                  15
```

```
Ser Leu Arg Leu Ser Cys Ala Ala Ser Gly Phe Thr Phe Ser Asn Ser
            20                  25                  30

Asp Met Asn Trp Ala Arg Lys Ala Pro Gly Lys Gly Leu Glu Trp Val
        35                  40                  45

Ser Gly Val Ser Trp Asn Gly Ser Arg Thr His Tyr Val Asp Ser Val
    50                  55                  60

Lys Arg Arg Phe Ile Ile Ser Arg Asp Asn Ser Arg Asn Ser Leu Tyr
65                  70                  75                  80

Leu Gln Lys Asn Arg Arg Ala Glu Asp Met Ala Val Tyr Tyr Cys
                85                  90                  95

Val Arg

<210> SEQ ID NO 614
<211> LENGTH: 98
<212> TYPE: PRT
<213> ORGANISM: Homo sapiens

<400> SEQUENCE: 614

Thr Val Gln Leu Val Glu Ser Gly Gly Gly Leu Val Glu Pro Gly Gly
1               5                   10                  15

Ser Leu Arg Leu Ser Cys Ala Ala Ser Gly Phe Thr Phe Ser Asn Ser
            20                  25                  30

Asp Met Asn Trp Val Arg Gln Ala Pro Gly Lys Gly Leu Glu Trp Val
        35                  40                  45

Ser Gly Val Ser Trp Asn Gly Ser Arg Thr His Tyr Ala Asp Ser Val
    50                  55                  60

Lys Gly Arg Phe Ile Ile Ser Arg Asp Asn Ser Arg Asn Phe Leu Tyr
65                  70                  75                  80

Gln Gln Met Asn Ser Leu Arg Pro Glu Asp Met Ala Val Tyr Tyr Cys
                85                  90                  95

Val Arg

<210> SEQ ID NO 615
<211> LENGTH: 97
<212> TYPE: PRT
<213> ORGANISM: Homo sapiens

<400> SEQUENCE: 615

Glu Val His Leu Val Glu Ser Gly Gly Gly Leu Val Gln Pro Gly Gly
1               5                   10                  15

Ala Leu Arg Leu Ser Cys Ala Ala Ser Gly Phe Thr Phe Ser Asn Tyr
            20                  25                  30

Asp Met His Trp Val Arg Gln Ala Thr Gly Lys Gly Leu Glu Trp Val
        35                  40                  45

Ser Ala Asn Gly Thr Ala Gly Asp Thr Tyr Tyr Pro Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg

<210> SEQ ID NO 616
<211> LENGTH: 97
<212> TYPE: PRT
<213> ORGANISM: Homo sapiens
```

<400> SEQUENCE: 616

Glu Val Gln Leu Val Glu Thr Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg

<210> SEQ ID NO 617
<211> LENGTH: 97
<212> TYPE: PRT
<213> ORGANISM: Homo sapiens

<400> SEQUENCE: 617

Glu Val Gln Leu Val Gln Ser Gly Gly Gly Leu Val His Pro Gly Gly
1               5                   10                  15

Ser Leu Arg Leu Ser Cys Ala Gly Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ser Ala Ile Gly Thr Gly Gly Gly Thr Tyr Tyr Ala Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Met Ala Val Tyr Tyr Cys Ala
                85                  90                  95

Arg

<210> SEQ ID NO 618
<211> LENGTH: 97
<212> TYPE: PRT
<213> ORGANISM: Homo sapiens

<400> SEQUENCE: 618

Glu Val Gln Leu Val Gln Ser Gly Gly Gly Leu Val Gln Pro Gly Gly
1               5                   10                  15

Ser Leu Arg Leu Ser Cys Ala Gly Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ser Ala Ile Gly Thr Gly Gly Gly Thr Tyr Tyr Ala Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Met Ala Val Tyr Tyr Cys Ala
                85                  90                  95

Arg

<210> SEQ ID NO 619
<211> LENGTH: 98
<212> TYPE: PRT
<213> ORGANISM: Homo sapiens

<400> SEQUENCE: 619

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys

<210> SEQ ID NO 620
<211> LENGTH: 98
<212> TYPE: PRT
<213> ORGANISM: Homo sapiens

<400> SEQUENCE: 620

Glu Val Gln Leu Val Glu Ser Gly Gly Gly Leu Val Gln Pro Gly Gly
1               5                   10                  15

Ser Leu Arg Leu Ser Cys Ser Ala Ser Gly Phe Thr Phe Ser Ser Tyr
            20                  25                  30

Ala Met His Trp Val Arg Gln Ala Pro Gly Lys Gly Leu Glu Tyr Val
        35                  40                  45

Ser Ala Ile Ser Ser Asn Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Val Gln Met Ser Ser Leu Arg Ala Glu Asp Thr Ala Val Tyr Tyr Cys
                85                  90                  95

Val Lys

<210> SEQ ID NO 621
<211> LENGTH: 98
<212> TYPE: PRT
<213> ORGANISM: Homo sapiens

<400> SEQUENCE: 621

Glu Val Gln Leu Val Glu Ser Gly Gly Gly Leu Val Gln Pro Gly Gly
1               5                   10                  15

Ser Leu Arg Leu Ser Cys Ser Ala Ser Gly Phe Thr Phe Ser Ser Tyr
            20                  25                  30

Ala Met His Trp Val Arg Gln Ala Pro Gly Lys Gly Leu Glu Tyr Val
        35                  40                  45

Ser Ala Ile Ser Ser Asn Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Val Gln Met Ser Ser Leu Arg Ala Glu Asp Thr Ala Val Tyr Tyr Cys

Val Lys

<210> SEQ ID NO 622
<211> LENGTH: 98
<212> TYPE: PRT
<213> ORGANISM: Homo sapiens

<400> SEQUENCE: 622

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Tyr Val
        35                  40                  45

Ser Ala Ile Ser Ser Asn Gly Gly Ser Thr Tyr Tyr Ala Asn Ser Val
    50                  55                  60

Lys Gly Arg Phe Thr Ile Ser Arg Asp Asn Ser Lys Asn Thr Leu Tyr
65                  70                  75                  80

Leu Gln Met Gly Ser Leu Arg Ala Glu Asp Met Ala Val Tyr Tyr Cys
                85                  90                  95

Ala Arg

<210> SEQ ID NO 623
<211> LENGTH: 98
<212> TYPE: PRT
<213> ORGANISM: Homo sapiens

<400> SEQUENCE: 623

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Gly Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys

<210> SEQ ID NO 624
<211> LENGTH: 98
<212> TYPE: PRT
<213> ORGANISM: Homo sapiens

<400> SEQUENCE: 624

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Thr Asp Ser Val
    50                  55                  60

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg

<210> SEQ ID NO 625
<211> LENGTH: 98
<212> TYPE: PRT
<213> ORGANISM: Homo sapiens

<400> SEQUENCE: 625

Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Ser Ser Tyr
                 20                  25                  30

Ala Met His Trp Val Arg Gln Ala Pro Gly Lys Gly Leu Glu Trp Val
             35                  40                  45

Ala Val Ile Ser Tyr Asp Gly Ser Asn Lys Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg

<210> SEQ ID NO 626
<211> LENGTH: 98
<212> TYPE: PRT
<213> ORGANISM: Homo sapiens

<400> SEQUENCE: 626

Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Ser Ser Tyr
                 20                  25                  30

Ala Met His Trp Val Arg Gln Ala Pro Gly Lys Gly Leu Glu Trp Val
             35                  40                  45

Ala Val Ile Ser Tyr Asp Gly Ser Asn Lys Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Ser Ser Leu Arg Ala Glu Asp Thr Ala Val Tyr Tyr Cys
                 85                  90                  95

Ala Arg

<210> SEQ ID NO 627
<211> LENGTH: 98
<212> TYPE: PRT
<213> ORGANISM: Homo sapiens

<400> SEQUENCE: 627

Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Ser Ser Tyr
                 20                  25                  30
```

Ala Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg

<210> SEQ ID NO 628
<211> LENGTH: 98
<212> TYPE: PRT
<213> ORGANISM: Homo sapiens

<400> SEQUENCE: 628

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg

<210> SEQ ID NO 629
<211> LENGTH: 98
<212> TYPE: PRT
<213> ORGANISM: Homo sapiens

<400> SEQUENCE: 629

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg

<210> SEQ ID NO 630
<211> LENGTH: 98
<212> TYPE: PRT
<213> ORGANISM: Homo sapiens

<400> SEQUENCE: 630

Gln Val Gln Leu Val Glu Ser Gly Gly Gly Val Val Gln Pro Gly Arg
 1               5                  10                  15

```
                1               5                   10                  15
            Ser Leu Arg Leu Ser Cys Ala Ala Ser Gly Phe Thr Phe Ser Ser Tyr
                        20                  25                  30

Ala Met His Trp Val Arg Gln Ala Pro Gly Lys Gly Leu Glu Trp Val
                        35                  40                  45

Ala Val Ile Ser Tyr Asp Gly Ser Asn Lys Tyr Tyr Ala Asp Ser Val
                        50                  55                  60

Lys Gly Arg Phe Thr Ile Ser Arg Asp Asn Ser Lys Asn Thr Leu Tyr
            65                  70                  75                  80

Leu Gln Met Asn Ser Leu Arg Ala Glu Asp Thr Ala Val Tyr Tyr Cys
                        85                  90                  95

Ala Arg

<210> SEQ ID NO 631
<211> LENGTH: 98
<212> TYPE: PRT
<213> ORGANISM: Homo sapiens

<400> SEQUENCE: 631

Gln Val Gln Leu Val Glu Ser Gly Gly Gly Val Val Gln Pro Gly Arg
            1               5                   10                  15

Ser Leu Arg Leu Ser Cys Ala Ala Ser Gly Phe Thr Phe Ser Ser Tyr
                        20                  25                  30

Ala Met His Trp Val Arg Gln Ala Pro Gly Lys Gly Leu Glu Trp Val
                        35                  40                  45

Ala Val Ile Ser Tyr Asp Gly Ser Asn Lys Tyr Tyr Ala Asp Ser Val
                        50                  55                  60

Lys Gly Arg Phe Thr Ile Ser Arg Asp Asn Ser Lys Asn Thr Leu Tyr
            65                  70                  75                  80

Leu Gln Met Asn Ser Leu Arg Ala Glu Asp Thr Ala Val Tyr Tyr Cys
                        85                  90                  95

Ala Arg

<210> SEQ ID NO 632
<211> LENGTH: 98
<212> TYPE: PRT
<213> ORGANISM: Homo sapiens

<400> SEQUENCE: 632

Gln Val Gln Leu Val Glu Ser Gly Gly Gly Val Val Gln Pro Gly Arg
            1               5                   10                  15

Ser Leu Arg Leu Ser Cys Ala Ala Ser Gly Phe Thr Phe Ser Ser Tyr
                        20                  25                  30

Ala Met His Trp Val Arg Gln Ala Pro Gly Lys Gly Leu Glu Trp Val
                        35                  40                  45

Ala Val Ile Ser Tyr Asp Gly Ser Asn Lys Tyr Tyr Ala Asp Ser Val
                        50                  55                  60

Lys Gly Arg Phe Thr Ile Ser Arg Asp Asn Ser Lys Asn Thr Leu Tyr
            65                  70                  75                  80

Leu Gln Met Asn Ser Leu Arg Ala Glu Asp Thr Ala Val Tyr Tyr Cys
                        85                  90                  95

Ala Arg

<210> SEQ ID NO 633
<211> LENGTH: 98
<212> TYPE: PRT
```

-continued

<213> ORGANISM: Homo sapiens

<400> SEQUENCE: 633

Gln Val Gln Leu Val Glu Ser Gly Gly Gly Leu Val Gln Pro Gly Gly
1               5                   10                  15

Ser Leu Arg Leu Ser Cys Ser Ala Ser Gly Phe Thr Phe Ser Ser Tyr
            20                  25                  30

Ala Met His Trp Val Arg Gln Ala Pro Gly Lys Gly Leu Glu Tyr Val
        35                  40                  45

Ser Ala Ile Ser Ser Asn Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Val Gln Met Ser Ser Leu Arg Ala Glu Asp Thr Ala Val Tyr Tyr Cys
                85                  90                  95

Val Lys

<210> SEQ ID NO 634
<211> LENGTH: 98
<212> TYPE: PRT
<213> ORGANISM: Homo sapiens

<400> SEQUENCE: 634

Gln Val Gln Leu Val Glu Ser Gly Gly Gly Leu Val Gln Pro Gly Gly
1               5                   10                  15

Ser Leu Arg Leu Ser Cys Ser Ala Ser Gly Phe Thr Phe Ser Ser Tyr
            20                  25                  30

Ala Met His Trp Val Arg Gln Ala Pro Gly Lys Gly Leu Glu Tyr Val
        35                  40                  45

Ser Ala Ile Ser Ser Asn Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 635
<211> LENGTH: 98
<212> TYPE: PRT
<213> ORGANISM: Homo sapiens

<400> SEQUENCE: 635

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Ala Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 636
<211> LENGTH: 98
<212> TYPE: PRT
<213> ORGANISM: Homo sapiens

<400> SEQUENCE: 636

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 637
<211> LENGTH: 98
<212> TYPE: PRT
<213> ORGANISM: Homo sapiens

<400> SEQUENCE: 637

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys

<210> SEQ ID NO 638
<211> LENGTH: 97
<212> TYPE: PRT
<213> ORGANISM: Homo sapiens

<400> SEQUENCE: 638

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met His Trp Val Arg Gln Ala Thr Gly Lys Gly Leu Glu Trp Val
        35                  40                  45

Ser Ala Ile Gly Thr Ala Gly Asp Thr Tyr Tyr Pro Gly Ser Val Lys
    50                  55                  60

Gly Arg Phe Thr Ile Ser Arg Glu Asn Ala Lys Asn Ser Leu Tyr Leu
65                  70                  75                  80

```
Gln Met Asn Ser Leu Arg Ala Gly Asp Thr Ala Val Tyr Tyr Cys Ala
            85                  90                  95

Arg

<210> SEQ ID NO 639
<211> LENGTH: 98
<212> TYPE: PRT
<213> ORGANISM: Homo sapiens

<400> SEQUENCE: 639

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
             20                  25                  30

Glu Met Asn Trp Val Arg Gln Ala Pro Gly Lys Gly Leu Glu Trp Val
         35                  40                  45

Ser Tyr Ile Ser Ser Ser Gly Ser Thr Ile Tyr Tyr Ala Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
             85                  90                  95

Ala Arg

<210> SEQ ID NO 640
<211> LENGTH: 98
<212> TYPE: PRT
<213> ORGANISM: Homo sapiens

<400> SEQUENCE: 640

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
             20                  25                  30

Gly Met His Trp Val Arg Gln Ala Pro Gly Lys Gly Leu Glu Trp Val
         35                  40                  45

Ala Val Ile Ser Tyr Asp Gly Ser Asn Lys Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Leu Arg Ala Arg Leu Cys Ile Thr Val
             85                  90                  95

Arg Glu

<210> SEQ ID NO 641
<211> LENGTH: 98
<212> TYPE: PRT
<213> ORGANISM: Homo sapiens

<400> SEQUENCE: 641

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
             20                  25                  30

Gly Met His Trp Val Arg Gln Ala Pro Gly Lys Gly Leu Glu Trp Val
         35                  40                  45
```

```
Ala Val Ile Ser Tyr Asp Gly Ser Asn Lys Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg

<210> SEQ ID NO 642
<211> LENGTH: 98
<212> TYPE: PRT
<213> ORGANISM: Homo sapiens

<400> SEQUENCE: 642

Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Ser Ser Tyr
                 20                  25                  30

Gly Met His Trp Val Arg Gln Ala Pro Gly Lys Gly Leu Glu Trp Val
             35                  40                  45

Ala Val Ile Ser Tyr Asp Gly Ser Asn Lys Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg

<210> SEQ ID NO 643
<211> LENGTH: 98
<212> TYPE: PRT
<213> ORGANISM: Homo sapiens

<400> SEQUENCE: 643

Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Ser Ser Tyr
                 20                  25                  30

Gly Met His Trp Val Arg Gln Ala Pro Gly Lys Gly Leu Glu Trp Val
             35                  40                  45

Ala Val Ile Ser Tyr Asp Gly Ser Asn Lys Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg

<210> SEQ ID NO 644
<211> LENGTH: 98
<212> TYPE: PRT
<213> ORGANISM: Homo sapiens

<400> SEQUENCE: 644

Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Ser Ser Tyr
```

20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg

<210> SEQ ID NO 645
<211> LENGTH: 98
<212> TYPE: PRT
<213> ORGANISM: Homo sapiens

<400> SEQUENCE: 645

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Arg Leu Tyr
 65                  70                  75                  80

Leu Gln Met Asn Ser Leu Arg Ala Glu Asp Thr Ala Val Tyr Tyr Cys
                85                  90                  95

Ala Arg

<210> SEQ ID NO 646
<211> LENGTH: 98
<212> TYPE: PRT
<213> ORGANISM: Homo sapiens

<400> SEQUENCE: 646

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg

<210> SEQ ID NO 647
<211> LENGTH: 98
<212> TYPE: PRT
<213> ORGANISM: Homo sapiens

<400> SEQUENCE: 647

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 648
<211> LENGTH: 98
<212> TYPE: PRT
<213> ORGANISM: Homo sapiens

<400> SEQUENCE: 648

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Gly Thr Ala Val Tyr Tyr Cys
                85                  90                  95

Ala Arg

<210> SEQ ID NO 649
<211> LENGTH: 98
<212> TYPE: PRT
<213> ORGANISM: Homo sapiens

<400> SEQUENCE: 649

Gln Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Phe Ile Arg Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys

<210> SEQ ID NO 650

```
<211> LENGTH: 98
<212> TYPE: PRT
<213> ORGANISM: Homo sapiens

<400> SEQUENCE: 650

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys

<210> SEQ ID NO 651
<211> LENGTH: 98
<212> TYPE: PRT
<213> ORGANISM: Homo sapiens

<400> SEQUENCE: 651

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 652
<211> LENGTH: 98
<212> TYPE: PRT
<213> ORGANISM: Homo sapiens

<400> SEQUENCE: 652

Gln Val Gln Leu Val Glu Ser Gly Gly Gly Val Val Gln Pro Gly Arg
 1               5                  10                  15

Ser Leu Arg Leu Ser Cys Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

Ala Lys

<210> SEQ ID NO 653
<211> LENGTH: 95
<212> TYPE: PRT
<213> ORGANISM: Homo sapiens

<400> SEQUENCE: 653

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Arg Lys
                85                  90                  95

<210> SEQ ID NO 654
<211> LENGTH: 98
<212> TYPE: PRT
<213> ORGANISM: Homo sapiens

<400> SEQUENCE: 654

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 655
<211> LENGTH: 98
<212> TYPE: PRT
<213> ORGANISM: Homo sapiens

<400> SEQUENCE: 655

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Ala
    50                  55                  60

Lys Gly Arg Phe Thr Ile Ser Arg Asp Asn Ser Thr Asn Thr Leu Phe
65                  70                  75                  80

Leu Gln Met Asn Ser Leu Arg Ala Glu Asp Thr Ala Val Tyr Tyr Cys
                    85                  90                  95

Ala Arg

<210> SEQ ID NO 656
<211> LENGTH: 98
<212> TYPE: PRT
<213> ORGANISM: Homo sapiens

<400> SEQUENCE: 656

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Tyr Ile Ser Ser Ser Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                    85                  90                  95

Ala Arg

<210> SEQ ID NO 657
<211> LENGTH: 98
<212> TYPE: PRT
<213> ORGANISM: Homo sapiens

<400> SEQUENCE: 657

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                    85                  90                  95

Ala Arg

<210> SEQ ID NO 658
<211> LENGTH: 97
<212> TYPE: PRT
<213> ORGANISM: Homo sapiens

<400> SEQUENCE: 658

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

```
Ser Ser Ile Ser Ser Ser Ser Tyr Ile Tyr Tyr Ala Asp Ser Val Lys
    50                  55                  60
Gly Arg Phe Thr Ile Ser Arg Asp Asn Ala Lys Asn Ser Leu Tyr Leu
 65                  70                  75                  80
Gln Met Asn Ser Leu Arg Ala Glu Asp Thr Ala Val Tyr Tyr Cys Ala
                 85                  90                  95
Arg

<210> SEQ ID NO 659
<211> LENGTH: 98
<212> TYPE: PRT
<213> ORGANISM: Homo sapiens

<400> SEQUENCE: 659

Glu Val Gln Leu Val Glu Ser Gly Gly Gly Leu Val Lys Pro Gly Gly
  1               5                  10                  15
Ser Leu Arg Leu Ser Cys Ala Ala Ser Gly Phe Thr Phe Ser Ser Tyr
             20                  25                  30
Ser Met Asn Trp Val Arg Gln Ala Pro Gly Lys Gly Leu Glu Trp Val
         35                  40                  45
Ser Ser Ile Ser Ser Ser Ser Tyr Ile Tyr Tyr Ala Asp Ser Val
    50                  55                  60
Lys Gly Arg Phe Thr Ile Ser Arg Asp Asn Ala Lys Asn Ser Leu Tyr
 65                  70                  75                  80
Leu Gln Met Asn Ser Leu Arg Ala Glu Asp Thr Ala Val Tyr Tyr Cys
                 85                  90                  95
Ala Arg

<210> SEQ ID NO 660
<211> LENGTH: 98
<212> TYPE: PRT
<213> ORGANISM: Homo sapiens

<400> SEQUENCE: 660

Glu Val Gln Leu Val Glu Ser Gly Gly Gly Leu Val Gln Pro Gly Gly
  1               5                  10                  15
Ser Leu Arg Leu Ser Cys Ala Ala Ser Gly Phe Thr Phe Ser Ser Tyr
             20                  25                  30
Ser Met Asn Trp Val Arg Gln Ala Pro Gly Lys Gly Leu Glu Trp Val
         35                  40                  45
Ser Tyr Ile Ser Ser Ser Ser Thr Ile Tyr Tyr Ala Asp Ser Val
    50                  55                  60
Lys Gly Arg Phe Thr Ile Ser Arg Asp Asn Ala Lys Asn Ser Leu Tyr
 65                  70                  75                  80
Leu Gln Met Asn Ser Leu Arg Ala Glu Asp Thr Ala Val Tyr Tyr Cys
                 85                  90                  95
Ala Arg

<210> SEQ ID NO 661
<211> LENGTH: 97
<212> TYPE: PRT
<213> ORGANISM: Homo sapiens

<400> SEQUENCE: 661

Glu Asp Gln Leu Val Glu Ser Gly Gly Gly Leu Val Gln Pro Gly Gly
  1               5                  10                  15
Ser Leu Arg Pro Ser Cys Ala Ala Ser Gly Phe Ala Phe Ser Ser Tyr
```

```
            20                  25                  30
Val Leu His Trp Val Arg Arg Ala Pro Gly Lys Gly Pro Glu Trp Val
            35                  40                  45

Ser Ala Ile Gly Thr Gly Gly Asp Thr Tyr Tyr Ala Asp Ser Val Met
            50                  55                  60

Gly Arg Phe Thr Ile Ser Arg Asp Asn Ala Lys Ser Leu Tyr Leu
65                  70                  75                  80

Gln Met Asn Ser Leu Ile Ala Glu Asp Met Ala Val Tyr Tyr Cys Ala
                85                  90                  95

Arg

<210> SEQ ID NO 662
<211> LENGTH: 98
<212> TYPE: PRT
<213> ORGANISM: Homo sapiens

<400> SEQUENCE: 662

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Val Trp Val
            35                  40                  45

Ser Arg Ile Asn Ser Asp Gly Ser Ser Thr Ser Tyr Ala Asp Ser Val
            50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 663
<211> LENGTH: 98
<212> TYPE: PRT
<213> ORGANISM: Homo sapiens

<400> SEQUENCE: 663

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Val Trp Val
            35                  40                  45

Ser Arg Ile Asn Ser Asp Gly Ser Ser Thr Ser Tyr Ala Asp Ser Val
            50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 664
<211> LENGTH: 98
<212> TYPE: PRT
<213> ORGANISM: Homo sapiens

<400> SEQUENCE: 664
```

-continued

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 665
<211> LENGTH: 98
<212> TYPE: PRT
<213> ORGANISM: Homo sapiens

<400> SEQUENCE: 665

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Val Trp Val
        35                  40                  45

Ser Arg Ile Asn Ser Asp Gly Ser Ser Thr Ser Tyr Ala Asp Ser Met
    50                  55                  60

Lys Gly Gln Phe Thr Ile Ser Arg Asp Asn Ala Lys Asn Thr Leu Tyr
65                  70                  75                  80

Leu Gln Met Asn Ser Leu Arg Ala Glu Asp Met Ala Val Tyr Tyr Cys
                85                  90                  95

Thr Arg

<210> SEQ ID NO 666
<211> LENGTH: 98
<212> TYPE: PRT
<213> ORGANISM: Homo sapiens

<400> SEQUENCE: 666

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 667

<211> LENGTH: 98
<212> TYPE: PRT
<213> ORGANISM: Homo sapiens

<400> SEQUENCE: 667

Gln Val Gln Leu Val Gln Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Phe Ile Arg Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Lys Ser Leu Arg Ala Glu Asp Thr Ala Val Tyr Tyr Cys
                85                  90                  95

Thr Thr

<210> SEQ ID NO 668
<211> LENGTH: 98
<212> TYPE: PRT
<213> ORGANISM: Homo sapiens

<400> SEQUENCE: 668

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala

<210> SEQ ID NO 669
<211> LENGTH: 98
<212> TYPE: PRT
<213> ORGANISM: Homo sapiens

<400> SEQUENCE: 669

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asp Met Gly Asn Tyr
            20                  25                  30

Ala Val Ser Trp Tyr Gln Gln Leu Pro Gly Thr Ala Pro Lys Leu Leu
        35                  40                  45

Ile Tyr Glu Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Trp
65                  70                  75                  80

Pro Glu Asp Glu Ala Asp Tyr Tyr Cys Leu Ala Trp Asp Thr Ser Pro
                85                  90                  95

Arg Ala

<210> SEQ ID NO 670
<211> LENGTH: 98
<212> TYPE: PRT
<213> ORGANISM: Homo sapiens

<400> SEQUENCE: 670

```
Gln Ser Val Leu Thr Gln Pro Pro Ser Ala Ser Gly Thr Pro Gly Gln
  1               5                  10                  15
Arg Val Thr Ile Ser Cys Ser Gly Ser Ser Asn Ile Gly Ser Asn
             20                  25                  30
Thr Val Asn Trp Tyr Gln Gln Leu Pro Gly Thr Ala Pro Lys Leu Leu
         35                  40                  45
Ile Tyr Ser Asn Asn Gln Arg Pro Ser Gly Val Pro Asp Arg Phe Ser
     50                  55                  60
Gly Ser Lys Ser Gly Thr Ser Ala Ser Leu Ala Ile Ser Gly Leu Gln
 65                  70                  75                  80
Ser Glu Asp Glu Ala Asp Tyr Tyr Cys Ala Ala Trp Asp Asp Ser Leu
                 85                  90                  95
Asn Gly
```

<210> SEQ ID NO 671
<211> LENGTH: 98
<212> TYPE: PRT
<213> ORGANISM: Homo sapiens

<400> SEQUENCE: 671

```
Gln Ser Val Leu Thr Gln Pro Pro Ser Ala Ser Gly Thr Pro Gly Gln
  1               5                  10                  15
Arg Val Thr Ile Ser Cys Ser Gly Ser Ser Asn Ile Gly Ser Asn
             20                  25                  30
Tyr Val Tyr Trp Tyr Gln Gln Leu Pro Gly Thr Ala Pro Lys Leu Leu
         35                  40                  45
Ile Tyr Arg Asn Asn Gln Arg Pro Ser Gly Val Pro Asp Arg Phe Ser
     50                  55                  60
Gly Ser Lys Ser Gly Thr Ser Ala Ser Leu Ala Ile Ser Gly Leu Arg
 65                  70                  75                  80
Ser Glu Asp Glu Ala Asp Tyr Tyr Cys Ala Ala Trp Asp Asp Ser Leu
                 85                  90                  95
Ser Gly
```

<210> SEQ ID NO 672
<211> LENGTH: 98
<212> TYPE: PRT
<213> ORGANISM: Homo sapiens

<400> SEQUENCE: 672

```
Gln Ser Val Leu Thr Gln Pro Pro Ser Val Ser Glu Ala Pro Arg Gln
  1               5                  10                  15
Arg Val Thr Ile Ser Cys Ser Gly Ser Ser Ser Asn Ile Gly Asn Asn
             20                  25                  30
Ala Val Asn Trp Tyr Gln Gln Leu Pro Gly Lys Ala Pro Lys Leu Leu
         35                  40                  45
Ile Tyr Tyr Asp Asp Leu Leu Pro Ser Gly Val Ser Asp Arg Phe Ser
     50                  55                  60
```

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly

<210> SEQ ID NO 673
<211> LENGTH: 99
<212> TYPE: PRT
<213> ORGANISM: Homo sapiens

<400> SEQUENCE: 673

Gln Ser Val Leu Thr Gln Pro Pro Ser Val Ser Ala Pro Gly Gln
1               5                   10                  15

Arg Val Thr Ile Ser Cys Thr Gly Ser Ser Ser Asn Ile Gly Ala Gly
                20                  25                  30

Tyr Val Val His Trp Tyr Gln Gln Leu Pro Gly Thr Ala Pro Lys Leu
                35                  40                  45

Leu Ile Tyr Gly Asn Ser Asn Arg Pro Ser Gly Val Pro Asp Gln Phe
            50                  55                  60

Ser Gly Ser Lys Ser Gly Thr Ser Ala Ser Leu Ala Ile Thr Gly Leu
65                  70                  75                  80

Gln Ser Glu Asp Glu Ala Asp Tyr Tyr Cys Lys Ala Trp Asp Asn Ser
                85                  90                  95

Leu Asn Ala

<210> SEQ ID NO 674
<211> LENGTH: 99
<212> TYPE: PRT
<213> ORGANISM: Homo sapiens

<400> SEQUENCE: 674

Gln Ser Val Val Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
                20                  25                  30

Tyr Asp Val His Trp Tyr Gln Gln Leu Pro Gly Thr Ala Pro Lys Leu
                35                  40                  45

Leu Ile Tyr Gly Asn Ser Asn Arg Pro Ser Gly Val Pro Asp Arg Phe
            50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly

<210> SEQ ID NO 675
<211> LENGTH: 98
<212> TYPE: PRT
<213> ORGANISM: Homo sapiens

<400> SEQUENCE: 675

Ser Tyr Val Leu Thr Gln Pro Pro Ser Val Ser Gly Thr Pro Gly Gln
1               5                   10                  15

Arg Val Thr Ile Ser Cys Ser Gly Gly Arg Ser Asn Ile Gly Ser Asn
                20                  25                  30

Thr Val Lys Trp Tyr Gln Gln Leu Pro Gly Thr Ala Pro Lys Leu Leu

-continued

```
            35                  40                  45
Ile Tyr Gly Asn Asp Gln Arg Pro Ser Gly Val Pro Asp Arg Phe Ser
        50                  55                  60

Gly Ser Lys Ser Gly Thr Ser Ala Ser Leu Ala Ile Thr Gly Val Gln
 65                  70                  75                  80

Ala Glu Asp Glu Ala Asp Tyr Tyr Cys Gln Ser Tyr Asp Ser Ser Leu
                 85                  90                  95

Arg Gly
```

HUMAN ANTIBODIES THAT BIND THE P40 SUBUNIT OF HUMAN IL-12 AND METHODS FOR USING THE SAME

RELATED APPLICATIONS

This application is a continuation of U.S. patent application Ser. No. 12/253,103, filed Oct. 16, 2008, now abandoned, which is a continuation of U.S. patent application Ser. No. 10/884,830, filed Jul. 1, 2004, now U.S. Pat. No. 7,504,485, which is a divisional of U.S. patent application Ser. No. 09/534,717, filed Mar. 24, 2000, now U.S. Pat. No. 6,914,128, which is a non-provisional application claiming priority to U.S. provisional application Ser. No. 60/126,603, filed Mar. 25, 1999. The entire contents of each of the foregoing applications are hereby incorporated herein by reference.

BACKGROUND OF THE INVENTION

Human interleukin 12 (IL-12) has recently been characterized as a cytokine with a unique structure and pleiotropic effects (Kobayashi, et al. (1989) *J. Exp Med.* 170:827-845; Seder, et al. (1993) *Proc. Natl. Acad. Sci.* 90:10188-10192; Ling, et al. (1995) *J. Exp Med.* 154:116-127; Podlaski, et al. (1992) *Arch. Biochem. Biophys.* 294:230-237). IL-12 plays a critical role in the pathology associated with several diseases involving immune and inflammatory responses. A review of IL-12, its biological activities, and its role in disease can be found in Gately et al. (1998) *Ann. Rev. Immunol.* 16: 495-521.

Structurally, IL-12 is a heterodimeric protein comprising a 35 kDa subunit (p35) and a 40 kDa subunit (p40) which are both linked together by a disulfide bridge (referred to as the "p70 subunit"). The heterodimeric protein is produced primarily by antigen-presenting cells such as monocytes, macrophages and dendritic cells. These cell types also secrete an excess of the p40 subunit relative to p70 subunit. The p40 and p35 subunits are genetically unrelated and neither has been reported to possess biological activity, although the p40 homodimer may function as an IL-12 antagonist.

Functionally, IL-12 plays a central role in regulating the balance between antigen specific T helper type (Th1) and type 2 (Th2) lymphocytes. The Th1 and Th2 cells govern the initiation and progression of autoimmune disorders, and IL-12 is critical in the regulation of $Th_1$-lymphocyte differentiation and maturation. Cytokines released by the Th1 cells are inflammatory and include interferon γ (IFNγ), IL-2 and lymphotoxin (LT). Th2 cells secrete IL-4, IL-5, IL-6, IL-10 and IL-13 to facilitate humoral immunity, allergic reactions, and immunosuppression.

Consistent with the preponderance of Th1 responses in autoimmune diseases and the proinflammatory activities of IFNγ, IL-12 may play a major role in the pathology associated with many autoimmune and inflammatory diseases such as rheumatoid arthritis (RA), multiple sclerosis (MS), and Crohn's disease.

Human patients with MS have demonstrated an increase in IL-12 expression as documented by p40 mRNA levels in acute MS plaques. (Windhagen et al., (1995) *J. Exp. Med.* 182: 1985-1996). In addition, ex vivo stimulation of antigen-presenting cells with CD40L-expressing T cells from MS patients resulted in increased IL-12 production compared with control T cells, consistent with the observation that CD40/CD40L interactions are potent inducers of IL-12.

Elevated levels of IL-12 p70 have been detected in the synovia of RA patients compared with healthy controls (Morita et al (1998) *Arthritis and Rheumatism.* 41: 306-314). Cytokine messenger ribonucleic acid (mRNA) expression profile in the RA synovia identified predominantly Th1 cytokines. (Bucht et al., (1996) *Clin. Exp. Immunol.* 103: 347-367). IL-12 also appears to play a critical role in the pathology associated with Crohn's disease (CD). Increased expression of INFγ and IL-12 has been observed in the intestinal mucosa of patients with this disease (Fais et al. (1994) *J. Interferon Res.* 14:235-238; Parronchi et al., (1997) *Am. J. Path.* 150:823-832; Monteleone et al., (1997) *Gastroenterology.* 112:1169-1178, and Berrebi et al., (1998) *Am. J. Path* 152:667-672). The cytokine secretion profile of T cells from the lamina propria of CD patients is characteristic of a predominantly Th1 response, including greatly elevated IFNγ levels (Fuss, et al., (1996) *J. Immunol.* 157:1261-1270). Moreover, colon tissue sections from CD patients show an abundance of IL-12 expressing macrophages and IFNγ expressing T cells (Parronchi et al (1997) *Am. J. Path.* 150: 823-832).

Due to the role of human IL-12 in a variety of human disorders, therapeutic strategies have been designed to inhibit or counteract IL-12 activity. In particular, antibodies that bind to, and neutralize, IL-12 have been sought as a means to inhibit IL-12 activity. Some of the earliest antibodies were murine monoclonal antibodies (mAbs), secreted by hybridomas prepared from lymphocytes of mice immunized with IL-12 (see e.g., World Patent Application Publication No. WO 97/15327 by Strober et al.; Neurath et al. (1995) *J. Exp. Med.* 182:1281-1290; Duchmann et al. (1996) *J. Immunol.* 26:934-938). These murine IL-12 antibodies are limited for their use in vivo due to problems associated with administration of mouse antibodies to humans, such as short serum half life, an inability to trigger certain human effector functions and elicitation of an unwanted immune response against the mouse antibody in a human (the "human anti-mouse antibody" (HAMA) reaction).

In general, attempts to overcome the problems associated with use of fully-murine antibodies in humans, have involved genetically engineering the antibodies to be more "human-like." For example, chimeric antibodies, in which the variable regions of the antibody chains are murine-derived and the constant regions of the antibody chains are human-derived, have been prepared (Junghans, et al. (1990) *Cancer Res.* 50:1495-1502; Brown et al. (1991) *Proc. Natl. Acad. Sci.* 88:2663-2667; Kettleborough et al. (1991) *Protein Engineering.* 4:773-783). However, because these chimeric and humanized antibodies still retain some murine sequences, they still may elicit an unwanted immune reaction, the human anti-chimeric antibody (HACA) reaction, especially when administered for prolonged periods.

A preferred IL-12 inhibitory agent to murine antibodies or derivatives thereof (e.g., chimeric or humanized antibodies) would be an entirely human anti-IL-12 antibody, since such an agent should not elicit the HAMA reaction, even if used for prolonged periods. However, such antibodies have not been described in the art and, therefore are still needed.

SUMMARY OF THE INVENTION

The present invention provides human antibodies that bind human IL-12. The invention also relates to the treatment or prevention of acute or chronic diseases or conditions whose pathology involves IL-12, using the human anti-IL-12 antibodies of the invention.

In one aspect, the invention provides an isolated human antibody, or an antigen-binding portion thereof, that binds to human IL-12.

In one embodiment, the invention provides a selectively mutated human IL-12 antibody, comprising:

a human antibody or antigen-binding portion thereof, selectively mutated at a preferred selective mutagenesis position, contact or hypermutation position with an activity enhancing amino acid residue such that it binds to human IL-12.

In a preferred embodiment, the invention provides a selectively mutated human IL-12 antibody, comprising:

a human antibody or antigen-binding portion thereof, selectively mutated at a preferred selective mutagenesis position with an activity enhancing amino acid residue such that it binds to human IL-12.

In another preferred embodiment, the selectively mutated human IL-12 antibody or antigen-binding portion thereof is selectively mutated at more than one preferred selective mutagenesis position, contact or hypermutation positions with an activity enhancing amino acid residue. In another preferred embodiment, the selectively mutated human IL-12 antibody or antigen-binding portion thereof is selectively mutated at no more than three preferred selective mutagenesis positions, contact or hypermutation positions. In another preferred embodiment, the selectively mutated human IL-12 antibody or antigen-binding portion thereof is selectively mutated at no more than two preferred selective mutagenesis position, contact or hypermutation positions. In yet another preferred embodiment, the selectively mutated human IL-12 antibody or antigen-binding portion thereof, is selectively mutated such that a target specificity affinity level is attained, the target level being improved over that attainable when selecting for an antibody against the same antigen using phage display technology. In another preferred embodiment, the selectively mutated human IL-12 antibody further retains at least one desirable property or characteristic, e.g., preservation of non-cross reactivity with other proteins or human tissues, preservation of epitope recognition, production of an antibody with a close to a germline immunoglobulin sequence.

In another embodiment, the invention provides an isolated human antibody, or antigen-binding portion thereof, that binds to human IL-12 and dissociates from human IL-12 with a $K_{off}$ rate constant of $0.1\ s^{-1}$ or less, as determined by surface plasmon resonance, or which inhibits phytohemagglutinin blast proliferation in an in vitro phytohemagglutinin blast proliferation assay (PHA assay) with an $IC_{50}$ of $1\times10^{-6}$ M or less. More preferably, the isolated human antibody or an antigen-binding portion thereof, dissociates from human IL-12 with a $K_{off}$ rate constant of $1\times10^{-2}\ s^{-1}$ or less, or inhibits phytohemagglutinin blast proliferation in an in vitro PHA assay with an $IC_{50}$ of $1\times10^{-7}$ M or less. More preferably, the isolated human antibody, or an antigen-binding portion thereof, dissociates from human IL-12 with a $K_{off}$ rate constant of $1\times10^{-3}\ s^{-1}$ or less, or inhibits phytohemagglutinin blast proliferation in an in vitro PHA assay with an $IC_{50}$ of $1\times10^{-8}$ M or less. More preferably, the isolated human antibody, or an antigen-binding portion thereof, dissociates from human IL-12 with a $K_{off}$ rate constant of $1\times10^{-4}\ s^{-1}$ or less, or inhibits phytohemagglutinin blast proliferation in an in vitro PHA assay with an $IC_{50}$ of $1\times10^{-9}$ M or less. More preferably, the isolated human antibody, or an antigen-binding portion thereof, dissociates from human IL-12 with a $K_{off}$ rate constant of $1\times10^{-5}\ s^{-1}$ or less, or inhibits phytohemagglutinin blast proliferation in an in vitro PHA assay with an $IC_{50}$ of $1\times10^{-10}$ M or less. Even more preferably, the isolated human antibody, or an antigen-binding portion thereof, dissociates from human IL-12 with a $K_{off}$ rate constant of $1\times10^{-5}\ s^{-1}$ or less, or inhibits phytohemagglutinin blast proliferation in an in vitro PHA assay with an $IC_{50}$ of $1\times10^{-11}$ M or less.

In another embodiment, the invention provides an isolated human antibody, or an antigen-binding portion thereof, which has the following characteristics:
  a) inhibits phytohemagglutinin blast proliferation in an in vitro PHA assay with an $IC_{50}$ of $1\times10^{-6}$ M or less;
  b) has a heavy chain CDR3 comprising the amino acid sequence of SEQ ID NO: 1; and
  c) has a light chain CDR3 comprising the amino acid sequence of SEQ ID NO: 2.

In a preferred embodiment, the isolated human antibody, or an antigen-binding portion thereof, has a heavy chain CDR2 comprising the amino acid sequence of SEQ ID NO: 3; and has a light chain CDR2 comprising the amino acid sequence of SEQ ID NO: 4. In a preferred embodiment, the isolated human antibody, or an antigen-binding portion thereof, has a heavy chain CDR1 comprising the amino acid sequence of SEQ ID NO: 5; and has a light chain CDR1 comprising the amino acid sequence of SEQ ID NO: 6. In a preferred embodiment, the isolated human antibody, or antigen binding portion thereof, has a heavy chain variable region comprising the amino acid sequence of SEQ ID NO: 7; and has a light chain variable region comprising the amino acid sequence of SEQ ID NO: 8.

In another embodiment, the invention provides an isolated human antibody, or an antigen-binding portion thereof, which has the following characteristics:
  a) inhibits phytohemagglutinin blast proliferation in an in vitro PHA assay with an $IC_{50}$ of $1\times10^{-9}$ M or less;
  b) has a heavy chain CDR3 comprising the amino acid sequence of SEQ ID NO: 9; and
  c) has a light chain CDR3 comprising the amino acid sequence of SEQ ID NO: 10.

In a preferred embodiment, the isolated human antibody, or an antigen-binding portion thereof, has a heavy chain CDR2 comprising the amino acid sequence of SEQ ID NO: 11; and has a light chain CDR2 comprising the amino acid sequence of SEQ ID NO: 12. In a preferred embodiment, the isolated human antibody, or an antigen-binding portion thereof, has a heavy chain CDR1 comprising the amino acid sequence of SEQ ID NO: 13; and has a light chain CDR1 comprising the amino acid sequence of SEQ ID NO: 14. In a preferred embodiment, the isolated human antibody has a heavy chain variable region comprising the amino acid sequence of SEQ ID NO: 15; and has a light chain variable region comprising the amino acid sequence of SEQ ID NO: 16.

In another embodiment, the invention provides an isolated human antibody, or an antigen-binding portion thereof, which
  a) inhibits phytohemagglutinin blast proliferation in an in vitro PHA assay with an $IC_{50}$ of $1\times10^{-9}$ M or less;
  b) has a heavy chain CDR3 comprising the amino acid sequence of SEQ ID NO: 17; and
  c) has a light chain CDR3 comprising the amino acid sequence of SEQ ID NO: 18.

In a preferred embodiment, the isolated human antibody, or an antigen-binding portion thereof, has a heavy chain CDR2 comprising the amino acid sequence of SEQ ID NO: 19; and a light chain CDR2 comprising the amino acid sequence of SEQ ID NO: 20. In a preferred embodiment, the isolated human antibody, or an antigen-binding portion thereof, has a heavy chain CDR1 comprising the amino acid sequence of SEQ ID NO: 21; and a light chain CDR1 comprising the amino acid sequence of SEQ ID NO: 22. In a preferred embodiment, the isolated human antibody, or an antigen-binding portion thereof, has the heavy chain variable region comprising the amino acid sequence of SEQ ID NO: 23, and a light chain variable region comprising the amino acid sequence of SEQ ID NO: 24. In a preferred embodiment, the isolated human antibody comprises a heavy chain constant region selected from the group consisting of IgG1, IgG2, IgG3, IgG4, IgM, IgA and IgE constant regions or any allelic variation thereof as discussed in Kabat et al. (Kabat, E. A., et al. (1991) *Sequences of Proteins of Immunological Interest, Fifth Edition*, U.S. Department of Health and Human Services, NIH Publication No. 91-3242), included herein by reference. In a more preferred embodiment, the antibody heavy chain constant region is IgG1. In another preferred embodiment, the isolated human antibody is a Fab fragment, or a F(ab')$_2$ fragment or a single chain Fv fragment.

In another embodiment, the invention provides an isolated human antibody, or an antigen-binding portion thereof, which
 a) inhibits phytohemagglutinin blast proliferation in an in vitro PHA assay with an IC$_{50}$ of $1\times10^{-9}$ M or less;
 b) has a heavy chain CDR3 comprising the amino acid sequence selected from the group consisting of SEQ ID NO: 404-SEQ ID NO: 469; and
 c) has a light chain CDR3 comprising the amino acid sequence selected from the group consisting of SEQ ID NO: 534-SEQ ID NO: 579.

In a preferred embodiment, the isolated human antibody, or an antigen-binding portion thereof, has a heavy chain CDR2 comprising the amino acid sequence selected from the group consisting of SEQ ID NO:335-SEQ ID NO: 403; and a light chain CDR2 comprising the amino acid sequence selected from the group consisting of SEQ ID NO: 506-SEQ ID NO: 533. In a preferred embodiment, the isolated human antibody, or an antigen-binding portion thereof, has a heavy chain CDR1 comprising the amino acid sequence selected from the group consisting of SEQ ID NO: 288-SEQ ID NO: 334; and a light chain CDR1 comprising the amino acid sequence selected from the group consisting of SEQ ID NO: 470-SEQ ID NO: 505. In a preferred embodiment, the isolated human antibody, or an antigen-binding portion thereof, comprising a the heavy chain variable region comprising the amino acid sequence of SEQ ID NO: 23, and a light chain variable region comprising the amino acid sequence of SEQ ID NO: 24. In a preferred embodiment, the isolated human antibody comprises a heavy chain constant region, or an Fab fragment or a F(ab')$_2$ fragment or a single chain Fv fragment as described above.

In another embodiment, the invention provides an isolated human antibody, or an antigen-binding portion thereof, which
 a) inhibits phytohemagglutinin blast proliferation in an in vitro PHA assay with an IC$_{50}$ of $1\times10^{-9}$ M or less;
 b) has a heavy chain CDR3 comprising the amino acid sequence of SEQ ID NO: 25; and
 c) has a light chain CDR3 comprising the amino acid sequence of SEQ ID NO: 26.

In a preferred embodiment, the isolated human antibody, or an antigen-binding portion thereof, has a heavy chain CDR2 comprising the amino acid sequence of SEQ ID NO: 27; and a light chain CDR2 comprising the amino acid sequence of SEQ ID NO: 28. In a preferred embodiment, the isolated human antibody, or an antigen-binding portion thereof, has a heavy chain CDR1 comprising the amino acid sequence of SEQ ID NO: 29; and a light chain CDR1 comprising the amino acid sequence of SEQ ID NO: 30. In a preferred embodiment, the isolated human antibody, or an antigen-binding portion thereof, which has a heavy chain variable region comprising the amino acid sequence of SEQ ID NO: 31, and a light chain variable region comprising the amino acid sequence of SEQ ID NO: 32. In a preferred embodiment, the isolated human antibody comprises a heavy chain constant region, or an Fab fragment, or a F(ab')$_2$ fragment or a single chain Fv fragment as described above.

In another embodiment, the invention provides an isolated human antibody, or an antigen-binding portion thereof, which
 a) inhibits phytohemagglutinin blast proliferation in an in vitro PHA assay with an IC$_{50}$ of $1\times10^{-6}$ M or less;
 b) comprises a heavy chain CDR3 comprising the amino acid sequence of SEQ ID NO: 1, a heavy chain CDR2 comprising the amino acid sequence of SEQ ID NO: 3 and a heavy chain CDR1 comprising the amino acid sequence of SEQ ID NO: 5, or a mutant thereof having one or more amino acid substitutions at a contact position or a hypermutation position, wherein said mutant has a k$_{off}$ rate no more than 10-fold higher than the antibody comprising a heavy chain CDR3 comprising the amino acid sequence of SEQ ID NO: 1, a heavy chain CDR2 comprising the amino acid sequence of SEQ ID NO: 3, and a heavy chain CDR1 comprising the amino acid sequence of SEQ ID NO: 5; and
 c) comprises a light chain CDR3 comprising the amino acid sequence of SEQ ID NO: 2, a light chain CDR2 comprising the amino acid sequence of SEQ ID NO: 4, and a light chain CDR1 comprising the amino acid sequence of SEQ ID NO: 6, or a mutant thereof having one or more amino acid substitutions at a contact position or a hypermutation position, wherein said mutant has a k$_{off}$ rate no more than 10-fold higher than the antibody comprising a light chain CDR3 comprising the amino acid sequence of SEQ ID NO: 2, a light chain CDR2 comprising the amino acid sequence of SEQ ID NO: 4, and a light chain CDR1 comprising the amino acid sequence of SEQ ID NO: 6.

In another embodiment, the invention provides an isolated human antibody, or an antigen-binding portion thereof, which
 a) inhibits phytohemagglutinin blast proliferation in an in vitro PHA assay with an IC$_{50}$ of $1\times10^{-9}$ M or less;
 b) comprises a heavy chain CDR3 comprising the amino acid sequence of SEQ ID NO: 9, a heavy chain CDR2 comprising the amino acid sequence of SEQ ID NO: 11 and a heavy chain CDR1 comprising the amino acid sequence of SEQ ID NO: 13, or a mutant thereof having one or more amino acid substitutions at a contact position or a hypermutation position, wherein said mutant has a k$_{off}$ rate no more than 10-fold higher than the antibody comprising a heavy chain CDR3 comprising the amino acid sequence of SEQ ID NO: 9, a heavy chain CDR2 comprising the amino acid sequence of SEQ ID NO: 11, and a heavy chain CDR1 comprising the amino acid sequence of SEQ ID NO: 13; and
 c) comprises a light chain CDR3 comprising the amino acid sequence of SEQ ID NO: 10, a light chain CDR2 comprising the amino acid sequence of SEQ ID NO: 12, and a light chain CDR1 comprising the amino acid sequence of SEQ ID NO: 14, or a mutant thereof having one or more amino acid substitutions at a preferred selective mutagenesis position, contact position or a hypermutation position, wherein said mutant has a k$_{off}$ rate no more than 10-fold higher than the antibody comprising a light chain CDR3 comprising the amino acid sequence of SEQ ID NO: 10, a light chain CDR2 comprising the amino acid sequence of SEQ ID NO: 12, and a light chain CDR1 comprising the amino acid sequence of SEQ ID NO: 14.

In another embodiment, the invention provides an isolated human antibody, or an antigen-binding portion thereof, which
 a) inhibits phytohemagglutinin blast proliferation in an in vitro PHA assay with an IC$_{50}$ of $1\times10^{-9}$ M or less;
 b) comprises a heavy chain CDR3 comprising the amino acid sequence of SEQ ID NO: 17, a heavy chain CDR2 comprising the amino acid sequence of SEQ ID NO: 19 and a heavy chain CDR1 comprising the amino acid sequence of SEQ ID NO: 21, or a mutant thereof having one or more amino acid substitutions at a preferred selective mutagenesis position, contact position or a hypermutation position, wherein said mutant has a $k_{off}$ rate no more than 10-fold higher than the antibody comprising a heavy chain CDR3 comprising the amino acid sequence of SEQ ID NO: 17, a heavy chain CDR2 comprising the amino acid sequence of SEQ ID NO: 19, and a heavy chain CDR1 comprising the amino acid sequence of SEQ ID NO: 21; and c) comprises a light chain CDR3 comprising the amino acid sequence of SEQ ID NO: 18, a light chain CDR2 comprising the amino acid sequence of SEQ ID NO: 20, and a light chain CDR1 comprising the amino acid sequence of SEQ ID NO: 22, or a mutant thereof having one or more amino acid substitutions at preferred selective mutagenesis position, contact position or a hypermutation position, wherein said mutant has a $k_{off}$ rate no more than 10-fold higher than the antibody comprising a light chain CDR3 comprising the amino acid sequence of SEQ ID NO: 18, a light chain CDR2 comprising the amino acid sequence of SEQ ID NO: 20, and a light chain CDR1 comprising the amino acid sequence of SEQ ID NO: 22.

The invention also provides nucleic acid molecules encoding antibodies, or antigen binding portions thereof, of the invention. A preferred isolated nucleic acid encodes the heavy chain CDR3 comprising the amino acid sequence of SEQ ID NO: 17. The isolated nucleic acid encoding an antibody heavy chain variable region. In another embodiment, the isolated nucleic acid encodes the CDR2 of the antibody heavy chain variable region comprising the amino acid sequence of SEQ ID NO: 19. In another embodiment, the isolated nucleic acid encodes the CDR1 of the antibody heavy chain variable region comprising the amino acid sequence of SEQ ID NO: 21. In another embodiment, the isolated nucleic acid encodes an antibody heavy chain variable region comprising the amino acid sequence of SEQ ID NO: 23. In another embodiment, the isolated nucleic acid encodes the light chain CDR3 comprising the amino acid sequence of SEQ ID NO: 18. The isolated nucleic acid encoding an antibody light chain variable region. In another embodiment, the isolated nucleic acid encodes the CDR2 of the antibody light chain variable region comprising the amino acid sequence of SEQ ID NO: 20. In another embodiment, the isolated nucleic acid encodes the CDR1 of the antibody light chain variable region comprising the amino acid sequence of SEQ ID NO: 22. In another embodiment, the isolated nucleic acid encodes an antibody light chain variable region comprising the amino acid sequence of SEQ ID NO: 24.

In another embodiment, the invention provides an isolated human antibody, or an antigen-binding portion thereof, which a) inhibits phytohemagglutinin blast proliferation in an in vitro PHA assay with an $IC_{50}$ of $1\times10^{-9}$ M or less;

b) comprises a heavy chain CDR3 comprising the amino acid sequence of SEQ ID NO: 25, a heavy chain CDR2 comprising the amino acid sequence of SEQ ID NO: 27 and a heavy chain CDR1 comprising the amino acid sequence of SEQ ID NO: 29, or a mutant thereof having one or more amino acid substitutions at a preferred selective mutagenesis position, contact position or a hypermutation position, wherein said mutant has a $k_{off}$ rate no more than 10-fold higher than the antibody comprising a heavy chain CDR3 comprising the amino acid sequence of SEQ ID NO: 25, a heavy chain CDR2 comprising the amino acid sequence of SEQ ID NO: 27, and a heavy chain CDR1 comprising the amino acid sequence of SEQ ID NO: 29; and c) comprises a light chain CDR3 comprising the amino acid sequence of SEQ ID NO: 26, a light chain CDR2 comprising the amino acid sequence of SEQ ID NO: 28, and a light chain CDR1 comprising the amino acid sequence of SEQ ID NO: 30, or a mutant thereof having one or more amino acid substitutions at a preferred selective mutagenesis position, contact position or a hypermutation position, wherein said mutant has a $k_{off}$ rate no more than 10-fold higher than the antibody comprising a light chain CDR3 comprising the amino acid sequence of SEQ ID NO: 26, a light chain CDR2 comprising the amino acid sequence of SEQ ID NO: 28, and a light chain CDR1 comprising the amino acid sequence of SEQ ID NO: 30.

A preferred isolated nucleic acid encodes the heavy chain CDR3 comprising the amino acid sequence of SEQ ID NO: 25. The isolated nucleic acid encoding an antibody heavy chain variable region. In another embodiment, the isolated nucleic acid encodes the CDR2 of the antibody heavy chain variable region comprising the amino acid sequence of SEQ ID NO: 27. In another embodiment, the isolated nucleic acid encodes the CDR1 of the antibody heavy chain variable region comprising the amino acid sequence of SEQ ID NO: 29. In another embodiment, the isolated nucleic acid encodes an antibody heavy chain variable region comprising the amino acid sequence of SEQ ID NO: 31. In another embodiment, the isolated nucleic acid encodes the light chain CDR3 comprising the amino acid sequence of SEQ ID NO: 26. The isolated nucleic acid encoding an antibody light chain variable region. In another embodiment, the isolated nucleic acid encodes the CDR2 of the antibody light chain variable region comprising the amino acid sequence of SEQ ID NO: 28. In another embodiment, the isolated nucleic acid encodes the CDR1 of the antibody light chain variable region comprising the amino acid sequence of SEQ ID NO: 30. In another embodiment, the isolated nucleic acid encodes an antibody light chain variable region comprising the amino acid sequence of SEQ ID NO: 32.

In another aspect, the invention provides an isolated human antibody, or an antigen-binding portion thereof, which has the following characteristics:

a) that binds to human IL-12 and dissociates from human IL-12 with a $k_{off}$ rate constant of 0.1 s$^{-1}$ or less, as determined by surface plasmon resonance, or which inhibits phytohemagglutinin blast proliferation in an in vitro phytohemagglutinin blast proliferation assay (PHA assay) with an $IC_{50}$ of $1\times10^{-6}$ M or less.

b) has a heavy chain variable region comprising an amino acid sequence selected from a member of the $V_H3$ germline family, wherein the heavy chain variable region has a mutation at a preferred selective mutagenesis position, contact or hypermutation position with an activity enhancing amino acid residue.

c) has a light chain variable region comprising an amino acid sequence selected from a member of the $V_\lambda 1$ germline family, wherein the light chain variable region has a mutation at a preferred selective mutagenesis position, contact position or hypermutation position with an activity enhancing amino acid residue.

In another embodiment, the invention provides an isolated human antibody, or an antigen-binding portion thereof, which has the following characteristics:

a) that binds to human IL-12 and dissociates from human IL-12 with a $k_{off}$ rate constant of 0.1 s$^{-1}$ or less, as determined by surface plasmon resonance, or which inhibits phytohemagglutinin blast proliferation in an in vitro phytohemagglutinin blast proliferation assay (PHA assay) with an $IC_{50}$ of $1\times10^{-6}$ M or less.
  b) has a heavy chain variable region comprising an amino acid sequence selected from the group consisting of SEQ ID NOs: 595-667, wherein the heavy chain variable region has a mutation at a preferred selective mutagenesis position, contact position or hypermutation position with an activity enhancing amino acid residue.
  c) has a light chain variable region comprising an amino acid sequence selected from the group consisting of SEQ ID NOs: 669-675, wherein the light chain variable region has a mutation at a preferred selective mutagenesis position, contact or hypermutation position with an activity enhancing amino acid residue.

In another embodiment, the invention provides an isolated human antibody, or an antigen-binding portion thereof, which has the following characteristics:
  a) that binds to human IL-12 and dissociates from human IL-12 with a $k_{off}$ rate constant of 0.1 $s^{-1}$ or less, as determined by surface plasmon resonance, or which inhibits phytohemagglutinin blast proliferation in an in vitro phytohemagglutinin blast proliferation assay (PHA assay) with an $IC_{50}$ of $1\times10^{-6}$ M or less.
  b) has a heavy chain variable region comprising the COS-3 germline amino acid sequence, wherein the heavy chain variable region has a mutation at a preferred selective mutagenesis position, contact or hypermutation position with an activity enhancing amino acid residue.
  c) has a light chain variable region comprising the DPL8 germline amino acid sequence, wherein the light chain variable region has a mutation at a preferred selective mutagenesis position, contact or hypermutation position with an activity enhancing amino acid residue.

In another embodiment, the invention provides an isolated human antibody, or an antigen-binding portion thereof, which has the following characteristics:
  a) that binds to human IL-12 and dissociates from human IL-12 with a $k_{off}$ rate constant of 0.1 $s^{-1}$ or less, as determined by surface plasmon resonance, or which inhibits phytohemagglutinin blast proliferation in an in vitro phytohemagglutinin blast proliferation assay (PHA assay) with an $IC_{50}$ of $1\times10^{-6}$ M or less.
  b) has a heavy chain variable region comprising an amino acid sequence selected from a member of the $V_H3$ germline family, wherein the heavy chain variable region comprises a CDR2 that is structurally similar to CDR2s from other $V_H3$ germline family members, and a CDR1 that is structurally similar to CDR1s from other $V_H3$ germline family members, and wherein the heavy chain variable region has a mutation at a preferred selective mutagenesis position, contact or hypermutation position with an activity enhancing amino acid residue;
  c) has a light chain variable region comprising an amino acid sequence selected from a member of the $V_\lambda1$ germline family, wherein the light chain variable region comprises a CDR2 that is structurally similar to CDR2s from other $V_\lambda1$ germline family members, and a CDR1 that is structurally similar to CDR1s from other $V_\lambda1$ germline family members, and wherein the light chain variable region has a mutation at a preferred selective mutagenesis position, contact or hypermutation position with an activity enhancing amino acid residue.

In a preferred embodiment, the isolated human antibody, or antigen binding portion thereof, has a mutation in the heavy chain CDR3. In another preferred embodiment, the isolated human antibody, or antigen binding portion thereof, has a mutation in the light chain CDR3. In another embodiment, the isolated human antibody, or antigen binding portion thereof, has a mutation in the heavy chain CDR2. In another preferred embodiment, the isolated human antibody, or antigen binding portion thereof, has a mutation in the light chain CDR2. In another preferred embodiment, the isolated human antibody, or antigen binding portion thereof, has a mutation in the heavy chain CDR1. In another preferred embodiment, the isolated human antibody, or antigen binding portion thereof, has a mutation in the light chain CDR1.

In another aspect, the invention provides recombinant expression vectors carrying the antibody-encoding nucleic acids of the invention, and host cells into which such vectors have been introduced, are also encompassed by the invention, as are methods of making the antibodies of the invention by culturing the host cells of the invention.

In another aspect, the invention provides an isolated human antibody, or antigen-binding portion thereof, that neutralizes the activity of human IL-12, and at least one additional primate IL-12 selected from the group consisting of baboon IL-12, marmoset IL-12, chimpanzee IL-12, cynomolgus IL-12 and rhesus IL-12, but which does not neutralize the activity of the mouse IL-12.

In another aspect, the invention provides a pharmaceutical composition comprising the antibody or an antigen binding portion thereof, of the invention and a pharmaceutically acceptable carrier.

In another aspect, the invention provides a composition comprising the antibody or an antigen binding portion thereof, and an additional agent, for example, a therapeutic agent.

In another aspect, the invention provides a method for inhibiting human IL-12 activity comprising contacting human IL-12 with the antibody of the invention, e.g., J695, such that human IL-12 activity is inhibited.

In another aspect, the invention provides a method for inhibiting human IL-12 activity in a human subject suffering from a disorder in which IL-12 activity is detrimental, comprising administering to the human subject the antibody of the invention, e.g., J695, such that human IL-12 activity in the human subject is inhibited. The disorder can be, for example, Crohn's disease, multiple sclerosis or rheumatoid arthritis.

In another aspect, the invention features a method for improving the activity of an antibody, or an antigen binding portion thereof, to attain a predetermined target activity, comprising:
  a) providing a parent antibody a antigen-binding portion thereof;
  b) selecting a preferred selective mutagenesis position selected from group consisting of H30, H31, H31B, H32, H33, H52, H56, H58, L30, L31, L32, L50, L91, L92, L93, L94.
  c) individually mutating the selected preferred selective mutagenesis position to at least two other amino acid residues to hereby create a first panel of mutated antibodies, or antigen binding portions thereof;
  d) evaluating the activity of the first panel of mutated antibodies, or antigen binding portions thereof to determined if mutation of a single selective mutagenesis position produces an antibody or antigen binding portion thereof with the predetermined target activity or a partial target activity;
  e) combining in a stepwise fashion, in the parent antibody, or antigen binding portion thereof, individual mutations shown to have an improved activity, to form combination antibodies, or antigen binding portions thereof.

f) evaluating the activity of the combination antibodies, or antigen binding portions thereof to determined if the combination antibodies, or antigen binding portions thereof have the predetermined target activity or a partial target activity.

g) if steps d) or f) do not result in an antibody or antigen binding portion thereof having the predetermined target activity, or result an antibody with only a partial activity, additional amino acid residues selected from the group consisting of H35, H50, H53, H54, H95, H96, H97, H98, L30A and L96 are mutated to at least two other amino acid residues to thereby create a second panel of mutated antibodies or antigen-binding portions thereof;

h) evaluating the activity of the second panel of mutated antibodies or antigen binding portions thereof, to determined if mutation of a single amino acid residue selected from the group consisting of H35, H50, H53, H54, H95, H96, H97, H98, L30A and L96 results an antibody or antigen binding portion thereof, having the predetermined target activity or a partial activity;

i) combining in stepwise fashion in the parent antibody, or antigen-binding portion thereof, individual mutations of step g) shown to have an improved activity, to form combination antibodies, or antigen binding portions thereof;

j) evaluating the activity of the combination antibodies or antigen binding portions thereof, to determined if the combination antibodies, or antigen binding portions thereof have the predetermined target activity or a partial target activity;

k) if steps h) or j) do not result in an antibody or antigen binding portion thereof having the predetermined target activity, or result in an antibody with only a partial activity, additional amino acid residues selected from the group consisting of H33B, H52B and L31A are mutated to at least two other amino acid residues to thereby create a third panel of mutated antibodies or antigen binding portions thereof;

l) evaluating the activity of the third panel of mutated antibodies or antigen binding portions thereof, to determine if a mutation of a single amino acid residue selected from the group consisting of H33B, H52B and L31A resulted in an antibody or antigen binding portion thereof, having the predetermined target activity or a partial activity;

m) combining in a stepwise fashion in the parent antibody, or antigen binding portion thereof, individual mutation of step k) shown to have an improved activity, to form combination antibodies, or antigen binding portions, thereof;

n) evaluating the activity of the combination antibodies or antigen-binding portions thereof, to determine if the combination antibodies, or antigen binding portions thereof have the predetermined target activity to thereby produce an antibody or antigen binding portion thereof with a predetermined target activity.

In another aspect, the invention provides a method for improving the activity of an antibody, or antigen-binding portion thereof, comprising:

a) providing a parent antibody or antigen-binding portion thereof;

b) selecting a preferred selective mutagenesis position, contact or hypermutation position within a complementarity determining region (CDR) for mutation, thereby identifying a selected preferred selective mutagenesis position, contact or hypermutation position;

c) individually mutating said selected preferred selective mutagenesis position, contact or hypermutation position to at least two other amino acid residues to thereby create a panel of mutated antibodies, or antigen-binding portions thereof;

d) evaluating the activity of the panel of mutated antibodies, or antigen-binding portions thereof, relative to the parent antibody or antigen-binding portion thereof;

e) repeating steps b) through d) for at least one other contact or hypermutation position;

f) combining, in the parent antibody, or antigen-binding portion thereof, individual mutations shown to have improved activity, to form combination antibodies, or antigen-binding portions thereof; and g) evaluating the activity of the combination antibodies, or antigen-binding portions thereof, relative to the parent antibody or antigen-binding portion thereof; until an antibody, or antigen-binding portion thereof, with an improved activity, relative to the parent antibody, or antigen-binding portion thereof, is obtained.

In one embodiment, the invention provides a method for improving the activity of an antibody, or antigen-binding portion thereof, comprising:

a) providing a recombinant parent antibody or antigen-binding portion thereof; that was obtained by selection in a phage-display system but whose activity is not further improved by mutagenesis in said phage-display system;

b) selecting a preferred selective mutagenesis position, contact or hypermutation position within a complementarity determining region (CDR) for mutation, thereby identifying a selected contact or hypermutation position;

c) individually mutating said selected preferred selective mutagenesis position, contact or hypermutation position to at least two other amino acid residues to thereby create a panel of mutated antibodies, or antigen-binding portions thereof, and expressing said panel in a non-phage display system;

d) evaluating the activity of the panel of mutated antibodies, or antigen-binding portions thereof, relative to the parent antibody or antigen-binding portion thereof;

e) repeating steps b) through d) for at least one other contact or hypermutation position;

f) combining, in the parent antibody, or antigen-binding portion thereof, individual mutations shown to have improved activity, to form combination antibodies, or antigen-binding portions thereof; and g) evaluating the activity of the combination antibodies, or antigen-binding portions thereof, relative to the parent antibody or antigen-binding portion thereof; until an antibody, or antigen-binding portion thereof, with an improved activity, relative to the parent antibody, or antigen-binding portion thereof, is obtained.

In a preferred embodiment, the contact positions are selected from the group consisting of H30, H31, H31B, H32, H33, H35, H50, H52, H52A, H53, H54, H56, H58, H95, H96, H97, H98, H101, L30, L31, L32, L34, L50, L52, L53, L55, L91, L92, L93, L94 and L96. In another preferred embodiment, the hypermutation positions are selected from the group consisting of H30, H31, H31B, H32, H52, H56, H58, L30, L31, L32, L53 and L93. In a more preferred embodiment the residues for selective mutagenesis are selected from the preferred selective mutagenesis positions from the group consisting of H30, H31, H31B, H32, H33, H52, H56, H58, L30, L31, L32, L50, L91, L92, L93, L94. In a more preferred embodiment, the contact positions are selected from the group consisting of L50 and L94.

In another embodiment, the invention provides a method for improving the activity of an antibody, or antigen-binding portion thereof, comprising:
  a) providing a recombinant parent antibody or antigen-binding portion thereof;
  b) selecting a preferred selective mutagenesis position, contact or hypermutation position within a complementarity determining region (CDR) for mutation, thereby identifying a selected contact or hypermutation position;
  c) individually mutating said selected preferred selective mutagenesis position, contact or hypermutation position to at least two other amino acid residues to thereby create a panel of mutated antibodies, or antigen-binding portions thereof and expressing said panel in an appropriate expression system;
  d) evaluating the activity of the panel of mutated antibodies, or antigen-binding portions thereof, relative to the parent antibody or antigen-binding portion thereof thereby identifying an activity enhancing amino acid residue;
  e) evaluating the panel of mutated antibodies, or antigen-binding portions thereof, relative to the parent antibody or antigen-binding portion thereof for at least one other property or characteristics, wherein the property or characteristic is one that needs to be retained in the antibody; until an antibody, or antigen-binding portion thereof, with an improved activity and at least one retained property or characteristic, relative to the parent antibody, or antigen-binding portion thereof, is obtained.

In a preferred embodiment, the contact positions are selected from the group consisting of H30, H31, H31B, H32, H33, H35, H50, H52, H52A, H53, H54, H56, H58, H95, H96, H97, H98, H101, L30, L31, L32, L34, L50, L52, L53, L55, L91, L92, L93, L94 and L96 and the other characteristic is selected from 1) preservation of non-crossreactivity with other proteins or human tissues, 2) preservation of epitope recognition, i.e. recognizing p40 epitope preferably in the context of the p70 p40/p35 heterodimer preventing binding interference from free, soluble p40 and/or 3) to produce an antibody with a close to germline immunoglobulin sequence. In another preferred embodiment, the hypermutation positions are selected from the group consisting of H30, H31, H31B, H32, H52, H56, H58, L30, L31, L32, L53 and L93 and the other characteristic is selected from 1) preservation of non-crossreactivity with other proteins or human tissues, 2) preservation of epitope recognition, i.e. recognizing p40 epitope preferably in the context of the p70 p40/p35 heterodimer preventing binding interference from free, soluble p40 and/or 3) to produce an antibody with a close to germline immunoglobulin sequence. In a more preferred embodiment the residues for selective mutagenesis are selected from the preferred selective mutagenesis positions from the group consisting of H30, H31, H31B, H32, H33, H52, H56, H58, L30, L31, L32, L50, L91, L92, L93, L94 and the other characteristic is selected from 1) preservation of non-crossreactivity with other proteins or human tissues, 2) preservation of epitope recognition, i.e. recognizing p40 epitope preferably in the context of the p70 p40/p35 heterodimer preventing binding interference from free, soluble p40 and/or 3) to produce an antibody with a close to germline immunoglobulin sequence. In a more preferred embodiment, the contact positions are selected from the group consisting of L50 and L94 and the other characteristic is selected from 1) preservation of non-crossreactivity with other proteins or human tissues, 2) preservation of epitope recognition, i.e. recognizing p40 epitope preferably in the context of the p70 p40/p35 heterodimer preventing binding interference from free, soluble p40 and/or 3) to produce an antibody with a close to germline immunoglobulin sequence.

In another embodiment of the invention provides a method for improving the activity of an antibody, or antigen-binding portion thereof, comprising:
  a) providing a recombinant parent antibody or antigen-binding portion thereof; that was obtained by selection in a phage-display system but whose activity cannot be further improved by mutagenesis in said phage-display system;
  b) selecting a preferred selective mutagenesis position, contact or hypermutation position within a complementarity determining region (CDR) for mutation, thereby identifying a selected preferred selective mutagenesis position, contact or hypermutation position;
  c) individually mutating said selected preferred selective mutagenesis position, contact or hypermutation position to at least two other amino acid residues to thereby create a panel of mutated antibodies, or antigen-binding portions thereof, and expressing said panel in a non-phage display system;
  d) evaluating the activity of the panel of mutated antibodies, or antigen-binding portions thereof, relative to the parent antibody or antigen-binding portion thereof thereby identifying an activity enhancing amino acid residue;
  e) evaluating the panel of mutated antibodies, or antigen-binding portions thereof, relative to the parent antibody or antigen-binding portion thereof for at least one other property or characteristic, wherein the property or characteristic is one that needs to be retained, until an antibody, or antigen-binding portion thereof, with an improved activity and at least one retained property or characteristic, relative to the parent antibody, or antigen-binding portion thereof, is obtained.
  f) repeating steps a) through e) for at least one other preferred selective mutagenesis position, contact or hypermutation position;
  g) combining, in the parent antibody, or antigen-binding portion thereof, at least two individual activity enhancing amino acid residues shown to have improved activity and at least on retained property or characteristic, to form combination antibodies, or antigen-binding portions thereof; and
  h) evaluating the activity of the combination antibodies, or antigen-binding portions thereof, relative to the parent antibody or antigen-binding portion thereof; until an antibody, or antigen-binding portion thereof, with an improved activity and at least one retained property or characteristic, relative to the parent antibody, or antigen-binding portion thereof, is obtained.

In a preferred embodiment, the contact positions are selected from the group consisting of H30, H31, H31B, H32, H33, H35, H50, H52, H52A, H53, H54, H56, H58, H95, H96, H97, H98, H101, L30, L31, L32, L34, L50, L52, L53, L55, L91, L92, L93, L94 and L96 and the other characteristic is selected from 1) preservation of non-crossreactivity with other proteins or human tissues, 2) preservation of epitope recognition, i.e. recognizing p40 epitope preferably in the context of the p70 p40/p35 heterodimer preventing binding interference from free, soluble p40 and/or 3) to produce an antibody with a close to germline immunoglobulin sequence. In another preferred embodiment, the hypermutation positions are selected from the group consisting of H30, H31, H31B, H32, H52, H56, H58, L30, L31, L32, L53 and L93 and the other characteristic is selected from 1) preservation of non-crossreactivity with other proteins or human tissues, 2) preservation of epitope recognition, i.e. recognizing p40 epitope preferably in the context of the p70 p40/p35 heterodimer preventing binding interference from free, soluble p40 and/or 3) to produce an antibody with a close to germline immunoglobulin sequence. In a more preferred embodiment the residues for selective mutagenesis are selected from the preferred selective mutagenesis positions from the group consisting of H30, H31, H31B, H32, H33, H52, H56, H58, L30, L31, L32, L50, L91, L92, L93, L94 and the other characteristic is selected from 1) preservation of non-crossreactivity with other proteins or human tissues, 2) preservation of epitope recognition, i.e. recognizing p40 epitope preferably in the context of the p70 p40/p35 heterodimer preventing binding interference from free, soluble p40 and/or 3) to produce an antibody with a close to germline immunoglobulin sequence. In a more preferred embodiment, the contact positions are selected from the group consisting of L50 and L94 and the other characteristic is selected from 1) preservation of non-crossreactivity with other proteins or human tissues, 2) preservation of epitope recognition, i.e. recognizing p40 epitope preferably in the context of the p70 p40/p35 heterodimer preventing binding interference from free, soluble p40 and/or 3) to produce an antibody with a close to germline immunoglobulin sequence.

In another embodiment, the invention provides a method for improving the activity of an antibody, or antigen-binding portion thereof, comprising:
  a) providing a recombinant parent antibody or antigen-binding portion thereof; that was obtained by selection in a phage-display system but whose activity cannot be further improved by mutagenesis in said phage-display system;
  b) selecting a contact or hypermutation position within a complementarity determining region (CDR) for mutation, thereby identifying a selected contact or hypermutation position;
  c) individually mutating said selected contact or hypermutation position to at least two other amino acid residues to thereby create a panel of mutated antibodies, or antigen-binding portions thereof, and expressing said panel in a non-phage display system;
  d) evaluating the activity of the panel of mutated antibodies, or antigen-binding portions thereof, relative to the parent antibody or antigen-binding portion thereof thereby identifying an activity enhancing amino acid residue;
  e) evaluating the panel of mutated antibodies, or antigen-binding portions thereof, relative to the parent antibody or antigen-binding portion thereof for at least one other property or characteristics, wherein the property or characteristic is one that needs to be retained;
until an antibody, or antigen-binding portion thereof, with an improved activity and at least one retained property or characteristic, relative to the parent antibody, or antigen-binding portion thereof, is obtained.

In a preferred embodiment, the contact positions are selected from the group consisting of H30, H31, H31B, H32, H33, H35, H50, H52, H52A, H53, H54, H56, H58, H95, H96, H97, H98, H101, L30, L31, L32, L34, L50, L52, L53, L55, L91, L92, L93, L94 and L96 and the other characteristic is selected from 1) preservation of non-crossreactivity with other proteins or human tissues, 2) preservation of epitope recognition, i.e. recognizing p40 epitope preferably in the context of the p70 p40/p35 heterodimer preventing binding interference from free, soluble p40 and/or 3) to produce an antibody with a close to germline immunoglobulin sequence.

In another preferred embodiment, the hypermutation positions are selected from the group consisting of H30, H31, H31B, H32, H52, H56, H58, L30, L31, L32, L53 and L93 and the other characteristic is selected from 1) preservation of non-crossreactivity with other proteins or human tissues, 2) preservation of epitope recognition, i.e. recognizing p40 epitope preferably in the context of the p70 p40/p35 heterodimer preventing binding interference from free, soluble p40 and/or 3) to produce an antibody with a close to germline immunoglobulin sequence. In a more preferred embodiment the residues for selective mutagenesis are selected from the preferred selective mutagenesis positions from the group consisting of H30, H31, H31B, H32, H33, H52, H56, H58, L30, L31, L32, L50, L91, L92, L93, L94 and the other characteristic is selected from 1) preservation of non-crossreactivity with other proteins or human tissues, 2) preservation of epitope recognition, i.e. recognizing p40 epitope preferably in the context of the p70 p40/p35 heterodimer preventing binding interference from free, soluble p40 and/or 3) to produce an antibody with a close to germline immunoglobulin sequence. In a more preferred embodiment, the contact positions are selected from the group consisting of L50 and L94 and the other characteristic is selected from 1) preservation of non-crossreactivity with other proteins or human tissues, 2) preservation of epitope recognition, i.e. recognizing p40 epitope preferably in the context of the p70 p40/p35 heterodimer preventing binding interference from free, soluble p40 and/or 3) to produce an antibody with a close to germline immunoglobulin sequence.

In another embodiment, the invention provides a method for improving the activity of an antibody, or antigen-binding portion thereof, comprising:
  a) providing a recombinant parent antibody or antigen-binding portion thereof; that was obtained by selection in a phage-display system but whose activity cannot be further improved by mutagenesis in said phage-display system;
  b) selecting a preferred selective mutagenesis position, contact or hypermutation position within a complementarity determining region (CDR) for mutation, thereby identifying a selected preferred selective mutagenesis position contact or hypermutation position;
  c) individually mutating said selected preferred selective mutagenesis position, contact or hypermutation position to at least two other amino acid residues to thereby create a panel of mutated antibodies, or antigen-binding portions thereof, and expressing said panel in a non-phage display system;
  d) evaluating the activity of the panel of mutated antibodies, or antigen-binding portions thereof, relative to the parent antibody or antigen-binding portion thereof thereby identifying an activity enhancing amino acid residue;
  e) evaluating the panel of mutated antibodies, or antigen-binding portions thereof, relative to the parent antibody or antigen-binding portion thereof for at least one other property or characteristic, wherein the property or characteristic is one that needs to be retained, until an antibody, or antigen-binding portion thereof, with an improved activity and at least one retained property or characteristic, relative to the parent antibody, or antigen-binding portion thereof, is obtained.
  f) repeating steps a) through e) for at least one other preferred selective mutagenesis position, contact or hypermutation position;
  g) combining, in the parent antibody, or antigen-binding portion thereof, at least two individual activity enhancing amino acid residues shown to have improved activity and at least on retained other characteristic, to form combination antibodies, or antigen-binding portions thereof; and h) evaluating the activity of the combination antibodies, or antigen-binding portions thereof, relative to the parent antibody or antigen-binding portion thereof; until an antibody, or antigen-binding portion thereof, with an improved activity and at least one retained property or characteristic, relative to the parent antibody, or antigen-binding portion thereof, is obtained.

In a preferred embodiment, the contact positions are selected from the group consisting of H30, H31, H31B, H32, H33, H35, H50, H52, H52A, H53, H54, H56, H58, H95, H96, H97, H98, H101, L30, L31, L32, L34, L50, L52, L53, L55, L91, L92, L93, L94 and L96 and the other characteristic is selected from 1) preservation of non-crossreactivity with other proteins or human tissues, 2) preservation of epitope recognition, i.e. recognizing p40 epitope preferably in the context of the p70 p40/p35 heterodimer preventing binding interference from free, soluble p40 and/or 3) to produce an antibody with a close to germline immunoglobulin sequence. In another preferred embodiment, the hypermutation positions are selected from the group consisting of H30, H31, H31B, H32, H52, H56, H58, L30, L31, L32, L53 and L93 and the other characteristic is selected from 1) preservation of non-crossreactivity with other proteins or human tissues, 2) preservation of epitope recognition, i.e. recognizing p40 epitope preferably in the context of the p70 p40/p35 heterodimer preventing binding interference from free, soluble p40 and/or 3) to produce an antibody with a close to germline immunoglobulin sequence. In a more preferred embodiment the residues for selective mutagenesis are selected from the preferred selective mutagenesis positions from the group consisting of H30, H31, H31B, H32, H33, H52, H56, H58, L30, L31, L32, L50, L91, L92, L93, L94 and the other characteristic is selected from 1) preservation of non-crossreactivity with other proteins or human tissues, 2) preservation of epitope recognition, i.e. recognizing p40 epitope preferably in the context of the p70 p40/p35 heterodimer preventing binding interference from free, soluble p40 and/or 3) to produce an antibody with a close to germline immunoglobulin sequence. In a more preferred embodiment, the contact positions are selected from the group consisting of L50 and L94 and the other characteristic is selected from 1) preservation of non-crossreactivity with other proteins or human tissues, 2) preservation of epitope recognition, i.e. recognizing p40 epitope preferably in the context of the p70 p40/p35 heterodimer preventing binding interference from free, soluble p40 and/or 3) to produce an antibody with a close to germline immunoglobulin sequence.

In another embodiment, the invention provides a method for improving the activity of an antibody, or antigen-binding portion thereof, comprising:

a) providing a parent antibody or antigen-binding portion thereof;

b) selecting an amino acid residue within a complementarity determining region (CDR) for mutation other than H30, H31, H31B, H32, H33, H35, H50, H52, H52A, H53, H54, H56, H58, H95, H96, H97, H98, H101, L30, L31, L32, L34, L50, L52, L53, L55, L91, L92, L93, L94 and L96;

c) individually mutating said selected position to at least two other amino acid residues to thereby create a panel of mutated antibodies, or antigen-binding portions thereof;

d) evaluating the activity of the panel of mutated antibodies, or antigen-binding portions thereof, relative to the parent antibody or antigen-binding portion thereof thereby identifying an activity enhancing amino acid residue;

e) evaluating the panel of mutated antibodies, or antigen-binding portions thereof, relative to the parent antibody or antigen-binding portion thereof, for changes in at least one other property or characteristic;

until an antibody, or antigen-binding portion thereof, with an improved activity, relative to the parent antibody, or antigen-binding portion thereof, is obtained.

Preferably, the other characteristic or property is selected from 1) preservation of non-crossreactivity with other proteins or human tissues, 2) preservation of epitope recognition, i.e. recognizing p40 epitope preferably in the context of the p70 p40/p35 heterodimer preventing binding interference from free, soluble p40 and/or 3) to produce an antibody with a close to germline immunoglobulin sequence In another embodiment, the invention provides a method for improving the activity of an antibody, or antigen-binding portion thereof, comprising:

a) providing a parent antibody or antigen-binding portion thereof;

b) selecting an amino acid residue within a complementarity determining region (CDR) for mutation other than H30, H31, H31B, H32, H33, H35, H50, H52, H52A, H53, H54, H56, H58, H95, H96, H97, H98, H101, L30, L31, L32, L34, L50, L52, L53, L55, L91, L92, L93, L94 and L96;

c) individually mutating said selected position to at least two other amino acid residues to thereby create a panel of mutated antibodies, or antigen-binding portions thereof;

d) evaluating the activity of the panel of mutated antibodies, or antigen-binding portions thereof, relative to the parent antibody or antigen-binding portion thereof, thereby identifying an activity enhancing amino acid residue;

e) repeating steps b) through d) for at least one other CDR position which is neither the position selected under b) nor a position at H30, H31, H31B, H32, H33, H35, H50, H52, H52A, H53, H54, H56, H58, H95, H96, H97, H98, H101, L30, L31, L32, L34, L50, L52, L53, L55, L91, L92, L93, L94 and L96;

f) combining, in the parent antibody, or antigen-binding portion thereof, at least two individual activity enhancing amino acid residues shown to have improved activity, to form combination antibodies, or antigen-binding portions thereof; and g) evaluating the activity of the combination antibodies, or antigen-binding portions thereof with two activity enhancing amino acid residues, relative to the parent antibody or antigen-binding portion thereof until an antibody, or antigen-binding portion thereof, with an improved activity, relative to the parent antibody, or antigen-binding portion thereof, is obtained.

In another embodiment, the invention provides a method for improving the activity of an antibody, or antigen-binding portion thereof, comprising:

a) providing a recombinant parent antibody or antigen-binding portion thereof; that was obtained by selection in a phage-display system but whose activity cannot be further improved by mutagenesis in said phage-display system;

b) selecting an amino acid residue within a complementarity determining region (CDR) for mutation other than H30, H31, H31B, H32, H33, H35, H50, H52, H52A, H53, H54, H56, H58, H95, H96, H97, H98, H101, L30, L31, L32, L34, L50, L52, L53, L55, L91, L92, L93, L94 and;

c) individually mutating said selected contact or hypermutation position to at least two other amino acid residues to thereby create a panel of mutated antibodies, or antigen-binding portions thereof, and expressing said panel in a non-phage display system;

d) evaluating the activity of the panel of mutated antibodies, or antigen-binding portions thereof, relative to the parent antibody or antigen-binding portion thereof thereby identifying an activity enhancing amino acid residue;

e) evaluating the panel of mutated antibodies, or antigen-binding portions thereof, relative to the parent antibody or antigen-binding portion thereof, for changes in at least one other property or characteristic until an antibody, or antigen-binding portion thereof, with an improved activity, relative to the parent antibody, or antigen-binding portion thereof, is obtained.

Preferably, the other characteristic or property is selected from 1) preservation of non-crossreactivity with other proteins or human tissues, 2) preservation of epitope recognition, i.e. recognizing p40 epitope preferably in the context of the p70 p40/p35 heterodimer preventing binding interference from free, soluble p40 and/or 3) to produce an antibody with a close to germline immunoglobulin sequence.

In another embodiment, the invention provides a method for improving the activity of an antibody, or antigen-binding portion thereof, comprising:

a) providing a parent antibody or antigen-binding portion thereof that was obtained by selection in a phage-display system but whose activity cannot be further improved by mutagenesis in said phage-display system;

b) selecting an amino acid residue within a complementarity determining region (CDR) for mutation other than H30, H31, H31B, H32, H33, H35, H50, H52, H52A, H53, H54, H56, H58, H95, H96, H97, H98, H101, L30, L31, L32, L34, L50, L52, L53, L55, L91, L92, L93, L94 and L96;

c) individually mutating said selected position to at least two other amino acid residues to thereby create a panel of mutated antibodies, or antigen-binding portions thereof and expression in a non-phage display system;

d) evaluating the activity of the panel of mutated antibodies, or antigen-binding portions thereof, relative to the parent antibody or antigen-binding portion thereof thereby identifying an activity enhancing amino acid residue;

e) repeating steps b) through d) for at least one other position within the CDR which is neither the position selected under b) nor a position at H30, H31, H31B, H32, H33, H35, H50, H52, H52A, H53, H54, H56, H58, H95, H96, H97, H98, H101, L30, L31, L32, L34, L50, L52, L53, L55, L91, L92, L93, L94;

f) combining, in the parent antibody, or antigen-binding portion thereof, at least two individual activity enhancing amino acid residues shown to have improved activity, to form combination antibodies, or antigen-binding portions thereof; and g) evaluating the activity and other property or characteristic of the combination antibodies, or antigen-binding portions thereof with two activity enhancing amino acid residues, relative to the parent antibody or antigen-binding portion thereof; until an antibody, or antigen-binding portion thereof, with an improved activity, relative to the parent antibody, or antigen-binding portion thereof, is obtained.

Preferably, the other characteristic or property is selected from 1) preservation of non-crossreactivity with other proteins or human tissues, 2) preservation of epitope recognition, i.e. recognizing p40 epitope preferably in the context of the p70 p40/p35 heterodimer preventing binding interference from free, soluble p40 and/or 3) to produce an antibody with a close to germline immunoglobulin sequence.

In another embodiment, the invention provides a method for improving the activity of an antibody, or antigen-binding portion thereof, comprising:

a) providing a parent antibody or antigen-binding portion thereof;

b) selecting an amino acid residue within a complementarity determining region (CDR) for mutation other than H30, H31, H31B, H32, H33, H35, H50, H52, H52A, H53, H54, H56, H58, H95, H96, H97, H98, H101, L30, L31, L32, L34, L50, L52, L53, L55, L91, L92, L93, L94 and L96;

c) individually mutating said selected position to at least two other amino acid residues to thereby create a panel of mutated antibodies, or antigen-binding portions thereof;

d) evaluating the activity of the panel of mutated antibodies, or antigen-binding portions thereof, relative to the parent antibody or antigen-binding portion thereof, thereby identifying an activity enhancing amino acid residue;

e) evaluating the panel of mutated antibodies or antigen-binding portions thereof, relative to the parent antibody or antigen-portion thereof, for changes in at least one other property or characteristic;

f) repeating steps b) through e) for at least one other CDR position which is neither the position selected under b) nor a position at H30, H31, H31B, H32, H33, H35, H50, H52, H52A, H53, H54, H56, H58, H95, H96, H97, H98, H101, L30, L31, L32, L34, L50, L52, L53, L55, L91, L92, L93, L94 and L96;

g) combining, in the parent antibody, or antigen-binding portion thereof, at least two individual activity enhancing amino acid residues shown to have improved activity and not affecting at least one other property or characteristic, to form combination antibodies, or antigen-binding portions thereof; and h) evaluating the activity and the retention of at least one other characteristic or property of the combination antibodies, or antigen-binding portions thereof with two activity enhancing amino acid residues, relative to the parent antibody or antigen-binding portion thereof until an antibody, or antigen-binding portion thereof, with an improved activity and at least one retained property or characteristic, relative to the parent antibody, or antigen-binding portion thereof, is obtained.

In another embodiment the invention provides a method to improve the affinity of an antibody or antigen-binding portion thereof, comprising:

a) providing a parent antibody or antigen-binding portion thereof that was obtained by selection in a phage-display system but whose activity cannot be further improved by mutagenesis in said phage-display system;

b) selecting an amino acid residue within a complementarity determining region (CDR) for mutation other than H30, H31, H31B, H32, H33, H35, H50, H52, H52A, H53, H54, H56, H58, H95, H96, H97, H98, H101, L30, L31, L32, L34, L50, L52, L53, L55, L91, L92, L93, L94 and L96;
  c) individually mutating said selected position to at least two other amino acid residues to thereby create a panel of mutated antibodies, or antigen-binding portions thereof and expression in a non-phage display system;
  d) evaluating the activity of the panel of mutated antibodies, or antigen-binding portions thereof, relative to the parent antibody or antigen-binding portion thereof thereby identifying an activity enhancing amino acid residue;
  e) evaluating the panel of mutated antibodies, or antigen-binding portions thereof, relative to the parent antibody or antigen-binding portion thereof, for changes in at least one other characteristic or property until an antibody, or antigen-binding portion thereof, with an improved activity, relative to the parent antibody, or antigen-binding portion thereof, is obtained.

In another embodiment, the invention provides a method for improving the activity of an antibody, or antigen-binding portion thereof, comprising:
  a) providing a parent antibody or antigen-binding portion thereof;
  b) selecting an amino acid residue within a complementarity determining region (CDR) for mutation at a position other than H30, H31, H31B, H32, H33, H35, H50, H52, H52A, H53, H54, H56, H58, H95, H96, H97, H98, H101, L30, L31, L32, L34, L50, L52, L53, L55, L91, L92, L93, L94 and L96;
  c) individually mutating said selected position to at least two other amino acid residues to thereby create a panel of mutated antibodies, or antigen-binding portions thereof;
  d) evaluating the activity of the panel of mutated antibodies, or antigen-binding portions thereof, relative to the parent antibody or antigen-binding portion thereof, thereby identifying an activity enhancing amino acid residue;
  e) evaluating the panel of mutated antibodies or antigen-binding portions thereof, relative to the parent antibody or antigen-portion thereof, for changes in at least one other property or characteristic;
  f) repeating steps b) through e) for at least one other CDR position which is neither the position selected under b) nor a position at H30, H31, H31B, H32, H33, H35, H50, H52, H52A, H53, H54, H56, H58, H95, H96, H97, H98, H101, L30, L31, L32, L34, L50, L52, L53, L55, L91, L92, L93, L94 and L96;
  g) combining, in the parent antibody, or antigen-binding portion thereof, at least two individual activity enhancing amino acid residues shown to have improved activity but not affecting at least one other property or characteristic, to form combination antibodies, or antigen-binding portions thereof with at least one retained property or characteristic; and
  h) evaluating the activity and the retention of at least one property of characteristic of the combination antibodies, or antigen-binding portions thereof with two activity enhancing amino acid residues, relative to the parent antibody or antigen-binding portion thereof until an antibody, or antigen-binding portion thereof, with an improved activity and at least one retained property or characteristic, relative to the parent antibody, or antigen-binding portion thereof, is obtained.

Preferably, the other characteristic or property is selected from 1) preservation of non-crossreactivity with other proteins or human tissues, 2) preservation of epitope recognition, i.e. recognizing p40 epitope preferably in the context of the p70 p40/p35 heterodimer preventing binding interference from free, soluble p40 and/or 3) to produce an antibody with a close to germline immunoglobulin sequence In another embodiment, the invention provides a method for improving the activity of an antibody, or antigen-binding portion thereof, without affecting other characteristics, comprising:
  a) providing a parent antibody or antigen-binding portion thereof;
  b) selecting an amino acid residue within a complementarity determining region (CDR) for mutation other than H30, H31, H31B, H32, H33, H35, H50, H52, H52A, H53, H54, H56, H58, H95, H96, H97, H98, H101, L30, L31, L32, L34, L50, L52, L53, L55, L91, L92, L93, L94 and L96;
  c) individually mutating said selected position to at least two other amino acid residues to thereby create a panel of mutated antibodies, or antigen-binding portions thereof;
  d) evaluating the activity of the panel of mutated antibodies, or antigen-binding portions thereof, relative to the parent antibody or antigen-binding portion thereof thereby identifying an activity enhancing amino acid residue;
  e) evaluating the panel of mutated antibodies, or antigen-binding portions thereof, relative to the parent antibody or antigen-binding portion thereof, for changes in at least one other property or characteristic until an antibody, or antigen-binding portion thereof, with an improved activity and retained other characteristic or property, relative to the parent antibody, or antigen-binding portion thereof, is obtained.

In another embodiment, the invention provides a method for improving the activity of an antibody, or antigen-binding portion thereof, comprising:
  a) providing a parent antibody or antigen-binding portion thereof that was obtained by selection in a phage-display system but whose activity cannot be further improved by mutagenesis in said phage-display system;
  b) selecting an amino acid residue within a complementarity determining region (CDR) for mutation other than H30, H31, H31B, H32, H33, H35, H50, H52, H52A, H53, H54, H56, H58, H95, H96, H97, H98, H101, L30, L31, L32, L34, L50, L52, L53, L55, L91, L92, L93, L94 and L96;
  c) individually mutating said selected position to at least two other amino acid residues to thereby create a panel of mutated antibodies, or antigen-binding portions thereof and expression in a non-phage display system;
  d) evaluating the activity and retention of at least one other characteristic or property of the panel of mutated antibodies, or antigen-binding portions thereof, relative to the parent antibody or antigen-binding portion thereof, thereby identifying an activity enhancing amino acid residue;
  e) repeating steps b) through d) for at least one other CDR position which is neither the position selected under b nor other than H30, H31, H31B, H32, H33, H35, H50, H52, H52A, H53, H54, H56, H58, H95, H96, H97, H98, H101, L30, L31, L32, L34, L50, L52, L53, L55, L91, L92, L93, L94 and L96;
  f) combining, in the parent antibody, or antigen-binding portion thereof, at least two individual activity enhancing amino acid residues shown to have improved activity and not to affect at least one other characteristic or property, to form combination antibodies, or antigen-binding portions thereof; and g) evaluating the activity and retention of at least one other characteristic or property of the combination antibodies, or antigen-binding portions thereof with two activity enhancing amino acid residues, relative to the parent antibody or antigen-binding portion thereof until an antibody, or antigen-binding portion thereof, with an improved activity and at least one other retained characteristic or property, relative to the parent antibody, or antigen-binding portion thereof, is obtained.

Preferably, the other characteristic or property is selected from 1) preservation of non-crossreactivity with other proteins or human tissues, 2) preservation of epitope recognition, i.e. recognizing p40 epitope preferably in the context of the p70 p40/p35 heterodimer preventing binding interference from free, soluble p40 and/or 3) to produce an antibody with a close to germline immunoglobulin sequence

BRIEF DESCRIPTION OF THE DRAWINGS

FIGS. 1A-1B show the heavy chain variable region amino acid sequence alignments of a series of human antibodies that bind human IL-12 compared to germline sequences Cos-3/JH3 and Dp118 Lv1042. Kabat numbering is used to identify amino acid positions. For the Joe 9 wild type, the full sequence is shown. For the other antibodies, only those amino acids positions that differ from Joe 9 wild type are shown.

FIGS. 1C-1D show the light chain variable region amino acid sequence alignments of a series of human antibodies that bind human IL-12. Kabat numbering is used to identify amino acid positions. For the Joe 9 wild type, the full sequence is shown. For the other antibodies, only those amino acids positions that differ from Joe 9 wild type are shown.

FIG. 3A-B demonstrates the in vivo efficacy of the human anti-IL-12 antibody J695, on plasma neopterin levels in cynomolgus monkeys.

DETAILED DESCRIPTION OF THE INVENTION

Figures 1, 2A:
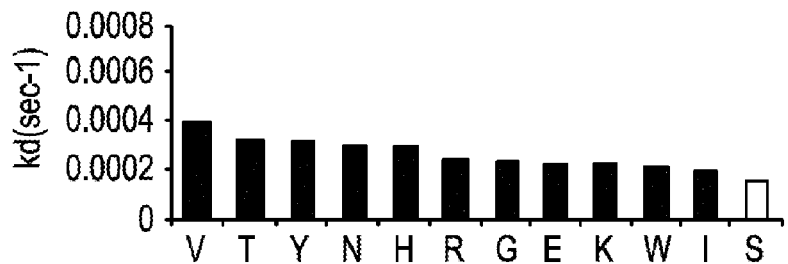
FIGS. 2A-2E show the CDR positions in the heavy chain of the Y61 antibody that were mutated by site-directed mutagenesis and the respective amino acid substitutions at each position. The graphs presented in FIGS. 2A-1 through 2A-4, 2B-1 through 2B-4, 2C-1 through 2C-2, 2D-1 through 2D-4 and 2E-1 through 2E-2 show the off-rates for the substituted antibodies (black bars) as compared to unmutated Y61 (open bar).
Figures 2, 2A:
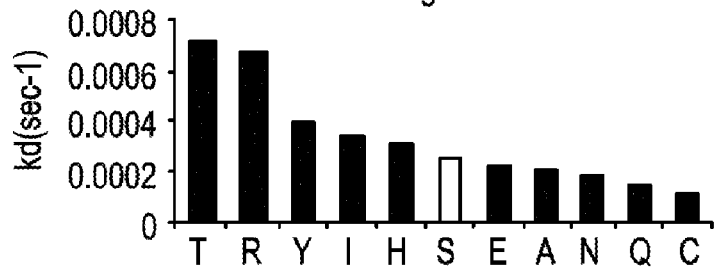

In order that the present invention may be more readily understood, certain terms are first defined.

The term "activity enhancing amino acid residue" includes an amino acid residue which improves the activity of the antibody. It should be understood that the activity enhancing amino acid residue may replace an amino acid residue at a contact, hypermutation or preferred selective mutagenesis position and, further, more than one activity enhancing amino acid residue can be present within one or more CDRs. An activity enhancing amino acid residue include, an amino acid residue that improves the binding specificity/affinity of an antibody, for example anti-human IL-12 antibody binding to human IL-12. The activity enhancing amino acid residue is also intended to include an amino acid residue that improves the neutralization potency of an antibody, for example, the human IL-12 antibody which inhibits human IL-12.

The term "antibody" includes an immunoglobulin molecule comprised of four polypeptide chains, two heavy (H) chains and two light (L) chains inter-connected by disulfide bonds. Each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDRs), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4.

The term "antigen-binding portion" of an antibody (or "antibody portion") includes fragments of an antibody that retain the ability to specifically bind to an antigen (e.g., hIL-12). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) *Proc. Natl. Acad. Sci. USA* 90:6444-6448; Poljak, R. J., et al. (1994) *Structure* 2:1121-1123). Still further, an antibody or antigen-binding portion thereof may be part of a larger immunoadhesion molecules, formed by covalent or non-covalent association of the antibody or antibody portion with one or more other proteins or peptides. Examples of such immunoadhesion molecules include use of the streptavidin core region to make a tetrameric scFv molecule (Kipriyanov, S. M., et al. (1995) *Human Antibodies and Hybridomas* 6:93-101) and use of a cysteine residue, a marker peptide and a C-terminal polyhistidine tag to make bivalent and biotinylated scFv molecules (Kipriyanov, S. M., et al. (1994) *Mol. Immunol.* 31:1047-1058). Antibody portions, such as Fab and F(ab')$_2$ fragments, can be prepared from whole antibodies using conventional techniques, such as papain or pepsin digestion, respectively, of whole antibodies. Moreover, antibodies, antibody portions and immunoadhesion molecules can be obtained using standard recombinant DNA techniques, as described herein. Preferred antigen binding portions are complete domains or pairs of complete domains.

The term "backmutation" refers to a process in which some or all of the somatically mutated amino acids of a human antibody are replaced with the corresponding germline residues from a homologous germline antibody sequence. The heavy and light chain sequences of the human antibody of the invention are aligned separately with the germline sequences in the VBASE database to identify the sequences with the highest homology. Differences in the human antibody of the invention are returned to the germline sequence by mutating defined nucleotide positions encoding such different amino acid. The role of each amino acid thus identified as candidate for backmutation should be investigated for a direct or indirect role in antigen binding and any amino acid found after mutation to affect any desirable characteristic of the human antibody should not be included in the final human antibody; as an example, activity enhancing amino acids identified by the selective mutagenesis approach will not be subject to backmutation. To minimize the number of amino acids subject to backmutation those amino acid positions found to be different from the closest germline sequence but identical to the corresponding amino acid in a second germline sequence can remain, provided that the second germline sequence is identical and colinear to the sequence of the human antibody of the invention for at least 10, preferably 12 amino acids, on both sides of the amino acid in question. Backmuation may occur at any stage of antibody optimization; preferably, backmutation occurs directly before or after the selective mutagenesis approach. More preferably, backmutation occurs directly before the selective mutagenesis approach.

The phrase "human interleukin 12" (abbreviated herein as hIL-12, or IL-12), as used herein, includes a human cytokine that is secreted primarily by macrophages and dendritic cells. The term includes a heterodimeric protein comprising a 35 kD subunit (p35) and a 40 kD subunit (p40) which are both linked together with a disulfide bridge. The heterodimeric protein is referred to as a "p70 subunit". The structure of human IL-12 is described further in, for example, Kobayashi, et al. (1989) *J. Exp Med.* 170:827-845; Seder, et al. (1993) *Proc. Natl. Acad. Sci.* 90:10188-10192; Ling, et al. (1945) *J. Exp Med.* 154:116-127; Podlaski, et al. (1992) *Arch. Biochem. Biophys.* 294:230-237. The term human IL-12 is intended to include recombinant human IL-12 (rh IL-12), which can be prepared by standard recombinant expression methods.

The terms "Kabat numbering", "Kabat definitions" and "Kabat labeling" are used interchangeably herein. These terms, which are recognized in the art, refer to a system of numbering amino acid residues which are more variable (i.e. hypervariable) than other amino acid residues in the heavy and light chain variable regions of an antibody, or an antigen binding portion thereof (Kabat et al. (1971) *Ann. NY Acad. Sci.* 190:382-391 and, Kabat, E. A., et al. (1991) *Sequences of Proteins of Immunological Interest, Fifth Edition*, U.S. Department of Health and Human Services, NIH Publication No. 91-3242). For the heavy chain variable region, the hypervariable region ranges from amino acid positions 31 to 35 for CDR1, amino acid positions 50 to 65 for CDR2, and amino acid positions 95 to 102 for CDR3. For the light chain variable region, the hypervariable region ranges from amino acid positions 24 to 34 for CDR1, amino acid positions 50 to 56 for CDR2, and amino acid positions 89 to 97 for CDR3.

The Kabat numbering is used herein to indicate the positions of amino acid modifications made in antibodies of the invention. For example, the Y61 anti-IL-12 antibody can be mutated from serine (S) to glutamic acid (E) at position 31 of the heavy chain CDR1 (H31S→E), or glycine (G) can be mutated to tyrosine (Y) at position 94 of the light chain CDR3 (L94G→Y).

The term "human antibody" includes antibodies having variable and constant regions corresponding to human germline immunoglobulin sequences as described by Kabat et al. (See Kabat, et al. (1991) *Sequences of Proteins of Immunological Interest, Fifth Edition*, U.S. Department of Health and Human Services, NIH Publication No. 91-3242). The human antibodies of the invention may include amino acid residues not encoded by human germline immunoglobulin sequences (e.g., mutations introduced by random or site-specific mutagenesis in vitro or by somatic mutation in vivo), for example in the CDRs and in particular CDR3. The mutations preferably are introduced using the "selective mutagenesis approach" described herein. The human antibody can have at least one position replaced with an amino acid residue, e.g., an activity enhancing amino acid residue which is not encoded by the human germline immunoglobulin sequence. The human antibody can have up to twenty positions replaced with amino acid residues which are not part of the human germline immunoglobulin sequence. In other embodiments, up to ten, up to five, up to three or up to two positions are replaced. In a preferred embodiment, these replacements are within the CDR regions as described in detail below. However, the term "human antibody", as used herein, is not intended to include antibodies in which CDR sequences derived from the germline of another mammalian species, such as a mouse, have been grafted onto human framework sequences.

The phrase "recombinant human antibody" includes human antibodies that are prepared, expressed, created or isolated by recombinant means, such as antibodies expressed using a recombinant expression vector transfected into a host cell (described further in Section II, below), antibodies isolated from a recombinant, combinatorial human antibody library (described further in Section III, below), antibodies isolated from an animal (e.g., a mouse) that is transgenic for human immunoglobulin genes (see e.g., Taylor, L. D., et al. (1992) *Nucl. Acids Res.* 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences (See Kabat, E. A., et al. (1991) *Sequences of Proteins of Immunological Interest, Fifth Edition*, U.S. Department of Health and Human Services, NIH Publication No. 91-3242). In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo. In certain embodiments, however, such recombinant human antibodies are the result of selective mutagenesis approach or backmutation or both.

An "isolated antibody" includes an antibody that is substantially free of other antibodies having different antigenic specificities (e.g., an isolated antibody that specifically binds hIL-12 is substantially free of antibodies that specifically bind antigens other than hIL-12). An isolated antibody that specifically binds hIL-12 may bind IL-12 molecules from other species (discussed in further detail below). Moreover, an isolated antibody may be substantially free of other cellular material and/or chemicals.

A "neutralizing antibody" (or an "antibody that neutralized hIL-12 activity") includes an antibody whose binding to hIL-12 results in inhibition of the biological activity of hIL-12. This inhibition of the biological activity of hIL-12 can be assessed by measuring one or more indicators of hIL-12 biological activity, such as inhibition of human phytohemagglutinin blast proliferation in a phytohemagglutinin blast proliferation assay (PHA), or inhibition of receptor binding in a human IL-12 receptor binding assay (see Example 3-Interferon-gamma Induction Assay). These indicators of hIL-12 biological activity can be assessed by one or more of several standard in vitro or in vivo assays known in the art (see Example 3).

The term "activity" includes activities such as the binding specificity/affinity of an antibody for an antigen, for example, an anti-hIL-12 antibody that binds to an IL-12 antigen and/or the neutralizing potency of an antibody, for example, an anti-hIL-12 antibody whose binding to hIL-12 inhibits the biological activity of hIL-12, e.g. inhibition of PHA blast proliferation or inhibition of receptor binding in a human IL-12 receptor binding assay (see Example 3).

The phrase "surface plasmon resonance" includes an optical phenomenon that allows for the analysis of real-time biospecific interactions by detection of alterations in protein concentrations within a biosensor matrix, for example using the BIAcore system (Pharmacia Biosensor AB, Uppsala, Sweden and Piscataway, N.J.). For further descriptions, see Example 5 and Jonsson, U., et al. (1993) *Ann. Biol. Clin.* 51:19-26; Jönsson, U., et al. (1991) *Biotechniques* 11:620-627; Johnsson, B., et al. (1995) *J. Mol. Recognit.* 8:125-131; and Johnnson, B., et al. (1991) *Anal. Biochem.* 198:268-277.

The term "$K_{off}$", as used herein, is intended to refer to the off rate constant for dissociation of an antibody from the antibody/antigen complex.

The term "$K_d$", as used herein, is intended to refer to the dissociation constant of a particular antibody-antigen interaction.

The phrase "nucleic acid molecule" includes DNA molecules and RNA molecules. A nucleic acid molecule may be single-stranded or double-stranded, but preferably is double-stranded DNA.

The phrase "isolated nucleic acid molecule", as used herein in reference to nucleic acids encoding antibodies or antibody portions (e.g., VH, VL, CDR3) that bind hIL-12 including "isolated antibodies"), includes a nucleic acid molecule in which the nucleotide sequences encoding the antibody or antibody portion are free of other nucleotide sequences encoding antibodies or antibody portions that bind antigens other than hIL-12, which other sequences may naturally flank the nucleic acid in human genomic DNA. Thus, for example, an isolated nucleic acid of the invention encoding a VH region of an anti-IL-12 antibody contains no other sequences encoding other VH regions that bind antigens other than IL-12. The phrase "isolated nucleic acid molecule" is also intended to include sequences encoding bivalent, bispecific antibodies, such as diabodies in which VH and VL regions contain no other sequences other than the sequences of the diabody.

The term "vector" includes a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The phrase "recombinant host cell" (or simply "host cell") includes a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

The term "modifying", as used herein, is intended to refer to changing one or more amino acids in the antibodies or antigen-binding portions thereof. The change can be produced by adding, substituting or deleting an amino acid at one or more positions. The change can be produced using known techniques, such as PCR mutagenesis.

The phrase "contact position" includes an amino acid position of in the CDR1, CDR2 or CDR3 of the heavy chain variable region or the light chain variable region of an antibody which is occupied by an amino acid that contacts antigen in one of the twenty-six known antibody-antigen structures. If a CDR amino acid in any of the 26 known solved structures of antibody-antigen complexes contacts the antigen, then that amino acid can be considered to occupy a contact position. Contact positions have a higher probability of being occupied by an amino acid which contact antigen than non-contact positions. Preferably a contact position is a CDR position which contains an amino acid that contacts antigen in greater than 3 of the 26 structures (>11.5%). Most preferably a contact position is a CDR position which contains an amino acid that contacts antigen in greater than 8 of the 25 structures (>32%).

The term "hypermutation position" includes an amino acid residue that occupies position in the CDR1, CDR2 or CDR3 region of the heavy chain variable region or the light chain variable region of an antibody that is considered to have a high frequency or probability for somatic hypermutation during in vivo affinity maturation of the antibody. "High frequency or probability for somatic hypermutation" includes frequencies or probabilities of a 5 to about 40% chance that the residue will undergo somatic hypermutation during in vivo affinity maturation of the antibody. It should be understood that all ranges within this stated range are also intended to be part of this invention, e.g., 5 to about 30%, e.g., 5 to about 15%, e.g., 15 to about 30%.

The term "preferred selective mutagenesis position" includes an amino acid residue that occupies a position in the CDR1, CDR2 or CDR3 region of the heavy chain variable region or the light chain variable region which can be considered to be both a contact and a hypermutation position.

The phrase "selective mutagenesis approach" includes a method of improving the activity of an antibody by selecting and individually mutating CDR amino acids at at least one preferred selective mutagenesis position, hypermutation, and/or contact position. A "selectively mutated" human antibody is an antibody which contains a mutation at a position selected using a selective mutagenesis approach. In another embodiment, the selective mutagenesis approach is intended to provide a method of preferentially mutating selected individual amino acid residues in the CDR1, CDR2 or CDR3 of the heavy chain variable region (hereinafter H1, H2, and H3, respectively), or the CDR1, CDR2 or CDR3 of the light chain variable region (hereinafter referred to as L1, L2, and L3, respectively) of an antibody. Amino acid residues may be selected from preferred selective mutagenesis positions, contact positions, or hypermutation positions. Individual amino acids are selected based on their position in the light or heavy chain variable region. It should be understood that a hypermutation position can also be a contact position. In an embodiment, the selective mutagenesis approach is a "targeted approach". The language "targeted approach" is intended to include a method of preferentially mutating selected individual amino acid residues in the CDR1, CDR2 or CDR3 of the heavy chain variable region or the CDR1, CDR2 or CDR3 of the light chain variable region of an antibody in a targeted manner, e.g., a "Group-wise targeted approach" or "CDR-wise targeted approach". In the "Group-wise targeted approach", individual amino acid residues in particular groups are targeted for selective mutations including groups I (including L3 and H3), II (including H2 and L1) and III (including L2 and H1), the groups being listed in order of preference for targeting. In the "CDR-wise targeted approach", individual amino acid residues in particular CDRs are targeted for selective mutations with the order of preference for targeting as follows: H3, L3, H2, L1, H1 and L2. The selected amino acid residue is mutated, e.g., to at least two other amino acid residues, and the effect of the mutation on the activity of the antibody is determined. Activity is measured as a change in the binding specificity/affinity of the antibody, and/or neutralization potency of the antibody. It should be understood that the selective mutagenesis approach can be used for the optimization of any antibody derived from any source including phage display, transgenic animals with human IgG germline genes, human antibodies isolated from human B-cells. Preferably, the selective mutagenesis approach is used on antibodies which can not be optimized further using phage display technology. It should be understood that antibodies from any source including phage display, transgenic animals with human IgG germline genes, human antibodies isolated from human B-cells can be subject to backmutation prior to or after the selective mutagenesis approach.

The term "activity enhancing amino acid residue" includes an amino acid residue which improves the activity of the antibody. It should be understood that the activity enhancing amino acid residue may replace an amino acid residue at a preferred selective mutagenesis position, contact position, or a hypermutation position and, further, more than one activity enhancing amino acid residue can be present within one or more CDRs. An activity enhancing amino acid residue include, an amino acid residue that improves the binding specificity/affinity of an antibody, for example anti-human IL-12 antibody binding to human IL-12. The activity enhancing amino acid residue is also intended to include an amino acid residue that improves the neutralization potency of an antibody, for example, the human IL-12 antibody which inhibits human IL-12.

Various aspects of the invention are described in further detail in the following subsections.

I. Human Antibodies that Bind Human IL-12

This invention provides isolated human antibodies, or antigen-binding portions thereof, that bind to human IL-12. Preferably, the human antibodies of the invention are recombinant, neutralizing human anti-hIL-12 antibodies. Antibodies of the invention that bind to human IL-12 can be selected, for example, by screening one or more human $V_L$ and $V_H$ cDNA libraries with hIL-12, such as by phage display techniques as described in Example 1. Screening of human $V_L$ and $V_H$ cDNA libraries initially identified a series of anti-IL-12 antibodies of which one antibody, referred to herein as "Joe 9" (or "Joe 9 wild type"), was selected for further development. Joe 9 is a relatively low affinity human IL-12 antibody (e.g., a $K_{off}$ of about 0.1 $sec^{-1}$), yet is useful for specifically binding and detecting hIL-12. The affinity of the Joe 9 antibody was improved by conducting mutagenesis of the heavy and light chain CDRs, producing a panel of light and heavy chain variable regions that were "mixed and matched" and further mutated, leading to numerous additional anti-hIL-12 antibodies with increased affinity for hIL-12 (see Example 1, Table 2 (see Appendix A) and the sequence alignments of FIGS. 1A-D).

Of these antibodies, the human anti-hIL-12 antibody referred to herein as Y61 demonstrated a significant improvement in binding affinity (e.g., a $K_{off}$ of about $2 \times 10^{-4}$ $sec^{-1}$). The Y61 anti-hIL-12 antibody was selected for further affinity maturation by individually mutating specific amino acids residues within the heavy and light chain CDRs. Amino acids residues of Y61 were selected for site-specific mutation (selective mutagenesis approach) based on the amino acid residue occupying a preferred selective mutagenesis position, contact and/or a hypermutation position. A summary of the substitutions at selected positions in the heavy and light chain CDRs is shown in FIGS. 2A-2H. A preferred recombinant neutralizing antibody of the invention, referred to herein as J695, resulted from a Gly to Tyr substitution at position 50 of the light chain CDR2 of Y61, and a Gly to Tyr substitution at position 94 of the light chain CDR3 of Y61.

Amino acid sequence alignments of the heavy and light chain variable regions of a panel of anti-IL-12 antibodies of the invention, on the lineage from Joe 9 wild type to J695, are shown in FIGS. 1A-1D. These sequence alignments allowed for the identification of consensus sequences for preferred heavy and light chain variable regions of antibodies of the invention that bind hIL-12, as well as consensus sequences for the CDR3, CDR2, and CDR1, on the lineage from Joe 9 to J695. Moreover, the Y61 mutagenesis analysis summarized in FIGS. 2A-2H allowed for the identification of consensus sequences for heavy and light chain variable regions that bind hIL-12, as well as consensus sequences for the CDR3, CDR2, and CDR1 that bind hIL-12 on the lineage from Y61 to J695 that encompasses sequences with modifications from Y61 yet that retain good hIL-12 binding characteristics. Preferred CDR, VH and VL sequences of the invention (including consensus sequences) as identified by sequence identifiers in the attached Sequence Listing, are summarized below.

| SEQ ID NO: | ANTIBODY CHAIN | REGION | SEQUENCE |
|---|---|---|---|
| 1 | Consensus Joe 9 to J695 | CDR H3 | (H/S)-G-S-(H/Y)-D-(N/T/Y) |
| 2 | Consensus Joe 9 to J695 | CDR L3 | Q-(S/T)-Y-(D/E)-(S/R/K)-(S/G/Y)-(L/P/T/S)-(R/S/T/W/H)-(G/P)-(S/T/A/L)-(R/S/M/T/L)-(V/I/T/M/L) |
| 3 | Consensus Joe 9 to J695 | CDR H2 | F-I-R-Y-D-G-S-N-K-Y-Y-A-D-S-V-K-G |
| 4 | Consensus Joe 9 to J695 | CDR L2 | (G/Y)-N-(D/S)-(Q/N)-R-P-S |
| 5 | Consensus Joe 9 to J695 | CDR H1 | F-T-F-S-(S/E)-Y-G-M-H |
| 6 | Consensus Joe 9 to J695 | CDR L1 | (S/T)-G-(G/S)-(R/S)-S-N-I-(G/V)-(S/A)-(N/G/Y)-(T/D)-V-(K/H) |
| 7 | Consensus Joe 9 to J695 | VH | (full VH sequence; see sequence listing) |
| 8 | Consensus Joe 9 to J695 | VL | (full VL sequence; see sequence listing) |
| 9 | Consensus Y61 to J695 | CDR H3 | H-(G/V/C/H)-(S/T)-(H/T/V/R/I)-(D/S)-(N/K/A/T/S/P/W/H) |
| 10 | Consensus Y61 to J695 | CDR L3 | Q-S-Y-(D/S)-(Xaa)-(G/D/Q/L/P/R/H/N/Y)-T-H-P-A-L-L |
| 11 | Consensus Y61 to J695 | CDR H2 | (F/T/Y)-I-(R/A)-Y-(D/S/E/A)-(G/R)-S-(Xaa)-K-(Y/E)-Y-A-D-S-V-K-G |
| 12 | Consensus Y61 to J695 | CDR L2 | (G/Y/S/T/N/Q)-N-D-Q-R-P-S |
| 13 | Consensus Y61 to J695 | CDR H1 | F-T-F-(Xaa)-(Xaa)-(Y/H)-(G/M/A/N/S)-M-H |
| 14 | Consensus Y61 to J695 | CDR L1 | S-G-G-R-S-N-I-G-(S/C/R/N/D/T)-(N/M/I)-(T/Y/D/H/K/P)-V-K |
| 15 | Consensus Y61 to J695 | VH | (full VH sequence; see sequence listing) |
| 16 | Consensus Y61 to J695 | VL | (full VL sequence; see sequence listing) |
| 17 | Y61 | CDR H3 | H-G-S-H-D-N |
| 18 | Y61 | CDR L3 | Q-S-Y-D-R-G-T-H-P-A-L-L |
| 19 | Y61 | CDR H2 | F-I-R-Y-D-G-S-N-K-Y-Y-A-D-S-V-K-G |
| 20 | Y61 | CDR L2 | G-N-D-Q-R-P-S |
| 21 | Y61 | CDR H1 | F-T-F-S-S-Y-G-M-H |
| 22 | Y61 | CDR L1 | S-G-G-R-S-N-I-G-S-N-T-V-K |
| 23 | Y61 | VH | (full VH sequence; see sequence listing) |
| 24 | Y61 | VL | (full VL sequence; see sequence listing) |
| 25 | J695 | CDR H3 | H-G-S-H-D-N |
| 26 | J695 | CDR L3 | Q-S-Y-D-R-Y-T-H-P-A-L-L |
| 27 | J695 | CDR H2 | F-I-R-Y-D-G-S-N-K-Y-Y-A-D-S-V-K-G |
| 28 | J695 | CDR L2 | Y-N-D-Q-R-P-S |
| 29 | J695 | CDR H1 | F-T-F-S-S-Y-G-M-H |
| 30 | J695 | CDR L1 | S-G-S-R-S-N-I-G-S-N-T-V-K |

-continued

| SEQ ID NO: | ANTIBODY | CHAIN | REGION SEQUENCE |
|---|---|---|---|
| 31 | J695 | VH | (full VH sequence; see sequence listing) |
| 32 | J695 | VL | (full VL sequence; see sequence listing) |

Antibodies produced from affinity maturation of Joe 9 wild type were functionally characterized by surface plasmon resonance analysis to determine the $K_d$ and $K_{off}$ rate. A series of antibodies were produced having a $K_{off}$ rate within the range of about 0.1 s$^{-1}$ to about 1×10$^{-5}$ s$^{-1}$, and more preferably a $K_{off}$ of about 1×10$^{-4}$ s$^{-1}$ to 1×10$^{-5}$ s$^{-1}$ or less. Antibodies were also characterized in vitro for their ability to inhibit phytohemagglutinin (PHA) blast proliferation, as described in Example 3. A series of antibodies were produced having an IC$_{50}$ value in the range of about 1×10$^{-6}$ M to about 1×10$^{-11}$ M, more preferably about 1×10$^{-10}$M to 1×10$^{-11}$M or less.

Accordingly, in one aspect, the invention provides an isolated human antibody, or antigen-binding portion thereof, that binds to human IL-12 and dissociates from human IL-12 with a $K_{off}$ rate constant of 0.1 s$^{-1}$ or less, as determined by surface plasmon resonance, or which inhibits phytohemagglutinin blast proliferation in an in vitro phytohemagglutinin blast proliferation assay (PHA assay) with an IC$_{50}$ of 1×10$^{-6}$ M or less. In preferred embodiments, the isolated human IL-12 antibody, or an antigen-binding portion thereof, dissociates from human IL-12 with a $K_{off}$ rate constant of 1×10$^{-2}$ s$^{-1}$ or less, or inhibits phytohemagglutinin blast proliferation in an in vitro PHA assay with an IC$_{50}$ of 1×10$^{-7}$ M or less. In more preferred embodiments, the isolated human IL-12 antibody, or an antigen-binding portion thereof, dissociates from human IL-12 with a $K_{off}$ rate constant of 1×10$^{-3}$ s$^{-1}$ or less, or inhibits phytohemagglutinin blast proliferation in an in vitro PHA assay with an IC$_{50}$ of 1×10$^{-8}$ M or less. In more preferred embodiments, the isolated human IL-12 antibody, or an antigen-binding portion thereof, dissociates from human IL-12 with a $K_{off}$ rate constant of 1×10$^{-4}$ s$^{-1}$ or less, or inhibits phytohemagglutinin blast proliferation in an in vitro PHA assay with an IC$_{50}$ of 1×10$^{-9}$ M or less. In more preferred embodiments, the isolated human IL-12 antibody, or an antigen-binding portion thereof, dissociates from human IL-12 with a $K_{off}$ rate constant of 1×10$^{-5}$ s$^{-1}$ or less, or inhibits phytohemagglutinin blast proliferation in an in vitro PHA assay with an IC$_{50}$ of 1×10$^{-10}$ M or less. In even more preferred embodiments, the isolated human IL-12 antibody, or an antigen-binding portion thereof, dissociates from human IL-12 with a $K_{off}$ rate constant of 1×10$^{-5}$ s$^{-1}$ or less, or inhibits phytohemagglutinin blast proliferation in an in vitro PHA assay with an IC$_{50}$ of 1×10$^{-11}$ M or less.

The dissociation rate constant ($K_{off}$) of an IL-12 antibody can be determined by surface plasmon resonance (see Example 5). Generally, surface plasmon resonance analysis measures real-time binding interactions between ligand (recombinant human IL-12 immobilized on a biosensor matrix) and analyte (antibodies in solution) by surface plasmon resonance (SPR) using the BIAcore system (Pharmacia Biosensor, Piscataway, N.J.). Surface plasmon analysis can also be performed by immobilizing the analyte (antibodies on a biosensor matrix) and presenting the ligand (recombinant IL-12 in solution). Neutralization activity of IL-12 antibodies, or antigen binding portions thereof, can be assessed using one or more of several suitable in vitro assays (see Example 3).

It is well known in the art that antibody heavy and light chain CDRs play an important role in the binding specificity/affinity of an antibody for an antigen. Accordingly, the invention encompasses human antibodies having light and heavy chain CDRs of Joe 9, as well as other antibodies having CDRs that have been modified to improve the binding specificity/affinity of the antibody. As demonstrated in Example 1, a series of modifications to the light and heavy chain CDRs results in affinity maturation of human anti-hIL-12 antibodies. The heavy and light chain variable region amino acid sequence alignments of a series of human antibodies ranging from Joe 9 wild type to J695 that bind human IL-12 is shown in FIGS. 1A-1D. Consensus sequence motifs for the CDRs of antibodies can be determined from the sequence alignment (as summarized in the table above). For example, a consensus motif for the VH CDR3 of the lineage from Joe 9 to J695 comprises the amino acid sequence: (H/S)-G-S-(H/Y)-D-(N/T/Y) (SEQ ID NO: 1), which encompasses amino acids from position 95 to 102 of the consensus HCVR shown in SEQ ID NO: 7. A consensus motif for the VL CDR3 comprises the amino acid sequence: Q-(S/T)-Y-(D/E)-(S/R/K)-(S/G/Y)-(L/F/T/S)-(R/S/T/W/H)-(G/P)-(S/T/A/L)-(R/S/M/T/L-V/I/T/M/L) (SEQ ID NO: 2), which encompasses amino acids from position 89 to 97 of the consensus LCVR shown in SEQ ID NO: 8.

Accordingly, in another aspect, the invention provides an isolated human antibody, or an antigen-binding portion thereof, which has the following characteristics:
  a) inhibits phytohemagglutinin blast proliferation in an in vitro PHA assay with an IC$_{50}$ of 1×10$^{-6}$ M or less;
  b) has a heavy chain CDR3 comprising the amino acid sequence of SEQ ID NO: 1; and
  c) has a light chain CDR3 comprising the amino acid sequence of SEQ ID NO: 2.

In a preferred embodiment, the antibody further comprises a VH CDR2 comprising the amino acid sequence: F-I-R-Y-D-G-S-N-K-Y-Y-A-D-S-V-K-G (SEQ ID NO: 3) (which encompasses amino acids from position 50 to 65 of the consensus HCVR comprising the amino acid sequence SEQ ID NO: 7) and further comprises a VL CDR2 comprising the amino acid sequence: (G/Y)-N-(D/S)-(Q/N)-R-P-S (SEQ ID NO: 4) (which encompasses amino acids from position 50 to 56 of the consensus LCVR comprising the amino acid sequence SEQ ID NO: 8).

In another preferred embodiment, the antibody further comprises a VH CDR1 comprising the amino acid sequence: F-T-F-S-(S/E)-Y-G-M-H (SEQ ID NO: 5) (which encompasses amino acids from position 27 to 35 of the consensus HCVR comprising the amino acid sequence SEQ ID NO: 7) and further comprises a VL CDR1 comprising the amino acid sequence: (S/T)-G-(G/S)-(R/S)-S-N-I-(GN)-(S/A)-(N/G/Y)-(T/D)-V-(K/H) (SEQ ID NO: 6) (which encompasses amino acids from position 24 to 34 of the consensus LCVR comprising the amino acid sequence SEQ ID NO: 8).

In yet another preferred embodiment, the antibody of the invention comprises a HCVR comprising the amino acid sequence of SEQ ID NO: 7 and a LCVR comprising the amino acid sequence of SEQ ID NO: 8.

Additional consensus motifs can be determined based on the mutational analysis performed on Y61 that led to the J695 antibody (summarized in FIGS. 2A-2H). As demonstrated by the graphs shown in FIGS. 2A-2H, certain residues of the heavy and light chain CDRs of Y61 were amenable to substitution without significantly impairing the hIL-12 binding properties of the antibody. For example, individual substitutions at position 30 in CDR H1 with twelve different amino acid residues did not significantly reduce the $K_{off}$ rate of the antibody, indicating that is position is amenable to substitution with a variety of different amino acid residues. Thus, based on the mutational analysis (i.e., positions within Y61 that were amenable to substitution by other amino acid residues) consensus motifs were determined. The consensus motifs for the heavy and light chain CDR3s are shown in SEQ ID NOs: 9 and 10, respectively, consensus motifs for the heavy and light chain CDR2s are shown in SEQ ID NOs: 11 and 12, respectively, and consensus motifs for the heavy and light chain CDR1s are shown in SEQ ID NOs: 13 and 14, respectively. Consensus motifs for the VH and VL regions are shown in SEQ ID NOs: 15 and 16, respectively.

Accordingly, in one aspect, the invention features an isolated human antibody, or an antigen-binding portion thereof, which has the following characteristics:
 a) inhibits phytohemagglutinin blast proliferation in an in vitro PHA assay with an $IC_{50}$ of $1 \times 10^{-9}$ M or less;
 b) has a heavy chain CDR3 comprising the amino acid sequence of SEQ ID NO: 9; and
 c) has a light chain CDR3 comprising the amino acid sequence of SEQ ID NO: 10.

In a preferred embodiment, the antibody further comprises a VH CDR2 comprising the amino acid sequence of SEQ ID NO: 11 and further comprises a VL CDR2 comprising the amino acid sequence of SEQ ID NO: 12.

In another preferred embodiment, the antibody further comprises a VH CDR1 comprising the amino acid sequence of SEQ ID NO: 13 and further comprises a VL CDR1 comprising the amino acid sequence of SEQ ID NO: 14.

In yet another preferred embodiment, the antibody of the invention comprises a HCVR comprising the amino acid sequence of SEQ ID NO: 15 and a LCVR comprising the amino acid sequence of SEQ ID NO: 16.

A preferred antibody of the invention, the human anti-hIL-12 antibody Y61, was produced by affinity maturation of Joe 9 wild type by PCR mutagenesis of the CDR3 (as described in Example 1). Y61 had an improved specificity/binding affinity determined by surface plasmon resonance and by in vitro neutralization assays. The heavy and light chain CDR3s of Y61 are shown in SEQ ID NOs: 17 and 18, respectively, the heavy and light chain CDR2s of Y61 are shown in SEQ ID NOs: 19 and 20, respectively, and the heavy and light chain CDR1s of Y61 are shown in SEQ ID NOs: 21 and 22, respectively. The VH of Y61 has the amino acid sequence of SEQ ID NO: 23 and the VL of Y61 has the amino acid sequence of SEQ ID NO: 24 (these sequences are also shown in FIGS. 1A-1D, aligned with Joe9).

Accordingly, in another aspect, the invention features an isolated human antibody, or an antigen-binding portion thereof, which
 a) inhibits phytohemagglutinin blast proliferation in an in vitro PHA assay with an $IC_{50}$ of $1 \times 10^{-9}$ M or less;
 b) has a heavy chain CDR3 comprising the amino acid sequence of SEQ ID NO: 17; and
 c) has a light chain CDR3 comprising the amino acid sequence of SEQ ID NO: 18.

In a preferred embodiment, the isolated human antibody, or an antigen-binding portion thereof, has a heavy chain CDR2 comprising the amino acid sequence of SEQ ID NO: 19 and a light chain CDR2 comprising the amino acid sequence of SEQ ID NO: 20.

In another preferred embodiment, the isolated human antibody, or an antigen-binding portion thereof has a heavy chain CDR1 comprising the amino acid sequence of SEQ ID NO: 21 and a light chain CDR1 comprising the amino acid sequence of SEQ ID NO: 22.

In yet another preferred embodiment, the isolated human antibody, or an antigen-binding portion thereof, comprising a the heavy chain variable region comprising the amino acid sequence of SEQ ID NO: 23, and a light chain variable region comprising the amino acid sequence of SEQ ID NO: 24.

In certain embodiments, the full length antibody comprises a heavy chain constant region, such as IgG1, IgG2, IgG3, IgG4, IgM, IgA and IgE constant regions, and any allotypic variant therein as described in Kabat (, Kabat, E. A., et al. (1991) *Sequences of Proteins of Immunological Interest, Fifth Edition*, U.S. Department of Health and Human Services, NIH Publication No. 91-3242). Preferably, the antibody heavy chain constant region is an IgG1 heavy chain constant region. Alternatively, the antibody portion can be an Fab fragment, an F(ab'$_2$) fragment or a single chain Fv fragment.

Modifications of individual residues of Y61 led to the production of a panel of antibodies shown in FIGS. 2A-2H. The specificity/binding affinity of each antibody was determined by surface plasmon resonance and/or by in vitro neutralization assays.

Accordingly, in another aspect, the invention features an isolated human antibody, or an antigen-binding portion thereof, which
 a) inhibits phytohemagglutinin blast proliferation in an in vitro PHA assay with an $IC_{50}$ of $1 \times 10^{-9}$ M or less;
 b) has a heavy chain CDR3 comprising the amino acid sequence selected from the group consisting of SEQ ID NO: 404-SEQ ID NO: 469; and
 c) has a light chain CDR3 comprising the amino acid sequence selected from the group consisting of SEQ ID NO: 534-SEQ ID NO: 579.

In preferred embodiment, the isolated human antibody, or an antigen-binding portion thereof, has a heavy chain CDR2 comprising the amino acid sequence selected from the group consisting of SEQ ID NO:335-SEQ ID NO: 403; and a light chain CDR2 comprising the amino acid sequence selected from the group consisting of SEQ ID NO: 506-SEQ ID NO: 533.

In another preferred embodiment, the isolated human antibody, or an antigen-binding portion thereof, has a heavy chain CDR1 comprising the amino acid sequence selected from the group consisting of SEQ ID NO: 288-SEQ ID NO: 334; and a light chain CDR1 comprising the amino acid sequence selected from the group consisting of SEQ ID NO: 470-SEQ ID NO: 505.

In yet another preferred embodiment, the isolated human antibody, or an antigen-binding portion thereof, comprising a the heavy chain variable region comprising the amino acid sequence of SEQ ID NO: 23, and a light chain variable region comprising the amino acid sequence of SEQ ID NO: 24.

In certain embodiments, the full length antibody comprising a heavy chain constant region such as IgG1, IgG2, IgG3, IgG4, IgM, IgA and IgE constant regions and any allotypic variant therein as described in Kabat, (Kabat, E. A., et al. (1991) *Sequences of Proteins of Immunological Interest, Fifth Edition*, U.S. Department of Health and Human Services, NIH Publication No. 91-3242). Preferably, the antibody heavy chain constant region is an IgG1 heavy chain constant region. Alternatively, the antibody portion can be a Fab fragment, an F(ab'$_2$) fragment or a single chain Fv fragment.

A particularly preferred recombinant, neutralizing antibody of the invention, J695, was produced by site-directed mutagenesis of contact and hypermutation amino acids residues of antibody Y61 (see Example 2 and section III below). J695 differs from Y61 by a Gly to Tyr substitution in Y61 at position 50 of the light chain CDR2 and by a Gly to Tyr substitution at position 94 of the light chain CDR3. The heavy and light chain CDR3s of J695 are shown in SEQ ID NOs: 25 and 26, respectively, the heavy and light chain CDR2s of J695 are shown in SEQ ID NOs: 27 and 28, respectively, and the heavy and light chain CDR1s of J695 are shown in SEQ ID NOs: 29 and 30, respectively. The VH of J695 has the amino acid sequence of SEQ ID NO: 31 and the VL of J695 has the amino acid sequence of SEQ ID NO: 32 (these sequences are also shown in FIGS. 1A-1D, aligned with Joe9).

Accordingly, in another aspect, the invention features an isolated human antibody, or an antigen-binding portion thereof, which
a) inhibits phytohemagglutinin blast proliferation in an in vitro PHA assay with an $IC_{50}$ of $1 \times 10^{-9}$ M or less;
b) has a heavy chain CDR3 comprising the amino acid sequence of SEQ ID NO: 25; and
c) has a light chain CDR3 comprising the amino acid sequence of SEQ ID NO: 26.

In preferred embodiment, the isolated human antibody, or an antigen-binding portion thereof, has a heavy chain CDR2 comprising the amino acid sequence of SEQ ID NO: 27, and a light chain CDR2 comprising the amino acid sequence of SEQ NO: 28.

In another preferred embodiment, the isolated human antibody, or an antigen-binding portion thereof, has a heavy chain CDR1 comprising the amino acid sequence of SEQ ID NO: 29, and a light chain CDR1 comprising the amino acid sequence of SEQ ID NO: 30.

In yet another preferred embodiment, the isolated human antibody, or an antigen-binding portion thereof, has a heavy chain variable region comprising the amino acid sequence of SEQ ID NO: 31, and a light chain variable region comprising the amino acid sequence of SEQ ID NO: 32.

In certain embodiments, the full length antibody comprises a heavy chain constant region, such as IgG1, IgG2, IgG3, IgG4, IgM, IgA and IgE constant regions and any allotypic variant therein as described in Kabat (, Kabat, E. A., et, al. (1991) *Sequences of Proteins of Immunological Interest, Fifth Edition*, U.S. Department of Health and Human Services, NIH Publication No. 91-3242). Preferably, the antibody heavy chain constant region is an IgG1 heavy chain constant region. Alternatively, the antibody portion can be an Fab fragment, an F(ab'$_2$) fragment or a single chain Fv fragment.

Additional mutations in the preferred consensus sequences for CDR3, CDR2, and CDR1 of antibodies on the lineage from Joe 9 to J695, or from the lineage Y61 to J695, can be made to provide additional anti-IL-12 antibodies of the invention. Such methods of modification can be performed using standard molecular biology techniques, such as by PCR mutagenesis, targeting individual contact or hypermutation amino acid residues in the light chain and/or heavy chain CDRs-, followed by kinetic and functional analysis of the modified antibodies as described herein (e.g., neutralization assays described in Example 3, and by BIAcore analysis, as described in Example 5).

Accordingly, in another aspect the invention features an isolated human antibody, or an antigen-binding portion thereof, which a) inhibits phytohemagglutinin blast proliferation in an in vitro PHA assay with an $IC_{50}$ of $1 \times 10^{-6}$ M or less;
b) comprises a heavy chain CDR3 comprising the amino acid sequence of SEQ ID NO: 1, a heavy chain CDR2 comprising the amino acid sequence of SEQ ID NO: 3 and a heavy chain CDR1 comprising the amino acid sequence of SEQ ID NO: 5, or a mutant thereof having one or more amino acid substitutions at a preferred selective mutagenesis position or a hypermutation position, wherein said mutant has a $k_{off}$ rate no more than 10-fold higher than the antibody comprising a heavy chain CDR3 comprising the amino acid sequence of SEQ ID NO: 1, a heavy chain CDR2 comprising the amino acid sequence of SEQ ID NO: 3, and a heavy chain CDR1 comprising the amino acid sequence of SEQ ID NO: 5; and
c) comprises a light chain CDR3 comprising the amino acid sequence of SEQ ID NO: 2, a light chain CDR2 comprising the amino acid sequence of SEQ ID NO: 4, and a light chain CDR1 comprising the amino acid sequence of SEQ ID NO: 6, or a mutant thereof having one or more amino acid substitutions at a preferred selective mutagenesis position or a hypermutation position, wherein said mutant has a $k_{off}$ rate no more than 10-fold higher than the antibody comprising a light chain CDR3 comprising the amino acid sequence of SEQ ID NO: 2, a light chain CDR2 comprising the amino acid sequence of SEQ ID NO: 4, and a light chain CDR1 comprising the amino acid sequence of SEQ ID NO: 6.

In another aspect the invention features an isolated human antibody, or an antigen-binding portion thereof, which
a) inhibits phytohemagglutinin blast proliferation in an in vitro PHA assay with an $IC_{50}$ of $1 \times 10^{-9}$ M or less;
b) comprises a heavy chain CDR3 comprising the amino acid sequence of SEQ ID NO: 9, a heavy chain CDR2 comprising the amino acid sequence of SEQ ID NO: 11 and a heavy chain CDR1 comprising the amino acid sequence of SEQ ID NO: 13, or a mutant thereof having one or more amino acid substitutions at a preferred selective mutagenesis position, contact position or a hypermutation position, wherein said mutant has a $k_{off}$ rate no more than 10-fold higher than the antibody comprising a heavy chain CDR3 comprising the amino acid sequence of SEQ ID NO: 9, a heavy chain CDR2 comprising the amino acid sequence of SEQ ID NO: 11, and a heavy chain CDR1 comprising the amino acid sequence of SEQ ID NO: 13; and
c) comprises a light chain CDR3 comprising the amino acid sequence of SEQ ID NO: 10, a light chain CDR2 comprising the amino acid sequence of SEQ ID NO: 12, and a light chain CDR1 comprising the amino acid sequence of SEQ ID NO: 14, or a mutant thereof having one or more amino acid substitutions at a preferred selective mutagenesis position, contact position or a hypermutation position, wherein said mutant has a $k_{off}$ rate no more than 10-fold higher than the antibody comprising a light chain CDR3 comprising the amino acid sequence of SEQ ID NO: 10, a light chain CDR2 comprising the amino acid sequence of SEQ ID NO: 12, and a light chain CDR1 comprising the amino acid sequence of SEQ ID NO: 14.

An ordinarily skilled artisan will also appreciate that additional mutations to the CDR regions of an antibody of the invention, for example in Y61 or in J695, can be made to provide additional anti-IL-12 antibodies of the invention. Such methods of modification can be performed using standard molecular biology techniques, as described above. The functional and kinetic analysis of the modified antibodies can be performed as described in Example 3 and Example 5, respectively. Modifications of individual residues of Y61 that led to the identification of J695 are shown in FIGS. 2A-2H and are described in Example 2.

Accordingly, in another aspect the invention features an isolated human antibody, or an antigen-binding portion thereof, which
 a) inhibits phytohemagglutinin blast proliferation in an in vitro PHA assay with an $IC_{50}$ of $1 \times 10^{-9}$ M or less;
 b) comprises a heavy chain CDR3 comprising the amino acid sequence of SEQ ID NO: 17, a heavy chain CDR2 comprising the amino acid sequence of SEQ ID NO: 19 and a heavy chain CDR1 comprising the amino acid sequence of SEQ ID NO: 21, or a mutant thereof having one or more amino acid substitutions at a preferred selective mutagenesis position or a hypermutation position, wherein said mutant has a $k_{off}$ rate no more than 10-fold higher than the antibody comprising a heavy chain CDR3 comprising the amino acid sequence of SEQ ID NO: 17, a heavy chain CDR2 comprising the amino acid sequence of SEQ ID NO: 19, and a heavy chain CDR1 comprising the amino acid sequence of SEQ ID NO: 21; and
 c) comprises a light chain CDR3 comprising the amino acid sequence of SEQ ID NO: 18, a light chain CDR2 comprising the amino acid sequence of SEQ ID NO: 20, and a light chain CDR1 comprising the amino acid sequence of SEQ ID NO: 22, or a mutant thereof having one or more amino acid substitutions at a preferred selective mutagenesis position or a hypermutation position, wherein said mutant has a $k_{off}$ rate no more than 10-fold higher than the antibody comprising a light chain CDR3 comprising the amino acid sequence of SEQ ID NO: 18, a light chain CDR2 comprising the amino acid sequence of SEQ ID NO: 20, and a light chain CDR1 comprising the amino acid sequence of SEQ ID NO: 22.

In another aspect the invention features an isolated human antibody, or an antigen-binding portion thereof, which
 a) inhibits phytohemagglutinin blast proliferation in an in vitro PHA assay with an $IC_{50}$ of $1 \times 10^{-9}$ M or less;
 b) comprises a heavy chain CDR3 comprising the amino acid sequence of SEQ ID NO: 25, a heavy chain CDR2 comprising the amino acid sequence of SEQ ID NO: 27 and a heavy chain CDR1 comprising the amino acid sequence of SEQ ID NO: 29, or a mutant thereof having one or more amino acid substitutions at a preferred selective mutagenesis position or a hypermutation position, wherein said mutant has a $k_{off}$ rate no more than 10-fold higher than the antibody comprising a heavy chain CDR3 comprising the amino acid sequence of SEQ ID NO: 25, a heavy chain CDR2 comprising the amino acid sequence of SEQ ID NO: 27, and a heavy chain CDR1 comprising the amino acid sequence of SEQ ID NO: 29; and
 c) comprises a light chain CDR3 comprising the amino acid sequence of SEQ ID NO: 26, a light chain CDR2 comprising the amino acid sequence of SEQ ID NO: 28, and a light chain CDR1 comprising the amino acid sequence of SEQ ID NO: 30, or a mutant thereof having one or more amino acid substitutions at a preferred selective mutagenesis position or a hypermutation position, wherein said mutant has a $k_{off}$ rate no more than 10-fold higher than the antibody comprising a light chain CDR3 comprising the amino acid sequence of SEQ ID NO: 26, a light chain CDR2 comprising the amino acid sequence of SEQ ID NO: 28, and a light chain CDR1 comprising the amino acid sequence of SEQ ID NO: 30.

In yet another embodiment, the invention provides isolated human antibodies, or antigen-binding portions thereof, that neutralize the activity of human IL-12, and at least one additional primate IL-12 selected from the group consisting of baboon IL-12, marmoset IL-12, chimpanzee IL-12, cynomolgus IL-12 and rhesus IL-12, but which do not neutralize the activity of the mouse IL-12.

II Selection of Recombinant Human Antibodies

Recombinant human antibodies of the invention can be isolated by screening of a recombinant combinatorial antibody library, preferably a scFv phage display library, prepared using human VL and VH cDNAs prepared from mRNA derived from human lymphocytes. Methodologies for preparing and screening such libraries are known in the art. In addition to commercially available kits for generating phage display libraries (e.g., the Pharmacia *Recombinant Phage Antibody System*, catalog no. 27-9400-01; and the Stratagene SurfZAP™ phage display kit, catalog no. 240612), examples of methods and reagents particularly amenable for use in generating and screening antibody display libraries can be found in, for example, Kang et al. PCT Publication No. WO 92/18619; Winter et al. PCT Publication No. WO 92/20791; Breitling et al. PCT Publication No. WO 93/01288; McCafferty et al. PCT Publication No. WO 92/01047; Garrard et al. PCT Publication No. WO 92/09690; Fuchs et al. (1991) *Bio/Technology* 9:1370-1372; Hay et al. (1992) *Hum Antibod Hybridomas* 3:81-85; Huse et al. (1989) *Science* 246:1275-1281; McCafferty et al., *Nature* (1990) 348:552-554; Griffiths et al. (1993) *EMBO J* 12:725-734; Hawkins et al. (1992) *J Mol Biol* 226:889-896; Clackson et al. (1991) *Nature* 352: 624-628; Gram et al. (1992) *PNAS* 89:3576-3580; Garrad et al. (1991) *Bio/Technology* 9:1373-1377; Hoogenboom et al. (1991) *Nuc Acid Res* 19:4133-4137; and Barbas et al. (1991) *PNAS* 88:7978-7982.

The antibody libraries used in this method are preferably scFv libraries prepared from human VL and VH cDNAs. The scFv antibody libraries are preferably screened using recombinant human IL-12 as the antigen to select human heavy and light chain sequences having a binding activity toward IL-12. To select for antibodies specific for the p35 subunit of IL-12 or the p70 heterodimer, screening assays were performed in the presence of excess free p40 subunit. Subunit preferences can be determined, for example by, micro-Friguet titration, as described in Example 1.

Once initial human VL and VH segments are selected, "mix and match" experiments, in which different pairs of the selected VL and VH segments are screened for IL-12 binding, are performed to select preferred VL/VH pair combinations (see Example 1). Additionally, to further improve the affinity and/or lower the off rate constant for hIL-12 binding, the VL and VH segments of the preferred VL/VH pair(s) can be randomly mutated, preferably within the CDR3 region of VH and/or VL, in a process analogous to the in vivo somatic mutation process responsible for affinity maturation of antibodies during a natural immune response. This in vitro affinity maturation can be accomplished by amplifying VH and VL regions using PCR primers complimentary to the VH CDR3 or VL CDR3, respectively, which primers have been "spiked" with a random mixture of the four nucleotide bases at certain positions such that the resultant PCR products encode VH and VL segments into which random mutations have been introduced into the VH and/or VL CDR3 regions. These randomly mutated VH and VL segments can be reselected and rescreened for binding to hIL-12 and sequences that exhibit high affinity and a low off rate for IL-12 binding can be selected. Table 2 (see Appendix A) shows antibodies that displayed altered binding specificity/affinity produced as a result of in vitro affinity maturation.

Following selection, isolation and screening of an anti-hIL-12 antibody of the invention from a recombinant immunoglobulin display library, nucleic acid encoding the selected antibody can be recovered from the phage particle(s) (e.g., from the phage genome) and subcloned into other expression vectors by standard recombinant DNA techniques. If desired, the nucleic acid can be further manipulated to create other antibody forms of the invention (e.g., linked to nucleic acid encoding additional immunoglobulin domains, such as additional constant regions). To express a recombinant human antibody isolated by screening of a combinatorial library, the DNA encoding the antibody is cloned into a recombinant expression vector and introduced into a mammalian host cells, as described in further detail in Section IV below.

Methods for selecting human IL-12 binding antibodies by phage display technology, and affinity maturation of selected antibodies by random or site-directed mutagenesis of CDR regions are described in further detail in Example 1.

As described in Example 1, screening of human VL and VH cDNA libraries identified a series of anti-IL-12 antibodies, of which the Joe 9 antibody was selected for further development. A comparison of the heavy chain variable region of Joe 9 with the heavy chain germline sequences selected from the VBASE database, revealed that Joe 9 was similar to the COS-3 germline sequence. COS-3 belongs to the $V_H3$ family of germline sequences.

The $V_H3$ family is part of the human VH germline repertoire which is grouped into seven families, $V_H1$-$V_H7$, based on nucleotide sequence homology (Tomlinson et al. (1992) *J. Mol. Biol.*, 227, 776-798 and Cook et al. (1995) *Immunology Today*, 16, 237-242). The $V_H3$ family contains the highest number of members and makes the largest contribution to the germline repertoire. For any given human $V_H3$-germline antibody sequence, the amino acid sequence identity within the entire $V_H3$ family is high (See e.g., Tomlinson et al. (1992) *J. Mol. Biol.*, 227, 776-798 and Cook et al. (1995) *Immunology Today*, 16, 237-242). The range of amino acid sequence identity between any two germline VH sequences of the $V_H3$ family varies from 69-98 residues out of approximately 100 VH residues, (i.e., 69-98% amino acid sequence homology between any two germline VH sequences). For most pairs of germline sequences there is at least 80 or more identical amino acid residues, (i.e., at least 80% amino acid sequence homology). The high degree of amino acid sequence homology between the $V_H3$ family members results in certain amino acid residues being present at key sites in the CDR and framework regions of the VH chain. These amino acid residues confer structural features upon the CDRs.

Studies of antibody structures have shown that CDR conformations can be grouped into families of canonical CDR structures based on the key amino acid residues that occupy certain positions in the CDR and framework regions. Consequently, there are similar local CDR conformations in different antibodies that have canonical structures with identical key amino acid residues (Chothia et al. (1987) *J. Mol. Biol.*, 196, 901-917 and Chothia et al. (1989) *Nature*, 342, 877-883). Within the $V_H3$ family there is a conservation of amino acid residue identity at the key sites for the CDR1 and CDR2 canonical structures (Chothia et al. (1992) *J. Mol. Biol.*, 227, 799-817).

The COS-3 germline VH gene, is a member of the $V_H3$ family and is a variant of the 3-30 (DP-49) germline VH allele. COS-3, differs from Joe9 VH amino acid sequences at only 5 positions. The high degree of amino acid sequence homology between Joe9 VH and COS-3, and between Joe9 VH and the other $V_H3$ family members also confers a high degree of CDR structural homology (Chothia et al. (1992) *J. Mol. Biol.*, 227, 799-817; Chothia et al. (1987) *J. Mol. Biol.*, 196, 901-917 and Chothia et al. (1989) *Nature*, 342, 877-883).

The skilled artisan will appreciate that based on the high amino acid sequence and canonical structural similarity to Joe 9, other $V_H3$ family members could also be used to generate antibodies that bind to human IL-12. This can be performed, for example, by selecting an appropriate VL by chain-shuffling techniques (Winter et al. (1994) *Annual Rev. Immunol.*, 12, 433-55), or by the grafting of CDRs from a rodent or other human antibody including CDRs from antibodies of this invention onto a $V_H3$ family framework.

The human V lambda germline repertoire is grouped into 10 families based on nucleotide sequence homology (Williams et al. (1996) *J. Mol. Biol.*, 264, 220-232). A comparison of the light chain variable region of Joe 9 with the light chain germline sequences selected from the VBASE database, revealed that Joe 9 was similar to the DPL8 lambda germline. The Joe9 VL differs from DPL8 sequence at only four framework positions, and is highly homologous to the framework sequences of the other $V_\lambda 1$ family members. Based on the high amino acid sequence homology and canonical structural similarity to Joe 9, other $V_\lambda 1$ family members may also be used to generate antibodies that bind to human IL-12. This can be performed, for example, by selecting an appropriate VH by chain-shuffling techniques (Winter et al. Supra, or by the grafting of CDRs from a rodent or other human antibody including CDRs from antibodies of this invention onto a $V_\lambda 1$ family framework.

The methods of the invention are intended to include recombinant antibodies that bind to hIL-12, comprising a heavy chain variable region derived from a member of the $V_H3$ family of germline sequences, and a light chain variable region derived from a member of the $V_\lambda 1$ family of germline sequences. Moreover, the skilled artisan will appreciate that any member of the $V_H3$ family heavy chain sequence can be combined with any member of the $V_\lambda 1$ family light chain sequence.

Those skilled in the art will also appreciate that DNA sequence polymorphisms that lead to changes in the amino acid sequences of the germline may exist within a population (e.g., the human population). Such genetic polymorphism in the germline sequences may exist among individuals within a population due to natural allelic variation. Such natural allelic variations can typically result in 1-5% variance in the nucleotide sequence of the a gene. Any and all such nucleotide variations and resulting amino acid polymorphisms in germline sequences that are the result of natural allelic variation are intended to be within the scope of the invention.

Accordingly, in one aspect, the invention features an isolated human antibody, or an antigen-binding portion thereof, which has the following characteristics:

a) that binds to human IL-12 and dissociates from human IL-12 with a $k_{off}$ rate constant of 0.1 s$^{-1}$ or less, as determined by surface plasmon resonance, or which inhibits phytohemagglutinin blast proliferation in an in vitro phytohemagglutinin blast proliferation assay (PHA assay) with an IC$_{50}$ of 1×10$^{-6}$M or less.

b) has a heavy chain variable region comprising an amino acid sequence selected from a member of the $V_H3$ germline family, wherein the heavy chain variable region has a mutation at a contact or hypermutation position with an activity enhancing amino acid residue.
c) has a light chain variable region comprising an amino acid sequence selected from a member of the $V_\lambda 1$ germline family, wherein the light chain variable region has a mutation at a preferred selective mutagenesis position, contact or hypermutation position with an activity enhancing amino acid residue.

In a preferred embodiment, the isolated human antibody, or antigen binding has mutation in the heavy chain CDR3.

In another preferred embodiment, the isolated human antibody, or antigen binding has mutation in the light chain CDR3.

In another preferred embodiment, the isolated human antibody, or antigen binding has mutation in the heavy chain CDR2.

In another preferred embodiment, the isolated human antibody, or antigen binding has mutation in the light chain CDR2.

In another preferred embodiment, the isolated human antibody, or antigen binding has mutation in the heavy chain CDR1.

In another preferred embodiment, the isolated human antibody, or antigen binding has mutation in the light chain CDR1.

An ordinarily skilled artisan will appreciate that based on the high amino acid sequence similarity between members of the $V_H 3$ germline family, or between members of the light chain $V_\lambda 1$ germline family, that mutations to the germlines sequences can provide additional antibodies that bind to human IL-12. Table 1 (see Appendix A) shows the germline sequences of the $V_H 3$ family members and demonstrates the significant sequence homology within the family members. Also shown in Table 1 are the germline sequences for $V_\lambda 1$ family members. The heavy and light chain sequences of Joe 9 are provided as a comparison. Mutations to the germline sequences of $V_H 3$ or $V_\lambda 1$ family members may be made, for example, at the same amino acid positions as those made in the antibodies of the invention (e.g. mutations in Joe 9). The modifications can be performed using standard molecular biology techniques, such as by PCR mutagenesis, targeting individual amino acid residues in the germline sequences, followed by kinetic and functional analysis of the modified antibodies as described herein (e.g., neutralization assays described in Example 3, and by BIAcore analysis, as described in Example 5).

Accordingly, in one aspect, the invention features isolated human antibody, or an antigen-binding portion thereof, which has the following characteristics:
a) has a heavy chain variable region comprising an amino acid sequence selected from the group consisting of SEQ ID NOs: 595-667, wherein the heavy chain variable region has a mutation at a preferred selective mutagenesis position, contact or hypermutation position with an activity enhancing amino acid residue.
b) has a light chain variable region comprising an amino acid sequence selected from the group consisting of SEQ ID NOs: 669-675, wherein the light chain variable region has a mutation at a preferred selective mutagenesis position, contact or hypermutation position with an activity enhancing amino acid residue.

An ordinarily skilled artisan will appreciate that based on the high amino acid sequence similarity between Joe 9 and COS-3 heavy chain germline sequence, and between Joe 9 and DPL8 lambda germline sequence, that other mutations to the CDR regions of these germlines sequences can provide additional antibodies that bind to human IL-12. Such methods of modification can be performed using standard molecular biology techniques as described above.

Accordingly, in one aspect, the invention features isolated human antibody, or an antigen-binding portion thereof, which has the following characteristics:
a) that binds to human IL-12 and dissociates from human IL-12 with a $k_{off}$ rate constant of $0.1 s^{-1}$ or less, as determined by surface plasmon resonance, or which inhibits phytohemagglutinin blast proliferation in an in vitro phytohemagglutinin blast proliferation assay (PHA assay) with an $IC_{50}$ of $1 \times 10^{-6}$M or less.
b) has a heavy chain variable region comprising the COS-3 germline amino acid sequence, wherein the heavy chain variable region has a mutation at a preferred selective mutagenesis position, contact or hypermutation position with an activity enhancing amino acid residue.
c) has a light chain variable region comprising the DPL8 germline amino acid sequence, wherein the light chain variable region has a mutation at a preferred selective mutagenesis position, contact or hypermutation position with an activity enhancing amino acid residue.

Due to certain amino acid residues occupying key sites in the CDR and framework regions in the light and heavy chain variable region, structural features are conferred at these regions. In particular, the CDR2 and CDR1 regions are subject to canonical structural classifications. Since there is a high degree of amino acids sequence homology between family members, these canonical features are present between family members. The skilled artisan will appreciate that modifications at the amino acid residues that confer these canonical structures would produce additional antibodies that bind to IL-12. The modifications can be performed using standard molecular biology techniques as described above.

Accordingly, in another aspect, the invention features an isolated human antibody, or an antigen-binding portion thereof, which has the following characteristics:
a) that binds to human IL-12 and dissociates from human IL-12 with a $k_{off}$ rate constant of $0.1$ $s^{-1}$ or less, as determined by surface plasmon resonance, or which inhibits phytohemagglutinin blast proliferation in an in vitro phytohemagglutinin blast proliferation assay (PHA assay) with an $IC_{50}$ of $1 \times 10^{-6}$M or less.
b) has a heavy chain variable region comprising an amino acid sequence selected from a member of the $V_H 3$ germline family, wherein the heavy chain variable region comprises a CDR2 that is structurally similar to CDR2s from other $V_H 3$ germline family members, and a CDR1 that is structurally similar to CDR1s from other $V_H 3$ germline family members, and wherein the heavy chain variable region has a mutation at a preferred selective mutagenesis position, contact or hypermutation position with an activity enhancing amino acid residue;
c) has a light chain variable region comprising an amino acid sequence selected from a member of the $V_\lambda 1$ germline family, wherein the light chain variable region comprises a CDR2 that is structurally similar to CDR2s from other $V_\lambda 1$ germline family members, and a CDR1 that is structurally similar to CDR1s from other $V_\lambda 1$ germline family members, and wherein the light chain variable region has a mutation at a preferred selective mutagenesis position, contact or hypermutation position with an activity enhancing amino acid residue.

Recombinant human antibodies of the invention have variable and constant regions which are homologous to human germline immunoglobulin sequences selected from the VBASE database. Mutations to the recombinant human antibodies (e.g., by random mutagenesis or PCR mutagenesis)

result in amino acids that are not encoded by human germline immunoglobulin sequences. Also, libraries of recombinant antibodies which were derived from human donors will contain antibody sequences that differ from their corresponding germline sequences due to the normal process of somatic mutation that occurs during B-cell development. It should be noted that if the "germline" sequences obtained by PCR amplification encode amino acid differences in the framework regions from the true germline configuration (i.e., differences in the amplified sequence as compared to the true germline sequence), it may be desirable to change these amino acid differences back to the true germline sequences (i.e., "backmutation" of framework residues to the germline configuration). Thus, the present invention can optionally include a backmutation step. To do this, the amino acid sequences of heavy and light chain encoded by the germline (as found as example in VBASE database) are first compared to the mutated immunoglobulin heavy and light chain framework amino acid sequences to identify amino acid residues in the mutated immunoglobulin framework sequence that differ from the closest germline sequences. Then, the appropriate nucleotides of the mutated immunoglobulin sequence are mutated back to correspond to the germline sequence, using the genetic code to determine which nucleotide changes should be made. Mutagenesis of the mutated immunoglobulin framework sequence is carried out by standard methods, such as PCR-mediated mutagenesis (in which the mutated nucleotides are incorporated into the PCR primers such that the PCR product contains the mutations) or site-directed mutagenesis. The role of each amino acid identified as candidate for backmutation should be investigated for a direct or indirect role in antigen binding and any amino acid found after mutation to affect any desirable characteristic of the human antibody should not be included in the final human antibody; as an example, activity enhancing amino acids identified by the selective mutagenesis approach will not be subject to backmutation. Assays to determine the characteristics of the antibody resulting from mutagenesis can include ELISA, competitive ELISA, in vitro and in vivo neutralization assays and/or (see e.g. Example 3) immunohistochemistry with tissue sections from various sources (including human, primate and/or other species).

To minimize the number of amino acids subject to backmutation those amino acid positions found to be different from the closest germline sequence but identical to the corresponding amino acid in a second germline sequence can remain, provided that the second germline sequence is identical and colinear to the sequence of the human antibody of the invention for at least 10, preferably 12 amino acids, on both sides of the amino acid in question. This would assure that any peptide epitope presented to the immune system by professional antigen presenting cells in a subject treated with the human antibody of the invention would not be foreign but identical to a self-antigen, i.e. the immunoglobulin encoded by that second germline sequence. Backmutation may occur at any stage of antibody optimization; preferably, backmutation occurs directly before or after the selective mutagenesis approach. More preferably, backmutation occurs directly before the selective mutagenesis approach.

III. Modifications to Preferred Selective Mutagenesis Positions, Contact and/or Hypermutation Positions Typically, selection of antibodies with improved affinities can be carried out using phage display methods, as described in section II above. This can be accomplished by randomly mutating combinations of CDR residues and generating large libraries containing antibodies of different sequences. However, for these selection methods to work, the antibody-antigen reaction must tend to equilibrium to allow, over time, preferential binding of higher affinity antibodies to the antigen. Selection conditions that would allow equilibrium to be established could not be determined (presumably due to additional non-specific interactions between the antigen and phage particle) when phage display methods were used to improve the affinity of selected anti-IL-12 antibodies, upon attaining a certain level of affinity achieved (i.e., that of antibody Y61). Accordingly, antibodies with even higher affinities could not be selected by phage display methods. Thus, for at least certain antibodies or antigens, phage display methods are limiting in their ability to select antibodies with a highly improved binding specificity/affinity. Accordingly, a method termed Selective Mutagenesis Approach which does not require phage display affinity maturation of antibodies, was established to overcome this limitation and is provided by the invention. Although this Selective Mutagenesis Approach was developed to overcome limitations using the phage display system, it should be noted that this method can also be used with the phage display system. Moreover, the selective mutagenesis approach can be used to improve the activity of any antibody.

To improve the activity (e.g., affinity or neutralizing activity) of an antibody, ideally one would like to mutate every CDR position in both the heavy and light chains to every other possible amino acid residue. However, since there are, on average, 70 CDR positions within an antibody, such an approach would be very time consuming and labor intensive. Accordingly, the method of the invention allows one to improve the activity of the antibody by mutating only certain selected residues within the heavy and/or light chain CDRs. Furthermore, the method of the invention allows improvement in activity of the antibody without affecting other desirable properties of the antibody.

Determining which amino acid residues of an antibody variable region are in contact with an antigen cannot be accurately predicted based on primary sequence or their positions within the variable region. Nevertheless, alignments of sequences from antibodies with different specificities conducted by Kabat et al. have identified the CDRs as local regions within the variable regions which differ significantly among antibodies (Kabat et al. (1971) *Ann. NY Acad, Sci.* 190:382-393, Kabat, E. A., et al. (1991) *Sequences of Proteins of Immunological Interest, Fifth Edition*, U.S. Department of Health and Human Services, NIH Publication No. 91-3242). Structural studies have shown that the antigen binding surface is formed by amino acid residues present in the CDRs. Other amino acid residues outside the CDR are also known to play structural roles or be directly involved in antigen binding. Therefore, for each antigen-antibody pair, amino acid residues within and outside of the CDRs may be important.

The sequence alignment studies by Tomlison et al identified a number of positions in the heavy and light chain CDR1 and CDR2, and in a portion of the kappa chain CDR3 which are frequent sites of somatic mutation. (Tomlison et al (1996) *J. Mol. Biol.* 256: 813-817). In particular, positions H31, H31B, H33, H33B, H52B, H56, H58, L30, L31, L31A, L50, L53, L91, L92, L93 and L94 were identified as frequent sites for somatic mutation. However, this analysis excludes the important heavy chain CDR3 regions, and sections of the light chain CDR3 which are known to lie in the center of an antibody binding site, and potentially provide important interactions with an antigen. Furthermore, Tomlison et al. propose that somatic diversity alone does not necessarily predict a role of a specific amino acid in antigen binding, and suggest conserved amino acid residues that contact the antigen, and diverse amino acid residues which do not contact the antigen. This conclusion is further supported by mutational studies on the role of somatic mutations to antibody affinity (Sharon, (1990), *PNAS*, 87:4814-7). Nineteen somatic mutations in a high-affinity anti-p-azophenylarsonate (Ars) antibody were simultaneously replaced with their corresponding germline residues, generating a germline version of the anti-Ars antibody which had a two-hundred fold loss in activity. The full affinity of the anti-Ars antibody could be recovered by restoring only three of the nineteen somatic mutations, demonstrating that many somatic mutations may be permitted that do not contribute to antigen binding activity.

The result can be explained in part by the nature of antibody diversity itself. Immature B-cells may produce initially low affinity antibodies that recognize a number of self or non-self antigens. Moreover, antibodies may undergo in the course of affinity maturation sequence variations that may cause self-reactivity. Hypermutation of such low affinity antibodies may serve to abolish self-reactivity ("negative selection") and increase affinity for the foreign antigen. Therefore, the analysis of primary and structural data of a large number of antibodies does not provide a method of predicting either (1) the role of somatic hyper-mutation sites in the affinity maturation process versus the process of decreasing affinity towards unwanted antigens, or (2) how a given amino acid contributes to the properties of a specific antigen-antibody pair.

Other attempts to address the role of specific amino acid residues in antigen recognition were made by analyzing a number of crystal structures of antigen-antibody complexes (MacCallum et al. (1996) *J. Mol. Biol.* 262: 732-745). The potential role of positions located within and outside the CDRs was indicated. Positions in CDRs involved in antigen binding in more than 10 of 26 analyzed structures included H31, H33, H50, H52, H53, H54, H56, H58, H95, H96, H97, H98 and H100 in the heavy chain and L30A, L32, L91, L92, L93, L94, L96 in the light chain. However, the authors noted that prediction of antigen contacts using these and other structural data may over and under predict contact positions, leading to the speculation that a different strategy may have to be applied to different antigens.

Pini et al. describe randomizing multiple residues in antibody CDR sequences in a large phage display library to rapidly increase antibody affinity (Pini et al. (1998) *J. Biol. Chem.* 273: 21769-21776). However, the high affinity antibodies discussed by Pini et al. had mutations in a total of eight positions, and a reductionary analysis of which changes are absolutely required to improve affinity of the antibody becomes impractical because of the large number of possible combinations to be tested for the smallest number of amino acids required.

Furthermore, randomizing multiple residues may not necessarily preserve other desired properties of the antibody. Desirable properties or characteristics of an antibody are art-recognized and include for example, preservation of non-cross reactivity, e.g., with other proteins or human tissues and preservation of antibody sequences that are close to human germline immunoglobulin sequences improvement of neutralization potency. Other desirable properties or characteristics include ability to preserve species cross reactivity, ability to preserve epitope specificity and ability to preserve high expression levels of protein in mammalian cells. The desirable properties or characteristics can be observed or measured using art-recognized techniques including but not limited to ELISA, competitive ELISA, in vitro and in vivo neutralization assays (see e.g. Example 3), immunohistochemistry with tissue sections from different sources including human, primate or other sources as the need may be, and studies to expression in mammalian cells using transient expression or stable expression.

In addition, the method of Pini et al may introduce more changes than the minimal number actually required to improve affinity and may lead to the antibodies triggering anti-human-antibody (HAMA) formation in human subjects. Further, as discussed elsewhere, the phage display as demonstrated here, or other related method including ribosome display may not work appropriately upon reaching certain affinities between antibody and antigen and the conditions required to reach equilibrium may not be established in a reasonable time frame because of additional interactions including interactions with other phage or ribosome components and the antigen.

The ordinarily skilled artisan may glean interesting scientific information on the origin of antibody diversity from the teachings of the references discussed above. The present invention, however, provides a method for increasing antibody affinity of a specific antigen-antibody pair while preserving other relevant features or desirable characteristics of the antibody. This is especially important when considering the desirability of imparting a multitude of different characteristics on a specific antibody including antigen binding.

If the starting antibody has desirable properties or characteristics which need to be retained, a selective mutagenesis approach can be the best strategy for preserving these desirable properties while improving the activity of the antibody. For example, in the mutagenesis of Y61, the aim was to increase affinity for hIL-12, and to improve the neutralization potency of the antibody while preserving desired properties. Desired properties of Y61 included (1) preservation of non-cross reactivity with other proteins or human tissues, (2) preservation of fine epitope specificity, i.e. recognizing a p40 epitope preferably in the context of the p70 (p40/p35) heterodimer, thereby preventing binding interference from free soluble p40; and (3) generation of an antibody with heavy and light chain amino acid sequences that were as close as possible to their respective germline immunoglobulin sequences.

In one embodiment, the method of the invention provides a selective mutagenesis approach as a strategy for preserving the desirable properties or characteristics of the antibody while improving the affinity and/or neutralization potency. The term "selective mutagenesis approach" is as defined above and includes a method of individually mutating selected amino acid residues. The amino acid residues to be mutated may first be selected from preferred selective mutagenesis positions, then from contact positions, and then from hypermutation positions. The individual selected position can be mutated to at least two other amino acid residue and the effect of the mutation both on the desired properties of the antibody, and improvement in antibody activity is determined.

The Selective Mutagenesis approach comprises the steps of:

selecting candidate positions in the order 1) preferred selective mutagenesis positions; 2) contact positions; 3) hypermutation positions and ranking the positions based on the location of the position within the heavy and light chain variable regions of an antibody (CDR3 preferred over CDR2 preferred over CDR1);

individually mutating candidate preferred selective mutagenesis positions, hypermutation and/or contact positions in the order of ranking, to all possible other amino acid residues and analyzing the effect of the individual mutations on the activity of the antibody in order to determine activity enhancing amino acid residues;

if necessary, making stepwise combinations of the individual activity enhancing amino acid residues and analyzing the effect of the various combinations on the activity of the antibodies; selecting mutant antibodies with activity enhancing amino acid residues and ranking the mutant antibodies based on the location and identity of the amino acid substitutions with regard to their immunogenic potential. Highest ranking is given to mutant antibodies that comprise an amino acid sequence which nearly identical to a variable region sequence that is described in a germline database, or has an amino acid sequence that is comparable to other human antibodies. Lower ranking is given to mutant antibodies containing an amino acid substitution that is rarely encountered in either germline sequences or the sequences of other human antibodies. The lowest ranking is given to mutant antibodies with an amino acid substitution that has not been encountered in a germline sequence or the sequence of another human antibody. As set forth above, mutant antibodies comprising at least one activity enhancing amino acid residue located in CDR3 is preferred over CDR2 which is preferred over CDR1. The CDRs of the heavy chain variable regions are preferred over those of the light chain variable region.

The mutant antibodies can also be studied for improvement in activity, e.g. when compared to their corresponding parental antibody. The improvement in activity of the mutant antibody can be determined for example, by neutralization assays, or binding specificity/affinity by surface plasmon resonance analysis (see Example 3). Preferably, the improvement in activity can be at least 2-20 fold higher than the parental antibody. The improvement in activity can be at least "$x_1$" to "$x_2$" fold higher than the parental antibody wherein "$x_1$" and "$x_2$" are integers between and including 2 to 20, including ranges within the state range, e.g. 2-15, e.g. 5-10.

The mutant antibodies with the activity enhancing amino acid residue also can be studied to determine whether at least one other desirable property has been retained after mutation. For example, with anti-hIL-12 antibodies testing for, (1) preservation of non-cross reactivity with other proteins or human tissues, (2) preservation of epitope recognition, i.e. recognizing a p40 epitope preferably in the context of the p70 (p40/p35) heterodimer, thereby preventing binding interference from free soluble p40; and (3) generation of antibodies with heavy and light chain amino acid sequences that were as close as possible to their respective germline immunoglobulin sequences, and determining which would be least likely to elicit a human immune response based on the number of differences from the germline sequence. The same observations can be made on an antibody having more than one activity enhancing amino acid residues, e.g. at least two or at least three activity enhancing amino acid residues, to determine whether retention of the desirable property or characteristic has occurred.

An example of the use of a "selective mutagenesis approach", in the mutagenesis of Y61 is described below. The individual mutations H31S→E, L50→Y, or L94G→Y each improved neutralization activity of the antibody. However, when combination clones were tested, the activity of the combined clone H31S→E+L50→Y+L94G→Y was no better than L50→Y+L94G→Y (J695). Therefore, changing the germline amino acid residue Ser to Glu at position 31 of CDR1 was unnecessary for the improved activity of J695 over Y61. The selective mutagenesis approach therefore, identified the minimal number of changes that contributed to the final activity, thereby reducing the immunogenic potential of the final antibody and preserving other desired properties of the antibody.

Isolated DNA encoding the VH and VL produced by the selected mutagenesis approach can be converted into full length antibody chain genes, to Fab fragment genes as to a scFV gene, as described in section IV. For expression of VH and VL regions produced by the selected mutagenesis approach, expression vectors encoding the heavy and light chain can be transfected into variety host cells as described in detail in section IV. Preferred host cells include either prokaryotic host cells, for example, *E. coli*, or eukaryotic host cells, for example, yeast cells, e.g., *S. cerevisae*. Most preferred eukaryotic host cells are mammalian host cells, described in detail in section IV.

The selective mutagenesis approach provides a method of producing antibodies with improved activities without prior affinity maturation of the antibody by other means. The selective mutagenesis approach provides a method of producing antibodies with improved affinities which have been subject to back mutations. The selective mutagenesis approach also provides a method of improving the activity of affinity matured antibodies.

The skilled artisan will recognize that the selective mutagenesis approach can be used in standard antibody manipulation techniques known in the art. Examples include, but are not limited to, CDR grafted antibodies, chimeric antibodies, scFV fragments, Fab fragments of a full length antibodies and human antibodies from other sources, e.g., transgenic mice.

Rapid large scale mutational analysis of antibodies include in vitro transcription and translation using ribosome display technology (see e.g., Hanes et al., (1997) *Proc. Natl. Acad. Sci.* 94: 4937-4942; Dall Acqua et al., (1998) *Curr. Opin. Struc. Biol.* 8: 443-450; He et al., (1997) *Nucleic Acid Res.* 25: 5132-5134), and U.S. Pat. Nos. 5,643,768 and 5,658,754 issued to Kawasaki. The selective mutagenesis approach also provides a method of producing antibodies with improved activities that can be selected using ribosomal display techniques.

In the methods of the invention, antibodies or antigen binding portions thereof are further modified by altering individual positions in the CDRs of the HCVR and/or LCVR. Although these modifications can be made in phage-displayed antibodies, the method is advantageous in that it can be performed with antibodies that are expressed in other types of host systems, such as bacterial, yeast or mammalian cell expression systems. The individual positions within the CDRs selected for modification are based on the positions being a contact and/or hypermutation position.

Preferred contact positions and hypermutation positions as defined herein are shown in Table 3 (see Appendix A) and their modification in accordance with the method of the invention is described in detail in Example 2. Preferred contact positions are selected from the group consisting of H30, H31, H31B, H32, H33, H35, H50, H52, H52A, H53, H54, H56, H58, H95, H96, H97, H98, H101, L30, L31, L32, L34, L50, L52, L53, L55, L91, L92, L93, L94 and L96. Preferred hypermutation positions are selected from the group consisting of H30, H31, H31B, H32, H52, H56, H58, L30, L31, L32, L53 and L93. More preferred amino acid residues (referred to as "preferred selective mutagenesis positions") are both contact and hypermutation positions and are selected from the group consisting of H30, H31, H31B, H32, H33, H52, H56, H58, L30, L31, L32, L50, L91, L92, L93, L94. Particularly preferred contact positions are selected from the group consisting of L50 and L94.

Preferred activity enhancing amino acid residues replace amino acid residues located at positions selected from the group consisting of H30, H31, H31B, H32, H33, H35, H50, H52, H52A, H53, H54, H56, H58, H95, H96, H97, H98, H101, L30, L31, L32, L34, L50, L52, L53, L55, L91, L92, L93, L94, and L96. More preferred activity enhancing amino acid residues replace amino acid residues located at positions H30, H31, H31B, H32, H33, H52, H56, H58, L30, L31, L32, L50, L91, L92, L93, L94. Particularly, preferred activity enhancing amino acid residues replace amino acid residues located at positions selected from the group consisting of L50 and L94.

In general, the method of the invention involves selecting a particular preferred selective mutagenesis position, contact and/or hypermutation position within a CDR of the heavy or light chain of a parent antibody of interest, or antigen binding portion thereof, randomly mutagenizing that individual position (e.g., by genetic means using a mutagenic oligonucleotide to generate a "mini-library" of modified antibodies), or mutating a position to specific desired amino acids, to identify activity enhancing amino acid residues expressing, and purifying the modified antibodies (e.g., in a non-phage display host system), measuring the activity of the modified antibodies for antigen (e.g., by measuring $k_{off}$ rates by BIAcore analysis), repeating these steps for other CDR positions, as necessary, and combining individual mutations shown to have improved activity and testing whether the combination(s) generate an antibody with even greater activity (e.g., affinity or neutralizing potency) than the parent antibody, or antigen-binding portion thereof.

Accordingly, in one embodiment, the invention provides a method for improving the activity of an antibody, or antigen-binding portion thereof, comprising:
 a) providing a parent antibody or antigen-binding portion thereof;
 b) selecting in order a 1) preferred selective mutagenesis position, 2) contact position, or 3) hypermutation position within a complementarity determining region (CDR) for mutation, thereby identifying a selected preferred selective mutagenesis position, contact or hypermutation position;
 c) individually mutating said selected preferred selective mutagenesis position, contact or hypermutation position to at least two other amino acid residues to thereby create a panel of mutated antibodies, or antigen-binding portions thereof;
 d) evaluating the activity of the panel of mutated antibodies, or antigen-binding portions thereof, relative to the parent antibody or antigen-binding portion thereof;
 e) optionally, repeating steps a) through d) for at least one other preferred selective mutagenesis position, contact or hypermutation position;
 f) combining, in the parent antibody, or antigen-binding portion thereof, individual mutations shown to have improved activity, to form combination antibodies, or antigen-binding portions thereof; and
 g) evaluating the activity of the combination antibodies, or antigen-binding portions thereof, relative to the parent antibody or antigen-binding portion thereof; until an antibody, or antigen-binding portion thereof, with an improved activity, relative to the parent antibody, or antigen-binding portion thereof, is obtained. Preferably, the selected antibody or antibodies have an improved activity without loss or with retention of at least one desirable characteristic or property of the parental antibody as described above. The desirable characteristic or property can be measured or observed by the ordinarily skilled artisan using art-recognized techniques.

Preferred contact positions are selected from the group consisting of H30, H31, H31B, H32, H33, H35, H50, H52, H52A, H53, H54, H56, H58, H95, H96, H97, H98, H101, L30, L31, L32, L34, L50, L52, L53, L55, L91, L92, L93, L94 and L96. Preferred hypermutation positions are selected from the group consisting of H30, H31, H31B, H32, H52, H56, H58, L30, L31, L32, L53 and L93. More preferred selective mutagenesis positions are selected from the group consisting of H30, H31, H31B, H32, H33, H52, H56, H58, L30, L31, L32, L50, L91, L92, L93 and L94. Particularly preferred contact positions are selected from the group consisting of L50 and L94.

In another embodiment, the invention provides a method for improving the activity of an antibody, or antigen-binding portion thereof, comprising:
 a) providing a parent antibody or antigen-binding portion thereof;
 b) selecting a preferred selective mutagenesis position, contact or hypermutation position within a complementarity determining region (CDR) for mutation;
 c) individually mutating said selected preferred selective mutagenesis position, contact or hypermutation position to at least two other amino acid residues to thereby create a panel of mutated antibodies, or antigen-binding portions thereof;
 d) evaluating the activity of the panel of mutated antibodies, or antigen-binding portions thereof, relative to the parent antibody or antigen-binding portion thereof, thereby identifying an activity enhancing amino acid residue;
 e) optionally, repeating steps a) through d) for at least one other preferred selective mutagenesis position, contact or hypermutation position;
 f) combining, in the parent antibody, or antigen-binding portion thereof, two individual activity enhancing amino acid residues shown to have improved activity, to form combination antibodies, or antigen-binding portions thereof; and
 g) evaluating the activity of the combination antibodies, or antigen-binding portions thereof with two activity enhancing amino acid residues, relative to the parent antibody or antigen-binding portion thereof; until an antibody, or antigen-binding portion thereof, with an improved activity, relative to the parent antibody, or antigen-binding portion thereof, is obtained.

Preferred contact positions are selected from the group consisting of H30, H31, H31B, H32, H33, H35, H50, H52, H52A, 1153, H54, H56, H58, H95, H96, H97, H98, H101, L30, L31, L32, L34, L50, L52, L53, L55, L91, L92, L93, L94 and L96. Preferred hypermutation positions are selected from the group consisting of H30, H31, H31B, H32, H52, H56, H58, L30, L31, L32, L53 and L93. More preferred selective mutagenesis positions are selected from the group consisting of H30, H31, H31B, H32, H33, H52, H56, H58, L30, L31, L32, L50, L91, L92, L93 and L94. Particularly preferred contact positions are selected from the group consisting of L50 and L94.

In another embodiment, the invention provides a method for improving the activity of an antibody, or antigen-binding portion thereof, comprising:
 a) providing a parent antibody or antigen-binding portion thereof;
 b) selecting a preferred selective mutagenesis position, contact or hypermutation position within a complementarity determining region (CDR) for mutation;
 c) individually mutating said selected preferred selective mutagenesis position, contact or hypermutation position to at least two other amino acid residues to thereby create a panel of mutated antibodies, or antigen-binding portions thereof;

d) evaluating the activity of the panel of mutated antibodies, or antigen-binding portions thereof, relative to the parent antibody or antigen-binding portion thereof, thereby identifying an activity enhancing amino acid residue;

e) optionally, repeating steps a) through d) for at least one other preferred selective mutagenesis position, contact or hypermutation position;

f) combining, in the parent antibody, or antigen-binding portion thereof, three individual activity enhancing amino acid residues shown to have improved activity, to form combination antibodies, or antigen-binding portions thereof; and g) evaluating the activity of the combination antibodies, or antigen-binding portions thereof with two activity enhancing amino acid residues, relative to the parent antibody or antigen-binding portion thereof;

until an antibody, or antigen-binding portion thereof, with an improved activity, relative to the parent antibody, or antigen-binding portion thereof, is obtained.

Preferably, the activity enhancing amino acid residue replaces amino acid residues located at positions selected from the group consisting of H30, H31, H31B, H32, H33, H35, H50, H52, H52A, H53, H54, H56, H58, H95, H96, H97, H98, H101, L30, L31, L32, L34, L50, L52, L53, L55, L91, L92, L93, L94 and L96.

Following mutagenesis of individual selected positions, mutated clones can be sequenced to identify which amino acid residues have been introduced into the selected position in each clone. A small number of clones (e.g., about 24) can be selected for sequencing, which statistically should yield 10-15 unique antibodies, whereas larger numbers of clones (e.g., greater than 60) can be sequenced to ensure that antibodies with every possible substitution at the selected position are identified.

In one embodiment, contact and/or hypermutation positions within the CDR3 regions of the heavy and/or light chains are first selected for mutagenesis. However, for antibodies that have already been affinity matured in vitro by random mutagenesis of the CDR3 regions via phage display selection, it may be preferably to first select contact and/or hypermutation positions within CDR1 or CDR2 of the heavy and/or light chain.

In a more preferred embodiment, preferred selective mutagenesis positions within the CDR3 regions of the heavy and/or light chains are first selected for mutagenesis. However, for antibodies that have already been affinity matured in vitro by random mutagenesis of the CDR3 regions via phage display selection, it may be preferably to first select preferred selective mutagenesis positions within CDR1 or CDR2 of the heavy and/or light chain.

In another preferred embodiment, the optimization of a selected antibody by the selective mutagenesis approach is done sequentially as follows: preferred selective mutagenesis positions selected from the group consisting of H30, H31, H31B, H32, H33, H52, H56, H58, L30, L31, L32, L50, L91, L92, L93, L94 are mutated first to at least 2 other amino acids each (preferably 5-14 other amino acids) and the resulting antibodies are characterized for increased affinity, neutralization potency (and possibly also for at least one other retained characteristic or property discussed elsewhere). If a mutation of a single preferred selective mutagenesis position does not increase the affinity or neutralization potency at all or sufficiently and if even the combination of multiple activity enhancing amino acids replacing amino acids in preferred selective mutagenesis positions does not result in an combination antibody which meets the target activity (including affinity and/or neutralization potency), additional amino acid residues will be selected for selective mutagenesis from the group consisting of H35, H50, H53, H54, H95, H96, H97, H98, L30A and L96 are mutated to at least 2 other amino acids each (preferably 5-14 other amino acids) and the resulting antibodies are characterized for increased affinity, neutralization potency (and possibly also for at least one other retained characteristic or property discussed elsewhere).

If a mutation of a single amino acid residue selected from the group Consisting of H35, H50, H53, H54, H95, H96, H97, H98, L30A and L96 does not increase the activity (including affinity and/or neutralization potency) at all or not sufficiently and if even the combination of multiple activity enhancing amino acids replacing amino acids in those positions does not result in an combination antibody which meets the targeted activity (including affinity and/or target neutralization potency), additional amino acid residues will be selected for selective mutagenesis from the group consisting of H33B, H52B, L31A and are mutated to at least 2 other amino acids each (preferably 5-14 other amino acids) and the resulting antibodies are characterized for increased affinity, neutralization potency (and possibly also for at least one other retained characteristic or property discussed elsewhere).

It should be understood that the sequential selective mutagenesis approach may end at any of the steps outline above as soon as an antibody with the desired activity (including affinity and neutralization potency) has been identified. If mutagenesis of the preselected positions has identified activity enhancing amino acids residues but the combination antibody still do not meet the targets set for activity (including affinity and neutralization potency) and/or if the identified activity enhancing amino acids also affect other desired characteristics and are therefore not acceptable, the remaining CDR residues may be subjected to mutagenesis (see section IV).

The method of the invention can be used to improve activity of an antibody, or antigen binding portion thereof, to reach a predetermined target activity (e.g. a predetermined affinity and/or neutralization potency, and/or a desired property or characteristic).

Accordingly, the invention provides a method of improving the activity of an antibody, or antigen-binding portion thereof, to attain a predetermined target activity, comprising:

a) providing a parent antibody a antigen-binding portion thereof;

b) selecting a preferred selective mutagenesis position selected from group consisting of H30, H31, H31B, H32, H33, H52, H56, H58, L30, L31, L32, L50, L91, L92, L93, L94.

c) individually mutating the selected preferred selective mutagenesis position to at least two other amino acid residues to hereby create a first panel of mutated antibodies, or antigen binding portions thereof;

d) evaluating the activity of the first panel of mutated antibodies, or antigen binding portions thereof to determined if mutation of a single selective mutagenesis position produces an antibody or antigen binding portion thereof with the predetermined target activity or a partial target activity;

e) combining in a stepwise fashion, in the parent antibody, or antigen binding portion thereof, individual mutations shown to have an improved activity, to form combination antibodies, or antigen binding portions thereof f) evaluating the activity of the combination antibodies, or antigen binding portions thereof to determined if the combination antibodies, or antigen binding portions thereof have the predetermined target activity or a partial target activity.

g) if steps d) or f) do not result in an antibody or antigen binding portion thereof having the predetermined target activity, or result an antibody with only a partial activity, additional amino acid residues selected from the group consisting of H35, H50, H53, H54, H95, H96, H97, H98, L30A and L96 are mutated to at least two other amino acid residues to thereby create a second panel of mutated antibodies or antigen-binding portions thereof;

h) evaluating the activity of the second panel of mutated antibodies or antigen binding portions thereof, to determined if mutation of a single amino acid residue selected from the group consisting of H35, H50, H53, H54, H95, H96, H97, H98, L30A and L96 results an antibody or antigen binding portion thereof, having the predetermined target activity or a partial activity;

i) combining in stepwise fashion in the parent antibody, or antigen-binding portion thereof, individual mutations of step g) shown to have an improved activity, to form combination antibodies, or antigen binding portions thereof;

j) evaluating the activity of the combination antibodies or antigen binding portions thereof, to determined if the combination antibodies, or antigen binding portions thereof have the predetermined target activity or a partial target activity;

k) if steps h) or j) do not result in an antibody or antigen binding portion thereof having the predetermined target activity, or result in an antibody with only a partial activity, additional amino acid residues selected from the group consisting of H33B, H52B and L31A are mutated to at least two other amino acid residues to thereby create a third panel of mutated antibodies or antigen binding portions thereof;

l) evaluating the activity of the third panel of mutated antibodies or antigen binding portions thereof, to determine if a mutation of a single amino acid residue selected from the group consisting of H33B, H52B and L31A resulted in an antibody or antigen binding portion thereof, having the predetermined target activity or a partial activity;

m) combining in a stepwise fashion in the parent antibody, or antigen binding portion thereof, individual mutation of step k) shown to have an improved activity, to form combination antibodies, or antigen binding portions, thereof;

n) evaluating the activity of the combination antibodies or antigen-binding portions thereof, to determine if the combination antibodies, or antigen binding portions thereof have the predetermined target activity to thereby produce an antibody or antigen binding portion thereof with a predetermined target activity.

A number of mutagenesis methods can be used, including PCR assembly, Kunkel (dut-ung-) and thiophosphate (Amersham Sculptor kit) oligonucleotide-directed mutagenesis.

A wide variety of host expression systems can be used to express the mutated antibodies, including bacterial, yeast, baculoviral and mammalian expression systems (as well as phage display expression systems). An example of a suitable bacterial expression vector is pUC119(Sfi). Other antibody expression systems are known in the art and/or are described below in section N.

The modified antibodies, or antigen binding portions thereof, produced by the method of the invention can be identified without the reliance on phage display methods for selection. Accordingly, the method of the invention is particularly advantageous for improving the activity of a recombinant parent antibody or antigen-binding portion thereof, that was obtained by selection in a phage-display system but whose activity cannot be further improved by mutagenesis in the phage-display system.

Accordingly, in another embodiment, the invention provides a method for improving the affinity of an antibody, or antigen-binding portion thereof, comprising:

a) providing a recombinant parent antibody or antigen-binding portion thereof; that was obtained by selection in a phage-display system but whose activity cannot be further improved by mutagenesis in said phage-display system;

b) selecting a preferred selective mutagenesis position, contact or hypermutation position within a complementarity determining region (CDR) for mutation, thereby identifying a selected contact or hypermutation position;

c) individually mutating said selected preferred selective mutagenesis position, contact or hypermutation position to at least two other amino acid residues to thereby create a panel of mutated antibodies, or antigen-binding portions thereof, and expressing said panel in a non-phage display system;

d) evaluating the activity of the panel of mutated antibodies, or antigen-binding portions thereof, relative to the parent antibody or antigen-binding portion thereof;

e) optionally repeating steps b) through d) for at least one other preferred selective mutagenesis position, contact or hypermutation position;

f) combining, in the parent antibody, or antigen-binding portion thereof, individual mutations shown to have improved activity, to form combination antibodies, or antigen-binding portions thereof; and g) evaluating the activity of the combination antibodies, or antigen-binding portions thereof, relative to the parent antibody or antigen-binding portion thereof; until an antibody, or antigen-binding portion thereof, with an improved activity, relative to the parent antibody, or antigen-binding portion thereof, is obtained.

Preferred contact positions are selected from the group consisting of H30, H31, H31B, H32, H33, H35, H50, H52, H52A, H53, H54, H56, H58, H95, H96, H97, H98, H101, L30, L31, L32, L34, L50, L52, L53, L55, L91, L92, L93, L94 and L96. Preferred hypermutation positions are selected from the group consisting of H30, H31, H31B, H32, H52, H56, H58, L30, L31, L32, L53 and L93. More preferred selective mutagenesis positions are selected from the group consisting of H30, H31, H31B, H32, H33, H52, H56, H58, L30, L31, L32, L50, L91, L92, L93 and L94. Particularly preferred contact positions are selected from the group consisting of L50 and L94.

With available methods it is not possible or it is extremely laborious to derive an antibody with increased binding affinity and neutralization potency while retaining other properties or characteristics of the antibodies as discussed above. The method of this invention, however, can readily identify such antibodies. The antibodies subjected to the method of this invention can come from any source.

Therefore, in another embodiment, the invention provides a method for improving the activity of an antibody, or antigen-binding portion thereof, comprising:

a) providing a recombinant parent antibody or antigen-binding portion thereof;

b) selecting a preferred selective mutagenesis position, contact or hypermutation position within a complementarity determining region (CDR) for mutation, thereby identifying a selected preferred selective mutagenesis position, contact or hypermutation position;

c) individually mutating said selected preferred selective mutagenesis position, contact or hypermutation position to at least two other amino acid residues to thereby create a panel of mutated antibodies, or antigen-binding portions thereof and expressing said panel in an appropriate expression system;

d) evaluating the activity of the panel of mutated antibodies, or antigen-binding portions thereof, relative to the parent antibody or antigen-binding portion thereof, thereby identifying an activity enhancing amino acid residue;

e) evaluating the panel of mutated antibodies, or antigen-binding portions thereof, relative to the parent antibody or antigen-binding portion thereof for at least one other property or characteristics, wherein the property or characteristic is one that needs to be retained in the antibody;

until an antibody, or antigen-binding portion thereof, with an improved activity and at least one retained property or characteristic, relative to the parent antibody, or antigen-binding portion thereof, is obtained.

In a preferred embodiment, the contact positions are selected from the group consisting of H30, H31, H31B, H32, H33, H35, H50, H52, H52A, H53, H54, H56, H58, H95, H96, H97, H98, H101, L30, L31, L32, L34, L50, L52, L53, L55, L91, L92, L93, L94 and L96 and the other characteristic is selected from 1) preservation of non-crossreactivity with other proteins or human tissues, 2) preservation of epitope recognition, i.e. recognizing p40 epitope preferably in the context of the p70 p40/p35 heterodimer preventing binding interference from free, soluble p40 and/or 3) to produce an antibody with a close to germline immunoglobulin sequence.

In another preferred embodiment, the hypermutation positions are selected from the group consisting of H30, H31, H31B, H32, H52, H56, H58, L30, L31, L32, L53 and L93 and the other characteristic is selected from 1) preservation of non-crossreactivity with other proteins or human tissues, 2) preservation of epitope recognition, i.e. recognizing p40 epitope preferably in the context of the p70 p40/p35 heterodimer preventing binding interference from free, soluble p40 and/or 3) to produce an antibody with a close to germline immunoglobulin sequence.

In a more preferred embodiment the residues for selective mutagenesis are selected from the preferred selective mutagenesis positions from the group consisting of H30, H31, H31B, H32, H33, H52, H56, H58, L30, L31, L32, L50, L91, L92, L93, L94 and the other characteristic is selected from 1) preservation of non-crossreactivity with other proteins or human tissues, 2) preservation of epitope recognition, i.e. recognizing p40 epitope preferably in the context of the p70 p40/p35 heterodimer preventing binding interference from free, soluble p40 and/or 3) to produce an antibody with a close to germline immunoglobulin sequence.

In a more preferred embodiment, the contact positions are selected from the group consisting of L50 and L94 and the other characteristic is selected from 1) preservation of non-crossreactivity with other proteins or human tissues, 2) preservation of epitope recognition, i.e. recognizing p40 epitope preferably in the context of the p70 p40/p35 heterodimer preventing binding interference from free, soluble p40 and/or 3) to produce an antibody with a close to germline immunoglobulin sequence.

If therefore, the affinity of an antibody for a specific antigen should be improved, but where the phage display (or related system including ribosome display) method is no longer applicable, and other desirable properties or characteristics should be retained, the method of the invention can be used. Accordingly, in another embodiment, the invention provides a method for improving the activity of an antibody, or antigen-binding portion thereof, comprising:

a) providing a recombinant parent antibody or antigen-binding portion thereof; that was obtained by selection in a phage-display system but whose activity cannot be further improved by mutagenesis in said phage-display system;

b) selecting a preferred selective mutagenesis position, contact or hypermutation position within a complementarity determining region (CDR) for mutation, thereby identifying a selected preferred selective mutagenesis position, contact or hypermutation position;

c) individually mutating said selected preferred selective mutagenesis position, contact or hypermutation position to at least two other amino acid residues to thereby create a panel of mutated antibodies, or antigen-binding portions thereof, and expressing said panel in a non-phage display system;

d) evaluating the activity of the panel of mutated antibodies, or antigen-binding portions thereof, relative to the parent antibody or antigen-binding portion thereof thereby identifying an activity enhancing amino acid residue;

e) evaluating the panel of mutated antibodies, or antigen-binding portions thereof, relative to the parent antibody or antigen-binding portion thereof for at least one other property or characteristic, wherein the property or characteristic is one that needs to be retained, until an antibody, or antigen-binding portion thereof, with an improved activity and at least one retained property or characteristic, relative to the parent antibody, or antigen-binding portion thereof, is obtained.

f) optionally, repeating steps a) through e) for at least one other preferred selective mutagenesis position, contact or hypermutation position;

g) combining, in the parent antibody, or antigen-binding portion thereof, at least two individual activity enhancing amino acid residues shown to have improved activity and at least one retained property or characteristic, to form combination antibodies, or antigen-binding portions thereof; and h) evaluating the activity of the combination antibodies, or antigen-binding portions thereof, relative to the parent antibody or antigen-binding portion thereof; until an antibody, or antigen-binding portion thereof, with an improved activity and at least one retained other property or characteristic, relative to the parent antibody, or antigen-binding portion thereof, is obtained.

In a preferred embodiment, the contact positions are selected from the group consisting of H30, H31, H31B, H32, H33, H35, H50, H52, H52A, H53, H54, H56, H58, H95, H96, H97, H98, H101, L30, L31, L32, L34, L50, L52, L53, L55, L91, L92, L93, L94 and L96 and the other characteristic is selected from 1) preservation of non-crossreactivity with other proteins or human tissues, 2) preservation of epitope recognition, i.e. recognizing p40 epitope preferably in the context of the p70 p40/p35 heterodimer preventing binding interference from free, soluble p40 and/or 3) to produce an antibody with a close to germline immunoglobulin sequence.

In another preferred embodiment, the hypermutation positions are selected from the group consisting of H30, H31, H31B, H32, H52, H56, H58, L30, L31, L32, L53 and L93 and the other characteristic is selected from 1) preservation of non-crossreactivity with other proteins or human tissues, 2) preservation of epitope recognition, i.e. recognizing p40 epitope preferably in the context of the p70 p40/p35 heterodimer preventing binding interference from free, soluble p40 and/or 3) to produce an antibody with a close to germline immunoglobulin sequence.

In a more preferred embodiment the residues for selective mutagenesis are selected from the preferred selective mutagenesis positions from the group consisting of H30, H31, H31B, H32, H33, H52, H56, H58, L30, L31, L32, L50, L91, L92, L93, L94 and the other characteristic is selected from 1) preservation of non-crossreactivity with other proteins or human tissues, 2) preservation of epitope recognition, i.e. recognizing p40 epitope preferably in the context of the p70 p40/p35 heterodimer preventing binding interference from free, soluble p40 and/or 3) to produce an antibody with a close to germline immunoglobulin sequence.

In a more preferred embodiment, the contact positions are selected from the group consisting of L50 and L94 and the other characteristic is selected from 1) preservation of non-crossreactivity with other proteins or human tissues, 2) preservation of epitope recognition, i.e. recognizing p40 epitope preferably in the context of the p70 p40/p35 heterodimer preventing binding interference from free, soluble p40 and/or 3) to produce an antibody with a close to germline immunoglobulin sequence.

In another embodiment, the invention provides a method for improving the activity of an antibody, or antigen-binding portion thereof, comprising:

a) providing a recombinant parent antibody or antigen-binding portion thereof; that was obtained by selection in a phage-display system but whose activity cannot be further improved by mutagenesis in said phage-display system;
b) selecting a preferred selective mutagenesis position, contact or hypermutation position within a complementarity determining region (CDR) for mutation, thereby identifying a selected contact or hypermutation position;
c) individually mutating said selected preferred selective mutagenesis position, contact or hypermutation position to at least two other amino acid residues to thereby create a panel of mutated antibodies, or antigen-binding portions thereof, and expressing said panel in a non-phage display system;
d) evaluating the activity of the panel of mutated antibodies, or antigen-binding portions thereof, relative to the parent antibody or antigen-binding portion thereof thereby identifying an activity enhancing amino acid residue;
e) evaluating the panel of mutated antibodies, or antigen-binding portions thereof, relative to the parent antibody or antigen-binding portion thereof for at least one other property or characteristic, wherein the property or characteristic is one that needs to be retained, until an antibody, or antigen-binding portion thereof, with an improved activity and at least one retained property or characteristic, relative to the parent antibody, or antigen-binding portion thereof, is obtained.

In a preferred embodiment, the contact positions are selected from the group consisting of H30, H31, H31B, H32, H33, H35, H50, H52, H52A, H53, H54, H56, H58, H95, H96, H97, H98, H101, L30, L31, L32, L34, L50, L52, L53, L55, L91, L92, L93, L94 and L96 and the other characteristic is selected from 1) preservation of non-crossreactivity with other proteins or human tissues, 2) preservation of epitope recognition, i.e. recognizing p40 epitope preferably in the context of the p70 p40/p35 heterodimer preventing binding interference from free, soluble p40 and/or 3) to produce an antibody with a close to germline immunoglobulin sequence.

In another preferred embodiment, the hypermutation positions are selected from the group consisting of H30, H31, H31B, H32, H52, H56, H58, L30, L31, L32, L53 and L93 and the other characteristic is selected from 1) preservation of non-crossreactivity with other proteins or human tissues, 2) preservation of epitope recognition, i.e. recognizing p40 epitope preferably in the context of the p70 p40/p35 heterodimer preventing binding interference from free, soluble p40 and/or 3) to produce an antibody with a close to germline immunoglobulin sequence.

In a more preferred embodiment the residues for selective mutagenesis are selected from the preferred selective mutagenesis positions from the group consisting of H30, H31, H31B, H32, H33, H52, H56, H58, L30, L31, L32, L50, L91, L92, L93, L94 and the other characteristic is selected from 1) preservation of non-crossreactivity with other proteins or human tissues, 2) preservation of epitope recognition, i.e. recognizing p40 epitope preferably in the context of the p70 p40/p35 heterodimer preventing binding interference from free, soluble p40 and/or 3) to produce an antibody with a close to germline immunoglobulin sequence.

In a more preferred embodiment, the contact positions are selected from the group consisting of L50 and L94 and the other characteristic is selected from 1) preservation of non-crossreactivity with other proteins or human tissues, 2) preservation of epitope recognition, i.e. recognizing p40 epitope preferably in the context of the p70 p40/p35 heterodimer preventing binding interference from free, soluble p40 and/or 3) to produce an antibody with a close to germline immunoglobulin sequence.

In another embodiment, the invention provides a method for improving the activity of an antibody, or antigen-binding portion thereof, comprising:

a) providing a recombinant parent antibody or antigen-binding portion thereof; that was obtained by selection in a phage-display system but whose activity cannot be further improved by mutagenesis in said phage-display system;
b) selecting a preferred selective mutagenesis position, contact or hypermutation position within a complementarity determining region (CDR) for mutation, thereby identifying a selected contact or hypermutation position;
c) individually mutating said selected preferred selective mutagenesis positions, contact or hypermutation position to at least two other amino acid residues to thereby create a panel of mutated antibodies, or antigen-binding portions thereof, and expressing said panel in a non-phage display system;
d) evaluating the activity of the panel of mutated antibodies, or antigen-binding portions thereof, relative to the parent antibody or antigen-binding portion thereof thereby identifying an activity enhancing amino acid residue;
e) evaluating the panel of mutated antibodies, or antigen-binding portions thereof, relative to the parent antibody or antigen-binding portion thereof for at least one other property or characteristic, wherein the property or characteristic is one that needs to be retained, until an antibody, or antigen-binding portion thereof, with an improved activity and at least one retained characteristic, relative to the parent antibody, or antigen-binding portion thereof, is obtained.

f) optionally, repeating steps a) through e) for at least one other preferred selective mutagenesis position, contact or hypermutation position;

g) combining, in the parent antibody, or antigen-binding portion thereof, at least two individual activity enhancing amino acid residues shown to have improved activity and at least on retained other characteristic, to form combination antibodies, or antigen-binding portions thereof; and h) evaluating the activity of the combination antibodies, or antigen-binding portions thereof, relative to the parent antibody or antigen-binding portion thereof; until an antibody, or antigen-binding portion thereof, with an improved activity and at least one retained property or characteristic, relative to the parent antibody, or antigen-binding portion thereof, is obtained.

In a preferred embodiment, the contact positions are selected from the group consisting of H30, H31, H31B, H32, H33, H35, H50, H52, H52A, H53, H54, H56, H58, H95, H96, H97, H98, H101, L30, L31, L32, L34, L50, L52, L53, L55, L91, L92, L93, L94 and L96 and the other characteristic is selected from 1) preservation of non-crossreactivity with other proteins or human tissues, 2) preservation of epitope recognition, i.e. recognizing p40 epitope preferably in the context of the p70 p40/p35, heterodimer preventing binding interference from free, soluble p40 and/or 3) to produce an antibody with a close to germline immunoglobulin sequence.

In another preferred embodiment, the hypermutation positions are selected from the group consisting of H30, H31, H31B, H32, H52, H56, H58, L30, L31, L32, L53 and L93 and the other characteristic is selected from 1) preservation of non-crossreactivity with other proteins or human tissues, 2) preservation of epitope recognition, i.e. recognizing p40 epitope preferably in the context of the p70 p40/p35 heterodimer preventing binding interference from free, soluble p40 and/or 3) to produce an antibody with a close to germline immunoglobulin sequence.

In a more preferred embodiment the residues for selective mutagenesis are selected from the preferred selective mutagenesis positions from the group consisting of H30, H31, H31B, H32, H33, H52, H56, H58, L30, L31, L32, L50, L91, L92, L93, L94 and the other characteristic is selected from 1) preservation of non-crossreactivity with other proteins or human tissues, 2) preservation of epitope recognition, i.e. recognizing p40 epitope preferably in the context of the p70 p40/p35 heterodimer preventing binding interference from free, soluble p40 and/or 3) to produce an antibody with a close to germline immunoglobulin sequence.

In a more preferred embodiment, the contact positions are selected from the group consisting of L50 and L94 and the other characteristic is selected from 1) preservation of non-crossreactivity with other proteins or human tissues, 2) preservation of epitope recognition, i.e. recognizing p40 epitope preferably in the context of the p70 p40/p35 heterodimer preventing binding interference from free, soluble p40 and/or 3) to produce an antibody with a close to germline immunoglobulin sequence.

IV. Modifications of Other CDR Residues

Ultimately, all CDR residues in a given antibody-antigen pair identified by any means to be required as activity enhancing amino acid residues and/or required directly or indirectly for binding to the antigen and/or for retaining other desirable properties or characteristics of the antibody. Such CDR residues are referred to as "preferred selective mutagenesis positions". It should be noted that in specific circumstances that preferred selective mutagenesis residues can be identified also by other means including co-crystallization of antibody and antigen and molecular modeling.

If the preferred attempts to identify activity enhancing amino acids focussing on the preferred selective mutagenesis positions, contact or hypermutation positions described above are exhausted, or if additional improvements are required, the remaining CDR residues may be modified as described below. It should be understood that the antibody could already be modified in any one or more contact or hypermutation positions according to the embodiments discussed above but may require further improvements. Therefore, in another embodiment, the invention provides a method for improving the activity of an antibody, or antigen-binding portion thereof, comprising:

a) providing a parent antibody or antigen-binding portion thereof;

b) selecting an amino acid residue within a complementarity determining region (CDR) for mutation other than H30, H31, H318, H32, H33, H35, H50, H52, H52A, H53, H54, H56, H58, H95, H96, H97, H98, H101, L30, L31, L32, L34, L50, L52, L53, L55, L91, L92, L93, L94 and L96;

c) individually mutating said selected position e.g., to at least two other amino acid residues to thereby create a mutated antibody or a panel of mutated antibodies, or antigen-binding portions thereof;

d) evaluating the activity of the mutated antibody or the panel of mutated antibodies, or antigen-binding portions thereof, relative to the parent antibody or antigen-binding portion thereof thereby identifying an activity enhancing amino acid residue;

e) evaluating the mutated antibody or the panel of mutated antibodies, or antigen-binding portions thereof, relative to the parent antibody or antigen-binding portion thereof, for changes in at least one other property or characteristic until an antibody, or antigen-binding portion thereof, with an improved activity, relative to the parent antibody, or antigen-binding portion thereof, is obtained.

Preferably, the other characteristic or property is selected from 1) preservation of non-crossreactivity with other proteins or human tissues, 2) preservation of epitope recognition, i.e. recognizing p40 epitope preferably in the context of the p70 p40/p35 heterodimer preventing binding interference from free, soluble p40 and/or 3) to produce an antibody with a close to germline immunoglobulin sequence If mutagenesis of a single residue is not sufficient other residues can be included; therefore, in another embodiment, the invention provides a method for improving the activity of an antibody, or antigen-binding portion thereof, comprising:

a) providing a parent antibody or antigen-binding portion thereof;

b) selecting an amino acid residue within a complementarity determining region (CDR) for mutation other than H30, H31, H31B, H32, H33, H35, H50, H52, H52A, H53, H54, H56, H58, H95, H96, H97, H98, H101, L30, L31, L32, L34, L50, L52, L53, L55, L91, L92, L93, L94 and L96;

c) individually mutating said selected position to at least two other amino acid residues to thereby create a panel of mutated antibodies, or antigen-binding portions thereof;

d) evaluating the activity of the panel of mutated antibodies, or antigen-binding portions thereof, relative to the parent antibody or antigen-binding portion thereof, thereby identifying an activity enhancing amino acid residue;

e) repeating steps b) through d) for at least one other CDR position which is neither the position selected under b) nor a position at H30, H31, H31B, H32, H33, H35, H50, H52, H52A, H53, H54, H56, H58, H95, H96, H97, H98, H101, L30, L31, L32, L34, L50, L52, L53, L55, L91, L92, L93, L94 and L96;

f) combining, in the parent antibody, or antigen-binding portion thereof, at least two individual activity enhancing amino acid residues shown to have improved activity, to form combination antibodies, or antigen-binding portions thereof; and g) evaluating the activity of the combination antibodies, or antigen-binding portions thereof with two activity enhancing amino acid residues, relative to the parent antibody or antigen-binding portion thereof until an antibody, or antigen-binding portion thereof, with an improved activity, relative to the parent antibody, or antigen-binding portion thereof, is obtained.

If the preferred attempts to identify activity enhancing amino acids focussing on the contact or hypermutation positions described above are exhausted, or if additional improvements are required, and the antibody in question can not further be optimized by mutagenesis and phage display (or related ribosome display) methods the remaining CDR residues may be modified as described below. It should be understood that the antibody could already be modified in any one or more preferred selective mutagenesis position, contact or hypermutation positions according to the embodiments discussed above but may require further improvements.

Therefore, in another embodiment, the invention provides a method for improving the activity of an antibody, or antigen-binding portion thereof, comprising:
a) providing a recombinant parent antibody or antigen-binding portion thereof; that was obtained by selection in a phage-display system but whose activity cannot be further improved by mutagenesis in said phage-display system;
b) selecting a selecting an amino acid residue within a complementarity determining region (CDR) for mutation other than H30, H31, H31B, H32, H33, H35, H50, H52, H52A, H53, H54, H56, H58, H95, H96, H97, H98, H101, L30, L31, L32, L34, L50, L52, L53, L55, L91, L92, L93, L94 and;
c) individually mutating said selected contact or hypermutation position to at least two other amino acid residues to thereby create a panel of mutated antibodies, or antigen-binding portions thereof, and expressing said panel in a non-phage display system;
d) evaluating the activity of the panel of mutated antibodies, or antigen-binding portions thereof, relative to the parent antibody or antigen-binding portion thereof thereby identifying an activity enhancing amino acid residue;
e) evaluating the panel of mutated antibodies, or antigen-binding portions thereof, relative to the parent antibody or antigen-binding portion thereof, for changes in at least one other property or characteristic, until an antibody, or antigen-binding portion thereof, with an improved activity, relative to the parent antibody, or antigen-binding portion thereof, is obtained.

Preferably, the other characteristic or property is selected from 1) preservation of non-crossreactivity with other proteins or human tissues, 2) preservation of epitope recognition, i.e. recognizing p40 epitope preferably in the context of the p70 p40/p35 heterodimer preventing binding interference from free, soluble p40 and/or 3) to produce an antibody with a close to germline immunoglobulin sequence.

If a single mutagenesis is not sufficient to increase the affinity of the antibody other residues may be included in the mutagenesis. Therefore, in another embodiment, the invention provides a method for improving the activity of an antibody, or antigen-binding portion thereof, comprising:
a) providing a parent antibody or antigen-binding portion thereof that was obtained by selection in a phage-display system but whose activity cannot be further improved by mutagenesis in said phage-display system;
b) selecting an amino acid residue within a complementarity determining region (CDR) for mutation other than H30, H31, H31B, H32, H33, H35, H50, H52, H52A, H53, H54, H56, H58, H95, H96, H97, H98, H101, L30, L31, L32, L34, L50, L52, L53, L55, L91, L92, L93, L94 and L96;
c) individually mutating said selected position to at least two other amino acid residues to thereby create a panel of mutated antibodies, or antigen-binding portions thereof and expression in a non-phage display system;
d) evaluating the activity of the panel of mutated antibodies, or antigen-binding portions thereof, relative to the parent antibody or antigen-binding portion thereof thereby identifying an activity enhancing amino acid residue;
e) repeating steps b) through d) for at least one other position which is neither the position selected under b) nor a position at H30, H31, H31B, H32, H33, H35, H50, H52, H52A, H53, H54, H56, H58, H95, H96, H97, H98, H101, L30, L31, L32, L34, L50, L52, L53, L55, L91, L92, L93, L94;
g) combining, in the parent antibody, or antigen-binding portion thereof, at least two individual activity enhancing amino acid residues shown to have improved activity, to form combination antibodies, or antigen-binding portions thereof; and
h) evaluating the activity and other property or characteristic of the combination antibodies, or antigen-binding portions thereof with two activity enhancing amino acid residues, relative to the parent antibody or antigen-binding portion thereof; until an antibody, or antigen-binding portion thereof, with an improved activity, relative to the parent antibody, or antigen-binding portion thereof, is obtained.

Preferably, the other characteristic or property is selected from 1) preservation of non-crossreactivity with other proteins or human tissues, 2) preservation of epitope recognition, i.e. recognizing p40 epitope preferably in the context of the p70 p40/p35 heterodimer preventing binding interference from free, soluble p40 and/or 3) to produce an antibody with a close to germline immunoglobulin sequence The preferred attempts to identify activity enhancing amino acids focussing on the preferred selective mutagenesis positions, contact or hypermutation positions described may be exhausted, or additional improvements may be required, and it is important to retain other properties or characteristics of the antibody.

Therefore, in another embodiment, the invention provides a method for improving the activity of an antibody, or antigen-binding portion thereof, without affecting other characteristics, comprising:
a) providing a parent antibody or antigen-binding portion thereof;
b) selecting an amino acid residue within a complementarity determining region (CDR) for mutation other than H30, H31, H31B, H32, H33, H35, H50, H52, H52A, H53, H54, H56, H58, H95, H96, H97, H98, H101, L30, L31, L32, L34, L50, L52, L53, L55, L91, L92, L93, L94 and L96;
c) individually mutating said selected position to at least two other amino acid residues to thereby create a panel of mutated antibodies, or antigen-binding portions thereof;
d) evaluating the activity of the panel of mutated antibodies, or antigen-binding portions thereof, relative to the parent antibody or antigen-binding portion thereof thereby identifying an activity enhancing amino acid residue;
e) evaluating the panel of mutated antibodies, or antigen-binding portions thereof, relative to the parent antibody or antigen-binding portion thereof, for changes in at least one other property or characteristic until an antibody, or antigen-binding portion thereof, with an improved activity and retained other property or characteristic, relative to the parent antibody, or antigen-binding portion thereof, is obtained.

Preferably, the other characteristic or property is selected from 1) preservation of non-crossreactivity with other proteins or human tissues, 2) preservation of epitope recognition, i.e. recognizing p40 epitope preferably in the context of the p70 p40/p35 heterodimer preventing binding interference from free, soluble p40 and/or 3) to produce an antibody with a close to germline immunoglobulin sequence If mutagenesis of a single residue is not sufficient other residues can be included; therefore, in another embodiment, the invention provides a method for improving the activity of an antibody, or antigen-binding portion thereof, comprising:
a) providing a parent antibody or antigen-binding portion thereof;
b) selecting an amino acid residue within a complementarity determining region (CDR) for mutation other than H30, H31, H31B, H32, H33, H35, H50, H52, H52A, H53, H54, H56, H58, H95, H96, H97, H98, H101, L30, L31, L32, L34, L50, L52, L53, L55, L91, L92, L93, L94 and L96;
c) individually mutating said selected position to at least two other amino acid residues to thereby create a panel of mutated antibodies, or antigen-binding portions thereof;
d) evaluating the activity of the panel of mutated antibodies, or antigen-binding portions thereof, relative to the parent antibody or antigen-binding portion thereof, thereby identifying an activity enhancing amino acid residue;
e) evaluating the panel of mutated antibodies or antigen-binding portions thereof, relative to the parent antibody or antigen-portion thereof, for changes in at least one other characteristic or property;
e) repeating steps b) through e) for at least one other CDR position which is neither the position selected under b) nor a position at H30, H31, H31B, H32, H33, H35, H50, H52, H52A, H53, H54, H56, H58, H95, H96, H97, H98, H101, L30, L31, L32, L34, L50, L52, L53, L55, L91, L92, L93, L94 and L96;
f) combining, in the parent antibody, or antigen-binding portion thereof, at least two individual activity enhancing amino acid residues shown to have improved activity and not affecting at least one other property or characteristic, to form combination antibodies, or antigen-binding portions thereof; and
g) evaluating the activity and the retention of at least one other property or characteristic of the combination antibodies, or antigen-binding portions thereof with two activity enhancing amino acid residues, relative to the parent antibody or antigen-binding portion thereof until an antibody, or antigen-binding portion thereof, with an improved activity and at least one retained other property or characteristic, relative to the parent antibody, or antigen-binding portion thereof, is obtained.

Mutagenesis of the preferred selective mutagenesis position, contact and hypermutation residues may not have increased the affinity of the antibody sufficiently, and mutagenesis and the phage display method (or related ribosome display method) may no longer be useful and at least one other characteristic or property of the antibody should be retained.

Therefore, in another embodiment the invention provides a method to improve the affinity of an antibody or antigen-binding portion thereof, comprising:
a) providing a parent antibody or antigen-binding portion thereof that was obtained by selection in a phage-display system but whose activity cannot be further improved by mutagenesis in said phage-display system;
b) selecting an amino acid residue within a complementarity determining region (CDR) for mutation other than H30, H31, H31B, H32, H33, H35, H50, H52, H52A, H53, H54, H56, H58, H95, H96, H97, H98, H101, L30, L31, L32, L34, L50, L52, L53, L55, L91, L92, L93, L94 and L96;
c) individually mutating said selected position to at least two other amino acid residues to thereby create a panel of mutated antibodies, or antigen-binding portions thereof and expression in a non-phage display system;
d) evaluating the activity of the panel of mutated antibodies, or antigen-binding portions thereof, relative to the parent antibody or antigen-binding portion thereof thereby identifying an activity enhancing amino acid residue;
e) evaluating the panel of mutated antibodies, or antigen-binding portions thereof, relative to the parent antibody or antigen-binding portion thereof, for changes in at least one other property or characteristic until an antibody, or antigen-binding portion thereof, with an improved activity, relative to the parent antibody, or antigen-binding portion thereof, is obtained.

Preferably, the other characteristic or property is selected from 1) preservation of non-crossreactivity with other proteins or human tissues, 2) preservation of epitope recognition, i.e. recognizing p40 epitope preferably in the context of the p70 p40/p35 heterodimer preventing binding interference from free, soluble p40 and/or 3) to produce an antibody with a close to germline immunoglobulin sequence If mutagenesis of a single residue is not sufficient other residues can be included; therefore, in another embodiment, the invention provides a method for improving the activity of an antibody, or antigen-binding portion thereof, comprising:
a) providing a parent antibody or antigen-binding portion thereof that was obtained by selection in a phage-display system but whose activity cannot be further improved by mutagenesis in said phage-display system;
b) selecting an amino acid residue within a complementarity determining region (CDR) for mutation other than H30, H31, H31B, H32, H33, H35, H50, H52, H52A, H53, H54, H56, H58, H95, H96, H97, H98, H101, L30, L31, L32, L34, L50, L52, L53, L55, L91, L92, L93, L94 and L96;
c) individually mutating said selected position to at least two other amino acid residues to thereby create a panel of mutated antibodies, or antigen-binding portions thereof and expression in a non-phage display system;

d) evaluating the activity and retention of at least one other property or characteristic of the panel of mutated antibodies, or antigen-binding portions thereof, relative to the parent antibody or antigen-binding portion thereof, thereby identifying an activity enhancing amino acid residue;

e) repeating steps b) through d) for at least one other CDR position which is neither the position selected under b) nor a position at H30, H31, H31B, H32, H33, H35, H50, H52, H52A, H53, H54, H56, H58, H95, H96, H97, H98, H101, L30, L31, L32, L34, L50, L52, L53, L55, L91, L92, L93, L94 and L96;

f) combining, in the parent antibody, or antigen-binding portion thereof, at least two individual activity enhancing amino acid residues shown to have improved activity and not to affect at least one other property or characteristic, to form combination antibodies, or antigen-binding portions thereof; and g) evaluating the activity and retention of at least one property or characteristic of the combination antibodies, or antigen-binding portions thereof with two activity enhancing amino acid residues, relative to the parent antibody or antigen-binding portion thereof until an antibody, or antigen-binding portion thereof, with an improved activity and at least one other retained characteristic or property, relative to the parent antibody, or antigen-binding portion thereof, is obtained.

V. Expression of Antibodies

An antibody, or antibody portion, of the invention can be prepared by recombinant expression of immunoglobulin light and heavy chain genes in a host cell. To express an antibody recombinantly, a host cell is transfected with one or more recombinant expression vectors carrying DNA fragments encoding the immunoglobulin light and heavy chains of the antibody such that the light and heavy chains are expressed in the host cell and, preferably, secreted into the medium in which the host cells are cultured, from which medium the antibodies can be recovered. Standard recombinant DNA methodologies are used to obtain antibody heavy and light chain genes, incorporate these genes into recombinant expression vectors and introduce the vectors into host cells, such as those described in Sambrook, Fritsch and Maniatis (eds), *Molecular Cloning; A Laboratory Manual, Second Edition*, Cold Spring Harbor, N.Y., (1989), Ausubel, F. M. et al. (eds.) *Current Protocols in Molecular Biology*, Greene Publishing Associates, (1989) and in U.S. Pat. No. 4,816,397 by Boss et al.

To obtain a DNA fragment encoding the heavy chain variable region of Joe 9 wt or a Joe 9 wt-related antibody, antibodies specific for human IL-12 were screened from human libraries and mutated, as described in section II. Once DNA fragments encoding Joe 9 wt or Joe 9 wt-related VH and VL segments are obtained, mutagenesis of these sequences is carried out by standard methods, such as PCR site directed mutagenesis (PCR-mediated mutagenesis in which the mutated nucleotides are incorporated into the PCR primers such that the PCR product contains the mutations) or other site-directed mutagenesis methods. Human IL-12 antibodies that displayed a level of activity and binding specificity/affinity that was desirable, for example J695, were further manipulated by standard recombinant DNA techniques, for example to convert the variable region genes to full-length antibody chain genes, to Fab fragment genes or to a scFv gene. In these manipulations, a VL- or VH-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the VH region can be converted to a full-length heavy chain gene by operatively linking the VH-encoding DNA to another DNA molecule encoding heavy chain constant regions (CH1, CH2 and CH3). The sequences of human heavy chain constant region genes are known in the art (see e.g., Kabat, E. A., et al. (1991) *Sequences of Proteins of Immunological Interest, Fifth Edition*, U.S. Department of Health and Human Services, NIH Publication No. 91-3242) and DNA fragments encompassing these regions can be obtained by standard PCR amplification. The heavy chain constant region can be an IgG1, IgG2, IgG3, IgG4, IgA, IgE, IgM or IgD constant region and any allotypic variant therein as described in Kabat (, Kabat, E. A., et al. (1991) *Sequences of Proteins of Immunological Interest, Fifth Edition*, U.S. Department of Health and Human Services, NIH Publication No. 91-3242), but most preferably is an IgG1 or IgG4 constant region. For a Fab fragment heavy chain gene, the VH-encoding DNA can be operatively linked to another DNA molecule encoding only the heavy chain CH1 constant region.

The isolated DNA encoding the VL region can be converted to a full-length light chain gene (as well as a Fab light chain gene) by operatively linking the VL-encoding DNA to another DNA molecule encoding the light chain constant region, CL. The sequences of human light chain constant region genes are known in the art (see e.g., Kabat, E. A., et al. (1991) *Sequences of Proteins of Immunological Interest, Fifth Edition*, U.S. Department of Health and Human Services, NIH Publication No. 91-3242) and DNA fragments encompassing these regions can be obtained by standard PCR amplification. The light chain constant region can be a kappa or lambda constant region, but most preferably is a lambda constant region.

To create a scFv gene, the VH- and VL-encoding DNA fragments are operatively linked to another fragment encoding a flexible linker, e.g., encoding the amino acid sequence $(Gly_4\text{-}Ser)_3$, such that the VH and VL sequences can be expressed as a contiguous single-chain protein, with the VL and VH regions joined by the flexible linker (see e.g., Bird et al. (1988) *Science* 242:423-426; Huston et al. (1988) *Proc. Natl. Acad. Sci. USA* 85:5879-5883; McCafferty et al., *Nature* (1990) 348:552-554).

To express the antibodies, or antibody portions of the invention, DNAs encoding partial or full-length light and heavy chains, obtained as described above, are inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector or, more typically, both genes are inserted into the same expression vector. The antibody genes are inserted into the expression vector by standard methods (e.g., ligation of complementary restriction sites on the antibody gene fragment and vector, or blunt end ligation if no restriction sites are present). Prior to insertion of the J695 or J695-related light or heavy chain sequences, the expression vector may already carry antibody constant region sequences. For example, one approach to converting the J695 or J695-related VH and VL sequences to full-length antibody genes is to insert them into expression vectors already encoding heavy chain constant and light chain constant regions, respectively, such that the VH segment is operatively linked to the CH segment(s) within the vector and the VL segment is operatively linked to the CL segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors of the invention carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel; Gene Expression Technology: Methods in Enzymology 185, Academic Press, San Diego, Calif. (1990). It will be appreciated by those skilled in the art that the design of the expression vector, including the selection of regulatory sequences may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from cytomegalovirus (CMV) (such as the CMV promoter/enhancer), Simian Virus 40 (SV40) (such as the SV40 promoter/enhancer), adenovirus, (e.g., the adenovirus major late promoter (AdMLP)) and polyoma. For further description of viral regulatory elements, and sequences thereof, see e.g., U.S. Pat. No. 5,168,062 by Stinski, U.S. Pat. No. 4,510,245 by Bell et al. and U.S. Pat. No. 4,968,615 by Schaffner et al., U.S. Pat. No. 5,464,758 by Bujard et al. and U.S. Pat. No. 5,654,168 by Bujard et al.

In addition to the antibody chain genes and regulatory sequences, the recombinant expression vectors of the invention may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399, 216, 4,634,665 and 5,179,017, all by Axel et al.). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr⁻ host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies of the invention in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody. Preferred mammalian host cells for expressing the recombinant antibodies of the invention include Chinese Hamster Ovary (CHO cells) (including dhfr-CHO cells, described in Urlaub and Chasin, (1980) Proc. Natl. Acad. Sci. USA 77:4216-4220, used with a DHFR selectable marker, e.g., as described in R. J. Kaufman and P. A. Sharp (1982) Mol. Biol. 159:601-621), NS0 myeloma cells, COS cells and SP2 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Host cells can also be used to produce portions of intact antibodies, such as Fab fragments or scFv molecules. It will be understood that variations on the above procedure are within the scope of the present invention. For example, it may be desirable to transfect a host cell with DNA encoding either the light chain or the heavy chain (but not both) of an antibody of this invention. Recombinant DNA technology may also be used to remove some or all of the DNA encoding either or both of the light and heavy chains that is not necessary for binding to hIL-12 The molecules expressed from such truncated DNA molecules are also encompassed by the antibodies of the invention. In addition, bifunctional antibodies may be produced in which one heavy and one light chain are an antibody of the invention and the other heavy and light chain are specific for an antigen other than hIL-12 by crosslinking an antibody of the invention to a second antibody by standard chemical crosslinking methods.

In a preferred system for recombinant expression of an antibody, or antigen-binding portion thereof, of the invention, a recombinant expression vector encoding both the antibody heavy chain and the antibody light chain is introduced into dhfr-CHO cells by calcium phosphate-mediated transfection. Within the recombinant expression vector, the antibody heavy and light chain genes are each operatively linked to enhancer/promoter regulatory elements (e.g., derived from SV40, CMV, adenovirus and the like, such as a CMV enhancer/AdMLP promoter regulatory element or an SV40 enhancer/AdMLP promoter regulatory element) to drive high levels of transcription of the genes. The recombinant expression vector also carries a DHFR gene, which allows for selection of CHO cells that have been transfected with the vector using methotrexate selection/amplification. The selected transformant host cells are culture to allow for expression of the antibody heavy and light chains and intact antibody is recovered from the culture medium. Standard molecular biology techniques are used to prepare the recombinant expression vector, transfect the host cells, select for transformants, culture the host cells and recover the antibody from the culture medium. Antibodies or antigen-binding portions thereof of the invention can be expressed in an animal (e.g., a mouse) that is transgenic for human immunoglobulin genes (see e.g., Taylor, L. D. et al. (1992) Nucl. Acids Res. 20: 6287-6295). Plant cells can also be modified to create transgenic plants that express the antibody or antigen binding portion thereof, of the invention.

In view of the foregoing, another aspect of the invention pertains to nucleic acid, vector and host cell compositions that can be used for recombinant expression of the antibodies and antibody portions of the invention. Preferably, the invention features isolated nucleic acids that encode CDRs of J695, or the full heavy and/or light chain variable region of J695. Accordingly, in one embodiment, the invention features an isolated nucleic acid encoding an antibody heavy chain variable region that encodes the J695 heavy chain CDR3 comprising the amino acid sequence of SEQ ID NO: 25. Preferably, the nucleic acid encoding the antibody heavy chain variable region further encodes a J695 heavy chain CDR2 which comprises the amino acid sequence of SEQ ID NO: 27. More preferably, the nucleic acid encoding the antibody heavy chain variable region further encodes a J695 heavy chain CDR1 which comprises the amino acid sequence of SEQ ID NO: 29. Even more preferably, the isolated nucleic acid encodes an antibody heavy chain variable region comprising the amino acid sequence of SEQ ID NO: 31 (the full VH region of J695).

In other embodiments, the invention features an isolated nucleic acid encoding an antibody light chain variable region that encodes the J695 light chain CDR3 comprising the amino acid sequence of SEQ ID NO: 26. Preferably, the nucleic acid encoding the antibody light chain variable region further encodes a J695 light chain CDR2 which comprises the amino acid sequence of SEQ ID NO: 28. More preferably, the nucleic acid encoding the antibody light chain variable region further encodes a J695 light chain CDR1 which comprises the amino acid sequence of SEQ ID NO: 30. Even more preferably, the isolated nucleic acid encodes an antibody light chain variable region comprising the amino acid sequence of SEQ ID NO: 32 (the full VL region of J695).

The invention also provides recombinant expression vectors encoding both an antibody heavy chain and an antibody light chain. For example, in one embodiment, the invention provides a recombinant expression vector encoding:

a) an antibody heavy chain having a variable region comprising the amino acid sequence of SEQ ID NO: 31; and
b) an antibody light chain having a variable region comprising the amino acid sequence of SEQ ID NO: 32.

The invention also provides host cells into which one or more of the recombinant expression vectors of the invention have been introduced. Preferably, the host cell is a mammalian host cell, more preferably the host cell is a CHO cell, an NS0 cell or a COS cell. Still further the invention provides a method of synthesizing a recombinant human antibody of the invention by culturing a host cell of the invention in a suitable culture medium until a recombinant human antibody of the invention is synthesized. The method can further comprise isolating the recombinant human antibody from the culture medium.

VI. Pharmaceutical Compositions and Pharmaceutical Administration

The antibodies and antibody-portions of the invention can be incorporated into pharmaceutical compositions suitable for administration to a subject. Typically, the pharmaceutical composition comprises an antibody or antibody portion of the invention and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the antibody or antibody portion.

The antibodies and antibody-portions of the invention can be incorporated into a pharmaceutical composition suitable for parenteral administration. Preferably, the antibody or antibody-portions will be prepared as an injectable solution containing 0.1-250 mg/ml antibody. The injectable solution can be composed of either a liquid or lyophilized dosage form in a flint or amber vial, ampule or pre-filled syringe. The buffer can be L-histidine (1-50 mM), optimally 5-10 mM, at pH 5.0 to 7.0 (optimally pH 6.0). Other suitable buffers include but are not limited to, sodium succinate, sodium citrate, sodium phosphate or potassium phosphate. Sodium chloride can be used to modify the toxicity of the solution at a concentration of 0-300 mM (optimally 150 mM for a liquid dosage form). Cryoprotectants can be included for a lyophilized dosage form, principally 0-10% sucrose (optimally 0.5-1.0%). Other suitable cryoprotectants include trehalose and lactose. Bulking agents can be included for a lyophilized dosage form, principally 1-10% mannitol (optimally 2-4%). Stabilizers can be used in both liquid and lyophilized dosage forms, principally 1-50 mM L-Methionine (optimally 5-10 mM). Other suitable bulking agents include glycine, arginine, can be included as 0-0.05% polysorbate-80 (optimally 0.005-0.01%). Additional surfactants include but are not limited to polysorbate 20 and BRIJ surfactants.

In a preferred embodiment, the pharmaceutical composition includes the antibody at a dosage of about 0.01 mg/kg-10 mg/kg. More preferred dosages of the antibody include 1 mg/kg administered every other week, or 0.3 mg/kg administered weekly.

The compositions of this invention may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application. Typical preferred compositions are in the form of injectable or infusible solutions, such as compositions similar to those used for passive immunization of humans with other antibodies. The preferred mode of administration is parenteral (e.g., intravenous, subcutaneous, intraperitoneal, intramuscular). In a preferred embodiment, the antibody is administered by intravenous infusion or injection. In another preferred embodiment, the antibody is administered by intramuscular or subcutaneous injection.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound (i.e., antibody or antibody portion) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile, lyophilized powders for the preparation of sterile injectable solutions, the preferred methods of preparation are vacuum drying and spray-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

The antibodies and antibody-portions of the present invention can be administered by a variety of methods known in the art, although for many therapeutic applications, the preferred route/mode of administration is subcutaneous injection, intravenous injection or infusion. As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

In certain embodiments, an antibody or antibody portion of the invention may be orally administered, for example, with an inert diluent or an assimilable edible carrier. The compound (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation.

Supplementary active compounds can also be incorporated into the compositions. In certain embodiments, an antibody or antibody portion of the invention is coformulated with and/or coadministered with one or more additional therapeutic agents that are useful for treating disorders in which IL-12 activity is detrimental. For example, an anti-hIL-12 antibody or antibody portion of the invention may be coformulated and/or coadministered with one or more additional antibodies that bind other targets (e.g., antibodies that bind other cytokines or that bind cell surface molecules). Furthermore, one or more antibodies of the invention may be used in combination with two or more of the foregoing therapeutic agents. Such combination therapies may advantageously utilize lower dosages of the administered therapeutic agents, thus avoiding possible toxicities or complications associated with the various monotherapies. It will be appreciated by the skilled practitioner that when the antibodies of the invention are used as part of a combination therapy, a lower dosage of antibody may be desirable than when the antibody alone is administered to a subject (e.g., a synergistic therapeutic effect may be achieved through the use of combination therapy which, in turn, permits use of a lower dose of the antibody to achieve the desired therapeutic effect).

Interleukin 12 plays a critical role in the pathology associated with a variety of diseases involving immune and inflammatory elements. These diseases include, but are not limited to, rheumatoid arthritis, osteoarthritis, juvenile chronic arthritis, Lyme arthritis, psoriatic arthritis, reactive arthritis, spondyloarthropathy, systemic lupus erythematosus, Crohn's disease, ulcerative colitis, inflammatory bowel disease, insulin dependent diabetes mellitus, thyroiditis, asthma, allergic diseases, psoriasis, dermatitis scleroderma, atopic dermatitis, graft versus host disease, organ transplant rejection, acute or chronic immune disease associated with organ transplantation, sarcoidosis, atherosclerosis, disseminated intravascular coagulation, Kawasaki's disease, Grave's disease, nephrotic syndrome, chronic fatigue syndrome, Wegener's granulomatosis, Henoch-Schoenlein purpurea, microscopic vasculitis of the kidneys, chronic active hepatitis, uveitis, septic shock, toxic shock syndrome, sepsis syndrome, cachexia, infectious diseases, parasitic diseases, acquired immunodeficiency syndrome, acute transverse myelitis, Huntington's chorea, Parkinson's disease, Alzheimer's disease, stroke, primary biliary cirrhosis, hemolytic anemia, malignancies, heart failure, myocardial infarction, Addison's disease, sporadic, polyglandular deficiency type I and polyglandular deficiency type II, Schmidt's syndrome, adult (acute) respiratory distress syndrome, alopecia, alopecia greata, seronegative arthopathy, arthropathy, Reiter's disease, psoriatic arthropathy, ulcerative colitic arthropathy, enteropathic synovitis, chlamydia, yersinia and salmonella associated arthropathy, spondyloarthopathy, atheromatous disease/arteriosclerosis, atopic allergy, autoimmune bullous disease, pemphigus vulgaris, pemphigus foliaceus, pemphigoid, linear IgA disease, autoimmune haemolytic anaemia, Coombs positive haemolytic anaemia, acquired pernicious anaemia, juvenile pernicious anaemia, myalgic encephalitis/Royal Free Disease, chronic mucocutaneous candidiasis, giant cell arteritis, primary sclerosing hepatitis, cryptogenic autoimmune hepatitis, Acquired Immunodeficiency Disease Syndrome, Acquired Immunodeficiency Related Diseases, Hepatitis C, common varied immunodeficiency (common variable hypogammaglobulinaemia), dilated cardiomyopathy, female infertility, ovarian failure, premature ovarian failure, fibrotic lung disease, cryptogenic fibrosing alveolitis, post-inflammatory interstitial lung disease, interstitial pneumonitis, connective tissue disease associated interstitial lung disease, mixed connective tissue disease associated lung disease, systemic sclerosis associated interstitial lung disease, rheumatoid arthritis associated interstitial lung disease, systemic lupus erythematosus associated lung disease, dermatomyositis/polymyositis associated lung disease, Sjögren's disease associated lung disease, ankylosing spondylitis associated lung disease, vasculitic diffuse lung disease, haemosiderosis associated lung disease, drug-induced interstitial lung disease, radiation fibrosis, bronchiolitis obliterans, chronic eosinophilic pneumonia, lymphocytic infiltrative lung disease, postinfectious interstitial lung disease, gouty arthritis, autoimmune hepatitis, type-1 autoimmune hepatitis (classical autoimmune or lupoid hepatitis), type-2 autoimmune hepatitis (anti-LKM antibody hepatitis), autoimmune mediated hypoglycemia, type B insulin resistance with acanthosis nigricans, hypoparathyroidism, acute immune disease associated with organ transplantation, chronic immune disease associated with organ transplantation, osteoarthrosis, primary sclerosing cholangitis, idiopathic leucopenia, autoimmune neutropenia, renal disease NOS, glomerulonephritides, microscopic vasculitis of the kidneys, lyme disease, discoid lupus erythematosus, male infertility idiopathic or NOS, sperm autoimmunity, multiple sclerosis (all subtypes), insulin-dependent diabetes mellitus, sympathetic ophthalmia, pulmonary hypertension secondary to connective tissue disease, Goodpasture's syndrome, pulmonary manifestation of polyarteritis nodosa, acute rheumatic fever, rheumatoid spondylitis, Still's disease, systemic sclerosis, Takayasu's disease/arteritis, autoimmune thrombocytopenia, idiopathic thrombocytopenia, autoimmune thyroid disease, hyperthyroidism, goitrous autoimmune hypothyroidism (Hashimoto's disease), atrophic autoimmune hypothyroidism, primary myxoedema, phacogenic uveitis, primary vasculitis and vitiligo. The human antibodies, and antibody portions of the invention can be used to treat autoimmune diseases, in particular those associated with inflammation, including, rheumatoid spondylitis, allergy, autoimmune diabetes; autoimmune uveitis.

Preferably, the antibodies of the invention or antigen-binding portions thereof, are used to treat rheumatoid arthritis, Crohn's disease, multiple sclerosis, insulin dependent diabetes mellitus and psoriasis, as described in more detail in section VII.

A human antibody, or antibody portion, of the invention also can be administered with one or more additional therapeutic agents useful in the treatment of autoimmune and inflammatory diseases.

Antibodies of the invention, or antigen binding portions thereof can be used alone or in combination to treat such diseases. It should be understood that the antibodies of the invention or antigen binding portion thereof can be used alone or in combination with an additional agent, e.g., a therapeutic agent, said additional agent being selected by the skilled artisan for its intended purpose. For example, the additional agent can be a therapeutic agent art-recognized as being useful to treat the disease or condition being treated by the antibody of the present invention. The additional agent also can be an agent which imparts a beneficial attribute to the therapeutic composition e.g., an agent which effects the viscosity of the composition.

It should further be understood that the combinations which are to be included within this invention are those combinations useful for their intended purpose. The agents set forth below are illustrative for purposes and not intended to be limited. The combinations which are part of this invention can be the antibodies of the present invention and at least one additional agent selected from the lists below. The combination can also include more than one additional agent, e.g., two or three additional agents if the combination is such that the formed composition can perform its intended function.

Preferred combinations are non-steroidal anti-inflammatory drug(s) also referred to as NSAIDS which include drugs like ibuprofen. Other preferred combinations are corticosteroids including prednisolone; the well known side-effects of steroid use can be reduced or even eliminated by tapering the steroid dose required when treating patients in combination with the anti-IL-12 antibodies of this invention. Non-limiting examples of therapeutic agents for rheumatoid arthritis with which an antibody, or antibody portion, of the invention can be combined include the following: cytokine suppressive anti-inflammatory drug(s) (CSAIDs); antibodies to or antagonists of other human cytokines or growth factors, for example, TNF, LT, IL-1, IL-2, IL-6, IL-7, IL-8, IL-15, IL-16, IL-18, EMAP-II, GM-CSF, FGF, and PDGF. Antibodies of the invention, or antigen binding portions thereof, can be combined with antibodies to cell surface molecules such as CD2, CD3, CD4, CD8, CD25, CD28, CD30, CD40, CD45, CD69, CD80 (B7.1), CD86 (B7.2), CD90, or their ligands including CD154 (gp39 or CD40L).

Preferred combinations of therapeutic agents may interfere at different points in the autoimmune and subsequent inflammatory cascade; preferred examples include TNF antagonists like chimeric, humanized or human TNF antibodies, D2E7, (U.S. application Ser. No. 08/599,226 filed Feb. 9, 1996), cA2 (Remicade™), CDP 571, anti-TNF antibody fragments (e.g., CDP870), and soluble p55 or p75 TNF receptors, derivatives thereof, (p75TNFR1gG (Enbrel™) or p55TNFR1gG (Lenercept), soluble IL-13 receptor (sIL-13), and also TNFα converting enzyme (TACE) inhibitors; similarly IL-1 inhibitors (e.g., Interleukin-1-converting enzyme inhibitors, such as Vx740, or IL-IRA etc.) may be effective for the same reason. Other preferred combinations include Interleukin 11, anti-P7s and p-selectin glycoprotein ligand (PSGL). Yet another preferred combination are other key players of the autoimmune response which may act parallel to, dependent on or in concert with IL-12 function; especially preferred are IL-18 antagonists including IL-18 antibodies or soluble IL-18 receptors, or IL-18 binding proteins. It has been shown that IL-12 and IL-18 have overlapping but distinct functions and a combination of antagonists to both may be most effective. Yet another preferred combination are non-depleting anti-CD4 inhibitors. Yet other preferred combinations include antagonists of the co-stimulatory pathway CD80 (B7.1) or CD86 (B7.2) including antibodies, soluble receptors or antagonistic ligands.

The antibodies of the invention, or antigen binding portions thereof, may also be combined with agents, such as methotrexate, 6-MP, azathioprine sulphasalazine, mesalazine, olsalazine chloroquinine/hydroxychloroquine, pencillamine, aurothiomalate (intramuscular and oral), azathioprine, cochicine, corticosteroids (oral, inhaled and local injection), beta-2 adrenoreceptor agonists (salbutamol, terbutaline, salmeteral), xanthines (theophylline, aminophylline), cromoglycate, nedocromil, ketotifen, ipratropium and oxitropium, cyclosporin, FK506, rapamycin, mycophenolate mofetil, leflunomide, NSAIDs, for example, ibuprofen, corticosteroids such as prednisolone, phosphodiesterase inhibitors, adensosine agonists, antithrombotic agents, complement inhibitors, adrenergic agents, agents which interfere with signalling by proinflammatory cytokines such as TNFα or IL-1 (e.g. IRAK, NIK, IKK, p38 or MAP kinase inhibitors), IL-1β converting enzyme inhibitors (e.g., Vx740), anti-P7s, p-selectin glycoprotein ligand (PSGL), TNFα converting enzyme (TACE) inhibitors, T-cell signalling inhibitors such as kinase inhibitors, metalloproteinase inhibitors, sulfasalazine, azathioprine, 6-mercaptopurines, angiotensin converting enzyme inhibitors, soluble cytokine receptors and derivatives thereof (e.g. soluble p55 or p75 TNF receptors and the derivatives p75TNFRIgG (Enbrel™) and p55TNFRIgG (Lenercept), sIL-1R1, sIL-1R11, sIL-6R, soluble IL-13 receptor (sIL-13)) and antiinflammatory cytokines (e.g. IL-4, IL-10, IL-11, IL-13 and TGFβ). Preferred combinations include methotrexate or leflunomide and in moderate or severe rheumatoid arthritis cases, cyclosporine.

Non-limiting examples of therapeutic agents for inflammatory bowel disease with which an antibody, or antibody portion, of the invention can be combined include the following: budenoside; epidermal growth factor; corticosteroids; cyclosporin, sulfasalazine; aminosalicylates; 6-mercaptopurine; azathioprine; metronidazole; lipoxygenase inhibitors; mesalamine; olsalazine; balsalazide; antioxidants; thromboxane inhibitors; IL-1 receptor antagonists; anti-IL-1β monoclonal antibodies; anti-IL-6 monoclonal antibodies; growth factors; elastase inhibitors; pyridinyl-imidazole compounds; antibodies to or antagonists of other human cytokines or growth factors, for example, TNF, LT, IL-1, IL-2, IL-6, IL-7, IL-8, IL-15, IL-16, IL-18, EMAP-II, GM-CSF, FGF, and PDGF. Antibodies of the invention, or antigen binding portions thereof, can be combined with antibodies to cell surface molecules such as CD2, CD3, CD4, CD8, CD25, CD28, CD30, CD40, CD45, CD69, CD90 or their ligands. The antibodies of the invention, or antigen binding portions thereof, may also be combined with agents, such as methotrexate, cyclosporin, FK506, rapamycin, mycophenolate mofetil, leflunomide, NSAIDs, for example, ibuprofen, corticosteroids such as prednisolone, phosphodiesterase inhibitors, adenosine agonists, antithrombotic agents, complement inhibitors, adrenergic agents, agents which interfere with signalling by proinflammatory cytokines such as TNFα or IL-1 (e.g. IRAK, NIK, IKK, p38 or MAP kinase inhibitors), IL-1β converting enzyme inhibitors (e.g., Vx740), anti-P7s, p-selectin glycoprotein ligand (PSGL), TNFα converting enzyme inhibitors, T-cell signalling inhibitors such as kinase inhibitors, metalloproteinase inhibitors, sulfasalazine, azathioprine, 6-mercaptopurines, angiotensin converting enzyme inhibitors, soluble cytokine receptors and derivatives thereof (e.g. soluble p55 or p75 TNF receptors, sIL-1R1, sIL-1R11, sIL-6R, soluble IL-13 receptor (sIL-13)) and antiinflammatory cytokines (e.g. IL-4, IL-10, IL-11, IL-13 and TGFβ).

Preferred examples of therapeutic agents for Crohn's disease in which an antibody or an antigen binding portion can be combined include the following: TNF antagonists, for example, anti-TNF antibodies, D2E7 (U.S. application Ser. No. 08/599,226, filed Feb. 9, 1996), cA2 (Remicade™), CDP 571, anti-TNF antibody fragments (e.g., CDP870), TNFR-Ig constructs (p75TNFRIgG (Enbrel™) and p55TNFRIgG (Lenercept)), anti-P7s, p-selectin glycoprotein ligand (PSGL), soluble IL-13 receptor (sIL-13), and PDE4 inhibitors. Antibodies of the invention or antigen binding portions thereof, can be combined with corticosteroids, for example, budenoside and dexamethasone. Antibodies of the invention or antigen binding portions thereof, may also be combined with agents such as sulfasalazine, 5-aminosalicylic acid and olsalazine, and agents which interfere with synthesis or action of proinflammatory cytokines such as IL-1, for example, IL-1β converting enzyme inhibitors (e.g., Vx740) and IL-1ra. Antibodies of the invention or antigen binding portion thereof may also be used with T cell signaling inhibitors, for example, tyrosine kinase inhibitors 6-mercaptopurines. Antibodies of the invention or antigen binding portions thereof, can be combined with IL-11.

Non-limiting examples of therapeutic agents for multiple sclerosis with which an antibody, or antibody portion, of the invention can be combined include the following: corticosteroids; prednisolone; methylprednisolone; azathioprine; cyclophosphamide; cyclosporine; methotrexate; 4-aminopyridine; tizanidine; interferon-β1a (Avonex; Biogen); interferon-β1b (Betaseron; Chiron/Berlex); Copolymer 1 (Cop-1; Copaxone; Teva Pharmaceutical Industries, Inc.); hyperbaric oxygen; intravenous immunoglobulin; clabribine; antibodies to or antagonists of other human cytokines or growth factors, for example, TNF, LT, IL-1, IL-2, IL-6, IL-7, IL-8, IL-15, IL-16, IL-18, EMAP-II, GM-CSF, FGF, and PDGF. Antibodies of the invention, or antigen binding portions thereof, can be combined with antibodies to cell surface molecules such as CD2, CD3, CD4, CD8, CD25, CD28, CD30, CD40, CD45, CD69, CD80, CD86, CD90 or their ligands. The antibodies of the invention, or antigen binding portions thereof, may also be combined with agents, such as methotrexate, cyclosporine, FK506, rapamycin, mycophenolate mofetil, leflunomide, NSAIDs, for example, ibuprofen, corticosteroids such as prednisolone, phosphodiesterase inhibitors, adensosine agonists, antithrombotic agents, complement inhibitors, adrenergic agents, agents which interfere with signalling by proinflammatory cytokines such as TNFα or IL-1 (e.g. IRAK, NIK, IKK, p38 or MAP kinase inhibitors), IL-1β converting enzyme inhibitors (e.g., Vx740), anti-P7s, p-selectin glycoprotein ligand (PSGL), TACE inhibitors, T-cell signalling inhibitors such as kinase inhibitors, metalloproteinase inhibitors, sulfasalazine, azathioprine, 6-mercaptopurines, angiotensin converting enzyme inhibitors, soluble cytokine receptors and derivatives thereof (e.g. soluble p55 or p75 TNF receptors, sIL-1R1, sIL-1R11, sIL-6R, soluble IL-13 receptor (sIL-13)) and antiinflammatory cytokines (e.g. IL-4, IL-10, IL-13 and TGFβ).

Preferred examples of therapeutic agents for multiple sclerosis in which the antibody or antigen binding portion thereof can be combined to include interferon-β, for example, IFNβ1a and IFNβ1b; copaxone, corticosteroids, IL-1 inhibitors, TNF inhibitors, and antibodies to CD40 ligand and CD80.

The pharmaceutical compositions of the invention may include a "therapeutically effective amount" or a "prophylactically effective amount" of an antibody or antibody portion of the invention. A "therapeutically effective amount" refers to an amount effective, at dosages and for periods of time necessary, to achieve the desired therapeutic result. A therapeutically effective amount of the antibody or antibody portion may vary according to factors such as the disease state, age, sex, and weight of the individual, and the ability of the antibody or antibody portion to elicit a desired response in the individual. A therapeutically effective amount is also one in which any toxic or detrimental effects of the antibody or antibody portion are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

An exemplary, non-limiting range for a therapeutically or prophylactically effective amount of an antibody or antibody portion of the invention is 0.01-20 mg/kg, more preferably 1-10 mg/kg, even more preferably 0.3-1 mg/kg. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

VII. Uses of the Antibodies of the Invention

Given their ability to bind to hIL-12, the anti-hIL-12 antibodies, or portions thereof, of the invention can be used to detect hIL-12 (e.g., in a biological sample, such as serum or plasma), using a conventional immunoassay, such as an enzyme linked immunosorbent assays (ELISA), an radioimmunoassay (RIA) or tissue immunohistochemistry. The invention provides a method for detecting hIL-12 in a biological sample comprising contacting a biological sample with an antibody, or antibody portion, of the invention and detecting either the antibody (or antibody portion) bound to hIL-12 or unbound antibody (or antibody portion), to thereby detect hIL-12 in the biological sample. The antibody is directly or indirectly labeled with a detectable substance to facilitate detection of the bound or unbound antibody. Suitable detectable substances include various enzymes, prosthetic groups, fluorescent materials, luminescent materials and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include $^{125}$I, $^{131}$I, $^{35}$S or $^{3}$H.

Alternative to labeling the antibody, hIL-12 can be assayed in biological fluids by a competition immunoassay utilizing rhIL-12 standards labeled with a detectable substance and an unlabeled anti-hIL-12 antibody. In this assay, the biological sample, the labeled rhIL-12 standards and the anti-hIL-12 antibody are combined and the amount of labeled rhIL-12 standard bound to the unlabeled antibody is determined. The amount of hIL-12 in the biological sample is inversely proportional to the amount of labeled rhIL-12 standard bound to the anti-hIL-12 antibody.

The Y61 and J695 antibodies of the invention can also be used to detect IL-12 from species other than humans, in particular IL-12 from primates. For example, Y61 can be used to detect IL-12 in the cynomolgus monkey and the rhesus monkey. J695 can be used to detect IL-12 in the cynomolgus monkey, rhesus monkey, and baboon. However, neither antibody cross reacts with mouse or rat IL-12 (see Example 3, subsection F).

The antibodies and antibody portions of the invention are capable of neutralizing hIL-12 activity in vitro (see Example 3) and in vivo (see Example 4). Accordingly, the antibodies and antibody portions of the invention can be used to inhibit IL-12 activity, e.g., in a cell culture containing hIL-12, in human subjects or in other mammalian subjects having IL-12 with which an antibody of the invention cross-reacts (e.g. primates such as baboon, cynomolgus and rhesus). In a preferred embodiment, the invention provides an isolated human antibody, or antigen-binding portion thereof, that neutralizes the activity of human IL-12, and at least one additional primate IL-12 selected from the group consisting of baboon IL-12, marmoset IL-12, chimpanzee IL-12, cynomolgus IL-12 and rhesus IL-12, but which does not neutralize the activity of the mouse IL-12. Preferably, the IL-12 is human IL-12. For example, in a cell culture containing, or suspected of containing hIL-12, an antibody or antibody portion of the invention can be added to the culture medium to inhibit hIL-12 activity in the culture.

In another embodiment, the invention provides a method for inhibiting IL-12 activity in a subject suffering from a disorder in which IL-12 activity is detrimental. IL-12 has been implicated in the pathophysiology of a wide variety of disorders (Windhagen et al., (1995) *J. Exp. Med.* 182: 1985-1996; Morita et al. (1998) *Arthritis and Rheumatism.* 41: 306-314; Bucht et al. (1996) *Clin. Exp. Immunol.* 103: 347-367; Fais et al. (1994) *J. Interferon Res.* 14:235-238; Parronchi et al., (1997) *Am. J. Path.* 150:823-832; Monteleone et al., (1997) *Gastroenterology.* 112:1169-1178, and Berrebi et al., (1998) *Am. J. Path* 152:667-672; Parronchi et al (1997) *Am. J. Path.* 150:823-832). The invention provides methods for inhibiting IL-12 activity in a subject suffering from such a disorder, which method comprises administering to the subject an antibody or antibody portion of the invention such that IL-12 activity in the subject is inhibited. Preferably, the IL-12 is human IL-12 and the subject is a human subject. Alternatively, the subject can be a mammal expressing a IL-12 with which an antibody of the invention cross-reacts. Still further the subject can be a mammal into which has been introduced hIL-12 (e.g., by administration of hIL-12 or by expression of an hIL-12 transgene). An antibody of the invention can be administered to a human subject for therapeutic purposes (discussed further below). Moreover, an antibody of the invention can be administered to a non-human mammal expressing a IL-12 with which the antibody cross-reacts for veterinary purposes or as an animal model of human disease. Regarding the latter, such animal models may be useful for evaluating the therapeutic efficacy of antibodies of the invention (e.g., testing of dosages and time courses of administration).

As used herein, the phrase "a disorder in which IL-12 activity is detrimental" is intended to include diseases and other disorders in which the presence of IL-12 in a subject suffering from the disorder has been shown to be or is suspected of being either responsible for the pathophysiology of the disorder or a factor that contributes to a worsening of the disorder. Accordingly, a disorder in which IL-12 activity is detrimental is a disorder in which inhibition of IL-12 activity is expected to alleviate the symptoms and/or progression of the disorder. Such disorders may be evidenced, for example, by an increase in the concentration of IL-12 in a biological fluid of a subject suffering from the disorder (e.g., an increase in the concentration of IL-12 in serum, plasma, synovial fluid, etc. of the subject), which can be detected, for example, using an anti-IL-12 antibody as described above. There are numerous examples of disorders in which IL-12 activity is detrimental. In one embodiment, the antibodies or antigen binding portions thereof, can be used in therapy to treat the diseases or disorders described herein. In another embodiment, the antibodies or antigen binding portions thereof, can be used for the manufacture of a medicine for treating the diseases or disorders described herein. The use of the antibodies and antibody portions of the invention in the treatment of a few non-limiting specific disorders is discussed further below:

A. Rheumatoid Arthritis

Interleukin-12 has been implicated in playing a role in inflammatory diseases such as rheumatoid arthritis. Inducible IL-12p40 message has been detected in synovia from rheumatoid arthritis patients and IL-12 has been shown to be present in the synovial fluids from patients with rheumatoid arthritis (see e.g., Morita et al., (1998) *Arthritis and Rheumatism* 41: 306-314). IL-12 positive cells have been found to be present in the sublining layer of the rheumatoid arthritis synovium. The human antibodies, and antibody portions of the invention can be used to treat, for example, rheumatoid arthritis, juvenile rheumatoid arthritis, Lyme arthritis, rheumatoid spondylitis, osteoarthritis and gouty arthritis. Typically, the antibody, or antibody portion, is administered systemically, although for certain disorders, local administration of the antibody or antibody portion may be beneficial. An antibody, or antibody portion, of the invention also can be administered with one or more additional therapeutic agents useful in the treatment of autoimmune diseases.

In the collagen induced arthritis (CIA) murine model for rheumatoid arthritis, treatment of mice with an anti-IL-12 mAb (rat anti-mouse IL-12 monoclonal antibody, C17.15) prior to arthritis profoundly suppressed the onset, and reduced the incidence and severity of disease. Treatment with the anti-IL-12 mAb early after onset of arthritis reduced severity, but later treatment of the mice with the anti-IL-12 mAb after the onset of disease had minimal effect on disease severity.

B. Crohn's Disease

Interleukin-12 also plays a role in the inflammatory bowel disease, Crohn's disease. Increased expression of IFN-γ and IL-12 occurs in the intestinal mucosa of patients with Crohn's disease (see e.g., Fais et al., (1994) *J. Interferon Res.* 14: 235-238; Parronchi et al., (1997) *Amer. J. Pathol.* 150: 823-832; Monteleone et al., (1997) *Gastroenterology* 112: 1169-1178; Berrebi et al., (1998) *Amer. J. Pathol.* 152: 667-672). Anti-IL-12 antibodies have been shown to suppress disease in mouse models of colitis, e.g., TNBS induced colitis IL-2 knockout mice, and recently in IL-10 knock-out mice. Accordingly, the antibodies, and antibody portions, of the invention, can be used in the treatment of inflammatory bowel diseases.

C. Multiple Sclerosis

Interleukin-12 has been implicated as a key mediator of multiple sclerosis. Expression of the inducible IL-12 p40 message or IL-12 itself can be demonstrated in lesions of patients with multiple sclerosis (Windhagen et al., (1995) *J. Exp. Med.* 182: 1985-1996, Drulovic et al., (1997) *J. Neurol. Sci.* 147: 145-150). Chronic progressive patients with multiple sclerosis have elevated circulating levels of IL-12. Investigations with T-cells and antigen presenting cells (APCs) from patients with multiple sclerosis revealed a self-perpetuating series of immune interactions as the basis of progressive multiple sclerosis leading to a Th1-type immune response. Increased secretion of IFN-γ from the T cells led to increased IL-12 production by APCs, which perpetuated the cycle leading to a chronic state of a Th1-type immune activation and disease (Balashov et al., (1997) *Proc. Natl. Acad. Sci.* 94: 599-603). The role of IL-12 in multiple sclerosis has been investigated using mouse and rat experimental allergic encephalomyelitis (EAE) models of multiple sclerosis. In a relapsing-remitting EAE model of multiple sclerosis in mice, pretreatment with anti-IL-12 mAb delayed paralysis and reduced clinical scores. Treatment with anti-IL-12 mAb at the peak of paralysis or during the subsequent remission period reduced clinical scores. Accordingly, the antibodies or antigen binding portions thereof of the invention may serve to alleviate symptoms associated with multiple sclerosis in humans.

D. Insulin-Dependent Diabetes Mellitus

Interleukin-12 has been implicated as an important mediator of insulin-dependent diabetes mellitus (IDDM). IDDM was induced in NOD mice by administration of IL-12, and anti-IL-12 antibodies were protective in an adoptive transfer model of IDDM. Early onset IDDM patients often experience a so-called "honeymoon period" during which some residual islet cell function is maintained. These residual islet cells produce insulin and regulate blood glucose levels better than administered insulin. Treatment of these early onset patients with an anti-IL-12 antibody may prevent further destruction of islet cells, thereby maintaining an endogenous source of insulin.

E. Psoriasis

Interleukin-12 has been implicated as a key mediator in psoriasis. Psoriasis involves acute and chronic skin lesions that are associated with a TH1-type cytokine expression profile. (Hamid et al. (1996) J. Allergy Clin. Immunol. 1:225-231; Turka et al. (1995) Mol. Med. 1:690-699). IL-12 p35 and p40 mRNAs were detected in diseased human skin samples. Accordingly, the antibodies or antigen binding portions thereof of the invention may serve to alleviate chronic skin disorders such psoriasis.

The present invention is further illustrated by the following examples which should not be construed as limiting in any way. The contents of all cited references, including literature references, issued patents, and published patent applications, as cited throughout this application are hereby expressly incorporated by reference. It should further be understood that the contents of all the tables attached hereto (see Appendix A) are incorporated by reference.

TABLE 1

VH3 Family Germline Amino Acid Sequences Numbering according to Kabat (Joe9 VH included for comparison)

| SEQ ID NO: | germ-line VH | 1 | 2 | 3 | 4 | 5 | 6 | 7 | 8 | CDR H1 (9-35) |
|---|---|---|---|---|---|---|---|---|---|---|
| 594 | dp-29 | E | V | Q | L | V | E | S | G | G G L V Q P G G S L R L S C A A S G F T F S D H Y M D |
| 595 | DP-30 | E | V | Q | L | V | E | S | G | G G L V Q P G G S L R L S C A A S G F T F S D H Y M S |
| 596 | HC15-7 | E | V | Q | L | V | E | S | G | G G L V Q P G G S L R L S C A A S G F T F S D H Y M S |
| 597 | VHD26 | E | V | Q | L | L | E | S | G | G G L V Q P G G S L R L S C A A S G F T F S D H Y M S |
| 598 | DP-31 | E | V | Q | L | V | E | S | G | G G L V Q P G R S L R L S C A A S G F T F D D Y A M H |
| 599 | DP-32 | E | V | Q | L | V | E | S | G | G G V V R P G G S L R L S C A A S G F T F D D Y G M S |
| 600 | DP-33 | E | V | Q | L | V | E | S | G | G V V V Q P G G S L R L S C A A S G F T F D D Y T M H |
| 601 | dp-35 | Q | V | Q | L | V | E | S | G | G G L V K P G G S L R L S C A A S G F T F S D Y Y M S |
| 602 | VH3-8 | Q | V | Q | L | L | E | S | G | G G L V K P G G S L R L S C A A S G F T F S D Y Y M S |
| 603 | yac-9 | E | V | Q | L | V | E | S | G | G G L V Q P G G S L K L S C A A S G F T F S G S A M H |
| 604 | dp-38 | E | V | Q | L | V | E | S | G | G G L V K P G G S L R L S C A A S G F T F S N A W M S |
| 605 | LSG2 | E | V | Q | L | V | E | S | G | G G L V K P G G S L R L S C A A S G F T F S N A W M S |
| 606 | LSG3 | E | V | Q | L | V | E | S | G | G G L V K P G G S L R L S C A A S G F T F S N A W M S |
| 607 | LSG4 | E | V | Q | L | V | E | S | G | G G L V K P G G S L R L S C A A S G F T F S N A W M S |
| 608 | LSG6 | E | V | Q | L | V | E | S | G | G G L V K P G G S L R L S C A A S G F T F S N A W M N |
| 609 | v3-15 | E | V | Q | L | V | E | S | G | G A L V K P G G S L R L S C A A S G F T F S N A W M S |
| 610 | dp-39 | E | V | Q | L | V | E | S | G | G G L V Q P G G S L R L S C P A S G F T F S N H Y M S |
| 611 | dp-40 | E | V | Q | L | V | E | S | G | G G L V Q P G G S L R L S C A A S G F T F S N H Y T S |
| 612 | dp-59 | E | V | Q | L | V | E | S | G | G G L V Q P G G S L R L S C A A S G F T F S N S D M N |
| 613 | v3-16p | E | V | Q | L | V | E | S | G | G G L V Q P G G S L R L S C A A S G F T F S N S D M N |
| 614 | v3-19p | T | V | Q | L | V | E | S | G | G G L V E P G G S L R L S C A A S G F T F S N S D M N |
| 615 | v3-13 | E | V | H | L | V | E | S | G | G G L V Q P G G A L R L S C A A S G F T F S N Y D M H |

TABLE 1-continued

VH3 Family Germline Amino Acid Sequences Numbering according to Kabat (Joe9 VH included for comparison)

| SEQ ID NO: | germline VH | | | | | | | |
|---|---|---|---|---|---|---|---|---|
| 616 | DP-42  | E | V | Q | L V E | T | G | G G L I Q P G G S L R L S C A A S G F T V S S N Y M S |
| 617 | dp-44  | E | V | Q | L V Q | S | G | G G L V H P G G S L R L S C A G S G F T F S S Y A M H |
| 618 | DP-45  | E | V | Q | L V Q | S | G | G G L V Q P G G S L R L S C A G S G F T F S S Y A M H |
| 619 | dp-47  | E | V | Q | L L E | S | G | G G L V Q P G G S L R L S C A A S G F T F S S Y A M S |
| 620 | flm    | E | V | Q | L V E | S | G | G G L V Q P G G S L R L S C S A S G F T F S S Y A M H |
| 621 | P1     | E | V | Q | L V E | S | G | G G L V Q P G G S L R L S C A A S G F T F S S Y A M H |
| 622 | v3-64  | E | V | Q | L V E | S | G | G G L V Q P G G S L R L S C A A S G F T F S S Y A M H |
| 623 | vh26   | E | V | Q | L L E | S | G | G G L V Q P Q Q S L R L S C A A S G F T F S S Y A M S |
| 624 | B25    | Q | V | Q | L V E | S | G | G G V V Q P G R S L R L S C A A S G F T F S S Y A M H |
| 625 | b32e   | Q | V | Q | L V E | S | G | G G V V Q P G R S L R L S C A A S G F T F S S Y A M H |
| 626 | B37    | Q | V | Q | L V E | S | G | G G V V Q P G R S L R L S C A A S G F T F S S Y A M H |
| 627 | B43    | Q | V | Q | L V E | S | G | G G V V Q P G R S L R L S C A A S G F T F S S Y A M H |
| 628 | B48    | Q | V | Q | L V E | S | G | G G V V Q P F R S L R L S C A A S G F T F S S Y A M H |
| 629 | B52    | Q | V | Q | L V E | S | G | G G V V Q P G R S L R L S C A A S G F T F S S Y A M H |
| 630 | B54    | Q | V | Q | L V E | S | G | G G V V Q P G R S L R L S C A A S G F T F S S Y A M H |
| 631 | cos-8  | Q | V | Q | L V E | S | G | G G V V Q P G R S L R L S C A A S G F T F S S Y A M H |
| 632 | dp-46  | Q | V | Q | L V E | S | G | G G V V Q P G R S L R L S C A A S G F T F S S Y A M H |
| 633 | F2M    | Q | V | Q | L V E | S | G | G G L V Q P G G S L R L S C S A S G F T F S S Y A M H |
| 634 | F3     | Q | V | Q | L V E | S | G | G G V V Q P G R S L R L S C A A S G F T F S S Y A M H |
| 635 | F7     | Q | V | Q | L V E | S | G | G G V V Q P G R S L R L S C A A S G F T F S S Y A M H |
| 636 | hv3005 | Q | V | Q | L V E | S | G | G G V V Q P G R S L R L S C A A S G F T F S S Y A M H |
| 637 | P2     | Q | V | Q | L V E | S | G | G G V V Q P G R S L R L S C A A S G F T F S S Y A M H |
| 638 | dp-48  | E | V | Q | L V E | S | G | G G L V Q P G G S L R L S C A A S G F T F S S Y D M H |
| 639 | dp-58  | E | V | Q | L V E | S | G | G G L V Q P G G S L R L S C A A S G F T F S S Y E M N |
| 640 | B1     | Q | V | Q | L V E | S | G | G G V V Q P G R S L R L S C A A S G F T F S S Y G M H |
| 641 | B13    | Q | V | Q | L V E | S | G | G G V V Q P G R S L R L S C A A S G F T F S S Y G M H |
| 642 | B18    | Q | V | Q | L V E | S | G | G G V V Q P G R S L R L S C A A S G F T F S S Y G M H |
| 643 | B26    | Q | V | Q | L V E | S | G | G G V V Q P G R S L R L S C A A S G F T F S S Y G M H |
| 644 | B28E   | Q | V | Q | L V E | S | G | G G V V Q P G R S L R L S C A A S G F T F S S Y G M H |
| 645 | B29E   | Q | V | Q | L V E | S | G | G G V V Q P G R S L R L S C A A S G F T F S S Y G M H |
| 646 | B29M   | Q | V | Q | L V E | S | G | G G V V Q P G R S L R L S C A A S G F T F S S Y G M H |
| 647 | B30    | Q | V | Q | L V E | S | G | G G V V Q P G R S L R L S C A A S G F T F S S Y G M H |
| 648 | B32M   | Q | V | Q | L V E | S | G | G G V V Q P G R S L R L S C A A S G F T F S S Y G M H |
| 649 | cos-3  | Q | V | Q | L V E | S | G | G G V V Q P G G S L R L S C A A S G F T F S S Y G M H |
| 650 | dp-49  | Q | V | Q | L V E | S | G | G G V V Q P G R S L R L S C A A S G F T F S S Y G M H |
| 651 | dp-50  | Q | V | Q | L V E | S | G | G G V V Q P G R S L R L S C A A S G F T F S S Y G M H |
| 652 | P6     | Q | V | Q | L V E | S | G | G G V V Q P G R S L R L S C A A S G F T F S S Y G M H |
| 653 | P9E    | Q | V | Q | L V E | S | G | G G V V Q P G R S L R L S C A A S G F T F S S Y G M H |
| 654 | v3-30  | Q | V | Q | L V E | S | G | G G V V Q P G R S L R L S C A A S G F T F S S Y G M H |
| 655 | v3-33  | Q | V | Q | L V E | S | G | G G V V Q P G R S L R L S C A A S G F T F S S Y G M H |
| 656 | dp-31  | E | V | Q | L V E | S | G | G G L V Q P G G S L R L S C A A S G F T F S S Y S M N |
| 657 | dp-77  | E | V | Q | L V E | S | G | G G L V K P G G S L R L S C A A S G F T F S S Y S M N |
| 658 | HHG4   | E | V | Q | L V E | S | G | G G L V Q P G G S L R L S C A A S G F T F S S Y S M N |
| 659 | v3-21  | E | V | Q | L V E | S | G | G G L V K P G G S L R L S C A A S G F T F S S Y S M N |
| 660 | v3-48  | E | V | Q | L V E | S | G | G G L V Q P G G S L R L S C A A S G F T F S S Y S M N |
| 661 | DP-52  | E | D | Q | L V E | S | G | G G L V Q P G G S L R P S C A A S G F A F S S Y V L H |
| 662 | cos-6  | E | V | Q | L V E | S | G | G G L V Q P G G S L R L S C A A S G F T F S S Y W M H |
| 663 | dp-53  | E | V | Q | L V E | S | G | G G L V Q P G G S L R L S C A A S G F T F S S Y W M H |
| 664 | dp-54  | E | V | Q | L V E | S | G | G G L V Q P G G S L R L S C A A S G F T F S S Y W M S |
| 665 | dp-87  | E | V | Q | L V E | S | G | G G L V Q P G G S L R L S C A A S G F T F S S Y W M H |
| 666 | VH3-11 | E | V | Q | L V E | S | G | G G L V Q P G G S L R L S C A A S G F T F S S Y W M S |
| 667 | JOE9 VH| Q | V | Q | L V Q | S | G | G G V V Q P G R S L R L S C A A S G F T F S S Y G M H |

|  |  | | | | | CDR H2 |
|---|---|---|---|---|---|---|
| SEQ ID NO: | germline VH | 3 6 | 3 3 3 7 8 9 | 4 0 | 4 1 | 5 5 5 4 4 4 4 4 4 4 4 5 5 5 2 2 2 5 5 5 5 5 5 5 6 6 6 6 2 3 4 5 6 7 8 9 0 1 2 A B C 3 4 5 6 7 8 9 0 1 2 3 4 5 |
| 594 | dp-29  | W | V R Q | A | P | G K G L E W V G R T R N K A N S Y T T E Y A A S V K G |
| 595 | DP-30  | W | V R Q | A | Q | G K G L E L V G L I R N K A N S Y T T E Y A A S V K G |
| 596 | HC15-7 | W | V R Q | A | Q | G K G L E L V G L I R N K A N S Y T T E Y A A S V K G |
| 597 | VHD26  | W | V R Q | A | Q | G K G L E L V G L I R N K A N S Y T T E Y A A S V K G |
| 598 | DP-31  | W | V R Q | A | P | G K G L E W V S G I S W . . N S G S I G Y A D S V K G |
| 599 | DP-32  | W | V R Q | A | P | G K G L E W V S G I N W . . N G G S T G Y A D S V K G |
| 600 | DP-33  | W | V R Q | A | P | G K G L E W V S L I S W . . D G G S T Y Y A D S V K G |
| 601 | dp-35  | W | I R Q | A | P | G K G L E W V S Y I . . S S S G S T I Y Y A D S V K G |
| 602 | VH3-8  | W | I R Q | A | P | G K G L E W V S Y I . . S S S S S Y T N Y A D S V K G |
| 603 | yac-9  | W | V R Q | A | S | G K G L E W V G R I R S K A N S Y A T A Y A A S V K G |
| 604 | dp-38  | W | V R Q | A | P | G K G L E W V G R I K S K T D G G T T D Y A A P V K G |
| 605 | LSG2   | W | V R Q | A | P | G K G L E W V G R I E S K T D G G T T D Y A A P V K G |
| 606 | LSG3   | W | V R Q | A | P | G K G L E W V G R I K S K T D G G T T D Y A A P V K G |
| 607 | LSG4   | W | V R Q | A | P | G K G L E W V G R I K S K T D G G T T N Y A A P V K G |
| 608 | LSG6   | W | V R Q | A | P | G K G L E W V G R I K S K T D G G T T D Y A A P V K G |
| 609 | v3-15  | W | V R Q | A | P | G K G L E W V G R I K S K T D G G T T D Y A A P V K G |
| 610 | dp-39  | W | V R Q | A | P | G K G L E W V G Y I . . S G D S G Y T N Y A D S V K G |

TABLE 1-continued

VH3 Family Germline Amino Acid Sequences Numbering according to Kabat (Joe9 VH included for comparison)

| | | | | | | | |
|---|---|---|---|---|---|---|---|
| 611 | dp-40 | W | V R Q | A | P | G K G L E W V G Y S . . S G N S G Y T N Y A D S V K G |
| 612 | dp-59 | W | V H Q | A | P | G K G L E W V S G V . . S W N G S R T H Y A D S V K G |
| 613 | v3-16p | W | A R K | A | P | G K G L E W V S G V . . S W N G S R T H Y V D S V K R |
| 614 | v3-19p | W | V R Q | A | P | G K G L E W V S G V . . S W N G S R T H Y A D S V K G |
| 615 | v3-13 | W | V R Q | A | T | G K G L E W V S A N . . G T A G . D T Y Y P G S V K G |
| 616 | DP-42 | W | V R Q | A | P | G K G L E W V S V I . Y . . S G G S T Y Y A D S V K G |
| 617 | dp-44 | W | V R Q | A | P | G K G L E W V S A I . . . G T G G G T Y Y A D S V K G |
| 618 | DP-45 | W | V R Q | A | P | G K G L E W V S A I . . . G T G G G T Y Y A D S V K G |
| 619 | dp-47 | W | V R Q | A | P | G K G L E W V S A I . . S G S G G S T Y Y A D S V K G |
| 620 | flm | W | V R Q | A | P | G K G L E Y V S A I . . S S N G G S T Y Y A D S V K G |
| 621 | P1 | W | V R Q | A | P | G K G L E Y V S A I . . S S N G G S T Y Y A D S V K G |
| 622 | v3-64 | W | V R Q | A | P | G L G L E Y V S A I . . S S N G G S T Y Y A N S V K G |
| 623 | vh26 | W | V R Q | A | P | G K G L E W V S A I . . S G S G G S T Y Y G D S V K G |
| 624 | B25 | W | V R Q | A | P | G K G L E W V A V I . . S Y D G S N K Y Y T D S V K G |
| 625 | b32e | W | V R Q | A | P | G K G L E W V A V I . . S Y D G S N K Y Y A D S V K G |
| 626 | B37 | W | V R Q | A | P | G K G L E W V A V I . . S Y D G S N K Y Y A D S V K G |
| 627 | B43 | W | V R Q | A | P | G K G L E W V A V I . . S Y D G S N K Y Y A D S V K G |
| 628 | B48 | W | V R Q | A | P | G K G L E W V A V I . . S Y D G S N K Y Y A D S V K G |
| 629 | B52 | W | V R Q | A | P | G K G L E W V A V I . . S Y D G S N K Y Y A D S V K G |
| 630 | B54 | W | V R Q | A | P | G K G L E W V A V I . . S Y D G S N K Y Y A D S V K G |
| 631 | cos-8 | W | V R Q | A | P | G K G L E W V A V I . . S Y D G S N K Y Y A D S V K G |
| 632 | dp-46 | W | V R Q | A | P | G K G L E W V A V I . . S Y D G S N K Y Y A D S V K G |
| 633 | F2M | W | V R Q | A | P | G K G L E Y V S A I . . S S N G G S T Y Y A D S V K G |
| 634 | F3 | W | V R Q | A | P | G K G L E Y V S A I . . S S N G G S T Y Y A D S V K G |
| 635 | F7 | W | V R Q | A | P | G K G L E W V A V I . . S Y D G S N K Y Y A D S V K G |
| 636 | hv3005 | W | V R Q | A | P | G K G L E W V A V I . . S Y D G S N K Y Y A D S V K G |
| 637 | P2 | W | V R Q | A | P | G K G L E W V A V I . . S Y D G S N K Y Y A D S V K G |
| 638 | dp-48 | W | V R Q | A | T | G K G L E W V S A I . . G T A G . D T Y Y P G S V K G |
| 639 | dp-58 | W | V R Q | A | P | G K G L E W V S Y I . . S S S G S T I Y Y A D S V K G |
| 640 | B1 | W | V R Q | A | P | G K G L E W V A V I . . S Y D G S N K Y Y A D S V K G |
| 641 | B13 | W | V R Q | A | P | G K G L E W V A V I . . S Y D G S N K Y Y A D S V K G |
| 642 | B18 | W | V R Q | A | P | G K G L E W V A V I . . S Y D G S N K Y Y A D S V K G |
| 643 | B26 | W | V R Q | A | P | G K G L E W V A V I . . S Y D G S N K Y Y A D S V K G |
| 644 | B28E | W | V R Q | A | P | G K G L E W V A V I . . S Y D G S N K Y Y A D S V K G |
| 645 | B29E | W | V R Q | A | P | G K G L E W V A V I . . S Y D G S N K Y Y A D S V K G |
| 646 | B29M | W | V R Q | A | P | G K G L E W V A V I . . S Y D G S N K Y Y A D S V K G |
| 647 | B30 | W | V R Q | A | P | G K G L E W V A V I . . W Y D G S N K Y Y A D S V K G |
| 648 | B32M | W | V R Q | A | P | G K G L E W V A V I . . S Y D G S N K Y Y A D S V K G |
| 649 | cos-3 | W | V R Q | A | P | G K G L E W V A F I . . R Y D G S N K Y Y A D S V K G |
| 650 | dp-49 | W | V R Q | A | P | G K G L E W V A V I . . S Y D G S N K Y Y A D S V K G |
| 651 | dp-50 | W | V R Q | A | P | G K G L E W V A V I . . W Y D G S N K Y Y A D S V K G |
| 652 | P6 | W | V R Q | A | P | G K G L E W V A V I . . W Y D G S N K Y Y A D S V K G |
| 653 | P9E | W | V R Q | A | P | G K G L E W V A V I . . S Y D G S N K Y Y A D S V K G |
| 654 | v3-30 | W | V R Q | A | P | G K G L E W V A V I . . S Y D G S N K Y Y A D S V K G |
| 655 | v3-33 | W | V R Q | A | P | G K G L E W V A V I . . W Y D G S N K Y Y A D S A K G |
| 656 | dp-31 | W | V R Q | A | P | G K G L E W V S Y I . . S S S S T I Y Y A D S V K G |
| 657 | dp-77 | W | V R Q | A | P | G K G L E W V S Y I . . S S S S Y I Y Y A D S V K G |
| 658 | HHG4 | W | V R Q | A | P | G K G L E W V S S I . . . S S S S  Y I Y Y A D S V K |
| 659 | v3-21 | W | V R Q | A | P | G K G L E W V S S I . . . S S S S S Y I Y Y A D S V K G |
| 660 | v3-48 | W | V R Q | A | P | G K G L E W V S Y I . . S S S S S T I Y Y A D S V K G |
| 661 | DP-52 | W | V R R | A | P | G K G P E W V S A I G . . . T G G D T Y Y A D S V M G |
| 662 | cos-6 | W | V R Q | A | P | G K G L V W V S R I . . N S D G S S T S Y A D S V K G |
| 663 | dp-53 | W | V R Q | A | P | G K G L V W V S R I . . N S D G S S T S Y A D S V K G |
| 664 | dp-54 | W | V R Q | A | P | G K G L E W V A N I . . K Q D G S E K Y Y V D S V K G |
| 665 | dp-87 | W | V R Q | A | P | G K G L V W V S R I . . N S D G S S T S Y A D S M K G |
| 666 | VH3-11 | W | V R Q | A | P | G K G L E W V A N I . . K Q D G S E K Y Y V D S V K G |
| 667 | JOE9 VH | W | V R Q | A | P | G K G L E W V A F I . . R Y D G S N K Y Y A D S V K G |

| SEQ ID NO: VH | germline | 6 6 6 6 7<br>6 7 8 9 0 | | | | 7 7 7 7 7 7 7 7 7 7 8 8 8 8 8 8 2 2 8 8 8 8 8 8 8 8 9 9 9 9<br>1 2 3 4 5 6 7 8 9 0 1 2 A B C 3 4 5 6 7 8 9 0 1 2 3 4 |
|---|---|---|---|---|---|---|

| | | | | | | |
|---|---|---|---|---|---|---|
| 594 | dp-29 | R F T | I | S | R D D S K N S L Y L Q M N S L K T E D T A V Y Y C A R |
| 595 | DP-30 | R L T | I | S | R E D S K N T L Y L Q M S S L K T E D L A V Y Y C A R |
| 596 | HC15-7 | R L T | I | S | R E D S K N T M Y L Q M N S L N K T E D L A V Y Y A R |
| 597 | VHD26 | R L T | I | S | R E D S K N T L Y L Q M S S L K T E D L A V Y Y C A R |
| 598 | DP-31 | R F T | I | S | R D N A K N S L Y L Q M N S L R A E D T A L Y Y C A R |
| 599 | DP-32 | R F T | I | S | R D N A K N S L Y L Q M N S L R A E D T A L Y H C A R |
| 600 | DP-33 | R F T | I | S | R D N S K N S L Y L Q M N S L R T E D T A L Y Y C A K |
| 601 | dp-35 | R F T | I | S | R D N A K N S L Y L Q M N S L R A E D T A L Y Y C A R |
| 602 | VH3-8 | R F T | I | S | R D N A K N S L Y L Q M N S L R A E D T A V Y Y C A R |
| 603 | yac-9 | R F T | I | S | R D D S K N T A Y L Q M N S L K T E D T A V Y Y C T R |
| 604 | dp-38 | R F T | I | S | R D D S K N T L Y L Q M N S L K T E D T A V Y Y C T T |
| 605 | LSG2 | R F T | I | S | R D D S K N T L Y L Q M N S L K T E D T A V Y Y C T T |
| 606 | LSG3 | R F T | I | S | R D D S K N T L Y L Q M N S L K T E D T A V Y Y C T T |
| 607 | LSG4 | R F T | I | S | R D D S K N T L Y L Q M N S L K T E D T A V Y Y C T T |

TABLE 1-continued

VH3 Family Germline Amino Acid Sequences Numbering according to
Kabat (Joe9 VH included for comparison)

| SEQ ID NO | gene | | | | | | | | |
|---|---|---|---|---|---|---|---|---|---|
| 608 | LSG6 | R F | T | I | | S | R D D S K N T L Y L Q M N S L K T E D T A V Y Y C T T |
| 609 | v3-15 | R F | T | I | | S | R D D S K N T L Y L Q M N S L K T E D T A V Y Y C T T |
| 610 | dp-39 | R F | T | I | | S | R D N A N N S P Y L Q M N S L R A E D T A V Y Y C V K |
| 611 | dp-40 | R F | T | I | | S | R D N A K N S L Y L Q M N S L R A E D T A V Y Y C V K |
| 612 | dp-59 | R F | I | I | | S | R D N S R N T L Y L Q T N S L R A E D T A V Y Y C V R |
| 613 | v3-16p | R F | I | I | | S | R D N S R N S L Y L Q K N R R A E D M A V Y Y C V R |
| 614 | v3-19p | R F | I | I | | S | R D N S R N F L Y Q Q M N S L R P E D M A V Y Y C V R |
| 615 | v3-13 | R F | T | I | | S | R E N A K N S L Y L Q M N S L R A G D T A V Y Y C A R |
| 616 | DP-42 | R F | T | I | | S | R D N S K N T L Y L Q M N S L R A E D T A V Y Y C A R |
| 617 | dp-44 | R F | T | I | | S | R D N A K N S L Y L Q M N S L R A E D M A V Y Y C A R |
| 618 | DP-45 | R F | T | I | | S | R D N A K N S L Y L Q M N S L R A E D M A V Y Y C A R |
| 619 | dp-47 | R F | T | I | | S | R D N S K N T L Y L Q M N S L R A E D T A V Y Y C A K |
| 620 | flm | R F | T | I | | S | R D N S K N T L Y V Q M S S L R A E D T A V Y Y C V K |
| 621 | P1 | R F | T | I | | S | R D N S K N T L Y V Q M N S L R A E D T A V Y Y C V K |
| 622 | v3-64 | R F | T | I | | S | R D N S K N T L Y L Q M G S L R A E D M A V Y Y C A R |
| 623 | vh26 | R F | T | I | | S | R D N S K N T L Y L Q M N S L R A E D T A V Y Y C A K |
| 624 | B25 | R F | T | I | | S | R D N S K N T L Y L Q M N S L R A E D T A V Y Y C A R |
| 625 | b32e | R F | T | I | | S | R D N S K N T L Y L Q M N S L R A E D T A V Y Y C A R |
| 626 | B37 | R F | T | I | | S | R D N S K N T L Y L Q M S S L R A E D T A V Y Y C A R |
| 627 | B43 | R F | T | I | | S | R D N S K N T L Y L Q M N S L R A E D T A V Y Y C A R |
| 628 | B48 | R F | T | I | | S | R D N S K N T L Y L Q M N S L R A E D T A V Y Y C A R |
| 629 | B52 | R F | T | I | | S | R D N S K N T L Y L Q M N S L R A E D T A V Y Y C A R |
| 630 | B54 | R F | T | I | | S | R D N S K N T L Y L Q M N S L R A E D T A V Y Y C A R |
| 631 | cos-8 | R F | T | I | | S | R D N S K N T L Y L Q M N S L R A E D T A V Y Y C A R |
| 632 | dp-46 | R F | T | I | | S | R D N S K N T L Y L Q M N S L R A E D T A V Y Y C A R |
| 633 | F2M | R F | T | I | | S | R D N S K N T L Y V Q M S S L R A E D T A V Y Y C V K |
| 634 | F3 | R F | T | I | | S | R D N S K N T L Y L Q M N S L R A E D T A V Y Y C A R |
| 635 | F7 | R F | A | I | | S | R D N S K N T L Y L Q M N S L R A E D T A V Y Y C A R |
| 636 | hv3005 | R F | T | I | | S | R D N S K N T L Y L Q M N S L R A E D T A V Y Y C A R |
| 637 | P2 | R F | T | I | | S | R D N S K N T L Y L Q M N S L R A E D T A V Y Y C A K |
| 638 | dp-48 | R F | T | I | | S | R E N A K N S L Y L Q M N S L R A G D T A V Y Y C A R |
| 639 | dp-58 | R F | T | I | | S | R D N A K N S L Y L Q M N S L R A E D T A V Y Y C A R |
| 640 | B1 | R F | T | I | | S | R D N S K N T L Y L Q M N S L R L A R L C I T V R E |
| 641 | B13 | R F | T | I | | S | R D N S K N T L Y L Q M N S L R A E D T A V Y Y C A R |
| 642 | B18 | R F | T | I | | S | R D N S K N T L Y L Q M N S L R A E D T A V Y Y C A R |
| 643 | B26 | R F | T | I | | S | R D N S K N T L Y L Q M N S L R A E D T A V Y Y C A R |
| 644 | B28E | R F | T | I | | S | R D N S K N T L Y L Q M N S L R A E D T A V Y Y C A R |
| 645 | B29E | R F | T | I | | S | R D N S K N R L Y L Q M N S L R A E D T A V Y Y C A R |
| 646 | B29M | R F | T | I | | S | R D N S K N T L Y L Q M N S L R A E D T A V Y Y C A R |
| 647 | B30 | R F | T | I | | S | R D N S K N T L Y L Q M N S L R A E D T A V Y Y C A R |
| 648 | B32M | R F | T | I | | S | R D N S K N T L Y L Q M N S L R A E G T A V Y Y C A R |
| 649 | cos-3 | R F | T | I | | S | R D N S K N T L Y L Q M N S L R A E D T A V Y Y C A R |
| 650 | dp-49 | R F | T | I | | S | R D N S K N T L Y L Q M N S L R A E D T A V Y Y C A K |
| 651 | dp-50 | R F | T | I | | S | R D N S K N T L Y L Q M N S L R A E D T A V Y Y C A R |
| 652 | P6 | R F | T | I | | S | R D N S K N T L Y L Q M N S L R A E D T A V Y Y C A K |
| 653 | P9E | R F | T | I | | S | R D N S K N T L Y L Q M N S L R A E D T A V R K - - - |
| 654 | v3-30 | R F | T | I | | S | R D N S K N T L Y L Q M N S L R A E D T A V Y Y C A R |
| 655 | v3-33 | R F | T | I | | S | R D N S T N T L F L Q M N S L R A E D T A V Y Y C A R |
| 656 | dp-31 | R F | T | I | | S | R D N A K N S L Y L Q M N S L R D E D T A V Y Y C A R |
| 657 | dp-77 | R F | T | I | | S | R D N A K N S L Y L Q M N S L R A E D T A V Y Y C A R |
| 658 | HHG4 | R F | T | I | | S | R D N A K N S L Y L Q M N S L R A E D T A V Y Y C A R |
| 659 | v3-21 | R F | T | I | | S | R D N A K N S L Y L Q M N S L R A E D T A V Y Y C A R |
| 660 | v3-48 | R F | T | I | | S | R D N A K N S L Y L Q M N S L R A E D T A V Y Y C A R |
| 661 | DP-52 | R F | T | I | | S | R D N A K K S L Y L Q M N S L I A E D M A V Y Y C A R |
| 662 | cos-6 | R F | T | I | | S | R D N A K N T L Y L Q M N S L R A E D T A V Y Y C A R |
| 663 | dp-53 | R F | T | I | | S | R D N A K N T L Y L Q M N S L R A E D T A V Y Y C A R |
| 664 | dp-54 | R F | T | I | | S | R D N A K N S L Y L Q M N S L R A E D T A V Y Y C A R |
| 665 | dp-87 | Q F | T | I | | S | R D N A K N S L Y L Q M N S L R A E D M A V Y Y C T R |
| 666 | VH3-11 | R F | T | I | | S | R D N A K N S L Y L Q M N S L R A E D T A V Y Y C A R |
| 667 | JOE9 VH | R F | T | I | | S | R D N S K N T L Y L Q M K S L R A E D T A V Y Y C T T |

| | | | | | | | | | | | CDR L1 |
|---|---|---|---|---|---|---|---|---|---|---|---|
| SEQ ID NO | gene* | VL | 1 | 2 | 3 | 4 5 6 7 | 8 | 9 | | | 1 1 1 1 1 1 1 1 1 2 2 2 2 2 2 2 7 7 7 2 2 3 3 3 3<br>0 1 2 3 4 5 6 7 8 9 0 1 2 4 5 6 7 A B C 8 9 0 1 2 3 4 |
| 668 | 1b | DPL5 | Q | | S V | L T Q P | | P | | S | V S A A P G Q K V T I S C S G S S S N I G N N Y . V S |
| 669 | 1d | DPL4 | Q | | S V | L T Q P | | P | | S | V S A A P G Q K V T I S C S G S S S D M G N Y A . V S |
| 670 | 1c | DPL2 | Q | | S V | L T Q P | | P | | S | A S G T P G Q R V T I S C S G S S S N I G S N T . V N |
| 671 | 1g | DPL3 | Q | | S V | L T Q P | | P | | S | A S G T P G Q R V T I S C S G S S S N I G S N Y . V Y |
| 672 | 1a | DPL1 | Q | | S V | L T Q P | | P | | S | V S E A P R Q R V T I S C S G S S S N I G N N . A V N |
| 673 | 1f | DPL9 | Q | | S V | L T Q P | | P | | S | V S G A P G Q R V T I S C T G S S S N I G A G Y V V H |

TABLE 1-continued

VH3 Family Germline Amino Acid Sequences Numbering according to Kabat (Joe9 VH included for comparison)

| 674 | 1e | DPL8 | Q | S | V | V | T Q P | P | S | V S G A P G Q R V T I S C T G S S S N I G A G Y D V H |
| 675 | | JOE9 VL | S | Y | V | L | T Q P | P | S | V S G T P G Q R V T I S C S G G R S N I G S N T . V K |

| | | | | | | | | | | CDR L2 | |
|---|---|---|---|---|---|---|---|---|---|---|---|
| SEQ ID NO: | gene*VL | | 5 | 6 | 7 | 8 9 0 1 | 2 | 3 | 5 5 5 5 5 5 5 5 5 6 6 6 6 6 6 6 6 6 7<br>4 5 6 7 8 9 0 1 2 3 4 5 6 7 8 9 0 |
| 668 | 1b | DPL5 | W | Y | Q | Q L P G | T | A | P K L L I Y D N N K R P S G I P D R F S G S K S G T S |
| 669 | 1d | DPL4 | W | Y | Q | Q L P G | T | A | P K L L I Y E N N K R P S G I P D R F S G S K S G T S |
| 670 | 1c | DPL2 | W | Y | Q | Q L P G | T | A | P K L L I Y S N N Q R P S G V P D R F S G S K S G T S |
| 671 | 1g | DPL3 | W | Y | Q | Q L P G | T | A | P K L L I Y R N N Q R P S G V P D R F S G S K S G T S |
| 672 | 1a | DPL1 | W | Y | Q | Q L P G | K | A | P K L L I Y D D L L P S G V S D R F S G S K S G T S |
| 673 | 1f | DPL9 | W | Y | Q | Q L P G | T | A | P K L L I Y G N S N R P S G V P D Q F S G S K S G T S |
| 674 | 1e | DPL8 | W | Y | Q | Q L P G | T | A | P K L L I Y G N S N R P S G V P D R F S G S K S G T S |
| 675 | | JOE9 VL | W | Y | Q | Q L P G | T | A | P K L L I Y G N D Q R P S G V P D R F S G S K S G T S |

| | | | CDR L3 |
|---|---|---|---|
| SEQ ID NO: | gene*VL | | 7 7 7 7 7 7 7 7 7 8 8 8 8 8 8 8 8 8 9 9 9 9 9 9 9 5 5<br>1 2 3 4 5 6 7 8 9 0 1 2 3 4 5 6 7 8 9 0 1 2 3 4 5 A B |
| 668 | 1b | DPL5 | A T L G I T G L Q T G D E A D Y Y C G T W D S S L S A |
| 669 | 1d | DPL4 | A T L G I T G L W P E D E A D Y Y C L A W D T S P R A |
| 670 | 1c | DPL2 | A S L A I S G L Q S E D E A D Y Y C A A W D D S L N G |
| 671 | 1g | DPL3 | A S L A I S G L R S E D E A D Y Y C A A W D D S L S G |
| 672 | 1a | DPL1 | A S L A I S G L Q S E D E A D Y Y C A A W D D S L N G |
| 673 | 1f | DPL9 | A S L A I T G L Q S E D E A D Y Y C K A W D N S L N A |
| 674 | 1e | DPL8 | A S L A I T G L Q A E D E A D Y Y C Q S Y D S S L S G |
| 675 | | JOE9 VL | A S L A I T G V Q A E D E A D Y Y C Q S Y D S S L R G |

*Williams, J M B, 1996, 264, 220-232

TABLE 2

| Clone | H3 SEQ ID NO:H3 | L3 SEQ ID NO:L3 | koff | RB assay IC50 (M) | PHA assay IC50 (M) | IFN gamma IC50 (M) |
|---|---|---|---|---|---|---|
| Joe9 wt | 77 SGSYDY | 110 QSYDSSLRGSRV | 1.00E-01 | 1.50E-06 | | 1.00E-06 |
| Joe9 wt IgG1 | 77 SGSYDY | 110 QSYDSSLRGSRV | | | | 5.00E-07 |
| 70-1 | 78 HGSHDN | 110 Joe9 wt | 1.34 e-2 | | | 2.00E-07 |
| 70-1 | 78 HGSHDN | 110 Joe9 wt | | | | 2.00E-07 |
| 70-2 | 79 HGSYDY | 110 Joe9 wt | 3.30E-02 | | | 3.50E-7 |
| 70-7 | 80 RRRSNY | 110 Joe9 wt | 1.29E-01 | | | 3.50E-7 |
| 70-13 | 81 SGSIDY | 110 Joe9 wt | 7.20E-02 | | | 3.50E-7 |
| 78-34 | 77 wt | 111 QSYDRGFTGSRV | 1.64 e-2 | 2.00E-07 | | 6.00E-07 |
| 78-25 | 77 wt | 112 QSYDSSLRGSRV | 5.00E-02 | | | |
| 78-28 | 77 wt | 112 QSYDSSLRGSRV | 4.66E-02 | | | |
| 78-35 | 77 wt | 113 QSYDSSLTGSRV | 4.99E-02 | 4.00E-07 | | |
| 79-1 | 77 wt | 114 QSYDSSLWGSRV | | 2.00E-07 | | 6.00E-07 |
| 101-14 | 79 70-2 | 111 78-34 | 7.52E-03 | | | |
| 101-9 | 79 10-2 | 113 78-35 | 8.54E-03 | | | |
| 101-19 | 81 70-13 | 111 78-34 | 4.52E-02 | | | |
| 101-8 | 81 70-13 | 111 78-34 | 1.01E-02 | | | |

TABLE 2-continued

| Clone | H3 SEQ ID NO:H3 | L3 SEQ ID NO:L3 | koff | RB assay IC50 (M) | PHA assay IC50 (M) | IFN gamma IC50 (M) |
|---|---|---|---|---|---|---|
| 101-4 | 81 70-13 | 113 78-35 | 9.76E-03 | | | |
| 101-5 | 81 70-13 | 113 78-35 | 4.45E-02 | | | |
| 101-11 (12) | 78 70-1 | 111 78-34 | 4.5 e-3 | | 3.00E-08 | |
| 101-11 IgG1 | 78 70-1 | 111 78-34 | | 1.60E-09 | | |
| 26-1 (2, 3) | 78 70-1 | 114 79-1 | 7.4 e-3 | | 6.00E-08 | |
| 136-9 | 82 HGSHDD | 115 QTYDISESGSRV | 3.20E-03 | | | |
| 136-10 | 82 HGSHDD | 116 QSYDRGFTGSRV | 1.40E-03 | 2.00E-09 | | |
| 136-14 | 83 HGSHDN | 117 QTYDRGFTGSRV | 1.10E-03 | 3.00E-10 | 1.00E-07 | |
| 136-15 | 83 HGSHDN | 118 QTYDKGFTGSSV | 7.4 e-4 | 1.00E-10 | 2.00E-09 | |
| 136-15 germline | 83 HGSHDN | 118 QTYDKGFTGSSV | 4.60E-04 | | 6.00E-09 | |
| 136-16 | 83 HGSHDN | 119 QSYDRRFTGSRV | 6.10E-04 | 3.00E-10 | 5.00E-09 | |
| 136-17 | 83 HGSHDN | 120 QSYDWNFTGSRV | 2.90E-05 | 2.00E-09 | 7.00E-09 | |
| 136-18 | 83 HGSHDN | 121 QSYDRGFTGSRV | 1.10E-03 | 8.00E-10 | | |
| 136-21 | 83 HGSHDN | 122 QSYDNGFTGSRV | 4.20E-04 | 2.00E-09 | | |
| 136-24 | 83 HGSHDN | 123 QSYDNAVTASKV | 8.90E-04 | 1.00E-09 | | |
| 101-11 | 84 TT HGSHDN WGQG | 124 QSYDRGFTGSRV | 4.5 × 10−3 | 2 × 10−9 | 2.00E-08 | |
| 136-15M1 | 85 AK...... | 124 QSYDRGFTGSRV | | 4.00E-10 | | |
| 149-4 | 86 .......S.. | 124............ | 1.37 × 10−3 | 8 × 10−11 | 3.00E-09 | |
| 149-5 | 87 .......T.... | 125 QSYDSSLWGTRV | 1.02 × 10−3 | 1.2 × 10−10 | 3.00E-09 | |
| 149-6 | 84 ............ | 124............ | 2.73 × 10−3 | 6 × 10−10 | 2.00E-09 | |
| 149-7 | 84 ............ | 126.....D...... | 1.13 × 10−3 | 9 × 10−10 | 3.00E-09 | |
| 149-8 | 88 K........... | | 2.33 × 10−3 | 3 × 10−9 | | |
| 149-9 | 89 K.......H. | 127...E......M. | 3.54 × 10−3 | 1.8 × 10−10 | | |
| 149-11 | 90 .......S.. | 128....N....A.. | 1.43 × 10−2 | 2 × 10−10 | 4.00E-09 | |
| 149-12 | 84 ............ | | 3.73 × 10−3 | neutralising | | |
| 149-13 | 84 ............ | | 2.22 × 10−3 | 5 × 10−10 | | |
| 149-14 | 91 ...R..N. .... | | | 1.5 × 10−10 | 6.00E-09 | |
| | 92 TT HGSHDN | 124 QSYDRGFTGSRV | | | | |
| 156-1 | 93 .. .....T | 126.....D...... | 5.00E-03 | | | |
| 156-2 | 93 .. .....T | 129.....R...... | | | | |
| 156-3 | 93 .. .....T | 128....N....A.. | 9.00E-03 | | | |
| 156-4 | 93 .. .....T | 127...E.....SM. | | | | |
| 156-5 | 93 .. .....T | 130.T..K.....S. | | | | |
| 156-6 | 92 .. ........ | 126.....D...... | 3.00E-03 | | | |
| 156-7 | 92 .. ........ | 129.....R...... | | | | |
| 156-8 | 92 .. ........ | 128....N....A.. | | | | |
| 156-9 | 92 .. ........ | 127...E.....SM. | | | | |
| 156-10 | 92 .. ........ | 130.T..K.....S. | | | | |

TABLE 2-continued

| Clone | H3 SEQ ID NO:H3 | L3 SEQ ID NO:L3 | koff | RB assay IC50 (M) | PHA assay IC50 (M) | IFN gamma IC50 (M) |
|---|---|---|---|---|---|---|
| 156-11 | 94 .K...... | 126.....D...... | | | | |
| 156-12 | 94 .K...... | 129.....R...... | | | | |
| 156-13 | 94 .K...... | 128....N....A.. | | | | |
| 156-14 | 94 .K...... | 127...E.....SM. | | | | |
| 156-15 | 94 .K...... | 130.T..K.....S. | | | | |
| 156-16 | 93 .. .....T | 124............ | | | | |
| 156-17 | 92 .. ....... | 125....SSLW.T.. | 6.00E-03 | | | |
| 156-18 | 93 .. .....T | 125....SSLW.T.. | | | | |
| | 92 TT HGSHDN | 124 QSYDRGFTGSRY | | | | |
| 103-1 | 95 .. Q.R... | 124............ | $2.9 \times 10^{-3}$ | | | |
| 103-2 | 96 K. R.R... | 130.T..K.....S. | $7.3 \times 10^{-4}$ | 7.00E-11 | | 1.00E-09 |
| 103-3 | 97 .. .....K | 124............ | $2.5 \times 10^{-3}$ | | | |
| 103-6 | | 131.....D...T.. | $4.5 \times 10^{-4}$ | | | |
| 103-7 | 98 .. .....D | 131.....D...T.. | $3.7 \times 10^{-4}$ | 1.40E-10 | | 1.00E-09 |
| 103-8 | 99 K. ...... | 130.T..K.....S. | $3.3 \times 10^{-4}$ | 6.00E-11 | | 1.50E-09 |
| 103-14 & 9 | 100 KT HGSHDN | 132 QSYDRGFTGSMV | 6.7 e-4 | 4.00E-11 | | 1.20E-09 |
| 103-8 & 2 | 100 KT HGSHDN | 133 QSYDKGFTGSSV | 5.3 e-4 | | | 1.50E-09 |
| 103-4 | 101 TT HGSHDN | 134 QSYDRGFTGARV | 1.6 e-4 | 8.60E-11 | | 9.00E-10 |
| 103-152 | 101 TT HGSHDN | 135 QSYERGFTGARV | | 8.60E-11 | | |
| | 102 TT SGSYDY | 136 QSYDRGFTGSRVF | | | | |
| 170-1 | 102 .. ....... | 137.........FK.. | 2.35E-03 | | | |
| 170-2 | 102 .. ....... | 138.......VSAY.. | 8.80E-04 | | | |
| 170-3 | 102 .. ....... | 139......L.VTK.. | 1.11E-03 | | | |
| 170-4 | 102 .. ....... | 140......Y.A.... | 8.11E-04 | | | |
| 170-7 | 102 .. ....... | 141.........K... | 5.30E-04 | | | |
| 170-11 | 102 .. ....... | 142......L..F... | 4.40E-04 | | | |
| 170-13 | 102 .. ....... | 143.........YK.. | 1.59E-03 | | | |
| 170-15 | 102 .. ....... | 144......L..Y.L. | 4.43E-03 | | | |
| 170-19 | 103 .. H..H.N | 145.........DYK. | 1.00E-03 | | | |
| 170-21 | 104 .. H..Q.N | 146.........P.L. | 3.89E-03 | | | |
| 170-22 | 102 .. ....... | 147......L...... | 5.60E-03 | | | |
| 170-23 | 103 .. H..H.N | 148.........A..W | 1.00E-03 | 2.00E-10 | | |
| 170-24 | 104 .. H..Q.N | 149.........Y... | 2.80E-04 | 5.00E-10 | | |
| 170-35 | 105 A. H..Q.N | 136............. | 1.00E-05 | | | |
| 170-38 | | 150.........P... | 2.10E-04 | | | |
| 170-39 | | 151......M.S.... | 2.79E-03 | | | |
| 170-36 | 83 HGSHDN | 152 QSYDRDSTGSRVF | 4.00E-04 | 2.00E-10 | | |

TABLE 2-continued

| Clone | H3 SEQ ID NO:H3 | L3 SEQ ID NO:L3 | koff | RB assay IC50 (M) | PHA assay IC50 (M) | IFN gamma IC50 (M) |
|---|---|---|---|---|---|---|
| 170-25 | 106 HGSQDT | 153 QSYDSSLRGSRVF | 5.00E-04 | 5.00E-11 | | |
|  | 106 SGSYDY | 136 QSYDRGFTGSRVF | | | | |
| 73-B1 | 107 SGSYDY | 154 H...SD....... | 3.25E-03 | >1E-8 | | |
| 73-B2 | 107 SGSYDY | 155 H.SES....... | 2.07E-03 | | | |
| 73-B6 | 107 SGSYDY | 156 H...NR....... | 2.51E-03 | >1E-8 | | |
| 73-C1 | 107 SGSYDY | 157 H..SR....... | 2.71E-03 | >1E-8 | | |
| 73-C2 | 107 SGSYDY | 158 ....SE....... | 3.79E-03 | | | |
| 73-C6 | 107 SGSYDY | 159 ....T......... | 3.96E-03 | | | |
| 73-D1 | 107 SGSYDY | 160 H...S........ | 3.99E-03 | | | |
| 73-D2 | 107 SGSYDY | 161 ....T......... | 3.56E-03 | | | |
| 73-D4 | 107 SGSYDY | 162 H...TK....... | 5.36E-03 | | | |
| 73-D5 | 107 SGSYDY | 163 H.S.S........ | 3.57E-03 | | | |
| 73-E3 | 107 SGSYDY | 164 ....SD....... | 4.98E-03 | | | |
| 73-E6 | 107 SGSYDY | 165 H..ES....... | 4.17E-03 | | | |
| 73-F3 | 107 SGSYDY | 166 ....APWS..... | 7.08E-03 | | | |
| 73-F5 | 107 SGSYDY | 167 ...DSD....K.. | 3.74E-03 | | | |
| 73-G2 | 107 SGSYDY | 168 HTN.S........ | 3.98E-03 | | | |
| 73-G3 | 107 SGSYDY | 169 H...TR....... | 3.50E-03 | | | |
| 73-G4 | 107 SGSYDY | 170 ....MR....... | 6.58E-03 | | | |
| 73-G5 | 107 SGSYDY | 171 H.S.SDS...... | 6.01E-03 | | | |
| 73-G6 | 107 SGSYDY | 172 ...NTD....... | 6.30E-03 | | | |
| 73-H2 | 107 SGSYDY | 173 ....S......... | 5.93E-03 | | | |
| 73-F6 | 107 SGSYDY | 174 H...M......... | 5.87E-03 | | | |
| 73-H3 | 107 SGSYDY | 175 H...N......... | 6.85E-03 | | | |
| 73-C5 | 107 SGSYDY | 176 H.H..D....... | 4.84E-03 | | | |
| 73-B7 | 108 HGSQDN | 177 QSYDSSLRGSRV | 2.50E-03 | 7.00E-09 | | |
|  |  | 136 QSYDRGFTGSRVF | 2.79E-03 | | | |
| M2 A2 | 83 HGSHDN | 178 ......IH..... | 4.00E-02 | | | |
| M2 A4 | 83 HGSHDN | 179 ....S..P..... | 8.49E-03 | | | |
| M2 A5 | 83 HGSHDN | 180 ....I.S...... | 4.01E-02 | | | |
| M2 B1 | 83 HGSHDN | 181 ....S.L...... | 7.97E-03 | | | |
| M2 B3 | 83 HGSHDN | 182 ....I.M...... | 4.60E-02 | | | |
| M2 B4 | 83 HGSHDN | 183 ....I.L...... | 4.42E-02 | | | |
| M2 B5 | 83 HGSHDN | 184 ....S.V...... | 8.38E-03 | | | |
| M2 B6 | 83 HGSHDN | 185 ......L.A.... | 2.81E-02 | | | |
| M2 C2 | 83 HGSHDN | 181 ....S.L...... | 4.85E-02 | | | |
| M2 C3 | 83 HGSHDN | 186 ....T.L...... | 4.62E-02 | | | |
| M2 C4 | 83 HGSHDN | 181 ....S.L...... | 8.16E-03 | | | |

TABLE 2-continued

| Clone | H3 SEQ ID NO:H3 | L3 SEQ ID NO:L3 | koff | RB assay IC50 (M) | PHA assay IC50 (M) | IFN gamma IC50 (M) |
|---|---|---|---|---|---|---|
| M2 C5 | 83 HGSHDN | 187....TAL...... | 4.71E-02 | | | |
| M2 D1 | 83 HGSHDN | 188....IR........ | 3.71E-02 | | | |
| M2 D2 | 83 HGSHDN | 189....IRS....... | 3.85E-02 | | | |
| M2 D3 | 83 HGSHDN | 190....NRL....... | 3.33E-02 | | | |
| M2 D4 | 83 HGSHDN | 191...ETS........ | 5.81E-02 | | | |
| M2 D5 | 83 HGSHDN | 192....SSS....... | 5.18E-02 | | | |
| M2 D6 | 83 HGSHDN | 193....S...A..... | 5.01E-02 | | | |
| M2 E1 | 83 HGSHDN | 194.T..K.....S.. | 5.32E-02 | | | |
| M2 E2 | 83 HGSHDN | 195....N......... | 4.77E-02 | | | |
| M2 E6 | 83 HGSHDN | 196....T...K.... | 9.77E-03 | | | |
| M2 F1 | 83 HGSHDN | 197....SDV....... | 6.16E-02 | | | |
| M2 H5 | 83 HGSHDN | 198....A......... | 9.90E-03 | | | |
| | | 124 QSYDRGFTGSRY | 2.79E-02 | | | |
| A5 | 83 HGSHDN | 199......THPSML | 1.12E-03 | | | |
| A12 | 83 HGSHDN | 200......TTPRPM | 1.43E-03 | | | |
| A4 | 83 HGSHDN | 201......RNPALT | 1.47E-03 | | | |
| A6 | 83 HGSHDN | 202......THPWLH | 1.87E-03 | | | |
| A10 | 83 HGSHDN | 203......NSPATV | 1.87E-03 | | | |
| A11 | 83 HGSHDN | 204......TFPSPQ | 2.07E-03 | | | |
| C2 | 83 HGSHDN | 205......LNPSAT | 2.23E-03 | | | |
| A8 | 83 HGSHDN | 206......KSNKML | 2.37E-03 | | | |
| B8 | 83 HGSHDN | 207......HTAHLY | 2.40E-03 | | | |
| C6 | 83 HGSHDN | 208......QTPSIT | 2.42E-03 | | | |
| A3 | 83 HGSHDN | 209......YPRNIL | 2.51E-03 | | | |
| B11 | 83 HGSHDN | 210......ITPGLA | 2.95E-03 | | | |
| B5 | 83 HGSHDN | 211......QPHAVL | 3.04E-03 | | | |
| C10 | 83 HGSHDN | 212......NSPIPT | 3.10E-03 | | | |
| C4 | 83 HGSHDN | 213......TPNNSF | 3.23E-03 | | | |
| C3 | 83 HGSHDN | 214....S.VDPGPY | 3.34E-03 | | | |
| B2 | 83 HGSHDN | 215......RPRHAL | 3.61E-03 | | | |
| A2 | 83 HGSHDN | 216......PYHPIR | 3.80E-03 | | | |
| C5 | 83 HGSHDN | 217......PHTQPT | 3.91E-03 | | | |
| A7 | 83 HGSHDN | 218......HNNFSP | 3.95E-03 | | | |
| C9 | 83 HGSHDN | 219......PTHLPH | 3.97E-03 | | | |
| B3 | 83 HGSHDN | 220......TPSYPT | 4.12E-03 | | | |
| C8 | 83 HGSHDN | 221....S.TSNLLP | 5.36E-03 | | | |
| B7 | 83 HGSHDN | 222......DSNHDL | 5.45E-03 | | | |

TABLE 2-continued

| Clone | H3 SEQ ID NO:H3 | L3 SEQ ID NO:L3 | | koff | RB assay IC50 (M) | PHA assay IC50 (M) | IFN gamma IC50 (M) |
|---|---|---|---|---|---|---|---|
| A1 | 83 HGSHDN | 223 | ......LPRLTH | 5.66E-03 | | | |
| C7 | 83 HGSHDN | 224 | ......IPTSYL | 5.83E-03 | | | |
| C12 | 83 HGSHDN | 225 | ......LRVQAP | 5.85E-03 | | | |
| B10 | 83 HGSHDN | 226 | ......LSDSPL | 6.04E-03 | | | |
| B6 | 83 HGSHDN | 227 | ....S.SLRRIL | 7.58E-03 | | | |
| A9 | 83 HGSHDN | 228 | ....S.SLRRIL | 7.98E-03 | | | |
| B9 | 83 HGSHDN | 229 | ......RAAHPQ | 8.66E-03 | | | |
| | | 124 QSYDRGHTGSRV | | | | | |
| 177-D7 | 83 HGSHDN | 230 | ......TQPABI | 4.07E-04 | | | |
| 177-G6 | 83 HGSHDN | 231 | ......THPTMI | 5.50E-04 | | | |
| 177-D9 | 83 HGSHDN | 232 | ......RIPABT | 6.32E-04 | | | |
| 177-C6 | 83 HGSHDN | 233 | ......THPVPA | 7.94E-04 | | | |
| 177-H5 | 83 HGSHDN | 234 | ......SBPIPA | 1.32E-03 | | | |
| 177-H9 | 83 HGSHDN | 235 | ......THPVPA | 1.58E-03 | | | |
| 177-H10 | 83 HGSHDN | 236 | ......THPTMY | 3.44E-03 | | | |
| 144-F1 | 83 HGSHDN | 237 | ......HHYTTF | 5.80E-04 | | | |
| 43-E3 | 83 HGSHDN | 238 | ......SHPAAE | 8.00E-04 | | | |
| 43-E9 | 83 HGSHDN | 239 | ......TIPSIE | 8.00E-04 | | | |
| 43-G2 | 83 HGSHDN | 240 | ......SSPAIM | 7.00E-04 | | | |
| 43-G3 | 83 HGSHDN | 241 | ......IWPNLN | 9.00E-04 | | | |
| 31-A6 | 83 HGSHDN | 242 | ......THPNLN | 5.00E-04 | | | |
| 31-B5 | 83 HGSHDN | 243 | ......THPSIS | 5.00E-04 | | | |
| | | 124 QSYDRGFTGSRV | | | | | |
| Y17 | 83 HGSHDN | 244 QSYDRGSAPMIN | | 8.90E-05 | 4.50E-10 | >1E-8 | |
| Y19 | 83 HGSHDN | 245 QSYDRGHHPAMS | | 2.26E-04 | 3.00E-11 | >1E-8 | |
| Y38 | 83 HGSHDN | 246 | ......THPSIT | 5.08E-04 | 5.50E-11 | 2.60E-09 | |
| Y45 | 83 HGSHDN | 247 | ......TDPAIV | 6.17E-04 | 4.00E-11 | 4.30E-09 | |
| Y61 | 83 HGSHDN | 248 | ......THPALL | 2.75 e-4 | 4E-11 | 1.40E-10 | |
| Y61 IgG | 83 HGSHDN | 248 | ......THPALL | 1.50E-04 | 1.60E-11 | 1.30E-10 | |
| Y61 IgG germline | 83 HGSHDN | 248 | ......THPALL | 1.50E-04 | 1.60E-11 | 1.30E-10 | 1.60E-10 |
| Y139 | 83 HGSHDN | 249 | ......SHPALT | 5.92E-04 | 3E-11 | 4.50E-10 | |
| Y139 IgG1 | 83 HGSHDN | 249 | ......SHPALT | | | 1.00E-09 | |
| Y174 | 83 HGSHDN | 250 | ......TTPAPE | 7.55E-04 | 6E-11 | 2.00E-09 | |
| Y177 | 83 HGSHDN | 251 | ......SHPTLI | 6.61E-04 | 5E-11 | 1.00E-09 | |
| A5 | 83 HGSHDN | 252 | ......THPSML | 4.50E-04 | 6.60E-11 | | |
| A12 | 83 HGSHDN | 253 | ......TTPRPM | 5.57E-04 | 2.50E-10 | | |
| D9 | 83 HGSHDN | 254 | ......RLPAQT | 8.21E-04 | 3.5E-09 | >> | |

TABLE 2-continued

| Clone | H3 SEQ ID NO:H3 | L3 SEQ ID NO:L3 | koff | RB assay IC50 (M) | PHA assay IC50 (M) | IFN gamma IC50 (M) |
|---|---|---|---|---|---|---|
| G6 | 83 HGSHDN | 255......THPLTI 5.08E-04 | | 1E-10 | 1.00E-09 | |
| G6 IgG1 | 83 HGSHDN | 255......THPLTI | | | 1.00E-09 | |
| C6 | 83 HGSHDN | 256 QSYDRGQTPSIT 1.07E-03 | | 3.5E-10 | 1.00E-08 | |
| Y55 | 83 HGSHDN | 257 QSYDRGTHFQMY 1.06E-03 | | 1.40E-10 | >1E-8 | |
| A4 | 83 HGSHDN | 258 QSYDRGRNPALT 6.30E-04 | | 2.50E-10 | | |
| AO3 | 83 HGSHDN | 259 QSYDRGTHPLTM 3.04E-04 | | 3.00E-11 | 4.00E-10 | |
| AO3 IgG1 | 83 HGSHDN | 260 QSYDRGTHPLTM 3.04 e-4 | | 2.90E-11 | 3.80E-10 | |
| A03 IgG germline | 83 HGSHDN | 260 QSYDRGTHPLTM 2.50E-04 | | 3.50E-11 | 1.75E-10 | |
| 99-B11 | 83 HGSHDN | 261 QSYDSGYTGSRV 5.40E-03 | | | | |
| 99-C11 | 83 HGSHDN | 262 QSYDSGFTGSRV 5.70E-03 | | | | |
| 99-H4 | 83 HGSHDN | 263 QSYDSRFTGSRV 4.80E-03 | | | | |
| 99-E9 | 83 HGSHDN | 262 QSYDSGFTGSRV 5.40E-03 | | | | |
| 99-H7 | 83 HGSHDN | 264 QSYPDGTPASRV 3.30E-03 | | | | |
| 99-H11 | 83 HGSHDN | 265 QSYSTHMPISRV 4.90E-03 | | | | |
| 99-F6 | 83 HGSHDN | 266 QSYDSGSTGSRV 4.90E-03 | | | | |
| 99-F7 | 83 HGSHDN | 267 QSYPNSYPISRV 4.80E-03 | | | | |
| 99-F8 | 83 HGSHDN | 268 QSYIRAPQQV 3.70E-03 | | | | |
| 99-F11 | 83 HGSHDN | 262 QSYDSGFTGSRV 5.40E-03 | | | | |
| 99-G7 | 83 HGSHDN | 269 QSYLKSRAFSRV 4.80E-03 | | | | |
| 99-G11 | 83 HGSHDN | 270 QSYDSRFTGSRV 4.30E-03 | | | | |
| | | 124 QSYDRGFTGSRV | | | | |
| L3.3R3M-B1 | 83 HGSHDN | 271......FTGSMV 5.46E + 00 | | | | |
| L3.3R3M-B3 | 83 HGSHDN | 272......FTGSMV 5.51E + 00 | | | | |
| L3.3R3M-C6 | 83 HGSHDN | 273......FTGFDG 6.17E + 00 | | | | |
| L3.3R3M-F9 | 83 HGSHDN | 274......TAPALS 4.99E + 00 | | | | |
| L3.3R3M-G8 | 83 HGSHDN | 275......SYPALR 5.55E + 00 | | | | |
| L3.3R3M-H6 | 83 HGSHDN | 276......NWPNSN 5.69E + 00 | | | | |
| L3.3R3M-H10 | 83 HGSHDN | 277......TAPSLL 5.35E + 00 | | | | |
| L3.3R3M-A3 | 83 HGSHDN | 278......FTGSMV 5.37E + 00 | | | | |
| L3.3R3M-F8 | 83 HGSHDN | 279......TTPRIR 4.99E + 00 | | | | |
| L3.3R3M-G1 | 83 HGSHDN | 280......FTGSMV 4.21E + 00 | | | | |
| L3.3R3M-G7 | 83 HGSHDN | 281......FTGSMV 4.24E + 00 | | | | |
| L3.3R3M-H11 | 83 HGSHDN | 282......MIPALT 3.95E + 00 | | | | |
| Y61-L94N | 109 CKT HGSHDN | 283 QSYDRNTHPALL | | | 8.00E-11 | |
| Y61-L94F | 109 CKT HGSHDN | 284 QSYDRFTHPALL | | | 6.00E-11 | |
| Y61-L94Y | 109 CKT HGSHDN | 285 QSYDRYTHPALL | | 2.00E-11 | 2.00E-11 | |
| Y61-L94Y IgG | 109 CKT HGSHDN | 285 QSYDRYTHPALL 1.27E-04 | | 6.00E-11 | 5.00E-11 | 4.00E-11 |

TABLE 2-continued

| Clone | H3 SEQ ID NO:H3 | L3 SEQ ID NO:L3 | koff | RB assay IC50 (M) | PHA assay IC50 (M) | IFN gamma IC50 (M) |
|---|---|---|---|---|---|---|
| Y61-L50Y | 109 CKT HGSHDN | 286 QSYDRGTHPALL | | 2.00E-11 | | 2.00E-11 |
| Y61-L50Y* IgG | 109 CKT HGSHDN | 286 QSYDRGTHPALL | 6.98E-05 | | 2.00E-11 | 3.00E-11 |
| Y61-L50Y-H31E** IgG | 109 CKT HGSHDN | 286 QSYDRGTHPALL | 2.99E-05 | | 6.00E-11 | 2.00E-11 |
| Y61-L50Y-H31E-L94Y** IgG | 109 CKT HGSHDN | 287 QSYDRYTHPALL | 4.64E-05 | | 1.00E-11 | 1.00E-11 |
| J695 (Y61-L94Y-L50Y IgG*) | 109 CKT HGSHDN | 287 QSYDRYTHPALL | 5.14E-05 | 5.00E-11 | 1.00E-11 | 5.00E-12 |

*CDR L2: L50G to Y
**CDR L2: L50G to Y; CDR H1: H31S to E

TABLE 3

|  | CDR H1 | CDR H2 | CDR H3 |
|---|---|---|---|
| Kabat Number | 2 2 2 3 3 3 3 3<br>7 8 9 0 1 2 3 4 5 | 5<br>5 5 2 5 5 5 5 5 5 6 6 6 6 6 6<br>0 1 2 A 3 4 5 6 7 8 9 0 1 2 3 4 | 1 1<br>9 9 9 9 0 0<br>5 6 7 8 1 2 |
| Y61 VH | F T F S S Y G M H | F I R Y D G S N K Y Y A D S V K | G H S H D N |
| Contact Positions | x x x x | x x x x x x x | x x x x x |
| Hypermutation Positions | x x x | x | x x | |

|  | CDR L1 | CDR L2 | CDR L3 |
|---|---|---|---|
| Kabat number | 2 2<br>2 2 2 2 7 7 2 2 3 3 3 3 3<br>4 5 6 7 A B 8 9 0 1 2 3 4 | 5 5 5 5 5 5 5<br>0 1 2 3 4 5 6 | 9 9 9<br>8 9 9 9 9 9 9 5 5 5 9 9<br>9 0 1 2 3 4 5 A B C 6 7 |
| Y61 VL | S G G R S N I G S N T V | K G N D Q R P | S Q S Y D R G T H P A L L |
| Contact Positions | x x x | x x x x x | x x x x x x |
| Hypermutation Positions | x x x | x | x | x contact and/or hypermutation position
x contact and/or hypermutation position mutated in Y61

TABLE 4

Neutralization Activity in the Presence of Excess Free IL-12 p40

| SEQ ID NO: | Clone | PHA assay IC50 (M) p70:p40 1:0 | PHA assay IC50 (M) p70:p40 1:20 | PHA assay IC50 (M) p70:p40 1:50 |
|---|---|---|---|---|
| VH: 47 VL: 48 | 136-15 | 2.00E-09 | 5.00E-09 | 4.00E-09 |
| VH: 51 VL: 52 | 149-5 | 6.50E-09 | 7.00E-09 | 4.00E-09 |
| VH: 53 VL: 54 | 149-6 | 9.00E-10 | 1.00E-09 | 1.00E-09 |
| VH: 84 VL: 126 | 149-7 | 3.50E-09 | 2.50E-09 | 4.00E-09 |
| VH: 23 VL: 24 | Y61 IgG | 1.80E-10 | | 1.80E-10 |
| VH: 65 VL: 66 | AO3 IgG1 | 2.50E-10 | | 2.20E-10 |
| VH: 31 VL: 32 | J695 | 1.00E-11 | | 3.50E-11 |

EXAMPLES

Example 1

Isolation of Anti-IL-12 Antibodies

A. Screening for IL-12 Binding Antibodies

Antibodies to hIL-12 were isolated by screening three separate scFv phage display libraries prepared using human VL and VH cDNAs from mRNA derived from human tonsils (referred to as scFv 1), tonsil and peripheral blood lymphocytes (PBL) (referred to as scFv 2), and bone marrow-derived lymphocytes (referred to as BMDL). Construction of the library and methods for selection are described in Vaughan et al. (1996) Nature Biotech. 14: 309-314.

The libraries were screened using the antigens, human IL-12 p70 subunit, human IL-12 p40 subunit, chimaeric IL-12 (mouse p40/human p35), mouse IL-12, biotinylated human IL-12 and biotinylated chimaeric IL-12. IL-12 specific antibodies were selected by coating the antigen onto immunotubes using standard procedures (Marks et al., (1991) J. Mol. Biol. 222: 581-597). The scFv library 2 was screened using either IL-12, or biotinylated-IL-12, and generated a significant number of IL-12 specific binders. Five different clonotypes were selected, determined by BstN1 enzymatic digestion patterns, and confirmed by DNA sequencing. The main clonotypes were VHDP58NLDPL11, VHDP77NLDPK31, VHDP47NL and VHDP77NLDPK31, all of which recognized the p40 subunit of IL-12.

Screening of the BMDL library with IL-12 p70 generated 3 different clonotypes. Two of these were found to be cross-reactive clones. The dominant clone was sequenced and consisted of VHDP35NLDP. This clone recognizes the p40 subunit of IL-12. Screening of the scFv library 1, using IL-12 p70, did not produce specific IL-12 antibodies.

In order to identify IL-12 antibodies which preferentially bind to the p70 heterodimer or the p35 subunit of IL-12, rather than the p40 subunit, the combined scFv 1+2 library, and the BMDL library were used. To select IL-12 antibodies that recognized the p70 heterodimer or p35 subunit, phage libraries were preincubated and selected in the presence of free p40. Sequencing of isolated clones revealed 9 different antibody lineages. Subunit preferences were further analyzed by 'micro-Friguet' titration. The supernatant containing scFv was titrated on biotin-captured IL-12 in an ELISA and the $ED_{50}$ determined. The concentration of scFv producing 50% ED was preincubated with increasing concentrations of free p70 or p40 (inhibitors). A decrease in the ELISA signal on biotin-IL-12 coated plates was measured and plotted against the concentration of free p70 or p40. This provided the $IC_{50}$ for each clone with respect to p70 and p40. If the titrations for both subunits overlaps, then the scFv binds to both p40 and p70. Any variation from this gives the degree of preference of p70 over p40.

B. Affinity Maturation of Antibody Lineage Specific for IL-12 (Joe 9)

The clones were tested for their ability to inhibit IL-12 binding to its receptor in an IL-12 receptor binding assay (referred to as RBA), and for their ability to inhibit IL-12 induced proliferation of PHA stimulated human blast cells (PHA assay), described in Example 3. Clone Joe 9 had the lowest $IC_{50}$ value in both the RBA and the PHA assay, with an $IC_{50}$ value of $1 \times 10^{-6}$ M in both assays. In addition the heavy chain variable region (VH) of Joe 9 had the least number of changes compared to the closest germline sequence COS-3, identified from the VBASE database. Table 1 (see Appendix A) shows the $V_H3$ family of germline sequences, of which COS-3 is a member, as well as members of $V_\lambda 1$ family of germline sequences. Therefore, Joe 9 was selected for affinity maturation. The amino acids sequences of VH and VL of the Joe9 wild type (Joe9 wt) antibody are shown in FIG. 1A-1D.

In order to increase the affinity of Joe 9, various mutations of the complementarity determining region 3 (CDR3) of both the heavy and light chains were made. The CDR3 variants were created by site-directed PCR mutagenesis using degenerate oligonucleotides specific for either the heavy chain CDR3 (referred to as "H3") or the light chain CDR3 (referred to as "L3"), with an average of three base substitutions in each CDR3 (referred to as "spike"). PCR mutagenesis of the heavy chain CDR3 was performed using the degenerate heavy chain oligonucleotide containing a random mixture of all four nucleotides, 5'TGTCCCTTGGCCCCA(G)(T)(A)(G)(T)(C)(A)(T)(A)(G)(C)(T)(C)(C)(C)(A)(C)(T) GGTCGTACAG-TAATA 3' (SEQ ID NO: 580), and oligonucleotide pUC Reverse Tag GAC ACC TCG ATC AGC GGA TAA CAA TTTCAC ACA GG (SEQ ID NO: 581) to generate a repertoire of heavy chain CDR3 mutants. The parent light chain was amplified using Joe 9 reverse oligonucleotide (5'TGG GGC CAA GGG ACA3' (SEQ ID NO:582) and the fdteteseq 24+21 oligonucleotide (5'-ATT CGT CCT ATA CCG TTC TAC TFT GTC GTC TTT CCA GAC GTT AGT-3' (SEQ ID NO: 583).

Complementarity between the two PCR products was used to drive annealing of the two fragments in a PCR assembly reaction and the full length recombined scFv library was amplified with pUC Reverse Tag (SEQ ID NO: 581) and fdTag 5'-ATT CGT CCT ATA CCG TTC-3' (SEQ ID NO: 584). PCR mutagenesis of the light chain was performed using the light chain oligonucleotide containing a mixture of all four nucleotides 5'GGTCCCAGTTCCGAAGACCCTC-GAACC(C)(C)(T)(C)(A)(G)(G)(C)(T) (G)(C)(T)(G)(T)(C) ATATGACTGGCAGTAATAGTCAGC 3' (SEQ ID NO: 585), and Joe 9 reverse oligonucleotide 5'TGG GGC CAA GGG ACA3' (SEQ ID NO: 586) to produce a repertoire of light chain CDR3 mutants. The parent heavy chain was amplified with pUC Reverse Tag (SEQ ID NO: 581) and HuJH3FOR oligonucleotide 5'TGAAGAGACGGTGAC-CATTGTCCC3' (SEQ ID NO: 587). Complementarity between the two PCR products was used to drive annealing of the two fragments in a PCR assembly reaction and the full length recombined scFv library was amplified with Reverse Tag GAC ACC TCG ATC AGC G (SEQ ID NO: 588) and HuJλ 2-3 FOR NOT oligonucleotide 5'GAG TCA TTC TCG ACT TGC GGC CGC ACC TAG GAC GGT CAG CTT GGT CCC 3' (SEQ ID NO: 589).

Heavy chain CDR3 mutants were selected using 1 nM biotinylated IL-12, and washed for 1 h at room temperature in PBS containing free IL-12 or p40 at a concentration of 7 nM. Clones were analyzed by phage ELISA and those that bound to IL-12 were tested in BIAcore kinetic binding studies using a low density IL-12 chip (see procedure for BIAcore analysis in Example 5). Generally, BIAcore analysis measures real-time binding interactions between ligand (recombinant human IL-12 immobilized on a biosensor matrix) and analyte (antibodies in solution) by surface plasmon resonance (SPR) using the BIAcore system (Pharmacia Biosensor, Piscataway, N.J.). The system utilizes the optical properties of SPR to detect alterations in protein concentrations within a dextran biosensor matrix. Proteins are covalently bound to the dextran matrix at known concentrations. Antibodies are injected through the dextran matrix and specific binding between injected antibodies and immobilized ligand results in an increased matrix protein concentration and resultant change in the SPR signal. These changes in SPR signal are recorded as resonance units (RU) and are displayed with respect to time along the y-axis of a sensorgram. To determine the off rate ($k_{off}$), on rate ($k_{on}$), association rate (Ka) and dissociation rate (Kd) constants, BIAcore kinetic evaluation software (version 2.1) was used. Clones that demonstrated an improvement in the $k_{off}$ rate were analyzed by neutralization assays which included inhibition by antibody of IL-12 binding to its receptor (RBA assay), inhibition of IL-12-induced proliferation in PHA stimulated human blast cells (PHA assay), and inhibition of IL-12-induced interferon gamma production by human blast cells (IFN gamma assay). A summary of the dissociation rates and/or $IC_{50}$ values from neutralization assays of heavy chain CDR3 spiked clones 70-1 through 70-13 is presented in Table 2 (see Appendix A). Clone 70-1 displayed a $k_{off}$ rate that was better than the parent Joe 9 clone, and had the lowest $IC_{50}$ value of $2.0 \times 10^{-7}$ M. Therefore clone 70-1 was selected for conversion to complete IgG1.

Light chain CDR3 mutants were selected using 1 nM biotin-IL-12 and washed with PBS containing 7 nM free p40. Clones were screened in phage ELISA and those that bound to IL-12 were tested in BIAcore binding analysis using low density IL-12 chips. Clones that displayed an off rate which was better than the parent Joe 9 clone were tested in neutralization assays which measured either, inhibition of IL-12 receptor binding, or inhibition of PHA blast cell proliferation. A summary of the dissociation rates and/or $IC_{50}$ values from neutralization assays of light chain CDR3 mutant clones, 78-34 through 79-1, is presented in Table 2 (see Appendix A).

Based on the $k_{off}$ rate, clones 78-34 and 78-35 displayed an improved $k_{off}$ rate compared to the parent Joe 9. Both of these clones were selected for combination analysis with heavy chain mutants.

C. Combination Clones

Mutant light and heavy chain clones that exhibited the best binding characteristics were used for combination and assembly of scFvs. Mutant clones with improved potency characteristics were combined by PCR overlap extension and pull-through of the mutated VH and VL segments as described above. Clones 101-14 through 26-1, shown in Table 2 (see Appendix A), were produced from the combination of heavy chain mutants (70-2, 70-13 and 70-1) with light chain mutants (78-34, 78-35 and 79-1). The $k_{off}$ rates and/or $IC_{50}$ values from neutralization assays for these clones are presented in Table 2.

BIAcore binding analysis identified clone 101-11, produced from the combination of the heavy chain CDR3 mutant clone 70-1 with the light chain CDR3 mutant clone 78-34, as having an off rate of 0.0045 $^s$-1. This $k_{off}$ rate was a significant improvement compared to the $k_{off}$ rates for either the heavy chain CDR3 mutant clone 70-1 (0.0134 $^s$-1), or for the light chain CDR3 mutant clone 78-34 (0.0164 $^s$-1) alone. Furthermore, clone 101-11 showed a significant improvement in neutralization assays. Accordingly, clone 101-11 was selected for affinity maturation as described below.

D. Affinity Maturation of Clone 101-11

Further affinity maturation of clone 101-11 consisted of repeat cycles of PCR mutagenesis of both the heavy and light chain CDR3s of 101-11 using spiked oligonucleotide primers. The clones were selected with decreasing concentrations of biotinylated IL-12 (bio-IL-12). The binding characteristics of the mutated clones was assessed by BIAcore binding analysis and RBA, PHA neutralization assays. The $k_{off}$ rates and/or $IC_{50}$ values for clones 136-9 through 170-25 are presented in Table 2 (see Appendix A). Clone 103-14 demonstrated an improved $IC_{50}$ value in both the receptor binding assay and the PHA blast assay. Clone 103-14 also demonstrated a low $k_{off}$ rate, and accordingly was selected for further affinity maturation.

E. Generation and Selection of Randomized Libraries of Clone 103-14 Light CDR3

The light chain CDR3 of clone 103-14 (QSYDRG-FTGSMV (SEQ ID NO: 590)) was systematically randomized in 3 segments using 3 different libraries as outlined below, where X is encoded by a randomized codon of sequence NNS with N being any nucleotide and S being either deoxycytosine or deoxyguanidine.

```
                                        (SEQ ID NO: 591)
        L3.1 = XXXXXXFTGSMV (SEQ ID NO: 592)
        L3.2 = QSYXXXXXXSMV (SEQ ID NO: 593)
        L3.3 = QSYDRGXXXXXX
```

Randomized mutagenesis of all three light chain CDRs (referred to as L3.1, L3.2, and L3.3) of clone 103-14 was performed. The heavy chain CDR3 (referred to as H3) of clone 103-14 was not mutated. Four randomized libraries based on clone 103-14 (H3 and L3.1, L3.2 & L3.3) were constructed and subjected to a large variety of selection conditions that involved using limiting antigen concentration and the presence or absence of excess free antigen (p40 and p70). The outputs from selections (clones 73-B1 through 99-G11) were screened primarily by BIAcore, and on occasion with RBA and are shown in Table 2 (see Appendix A).

Random mutagenesis of the light chain CDR of 103-14 generated clone Y61, which exhibited a significant improvement in $IC_{50}$ value compared to the parent clone 103-14. Y61 was selected for conversion to a whole IgG1. Whole Y61-IgG1 has an $IC_{50}$ value of approximately 130 pM determined by the PHA assay. The $IC_{50}$ value was not affected by a 50 fold molar excess of free p40, demonstrating that free p40 did not cross-react with Y61 anti-IL-12 antibody to thereby decrease the antibody binding to the heterodimer. The full length sequences of Y61 heavy chain variable region and light chain variable region are shown below.

Y61 Heavy Chain Variable Region Peptide Sequence

```
                                        (SEQ ID NO: 23)
                         CDR H1
    QVQLVESGGGVVQPGRSLRLSCAASFTFS SYGMH WVRQAPGK

CDR H2
    GLEWVAFIRYDGSNKYYADSVKG RFTISRDNSKNTLYLQMNSL

CDR H3
    RAEDTAVYYCKTHGSHDN WGQGTMVTVSS
```

Y61 Light Chain Variable Region Peptide Sequence

```
                                        (SEQ ID NO: 24)
                         CDR L1
    QSVLTQPPSVSGAPGQRVTISC SGGRSNIGSNTVK WYQQLPGTAPKLLI

CDR L2                                       CDR L3
    YGNDQRPS GVPDRFSGSKSGTSASLAITGLQAEDEADYYCQSYDRGTHPA

LL FGTGTKVTVLG
```

CDR residues are assigned according to the Kabat definitions.

Example 2

Mutation of Y61 at Hypermutation and Contact Positions

Typically selection of recombinant antibodies with improved affinities can be carried out using phage display methods. This is accomplished by randomly mutating combinations of CDR residues to generate large libraries containing single-chain antibodies of different sequences. Typically, antibodies with improved affinities are selected based on their ability to reach an equilibrium in an antibody-antigen reaction. However, when Y61 scFV was expressed on phage surface and incubated with IL-12, selection conditions could not be found that would allow the system to reach normal antibody-antigen equilibrium. The scFV-phage remained bound to IL-12, presumably due to a non-specific interaction, since purified Y61 scFv exhibits normal dissociation kinetics. Since the usual methods of phage-display affinity maturation to Y61 (i.e. library generation and selections by mutagenesis of multiple CDR residues) could not be utilized, a new strategy was developed in which individual CDR positions were mutated.

This strategy involves selection of appropriate CDR positions for mutation and is based on identification and selection of amino acids that are preferred selective mutagenesis positions, contact positions, and/or hypermutation positions. Contact positions are defined as residues that have a high probability of contact with an antigen when the antigen interacts with the antibody, while hypermutation positions are defined as residues considered to have a high probability for somatic hypermutation during in vivo affinity maturation of the antibody. Preferred selective mutagenesis positions are CDR positions that are both contact and hypermutation positions. The Y61 antibody was already optimized in the CDR3 regions using the procedure described in Example 1, therefore it was difficult to further improve the area which lies at the center of the antibody binding site using phage-display selection methods. Greater improvements in activity were obtained by mutation of potential contact positions outside the CDR3 regions by either removing a detrimental antigen-antibody contact or, engineering a new contact.

Amino acids residues of Y61 which were considered contact points with antigen, and those CDR positions which are sites of somatic hypermutations during in vivo affinity maturation, are shown in Table 3 (see Appendix A). For Y61 affinity maturation, 15 residues outside CDR3, 3 residues within the L3 loop, and 5 residues in the H3 loop were selected for PCR mutagenesis.

Y61 scFv gene was cloned into the pUC119(Sfi) plasmid vector for mutagenesis. Oligonucleotides were designed and synthesized with randomized codons to mutate each selected position. Following PCR mutagenesis, a small number of clones (~24) were sequenced and expressed in a host cell, for example, in a bacterial, yeast or mammalian host cell. The expressed antibody was purified and the $k_{off}$ measured using the BIAcore system. Clones with improved off-rates, as compared to Y61, were then tested in neutralization assays. This procedure was repeated for other CDR positions. Individual mutations shown to have improved neutralization activity were combined to generate an antibody with even greater neutralization potency.

The Y61 CDR positions that were mutated in order to improve neutralization potency, and the respective amino-acid substitutions at each position are shown in FIGS. 2A-2H. Off-rates, as determined by BIAcore analysis, are given. These off rates are also shown in the histograms to the right of each table.

Results of these substitutions at positions H30, H32, H33, H50, H53, H54, H58, H95, H97, H101, L50, L92, L93, demonstrated that all amino-acid substitutions examined resulted in antibodies with poorer off-rates than Y61. At positions H52, L32, and L50, only a one amino acid substitution was found to improve the off-rate of Y61, all other changes adversely affected activity. For L50, this single Gly-Tyr change significantly (5-10 times) improved the neutralization potency of Y61. The results demonstrated the importance of these positions to Y61 activity, and suggest that in most cases phage-display was able to select for the optimal residues. However, at positions H31, H56, L30, and L94, several substitutions were found to improve Y61 off-rate, suggesting that these positions were also important for antigen binding, although the phage display approach did not allow selection of the optimal residues.

Selective mutation of contact and hypermutation positions of Y61 identified amino acid residue L50 in the light chain CDR2, and residue L94 of the light chain CDR3, which improved the neutralization ability of Y61. A combination of these mutations produced an additive effect, generating an antibody, J695, that exhibited a significant increase in neutralization ability. The full length sequence of J695 heavy and light chain variable region sequences is shown below.

J695 Heavy Chain Variable Region Peptide Sequence

```
                                    (SEQ ID NO: 31)
                       CDR H1
QVQLVESGGGVVQPGRSLRLSCAASGFTFS SYGMH WVRQAPGK
         CDR H2
GLEWVAFIRYDGSNKYYADSVKG RFTISRDNSKNTLYLQMNSLR
         CDR H3
AEDTAVYYCKTHGSHDN WGQGTMVTVSS
```

J695 Light Chain Variable Region Peptide Sequence

```
                                    (SEQ ID NO: 32)
                    CDR L1
QSVLTQPPSVSGAPGQRVTISC SGSRSNIGSNTVK WYQQLPGTA
         CDR L2
PKLLIYYNDQRPS GVPDRFSGSKSGTSASLAITGLQAEDEADYYC
 CDR L3
 QSYDRYTHPALL FGTGTKVTVLG
```

CDR residues are assigned according to the Kabat definitions.

A summary of the heavy and light chain variable region sequence alignments showing the lineage development of clones that were on the path from Joe9 to J695 is shown in FIGS. 1A-1D. The CDRs and residue numbering are according to Kabat.

Example 3

Functional Activity of Anti-hIL-12 Antibodies

To examine the functional activity of the human anti-human IL-12 antibodies of the invention, the antibodies were used in several assays that measure the ability of an antibody to inhibit IL-12 activity.

A. Preparation of Human PHA-Activated Lymphoblasts

Human peripheral blood mononuclear cells (PBMC) were isolated from a leukopac collected from a healthy donor by Ficoll-Hypaque gradient centrifugation for 45 minutes at 1500 rpm as described in Current Protocols in Immunology, Unit 7.1. PBMC at the interface of the aqueous blood solution and the lymphocyte separation medium were collected and washed three times with phosphate-buffered saline (PBS) by centrifugation for 15 minutes at 1500 rpm to remove Ficoll-Paque particles.

The PBMC were then activated to form lymphoblasts as described in Current Protocols in Immunology, Unit 6.16. The washed PBMC were resuspended at $0.5–1 \times 10^6$ cells/ml in RPMI complete medium (RPMI 1640 medium, 10% fetal bovine serum (FBS), 100 U/ml penicillin, 100 µg/ml streptomycin), supplemented with 0.2% (v/v) PHA-P (Difco, Detroit, Mich.) and cultured for four days at 37° C. in a 5% $CO_2$ atmosphere. After four days, cell cultures were split 1:1 by volume in RPMI complete medium, plus 0.2% (v/v) PHA-P and 50 U/ml recombinant human IL-2. Recombinant human IL-2 was produced by transfection of an expression vector carrying the human IL-2 cDNA into COS cells (see Kaufman et al., (1991) *Nucleic Acids Res.* 19, 4484-4490), and purified as described in PCT/US96/01382. Cell cultures were then incubated for an additional one to three days. PHA blast cells were harvested, washed twice with RPMI complete medium and frozen in 95% FBS, 5% DMSO at $10 \times 10^6$ cells/ml.

PHA blast cells to be used for the IL-12 receptor binding assay (see section B) were collected after one day culture in the presence of IL-2, whereas PHA blast cells to be used for the PHA blast proliferation assay (see section C) and the interferon-gamma induction assay (see section D) were collected after three day culture in the presence of IL-2.

B. IL-12 Receptor Binding Assay

The ability of anti-IL-12 antibodies to inhibit binding of radiolabelled IL-12 to IL-12 receptors on PHA blasts were analyzed as follows. Various concentrations of anti-IL-12 antibody were preincubated for 1 hour at 37° C. with 50-100 pM $^{125}$I-hIL-12 (iodinated hIL-12 was prepared using the Bolton-Hunter labeling method to a specific activity of 20-40mCi/mg from NEN-Dupont) in binding buffer (RPMI 1640, 5% FBS, 25 mM Hepes pH 7.4). PHA blast cells isolated as described above, were washed once and resuspended in binding buffer to a cell density of $2 \times 10^7$ cells/ml. PHA blasts ($1 \times 10^6$ cells) were added to the antibody $^{125}$I-hIL-12 mixture and incubated for two hours at room temperature. Cell bound radioactivity was separated from free $^{125}$I-hIL-12 by centrifugation of the assay mixture for 30 seconds at room temperature, aspiration of the liquid and a wash with 0.1 ml binding buffer, followed by centrifugation at 4° C. for 4 min at 10,000×g. The cell pellet was examined for cell bound radioactivity using a gamma counter. Total binding was determined in the absence of antibody and non-specific binding was determined by inclusion of 25 nM unlabeled IL-12 in the assay. Incubations were carried out in duplicate.

In the IL-12 receptor binding assay using the Y61 and J695 human anti-IL-12 antibodies, both antibodies demonstrated a comparable inhibition of IL-12 receptor binding. Y61 inhibited IL-12 receptor binding with an $IC_{50}$ value of approximately $1.6 \times 10^{-11}$M, while J695 had an $IC_{50}$ value of approximately $1.1 \times 10^{-11}$M.

C. Human PHA Blast Proliferation Assay

Anti-IL-12 antibodies were evaluated for their ability to inhibit PHA blast proliferation (which proliferation is stimulated by IL-12). Serial dilutions of anti-IL-12 antibody were preincubated for 1 hour at 37° C., 5% $CO_2$ with 230 pg/ml hIL-12 in 100 ml RPMI complete medium in a microtiter plate (U-bottom, 96-well, Costar, Cambridge, Mass.). PHA blast cells isolated as described above, were washed once and resuspended in RPMI complete medium to a cell density of $3 \times 10^5$ cells/ml. PHA blasts (100 ml, $3 \times 10^4$ cells) were added to the antibody/hIL-12 mixture, incubated for 3 days at 37° C., 5% $CO_2$ and labeled for 4-6 hours with 0.5 mCi/well (3H)-Thymidine (Amersham, Arlington Heights, Ill.). The culture contents were harvested onto glass fiber filters by means of a cell harvester (Tomtec, Orange, Conn.) and ($^3$H)-Thymidine incorporation into cellular DNA was measured by liquid scintillation counting. All samples were assayed in duplicate.

The results of neutralization in the presence of varying concentrations of p70:p40 (i.e. the ratio of IL-12 heterodimer to free p40 subunit) is shown in Table 4 (see Appendix A).

Analysis of the Y61 human anti-IL-12 antibody in the PHA blast proliferation assay demonstrated that the antibody inhibited PHA blast proliferation with an $IC_{50}$ value of approximately $1.8 \times 10^{-10}$ M in the presence of IL-12 p70 alone, without any excess p40 (p70:p40 ratio of 1:0). In the presence of a 50-fold excess of free p40 (p70:p40 at a ratio of 1:50), the Y61 antibody inhibited PHA blast proliferation with an $IC_{50}$ value of approximately $1.8 \times 10^{-10}$M. This result demonstrates that the ability of Y61 to inhibit blast proliferation is not compromised by the presence of excess p40.

The human anti-IL-12 antibody, J695 inhibited PHA blast proliferation with an $IC_{50}$ value of approximately $1.0 \times 10^-$$_{11}$M in the presence of p70:p40 at a ratio of 1:0. In the presence of a p70:p40 ratio of 1:50, this antibody inhibited PHA blast proliferation with an $IC_{50}$ value of approximately $5.8 + 2.8 \times 10^{-12}$ M (n=2), demonstrating that the excess p40 had only a slight inhibitory effect on the antibody. Overall results demonstrate the improved neutralization activity of J695 in comparison with Y61 due to the mutations at L50 and L94.

D. Interferon-Gamma Induction Assay

The ability of anti-IL-12 antibodies to inhibit the production of IFNγ by PHA blasts (which production is stimulated by IL-12) was analyzed as follows. Various concentrations of anti-IL-12 antibody were preincubated for 1 hour at 37° C., 5% $CO_2$ with 200-400 pg/ml hIL-12 in 100 ml RPMI complete medium in a microtiter plate (U-bottom, 96-well, Costar). PHA blast cells isolated as described above, were washed once and resuspended in RPMI complete medium to a cell density of $1 \times 10^7$ cells/ml. PHA blasts (100 μl of $1 \times 10^6$ cells) were added to the antibody/hIL-12 mixture and incubated for 18 hours at 37° C. and 5% $CO_2$. After incubation, 150 μl of cell free supernatant was withdrawn from each well and the level of human IFNγ produced was measured by ELISA (Endogen Interferon gamma ELISA, Endogen, Cambridge, Mass.). Each supernatant was assayed in duplicate.

Analysis of human anti-hIL-12 antibody, Y61 in this assay demonstrated that Y61 inhibited human IFNγ production with an $IC_{50}$ value of approximately $1.6 \times 10^{-10}$M, while the human anti-IL-12 antibody, J695, inhibited human IFNγ production with an $IC_{50}$ value of approximately $5.0 \pm 2.3 \times 10^{-12}$M (n=3). The result demonstrates the substantial improvement in the affinity of J695 as a result of the modifications at L50 and L94.

E. Induction of Non-Human IL-12 from Isolated PBMC

To examine the cross-reactivity of the human anti-hIL-12 antibodies with IL-12 from other species, non-human IL-12 was produced as follows. PBMC were separated from fresh heparinized blood by density gradient centrifugation as described above using lymphoprep (Nycomed, Oslo, Norway) for cynomolgus monkey, baboon, and dog, PBMC, Accu-paque (Accurate Chemical & Sci. Corp., Westbury, N.Y.) for dog PBMC or Lympholyte-rat (Accurate Chemical & Sci. Corp., Westbury, N.Y.) for rat PBMC.

The PBMC were then induced to produce IL-12 as described (D'Andrea et al., (1992) *J. Exp. Med.* 176, 1387-1398, Villinger et al., (1995) *J. Immunol.* 155, 3946-3954, Buettner et al., (1998) *Cytokine* 10, 241-248). The washed PBMC were resuspended at $1 \times 10^6$ cells/ml in RPMI complete medium, supplemented with 0.0075% (wt/vol) of SAC (Pansorbin; Calbiochem-Behring Co., La Jolla, Calif.) or 1-5 mg/ml ConA (Sigma Chemical Co., St. Louis, Mo.) plus 0.0075% SAC and incubated for 18 hours at 37° C. in a 5% $CO_2$ atmosphere. Cell-free and SAC-free medium was collected by centrifugation and filtering through 0.2 mm filters.

IL-12 from the rhesus monkey was obtained as recombinant rhesus IL-12 from Emory University. School of Medicine, Atlanta, Ga.

F. Murine 2D6 Cell Proliferation Assay

The murine T cell clone 2D6 proliferates in response to murine IL-2, IL-4, IL-7 and IL-12 (Maruo et al., (1997) *J. Leukocyte Biol.* 61, 346-352). A significant proliferation was also detected in response to rat PBMC supernatants containing rat IL-12. The cells do not respond to dog, cynomolgus, baboon or human IL-12. Murine 2D6 cells were propagated in RPMI complete medium supplemented with 50 mM beta-mercaptoethanol (βME) and 30 ng/ml murine IL-12. One day prior to the assay, the murine IL-12 was washed out and the cells were incubated overnight in RPMI complete medium plus βME.

Serial dilutions of anti-IL-12 antibody were preincubated for 1 hour at 37° C., 5% $CO_2$ with 40 pg/ml murine IL-12 in 100 ml RPMI complete medium plus 13ME in a microtiter plate (U-bottom, 96-well, Costar). 2D6 cells were washed once and resuspended in RPMI complete medium containing βME to a cell density of $1 \times 10^5$ cells/ml. 2D6 cells (100 μl, $1 \times 10^4$ cells) were added to the antibody/hIL-12 mixture, incubated for 3 days at 37° C., 5% $CO_2$ and labeled for 4-6 hours with 0.5 mCi/well (3H)-Thymidine. The culture contents were harvested and counted by liquid scintillation counting. All samples were assayed in duplicate.

G. Species Cross-Reactivity of J695 with Non-Human IL-12

Species cross-reactivity of J695 with non-human IL-12 was analyzed using PBMC's isolated from several non-human species. The presence of non-human IL-12 activity in the rat, dog, cynomolgus and baboon PBMC supernatants was confirmed using several bioassays described above, such as the murine 2D6 cell proliferation assay, the human PHA blast proliferation assay and the interferon-gamma induction assay by blocking the non-human PBMC induced responses with rabbit and/or sheep polyclonal antibodies to murine and/or human IL-12. Cross-reactivity of the human anti-hIL-12 antibodies Y61 and J695 with non-human IL-12 in PBMC supernatants or purified murine and rhesus IL-12 was then assessed in the same bioassay(s) by determining the J695 antibody concentration at which 50% inhibition of the response was observed. The species cross-reactivity results are summarized in Table 5. The results demonstrate that Y61 and J695 are each able to recognize IL-12 from monkeys (e.g., cynomolgus and rhesus IL-12 for Y61, and cynomolgus, rhesus and baboon for J695) and that J695 is approximately 35 fold less active on dog IL-12; neither Y61 nor J695 cross reacts with mouse or rat IL-12.

H. Human Cytokine Specificity of J695

The specificity of J695 was tested in a competition ELISA in which a panel of human cytokines was tested for their ability to interfere with the binding of soluble J695 to immobilized human IL-12. The panel of human cytokines included IL-1α and IL-1β (Genzyme, Boston, Mass.), IL-2 (Endogen), IL-4, IL-10, IL-17, IFN-gamma, and TGF-β1 (R&D, Minneapolis, Minn.) IL-8 (Calbiochem), PDGF, IGF-I, and IGF-II (Boehringer Mannheim Corp., Indianapolis, Ind.), TNFα and lymphotoxin, IL-6, soluble IL-6 receptor, IL-11, IL-12 p70, IL-12 p40, M-CSF, and LIF. EBI-3, an IL-12 p40 related protein that is induced by Epstein-Barr virus infection in B lymphocytes (Devergne et al., (1996) *J. Virol.* 70, 1143-1153) was expressed as a human IgG-Fc chimera (EBI-3/Fc) Single-stranded salmon sperm DNA (Sigma) was also tested.

Flat-bottom ELISA immunoassay microtiter plates (96 well, high binding, Costar) were coated overnight at 4° C. with 0.1 ml human IL-12 (2 μg/ml in 0.1 M carbonate coating buffer (4 volumes 0.1 M $NaHCO_3$ plus 8.5 volumes 0.1 M $NaHCO_3$)). The plates were washed twice with PBS containing 0.05% Tween 20 (PBS-T), blocked with 200 μl of 1 mg/ml bovine serum albumin (BSA, Sigma) in PBS-T for 1 hour at room temperature, and again washed twice with PBS-T. Samples (100 μl) containing IL-12 antibody J695 (100 ng/ml) and each cytokine (2 nM) in PBS-T containing 50 μg/ml BSA (PBS-T/BSA) were added and incubated for 2 h at room temperature. The plates were washed 4 times and incubated for 1 h at room temperature with 100 μl mouse anti-human lambda-HRP (1:500 in PBS-T/BSA, Southern Biotech. Ass. Inc., Birmingham, Ala.). The plates were washed 4 times and developed with ABTS (Kirkegaard & Perry Lab., Gaithersburg, Md.) for 20-30 minutes in the dark. The $OD_{450}$ nm was read using a microplate reader (Molecular Devices, Menlo Park, Calif.). Percent binding was determined relative to J695 binding to the IL-12 coated plate in the absence of any soluble cytokine.

The results demonstrated that J695 binding to immobilized human IL-12 was blocked only by human IL-12 p70 and to a lesser extent, by human IL-12 p40 and not by any of the other cytokines tested.

I. Binding to a Novel IL-12 Molecule

An alternative IL-12 heterodimer has been described, in which the p35 subunit is replaced by a novel p19 molecule. P19 was identified using 3D homology searching for IL-6/IL-12 family members, and is synthesized by activated dendritic cells. P19 binds to p40 to form a p19/p40 dimer, which has IL-12—like activity, but is not as potent as the p35/p40 heterodimer in IFNγ induction. Antibodies which recognize p40 alone, but preferably in the context of a p70 molecule (e.g., J695 and Y61, see Example 3H) are expected to also neutralize both the p35/p40 molecules and the p19/p40 molecules.

Example 4

In Vivo Activity of Anti-hIL-12 Antibodies

The in vivo effects of IL-12 antibodies on IL-12 induced responses were examined in a model modified from one used by Bree et al. to study the effect of human IL-12 on peripheral hematology in cynomolgus monkey Bree et al., (1994) *Biochem Biophys Res. Comm.* 204: 1150-1157. In those previous studies, administration of human IL-12 at 1 μg/kg/day for a period of 5 days resulted in a decrease in white blood cell count (WBC), especially in the lymphocyte and monocyte subsets after 24 hours. A decrease in the platelet count was observed at 72 hours. Levels of plasma neopterin, a marker of

TABLE 5

Species Cross Reactivity Data
$IC_{50}$ (M)

| Antibody | | Mouse IL-12 | Rat IL-12 | Dog IL-12 | Cyno IL-12 | Rhesus IL-12 | Baboon IL-12 | Human IL-12 |
|---|---|---|---|---|---|---|---|---|
| Name | Specificity | Purified | PBMC sup | PBMC sup | PBMC sup | Purified | PBMC sup | Purified |
| C17.15 | rat-αmuIL12 | $3.0 \times 10^{-11}$ | | | | | | |
| R03B03 | rabbit-αmuIL12 | $1.5 \times 10^{-10}$ | $6.0 \times 10^{-10}$ | | | | | |
| C8.6.2 | mouse-αhuIL12 | | | | $1.2 \times 10^{-10}$ | $1.0 \times 10^{-10}$ | $2.0 \times 10^{-10}$ | $5.0 \times 10^{-11}$ |
| Y61 | human-αhuIL12 | Non-neutralizing | | | $2.2 \times 10^{-10}$ | $1.0 \times 10^{-10}$ | | $1.7 \times 10^{-10}$ |
| J695 | human-αhuIL12 | Non-neutralizing | Non-neutralizing | $3.5 \times 10^{-10}$ | $1.0 \times 10^{-11}$ | $1.0 \times 10^{-11}$ | $1.5 \times 10^{-11}$ | $5.0 \times 10^{-12}$ | monocyte activation in response to IFN-γ, began to elevate at 24 hours and were the highest at 72 hours.

In the first study with human anti-hIL-12 antibodies, fifteen healthy cynomolgus monkeys with an average weight of 5 kg, were sedated and divided into 5 groups (n=3). Group 1 received an intravenous (IV) administration of 10 mg/kg human intravenous immunoglobulin (WIG, Miles, Eckhart, Ind., purified using protein A Sepharose). Group 2 received an intravenous administration of 1 mg/kg C8.6.2 (neutralizing mouse anti-human IL-12 monoclonal antibody). Group 3 received an intravenous administration of 10 mg/kg C8.6.2. Group 4 received an intravenous administration of 1 mg/kg Y61 (human anti-human IL-12 antibody, purified from CHO cell conditioned medium). Group 5 received an intravenous administration of 10 mg/kg Y61.

One hour after the antibody administration all animals received a single subcutaneous (SC) injection of human IL-12 (1 μg/kg). Blood samples were taken at the following time points: baseline, 8, 24, 48, 96 and 216 hours, and analyzed for complete blood cell counts with differentials and serum chemistry. Serum human IL-12, C8.6.2 antibody, Y61 antibody, monkey IFN-gamma, monkey IL-10, monkey IL-6 and plasma neopterin levels were also measured.

Animals treated with IL-12 plus IVIG control antibody (Group 1) showed many of the expected hematological changes, including decreases in WBC, platelets, lymphocyte count and monocyte count. These decreases were not seen or were less pronounced in the animals treated with either the C8.6.2 or Y61 antibody at 1 or 10 mg/kg (Groups 2-5).

Serum or plasma samples were analyzed by ELISA specific for monkey IFN-gamma and monkey IL-10 (Biosource International, Camarillo, Calif.), monkey IL-6 (Endogen) and plasma neopterin (ICN Pharmaceuticals, Orangeburg, N.Y.). IFN-gamma, IL-10 or IL-6 were not detected in any of the IL-12 treated animals including the control animals treated with IL-12 plus IVIG. This was probably due to the low level exposure to IL-12 (only 1 dose of 1 μg/kg). Nevertheless, plasma neopterin levels increased about three fold in the IL-12 plus WIG treated animals but did not change in all C8.6.2 or Y61 treated animals, including the lower dose (1 mg/kg) Y61 treated animals, indicating that Y61 was effective in vivo in blocking this sensitive response to IL-12.

In a second study, in vivo activity and pharmacodynamics (PD) of J695 in cynomolgous monkeys were studied by administering exogenous rhIL-12 and determining if J695 could block or reduce the responses normally associated with rhIL-12 administration. Male cynomolgus monkeys (n=3 per group) were administered a single dose of 0.05, 0.2, or 1.0 mg/kg J695 or 1 mg/kg intravenous immunoglobulin (IVIG) as a bolus intravenous (IV) injection via a saphenous vein or subcutaneously (SC) in the dorsal skin. One hour following the administration of J695 or IVIG, all animals received a single SC dose of 1 μg/kg rhIL-12 in the dorsal skin. Blood samples were collected via the femoral vein up to 28 days after J695 administration. Serum was acquired from each blood sample and assayed for IL-12, J695, IFN-γ, and anti-J695 antibodies by ELISA. Neopterin was assayed by reverse-phase high performance liquid chromatography.

Figures 2, 2A, 3:

The levels of neopterin, normalized with respect to the levels of neopterin that were measured before administration of J695 or rhIL-12, are shown in FIG. 3. To compare the suppression of neopterin between groups, the area under the curve (AUC) normalized for neopterin levels was calculated for each animal (Table 6). Neopterin exposure (AUC) was suppressed in a dose-dependent manner between approximately 71 and 93% in the IV groups and between 71 and 100% in SC groups, relative to the IVIG control groups. These results suggest that the dose of J695 necessary for 50% inhibition of the neopterin response ($ED_{50}$) was less than 0.05 mg/kg when administered by either the IV or SC route.

TABLE 6

Dose-Dependent Suppression of IL-12 Induced Neopterin by J695 in Cynomolgus Monkeys

| Route of dosing IVIG or J695 and rhIL-12 | J695 Dose (mg/kg) | IVIG Dose (mg/kg) | AUC of Normalized Neopterin Levels | % Reduction of Neopterin AUC Compared with Control |
|---|---|---|---|---|
| Single IV injection | — | 1.0 | 1745 ± 845 | 0 |
| followed 1 hr later by a | 0.05 | — | 502 ± 135 | 71.3 |
| dose of 1 μg/kg human | 0.2 | — | 199 ± 316 | 88.6 |
| IL-12 given SC | 1.0 | — | 128 ± 292 | 92.7 |
| Single SC injection | — | 1.0 | 1480 ± 604 | 0 |
| followed 1 hour later | 0.05 | — | 426 ± 108 | 71.2 |
| by a dose of 1 μg/kg | 0.2 | — | 395 ± 45.9 | 73.3 |
| human IL-12 given SC | 1.0 | — | 0 ± 109 | 100 |

Treatment with J695 also prevented or reduced the changes in hematology normally associated with rhIL-12 administration (leukopenia and thrombocytopenia). At 24 hours after rhIL-12 administration lymphocyte counts were reduced by approximately 50% when compared to baseline values in the control IV and SC IVIG treated groups. Administration of J695 either SC or IV at all three dose levels prevented this reduction, resulting in lymphocyte counts at 24 hours approximately the same as baseline values. At 48 hours after IL-12 administration, platelet counts in the groups treated with IV and SC IVIG were reduced by approximately 25% when compared to baseline values.

An example dose schedule targeted to maintain serum levels above the 90% effect level would be 1 mg/kg IV and SC given approximately every other week, or 0.3 mg/kg given approximately every week, assuming slight accumulation during repeated dosing. This study demonstrates that antibody can be given safely to monkeys at such dosages. In independent toxicity studies, it was further found that up to 100 mg/kg of the antibody can be given safely to monkeys.

J695 was also effective in preventing IFN-γ production in mice treated with a chimeric IL-12, a molecule which combines the murine p35 subunit with the human IL-12 p40 subunit. In contrast to human IL-12 which is biologically inactive in mice, this chimeric IL-12 retains biological function in mice, including induction of IFN-γ. In addition, the human p40 subunit allows the molecule to be bound and neutralized by J695. Chimeric IL-12 at a dose of 0.05 mg/kg i.p. was administered to female C3H/HeJ mice (10/experimental group) in five daily doses on days 0, 1, 2, 3, and 4. J695 was given on days 0, 2 and 4 at doses of 0.05, 0.01, 0.002, 0.0004, 0.00008, and 0.000016 mg/kg i.p., 30' prior to the IL-12 injections. The control huIgG1γ was given IP. at a dose of 0.05 mg/kg on days 0, 2, and 4. The mice were bled on day 5, and serum IFN-γ levels were determined by ELISA. The results demonstrated that J695 caused dose-dependent inhibition of IFN-γ production with an $ED_{50}$ of approximately 0.001 mg/kg. Collectively, these results demonstrate that J695 is a potent inhibitor of Il-12 activity in vivo.

Example 5

Kinetic Analysis of Binding of Human Antibodies to Recombinant Human IL-12 (rhIL-12)

Real-time binding interactions between captured ligand (human anti-rhIL-12 antibody J695, captured on a biosensor matrix) and analyte (rhIL12 in solution) were measured by surface plasmon resonance (SPR) using the BIAcore system (Biacore AB, Uppsala, Sweden). The system utilizes the optical properties of SPR to detect alterations in protein concentration within a dextran biosensor matrix. Proteins are covalently bound to the dextran matrix at known concentrations. Antibodies are injected through the dextran matrix and specific binding between injected antibodies and immobilized ligand results in an increased matrix protein concentration and resultant change in the SPR signal. These changes in SPR signal are recorded as resonance units (RU) and are displayed with respect to time along the y-axis of a sensorgram.

To facilitate immobilization of goat anti-human IgG (Southern Biotechnology Associates, Cat. No. 2040-01, Birmingham, Ala.) on the biosensor matrix, goat anti-human IgG is covalently linked via free amine groups to the dextran matrix by first activating carboxyl groups on the matrix with 100 mM N-hydroxysuccinimide (NHS) and 400 mM N-Ethyl-N'-(3-dimethylaminopropyl)-carbodiimide hydrochloride (EDC). Next, goat anti-human IgG is injected across the activated matrix. Thirty-five microliters of goat anti-human IgG (25 µg/ml), diluted in sodium acetate, pH 4.5, is injected across the activated biosensor and free amines on the protein are bound directly to the activated carboxyl groups. Unreacted matrix EDC-esters are deactivated by an injection of 1 M ethanolamine. Standard amine coupling kits were commercially available (Biacore AB, Cat. No. BR-1000-50, Uppsala, Sweden).

J695 was diluted in HBS running buffer (Biacore AB, Cat. No. BR-1001-88, Uppsala, Sweden) to be captured on the matrix via goat anti-human IgG. To determine the capacity of rhIL12-specific antibodies to bind immobilized goat anti-human IgG, a binding assay was conducted as follows. Aliquots of J695 (25 µg/ml; 25 µl aliquots) were injected through the goat anti-human IgG polyclonal antibody coupled dextran matrix at a flow rate of 5 µl/min. Before injection of the protein and immediately afterward, HBS buffer alone flowed through each flow cell. The net difference in signal between the baseline and the point corresponding to approximately 30 seconds after completion of J695 injection was taken to represent the amount of IgG1 J695 bound (approximately 1200 RU's). Direct rhIL12 specific antibody binding to soluble rhIL12 was measured. Cytokines were diluted in HBS running buffer and 50 µl A aliquots were injected through the immobilized protein matrices at a flow rate of 5 µl/min. The concentrations of rhIL-12 employed were 10, 20, 25, 40, 50, 80, 100, 150 and 200 nM. Prior to injection of rhIL-12, and immediately afterwards, HBS buffer alone flowed through each flow cell. The net difference in baseline signal and signal after completion of cytokine injection was taken to represent the binding value of the particular sample. Biosensor matrices were regenerated using 100 mM HCl before injection of the next sample. To determine the dissociation constant (off-rate), association constant (on-rate), BIAcore kinetic evaluation software (version 2.1) was used.

Representative results of CHO derived J695 binding to rhIL-12 as compared to the COS derived J695, are shown in Table 7.

TABLE 7

Binding of CHO or COS derived J695 to rhIL-12.

| Source | rhIL12, nM | rhIL12 bound, RU's | Ab, bound, RU's | rhIL12/AB |
|---|---|---|---|---|
| CHO | 200 | 1112 | 1613 | 1.48 |
| CHO | 150 | 1033 | 1525 | 1.45 |
| CHO | 100 | 994 | 1490 | 1.43 |
| CHO | 80 | 955 | 1457 | 1.40 |
| CHO | 50 | 912 | 1434 | 1.36 |
| CHO | 40 | 877 | 1413 | 1.33 |
| CHO | 25 | 818 | 1398 | 1.25 |
| CHO | 20 | 773 | 1382 | 1.20 |
| CHO | 10 | 627 | 1371 | 0.98 |
| COS | 200 | 1172 | 1690 | 1.49 |
| COS | 150 | 1084 | 1586 | 1.46 |
| COS | 100 | 1024 | 1524 | 1.44 |
| COS | 80 | 985 | 1489 | 1.42 |
| COS | 50 | 932 | 1457 | 1.37 |
| COS | 40 | 894 | 1431 | 1.34 |
| COS | 25 | 833 | 1409 | 1.27 |
| COS | 20 | 783 | 1394 | 1.20 |
| COS | 10 | 642 | 1377 | 1.00 |

Molecular kinetic interactions between captured J695 and soluble rhIL-12 were quantitatively analyzed using BIAcore technology. Several independent experiments were performed and the results were analyzed by the available BIAcore mathematical analysis software to derive kinetic rate constants, as shown in Table 8.

TABLE 8

Apparent kinetic rate and affinity constants of J695 for rhIL-12.

| Antibody | Source | On-rate (M−1s−1), Avg. | Off-rate (s−1), Avg. | Kd (M), Avg. |
|---|---|---|---|---|
| J695 | CHO | 3.52E+05 | 4.72E−05 | 1.34E−10 |
| J695 | COS | 3.40E+05 | 2.61E−05 | 9.74E−11 |

There was a small difference between the calculated apparent constant (Kd) for the interaction between CHO derived J695 (Kd=$1.34^{-10}M^{-1}$) and COS derived J695 (Kd=$9.74 \times 10^{-11}M^{-1}$) antibodies. The apparent dissociation constant (Kd) between J695 and rhIL12 was estimated from the observed rate constants by the formula: Kd=off-rate/on-rate.

To determine the apparent association and dissociation rate constant for the interaction between J695 and rhIL-12, several binding reactions were performed using a fixed amount of J695 (2 µg/ml) and varying concentrations of rhIL-12. Real-time binding interaction sensorgrams between captured J695 and soluble rhIL12 showed that both forms of antibody were very similar for both the association and dissociation phase.

To further evaluate the capacity of captured IgG1 J695 mAb to bind soluble recombinant cytokine, a direct BIAcore method was used. In this method, goat anti-human IgG (25 µg/ml) coupled carboxymethyl dextran sensor surface was coated with IgG1 J695 (2 µg/ml) and recombinant cytokine was then added. When soluble rhIL12 was injected across a biosensor surface captured with CHO or COS derived IgG1 J695, the amount of signal increased as the concentration of cytokine in the solution increased. No binding was observed with rmIL12 (R&D Systems, Cat. No. 419-ML, Minneapolis, Minn.) or rh IL12 any concentration tested up to 1000 nM. These results support the conclusion that IgG1 J695 antibodies recognize a distinct determinant on rhIL-12.

Table 9 shows the results of an experiment using BIAcore to demonstrate human IgG1 J695 mAb binding to only soluble rhIL12 and none of the other recombinant cytokines:

TABLE 9

Epitope mapping of J695 using BIAcore technology.

| Soluble analyte | Captured ligand COS J695 | Captured ligand CHO J695 |
|---|---|---|
| rec. human IL12 | Positive | Positive |
| rec. murine IL12 | Negative | Negative |

Example 6

Further Studies of J695 Affinity for IL-12

Molecular kinetic interactions between J695 antibody and human IL-12 were quantitatively analyzed using BIAcore plasmon resonance technology, and apparent kinetic rate constants were derived.

BIAcore technology was used to measure the binding of soluble rhIL-12 to solid phase captured J695. A goat anti-human IgG antibody was immobilized on the biosensor chips, then a fixed amount of J695 was injected and captured on the surface. Varying concentrations of rhIL-12 were applied, and the binding of IL-12 at different concentrations to J695 was measured as a function of time. Apparent dissociation and association rate constants were calculated, assuming zero-order dissociation and first order association kinetics, as well as a simple one-to-one molecular interaction between J695 and IL-12. Three independent experiments were performed, and the values shown are averages for the three experiments. From these measurements, the apparent dissociation ($k_d$) and association ($k_a$) rate constants were derived and used to calculate a $K_d$ value for the interaction (see Table 10). The results indicated that J695 has a high affinity for rhIL-12.

TABLE 10

Kinetic Parameters for the Interaction Between J695 and Human IL-12

| Kinetic Parameter | Value |
|---|---|
| $k_d$ | $3.71 \pm 0.40 \times 10^{-5}\ s^{-1}$ |
| $k_a$ | $3.81 \pm 0.48 \times 10^{5}\ M^{-1}s^{-1}$ |
| $K_d$ | $9.74 \times 10^{-11}\ M$ (14 ng/mL) |

Example 7

Characteristics and Neutralization Activity of C17.15, a Rat Monoclonal Antibody to Murine Interleukin-12

To assess the relevance of IL-12 treatment studies in mouse models of inflammation to and autoimmunity using monoclonal antibodies specific for murine IL-12 to similar approaches in human disease, the interaction of C17.15, a rat anti-murine IL-12 monoclonal antibody with murine IL-12, was examined. The ability of C17.15 to neutralize murine IL-12 activity in a PHA blast proliferation assay, and to block murine IL-12 binding to cell surface receptors, was assessed, as were the kinetics of the C17.15-murine IL-12 binding interaction.

In a human PHA blast proliferation assay (See Example 3), serial dilutions of C17.15 or rat IgG2a (a control antibody) were preincubated with 230 pg/mL murine IL-12 for 1 hr at 37° C. PHA-stimulated blast cells were added to the antibody-IL-12 mixtures and incubated for 3 days at 37° C. The cells were subsequently labeled for 6 h with 1 µCi/well [$^3$H]-thymidine. The cultures were harvested and [$^3$H]-thymidine incorporation was measured. Background non-specific proliferation was measured in the absence of added murine IL-12. All samples were assayed in duplicate. The $IC_{50}$ (M) of C17.15 for recombinant murine IL-12 in this assay was found to be $1.4 \times 10^{-11}$, as compared to the $IC_{50}$ value of $5.8 \times 10^{-12}$ observed for J695 for recombinant human IL-12 under the same conditions (see Table 11).

TABLE 11

Comparison of the properties of anti-human IL-12 monoclonal antibody J695 and the rat anti-mouse IL-12 monoclonal antibody C17.15

| Antibody | Epitope | Biomolecular Interaction Assay | | | Receptor Binding Assay $IC_{50}$ (M) | PHA blast Assay $IC_{50}$ (M) |
|---|---|---|---|---|---|---|
| | | $k_a$, on-rate ($M^{-1}s^{-1}$) | $k_d$, off-rate ($s^{-1}$) | $K_d$ (M) | | |
| J695 | Hu p40 | $3.81 \times 10^5$ | $3.71 \times 10^{-5}$ | $9.74 \times 10^{-11}$ | $1.1 \times 10^{-11}$ | $5.8 \times 10^{-12}$ |
| C17.15 | Mu p40 | $3.80 \times 10^5$ | $1.84 \times 10^{-4}$ | $4.80 \times 10^{-10}$ | $1.5 \times 10^{-10}$ | $1.4 \times 10^{-11}$ |

The ability of C17.15 to inhibit the binding of murine IL-12 to cellular receptors was also measured. Serial dilutions of C17.15 were pre-incubated for 1 hr at 37° C. with 100 pM [$^{125}$I]-murine IL-12 in binding buffer. The 2D6 cells ($2 \times 10^6$) were added to the antibody/[$^{125}$I]-murine IL-12 mixture and incubated for 2 hours at room temperature. Cell-bound radioactivity was separated from free [$^{125}$I]-IL-12, and the remaining cell-bound radioactivity was determined. Total binding of the labeled murine IL-12 to receptors on 2D6 cells was determined in the absence of antibody, and non-specific binding was determined by the inclusion of 25 nM unlabelled murine IL-12 in the assay. Specific binding was calculated as the total binding minus the non-specific binding. Incubations were carried out in duplicate. The results showed that C17.15 has an $IC_{50}$ (M) of $1.5 \times 10^{-10}$ for inhibition of binding of murine IL-12 to cellular receptors.

The affinity of C17.15 for recombinant murine IL-12 was assessed by biomolecular interaction analysis. A goat anti-rat IgG antibody was immobilized on the biosensor chips, followed by an injection of a fixed amount of the C17.15 antibody, resulting in capture of C17.15 on the surface of the chip. Varying concentrations of recombinant murine IL-12 were applied to the C17.15 surface, and the binding of murine IL-12 to the immobilized C17.15 was measured as a function of time. Apparent dissociation and association rate constants were calculated, assuming a zero order dissociation and first order association kinetics as well as a simple one to one molecular interaction between the immobilized C17.15 and murine IL-12. From these measurements, the apparent dissociation ($k_d$, off-rate) and association ($k_a$, on-rate) rate constants were calculated. These results were used to calculate a IQ value for the interaction. An on-rate of $3.8 \times 10^5$ $M^{-1}s^{-1}$, an off-rate of $1.84 \times 10^{-4}$ $s^{-1}$, and a $K_d$ of $4.8 \times 10^{-10}$ was observed for the recombinant murine IL-12-C17.15 interaction.

The observed activities of C17.15 in neutralizing murine IL-12 activity and binding to cell surface receptors, as well as the kinetics of binding of C17.15 to murine IL-12 correlate with similar measurements for the J695-rhIL-12 interaction. This indicates that the modes of action of the rat anti-mouse IL-12 antibody C17.15 and anti-human IL-12 antibody J695 are nearly identical based upon on-rate, off-rate, $K_d$, $IC_{50}$, and the PHA blast assay. Therefore, C17.15 was used as a homologous antibody to J695 in murine models of inflammation and autoimmune disease to study the effects of IL-12 blockade on the initiation or progression of disease in these model animals (see Example 8).

Example 8

Treatment of Autoimmune or Inflammation-Based Diseases in Mice by α-Murine IL-12 Antibody Administration A. Suppression of Collagen-Induced Arthritis in Mice by the α-Il-12 Antibody C17.15

A correlation between IL-12 levels and rheumatoid arthritis (RA) has been demonstrated. For example, elevated levels of IL-12 p70 have been detected in the synovia of RA patients compared with healthy controls (Morita et al (1998) *Arthritis and Rheumatism.* 41: 306-314). Therefore, the ability of C17.15, a rat anti-mouse IL-12 antibody, to suppress collagen-induced arthritis in mice was assessed.

Male DBA/1 mice (10/group) were immunized with type II collagen on Day 0 and treated with C17.15, or control rat IgG, at 10 mg/kg intraperitoneally on alternate days from Day −1 (1 day prior to collagen immunization) to Day 12. The animals were monitored clinically for the development of arthritis in the paws until Day 90. The arthritis was graded as: 0—normal; 1—arthritis localized to one joint; 2—more than one joint involved but not whole paw; 3—whole paw involved; 4—deformity of paw; 5—ankylosis of involved joints. The arthritis score of a mouse was the sum of the arthritic grades in each individual paw of the mouse (max=20). The results are expressed as mean±SEM in each group.

Figures 2, 2A, 3, 4:
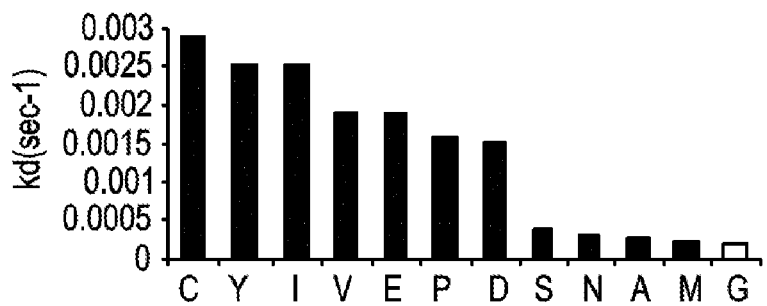
FIG. 4 shows a graph of mean arthritic score versus days after immunization of mice with collagen, demonstrating that treatment with C17.15 significantly decreases arthritis-related symptoms as compared to treatment with rat IgG.
Figures 1, 2B:
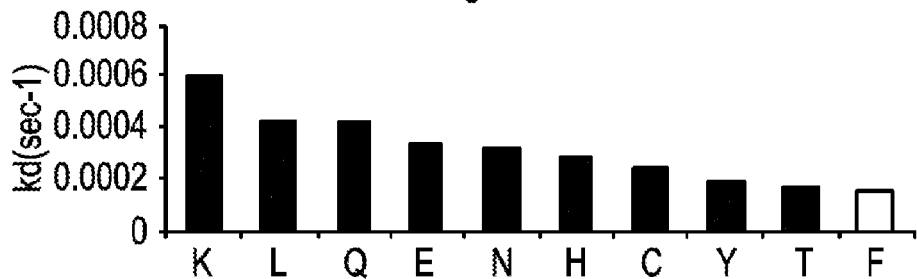
Figures 2, 2B:
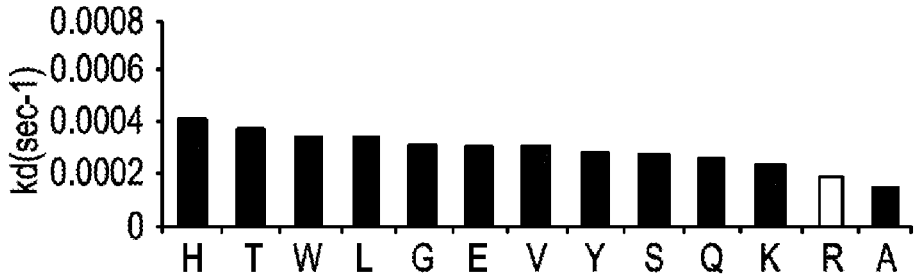
Figures 2, 2B, 3:
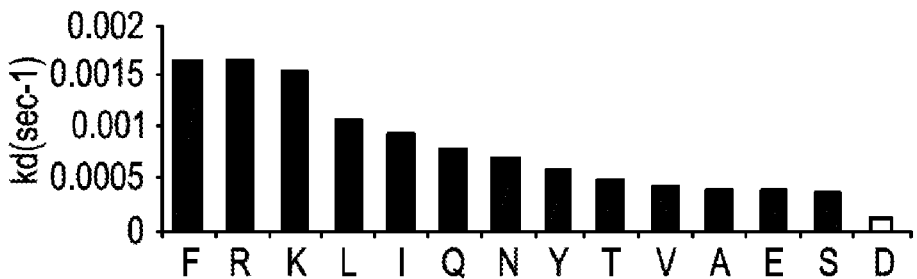
Figures 2, 2B, 3, 4:
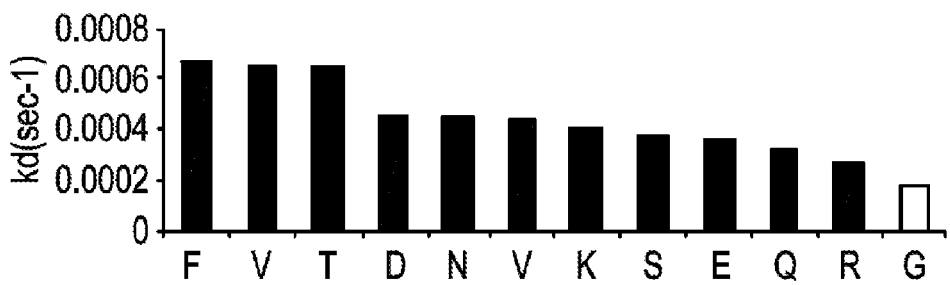
Figures 1, 2C:
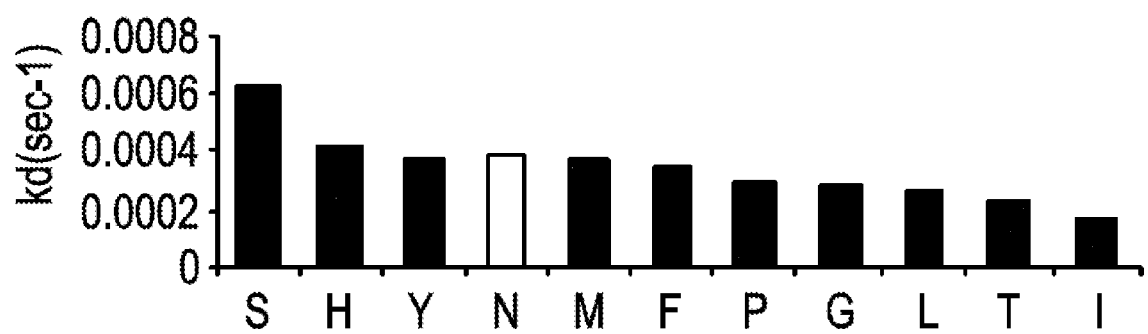
Figures 2, 2C:
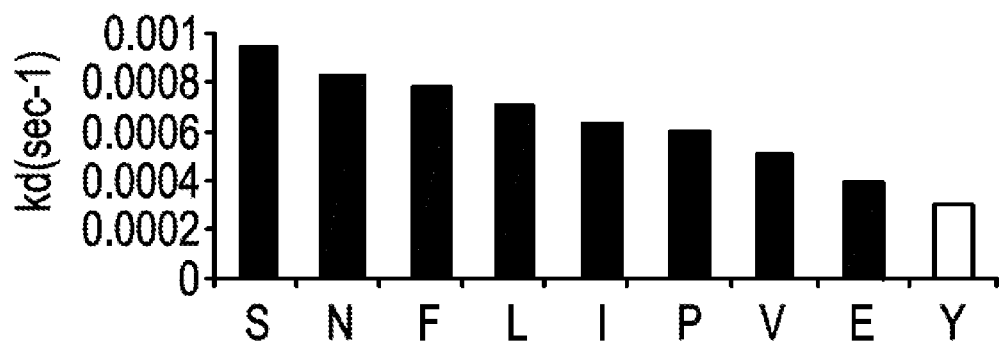
Figures 1, 2D:
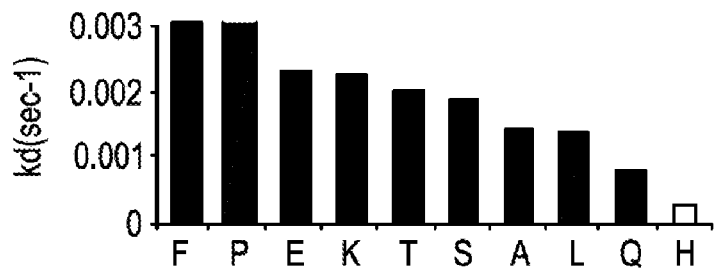
Figures 2, 2D:
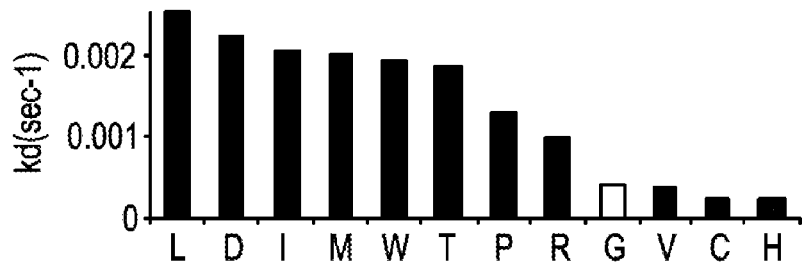
Figures 2, 2D, 3:
Figures 2, 2D, 3, 4:
Figures 1, 2E:
Figures 2, 2E:
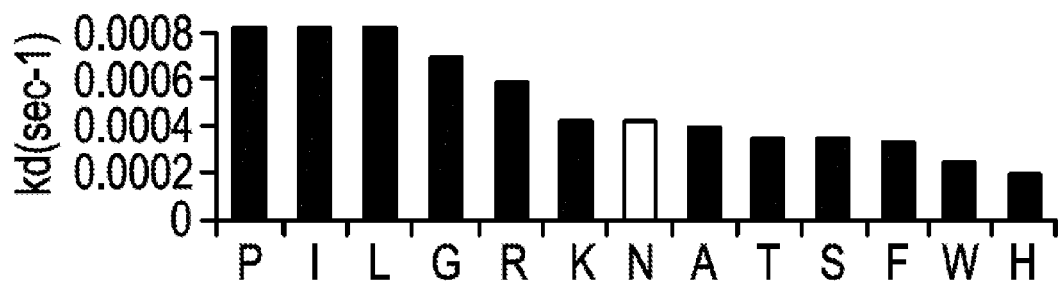
Figures 1, 2F:
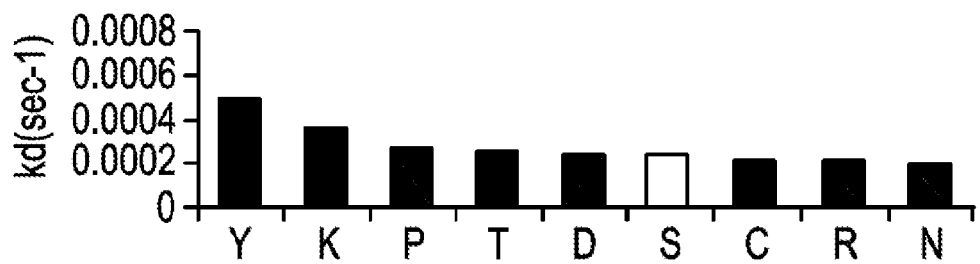
FIGS. 2F-2H show the CDR positions in the light chain of the Y61 antibody that were mutated by site-directed mutagenesis and the respective amino acid substitutions at each position. The graphs at the right of the figures show the off-rates for the substituted antibodies (black bars) as compared to unmutated Y61 (open bar).
Figures 2, 2F:
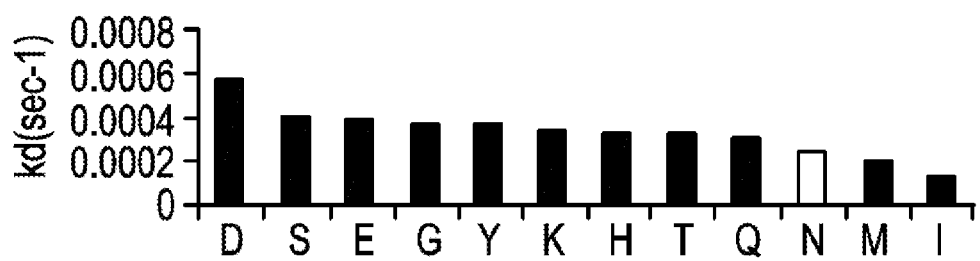
Figures 2, 2F, 3:
Figures 1, 2G:
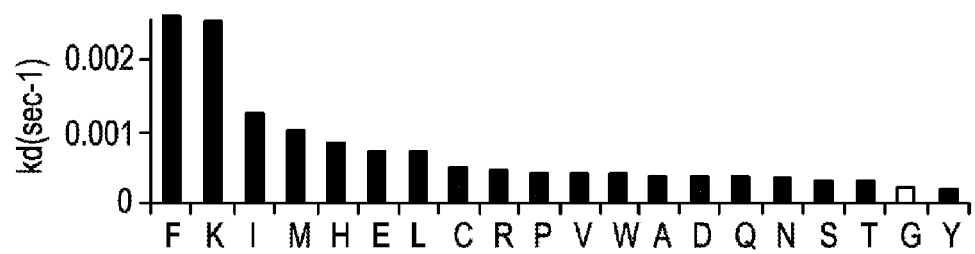
Figures 2, 2G:
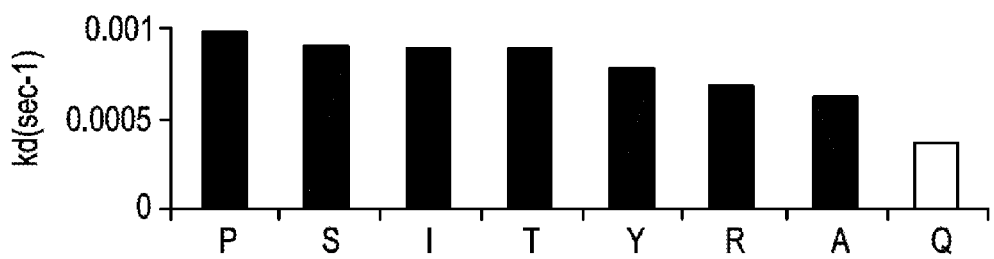
Figures 1, 2H:
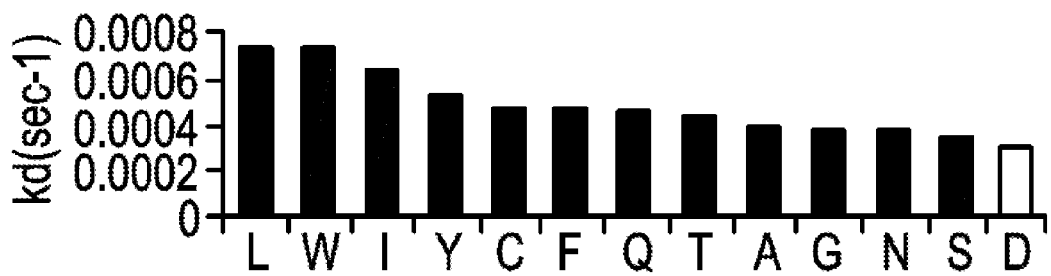
Figures 2, 2H:
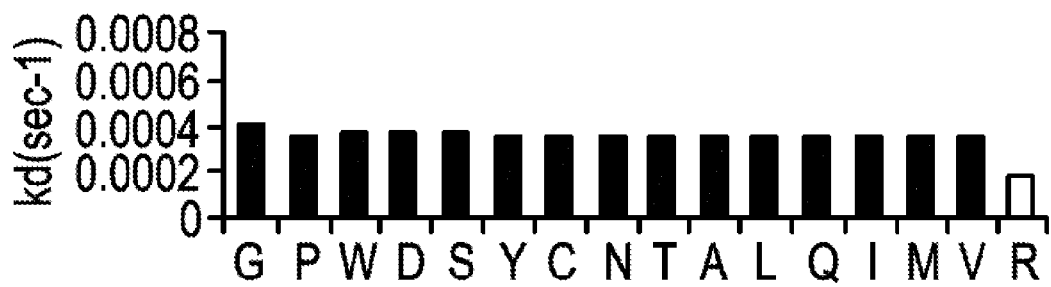
Figures 2, 2H, 3:
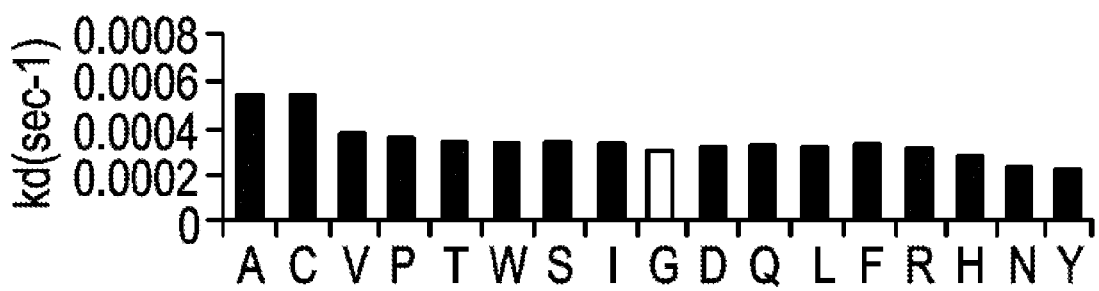
Figure 4:
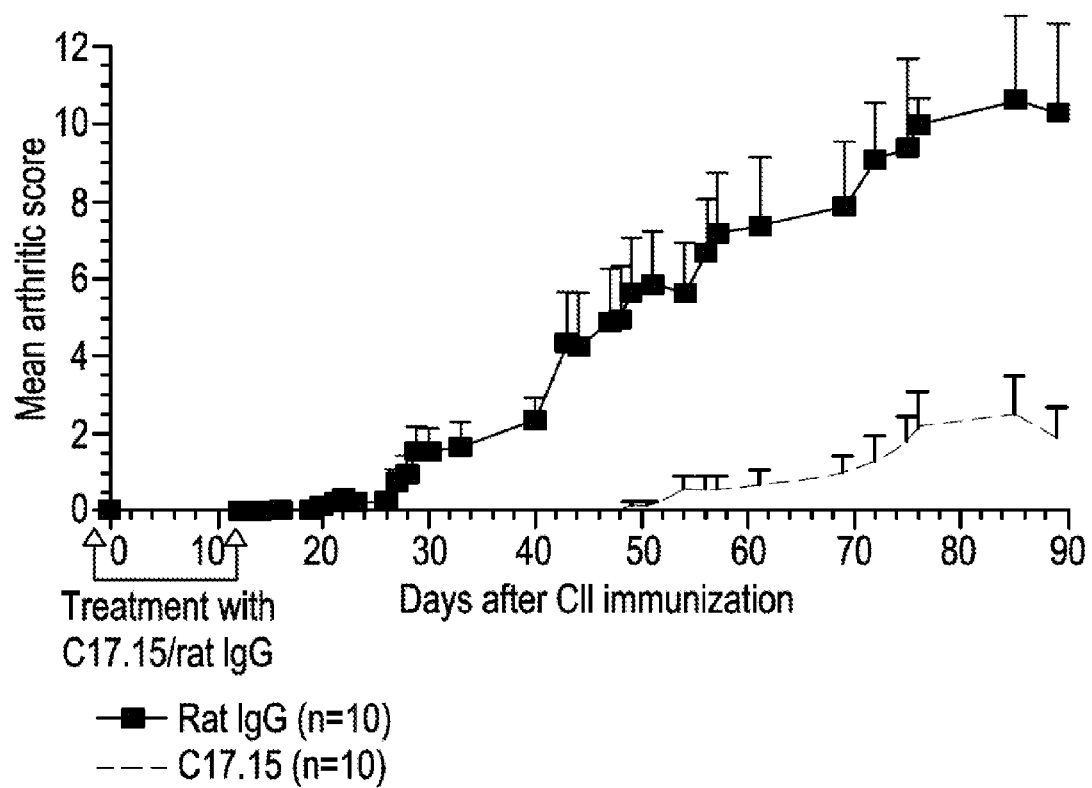

The results, as shown in FIG. 4, indicate that an arthritic score was measurable in the C17.15-treated mice only after day 50 post-treatment, and that the peak mean arthritic score obtained with the C17.15-treated mice was at least 5-fold lower than that measured in the IgG-treated mice. This demonstrated that the rat anti-mouse IL-12 antibody C17.15 prevented the development of collagen-induced arthritis in mice.

B. Suppression of Colitis in Mice by the Rat α-Murine IL-12 Antibody C17.15

IL-12 has also been demonstrated to play a role in the development/pathology of colitis. For example, anti-IL-12 antibodies have been shown to suppress disease in mouse models of colitis, e.g., TNBS induced colitis IL-2 knockout mice (Simpson et al. (1998) *J. Exp. Med.* 187(8): 1225-34). Similarly, anti-IL-2 antibodies have been demonstrated to suppress colitis formation in IL-10 knock-out mice. The ability of the rat anti-mouse IL-12 antibody, C17.15, to suppress TNBS colitis in mice was assessed in two studies (Davidson et al. (1998) *J. Immunol.* 161(6): 3143-9).

In the first study, colitis was induced in pathogen free SJL mice by the administration of a 150 μL 50% ethanol solution containing 2.0 mg TNBS delivered via a pediatric umbilical artery catheter into the rectum. Control animals were treated with a 150 μL 50% ethanol solution only. A single dose of 0.75, 0.5, 0.25, or 0.1 mg C17.15 or 0.75 mg control rat IgG2a was given intravenously via the tail vein at day 11, and the therapeutic effect of the treatment was assessed by weighing the animals on days 11 and 17, and histological scoring at day 17. The weight of the mice treated with C17.15 increased within 48 hours of antibody treatment and normalized on day 6 after treatment. The effect of treatment with C17.15 was confirmed histologically. Further, assessments of IFN-γ secretion by $CD4^+$ T-cells from spleen and colon of the treated mice, as well as IL-12 levels from spleen or colon-derived macrophages from the treated mice were also made (see Table 12).

In the second study, the dosing was optimized and the mice were treated with a total dose of 0.1 mg or 0.5 mg C17.15 or 0.1 mg control IgG2a, respectively, split between days 12 and 14. It was found that the administration of C17.15 in a single dose at the dosage of 0.1 mg/mouse or 0.25 mg/mouse led to only partial improvement in TNBS-induced colitis and did not result in a significant reduction in the $CD4^+$ T cell production of IFN-γ in vitro, but did result in a significant decrease in secretion of IL-12, compared to untreated controls. At a single dose of 0.5 mg/mouse or greater a response was observed. Taking the lowest dose of antibody tested and administering it in two divided injections (at days 12 and 14) improved the dosing regimen, indicating that multiple low doses can be more effective than a single bolus dose. The data obtained are shown in Table 12.

TABLE 12

Anti-mouse Il-12 mAb C17.15 Suppresses Established Colitis in Mice

| Disease Induction | Treatment | Weight (g) | | IFN-γ spleen $CD4^+$ cells (U/mL) | IL-12 spleen macrophages (pg/ml) |
|---|---|---|---|---|---|
| Day 0 | Day 11 | Day 11 | Day 17 | | |
| TNBS + Ethanol | Control IgG2a 0.75 mg | 16.0 | 15.26 | 3326 | 300 |
| TNBS + Ethanol | C17.15 0.75 mg | 16.0 | 20.21 | 1732 | 0 |
| TNBS + Ethanol | C17.15 0.5 mg | 16.36 | 19.94 | 1723 | 0 |
| TNBS + Ethanol | C17.15 0.25 mg | 16.28 | 17.7 | 3618 | 7 |
| TNBS + Ethanol | C17.15 0.1 mg | 16.2 | 17.98 | 3489 | 22 |
| Ethanol control | — | 20.76 | 21.16 | 1135 | 0 |

Administration of C17.15 monoclonal anti-IL-12 in two divided doses spaced one day apart totaling 0.1 mg/mouse or 0.05 mg/mouse led to complete reversal of colitis as assessed by wasting and macroscopic appearance of the colon. In addition, this dose schedule led to significant down-regulation of lamina propria T-cell production of IFN-γ and macrophage production of IL-12, so that the latter were comparable to levels seen in control ethanol-treated mice without TNBS-colitis. Thus, C17.15 administration to mouse models for TNBS colitis reversed the progression of the disease in a dose-dependent manner.

C. Suppression of Experimental Autoimmune Encephalomyelitis (EAE) in Mice by α-IL-12 Antibodies It is commonly believed that IL-12 plays a role in the pathogenesis of multiple sclerosis (MS). The inducible IL-12 p40 message has been shown to be expressed in acute plaques of MS patients but not in inflammatory brain infarct lesions (Windhagen, A. et al. (1995) *J. Exp. Med.* 182: 1985-1996). T cells from MS patients (but not control T cells) stimulate IL-12 production from antigen-presenting cells through unregulated CD40L expression (Balashov, K. E. et al. (1997) *Proc. Natl. Acad. Sci. USA* 94: 599-603). MS patients have enhanced IFN-γ secretion that can be blocked with α-IL-12 antibodies in vitro (Balashov, K. E. et al. (1997) *Proc. Natl. Acad. Sci. USA* 94: 599-603). Elevated levels of serum IL-12 are detected in MS patients, but not in other neurological diseases (Nicoletti, F. et al. (1996) *J. Neuroimmunol.* 70: 87-90). Increased IL-12 production has been shown to correlate with disease activity in MS patients (Cormabella, M. et al. (1998) *J. Clin. Invest.* 102: 671-678). The role of IL-12 in the pathogenesis of a murine model of multiple sclerosis, experimental autoimmune encephalomyelitis (EAE), has been studied (Leonard, J. P. et al. (1995) *J. Exp. Med.* 181: 281-386; Banerjee, S. et al. (1998) *Arthritis Rheum.* (1998) 41: S33; and Segal, B. M. et al. (1998) *J. Exp. Med.* 187: 537-546). The disease in this model is known to be induced by T cells of the $TH_1$ subset. Therefore, the ability of α-IL-12 antibodies to prevent the onset of acute EAE was assessed.

An α-IL-12 antibody was found to be able to inhibit the onset of acute EAE, to suppress the disease after onset, and to decrease the severity of relapses in mice immunized with the autoantigen, myelin basic protein (Banerjee, S. et al. (1998) *Arthritis Rheum.* (1998) 41: S33). The beneficial effects of α-IL-12 antibody treatment in the mice persisted for over two months after stopping treatment. It has also been demonstrated that anti-IL-12 antibodies suppress the disease in mice that are recipients of encephalitogenic T cells by adoptive transfer (Leonard, J. P. et al. (1995) *J. Exp. Med.* 181: 281-386).

Example 9

Clinical Pharmacology of J695

In a double blind, crossover study, 64 healthy, human male subjects were administered ascending doses of J695 or placebo. Measurement of complement fragment C3a prior to and 0.25 h after dosing did not demonstrate activation of the complement system. CRP and fibrinogen levels were only increased in subjects in whom symptoms of concurrent infections were observed.

All subjects survived and the overall tolerability of J695 was very good. In no case did treatment have to be stopped because of adverse events (AEs). The most commonly observed AEs were headache and common cold/bronchitis, neither of which were categorized as severe.

One of the study subjects, a 33-year-old single male, was suffering from psoriasis guttata at the start of the study. According to the randomized study design, this subject by chance received 5 mg/kg J695 by SC administration. Ten days prior to administration of the antibody, the subject showed only small discrete papular lesions on the arms and legs. At the time of the antibody administration, the subject displayed increased reddening, thickness of the erythematous plaques, and increased hyperkaratosis. One week after J695 administration, the subject reported an improvement in skin condition, including flattening of the lesions and a decrease in scaling. Shortly after the second administration of J695 (5 mg/kg IV), the subject's skin was totally cleared of psoriatic lesions, in the absence of any local treatment. Erythematous plaques covered with white scales reappeared concomitant with the expected clearance of J695 after the second administration of antibody.

Example 10

Comparison of J695 Produced by Two CHO Cell Lines

For recombinant expression of J695, a recombinant expression vector encoding both the antibody heavy chain and the antibody light chain is introduced into dhfr-CHO cells (Urlaub, G. and Chasin, L. A. (1980) *Proc. Natl. Acad. Sci. USA* 77:4216-4220) by calcium phosphate-mediated transfection. Within the recombinant expression vector, the antibody heavy and light chain genes are each operatively linked to enhancer/promoter regulatory elements (e.g., derived from SV40, CMV, adenovirus and the like, such as a CMV enhancer/AdMLP promoter regulatory element or an SV40 enhancer/AdMLP promoter regulatory element) to drive high levels of transcription of the genes. The recombinant expression vector also carries a DHFR gene, which allows for selection of CHO cells that have been transfected with the vector using methotrexate selection/amplification.

One hundred and fifty micrograms of an expression vector encoding the peptide sequences of the human antibody J695 were dissolved in 2.7 ml water in a 50 ml conical tube. Three hundred μL of 2.5 M $CaCl_2$ were added and this DNA mixture was added dropwise to 3 ml of 2×HEPES buffered saline in a 50 ml conical tube. After vortexing for 5 sec and incubating at room temperature for 20 min, 1 mL was distributed evenly over each plate (still in F12 medium), and the plates were incubated at 37° C. for 4 h. Liquid was removed by aspiration and 2 ml of 10% DMSO in F12 were added to each plate. The DMSO shock continued for 1 min, after which the DMSO was diluted by the addition of 5 ml PBS to each plate. Plates were washed twice in PBS, followed by the addition of 10 ml of alpha MEM, supplemented with H/T and 5% FBS (selective for cells expressing DHFR) and overnight incubation at 37° C. Cells were seeded into 96-well plates at a density of 100 cells per well, and plates were incubated at 37° C., 5% $CO_2$ for two weeks, with one change of medium per week.

Five days after the final medium change, culture supernatants were diluted 1:50 and tested using an ELISA specific for human IgG gamma chain. The clones yielding the highest ELISA signal were transferred from the 96-well plates to 12-well plates in 1.5 ml/well of Alpha MEM+5% dialyzed serum. After 3 days, another ELISA specific for human IgG gamma chain was performed, and the 12 clones with the greatest activity were split into the alpha MEM+5% dialyzed serum and 20 nM MTX. Cell line 031898 218 grew in the presence of 20 nM MTX without any apparent cell death or reduction in growth rate, produced 1.8 μg/ml hIgG in a three-day assay. T-25 cultures of 031898 218, growing in medium containing MTX, produced an average of 11.9 μg/ml of J695. The line, designated ALP903, was adapted to growth in suspension under serum-free conditions, where it produced 7.5 pg J695/cell/24 h.

ALP903 cells, after initial selection in alpha MEM/5% FBS/20 nM MTX medium, were passed again in 20 nM MTX. The cells were cultured under 100 nM MTX selection, followed by passaging in 500 nM MTX twice in the next 30 days. At that time the culture was producing 32 μg J695/mL/24 h. The culture was subcloned by limiting dilution. Subclone 218-22 produced 16.5 μg/mL in a 96-well plate in 2 days and 50.3 μg/mL of J695 in a 12-well dish in 2 days. Clone 218-22 was cultured in alpha MEM/5% dialyzed FBS/500 nM MTX for 38 days, followed by adaptation to serum-free spinner culture, as above. The average cell-specific productivity of the serum-free suspension culture, designated ALP 905, was 58 pg/cell/24 h.

The first cell line used to produce J695 (ALP 903) resulted in lower yields of the antibody from culture than a second cell line, ALP 905. To assure that the ALP 905-produced J695 was functionally identical to that produced from ALP 903, both batches of antibodies were assessed for IL-12 affinity, for the ability to block IL-12 binding to cellular receptors, for the ability to inhibit IFN-γ induction by IL-12, and for the ability to inhibit IL-12-mediated PHA blast proliferation.

The affinities of J695 batches ALP 903 and ALP 905 for IL-12 were determined by measuring the kinetic rate constants of binding to IL-12 by surface plasmon resonance studies (BIAcore analyses). The off-rate constant ($k_d$) and the on-rate constant ($k_a$) of antibody batches ALP903 and ALP905 for binding to rhIL-12 were determined in three experiments (as described in Example 3). The affinity, IQ, of binding to IL-12 was calculated by dividing the off-rate constant by the on-rate constant. $K_d$ was calculated for each separate experiment and then averaged. The results showed that the determined kinetic parameters and affinity of binding to rhIL-12 were very similar for J695 batches ALP 903 and ALP 905: the calculated $K_d$ was $1.19 \pm 0.22 \times 10^{-10}$ M for batch ALP 903 and $1.49 \pm 0.47 \times 10^{-10}$ M for batch ALP 905 (see Table 13).

The ability of J695 derived from both ALP 903 and ALP 905 to block binding of rhIL-12 to IL-12 receptors on human PHA-activated T-lymphoblasts was assessed (see Example 3). Each sample of J695 was tested at a starting concentration of $1 \times 10^{-8}$ with 10-fold serial dilutions. The antibody was preincubated for 1 hour at 37° C. with 50 pM [$^{125}$I]-human IL-12 in binding buffer. PHA blast cells were added to the antibody/[$^{125}$I]-human IL-12 mixture and incubated for 2 h at room temperature. Cell bound radioactivity was separated from free [$^{125}$I]-IL-12 by centrifugation and washing steps, and % inhibition was calculated. The $IC_{50}$ values for J695 were determined from the inhibition curves using 4-parameter curve fitting and were confirmed by two independent experiments. Incubations were carried out in duplicate. The results for the two batches of J695 were very similar (see Table 13).

The ability of J695 from both ALP 903 and ALP 905 cells to inhibit rhIL-12-induced IFN-γ production by human PHA-activated lymphoblasts in vitro was assessed. Serial dilutions of J695 were preincubated with 200 pg/mL rhIL-12 for 1 h at 37° C. PHA lymphoblast cells were added and incubated for 18 hours at 37° C. After incubation, cell free supernatant was withdrawn and the level of human IFN-γ determined by ELISA. The $IC_{50}$ values from the inhibition curves were plotted against the antibody concentration using 4-parameter curve fitting. The results demonstrate that the ability of the two batches to inhibit IFN-γ production is very similar.

The in vitro PHA blast cell proliferation assay was used to measure the neutralization capacity of ALP 903 and ALP 905 J695 for rhIL-12. Serial dilutions of J695 of each type were preincubated with 230 pg/mL human IL-12 for 1 h at 37° C. Next PHA blast cells were added and incubated for 3 days at 37° C. The cells were then labeled for 6 hours with 1 γCi/well [$^3$H]-thymidine. The cultures were harvested and [$^3$H]-thymidine incorporation measured. Non-specific proliferation (background) was measured in the absence of rhIL-12. The $IC_{50}$ values for ALP 903 and ALP 905 J695 were found to be very similar and are set forth in Table 13.

The activity of the J695 antibodies in neutralizing rhIL-12 activity, in blocking IL-12 binding to cell surface receptors, and in binding to rhIL-12 did not significantly differ from batch ALP 903 to batch ALP 905, and thus the antibodies produced from these two different cell types were equivalent.

TABLE 13

Comparison of the Properties of J695 lots ALP 903 and ALP 905

| Antibody | $k_a$, On-rate ($M^{-1}, s^{-1}$) | $k_d$, Off-rate ($s^{-1}$) | $K_d$(M) | RB assay $IC_{50}$ (M) | PHA blast Assay $IC_{50}$ (M) | IFN-γ Assay $IC_{50}$ (M) |
|---|---|---|---|---|---|---|
| J695 ALP 903 | $3.75 \times 10^5$ | $4.46 \times 10^{-5}$ | $1.19 \times 10^{-10}$ | $3.4 \times 10^{-11}$ | $5.5 \times 10^{-12}$ | $5.8 \times 10^{-12}$ |
| J695 ALP 905 | $3.91 \times 10^5$ | $5.59 \times 10^{-5}$ | $1.49 \times 10^{-10}$ | $3.0 \times 10^{-11}$ | $4.4 \times 10^{-12}$ | $4.3 \times 10^{-12}$ |

EQUIVALENTS

Those skilled in the art will recognize, or be able to ascertain using no more than routine experimentation, many equivalents to the specific embodiments of the invention described herein. Such equivalents are intended to be encompassed by the following claims.

The invention claimed is:

1. An isolated human antibody, or antigen-binding portion thereof, which is capable of binding to the p40 subunit of human interleukin 12 (IL-12) and dissociates from human IL-12 with a $k_{off}$ rate constant of about $1\times10^{-4}$ $s^{-1}$ to $1\times10^{-5}$ $s^{-1}$, as determined by surface plasmon resonance, wherein the antibody is capable of binding to a first heterodimer and is also capable of binding to a second heterodimer, wherein the first heterodimer comprises the p40 subunit of human IL-12 and the p35 subunit of human IL-12, and wherein the second heterodimer comprises the p40 subunit of human IL-12 and a p19 subunit.

2. The antibody of claim 1, or antigen-binding portion thereof, wherein the antibody neutralizes the biological activity of the first heterodimer.

3. The antibody of claim 1, or antigen-binding portion thereof, wherein the antibody neutralizes the biological activity of the second heterodimer.

4. The antibody of claim 1, or antigen-binding portion thereof, wherein the antibody neutralizes the biological activity of the first heterodimer and the second heterodimer.

5. The isolated antibody of claim 1, or antigen binding portion thereof, which dissociates from human IL-12 with a $K_d$ of $1.34\times10^{-10}$ M or less, as determined by surface plasmon resonance.

6. An isolated human antibody, or antigen-binding portion thereof, which is capable of binding to the p40 subunit of a first heterodimer comprising the p40 subunit of human IL-12 and the p35 subunit of human IL-12, and to the p40 subunit of a second heterodimer comprising the p40 subunit of human IL-12 and a p19 subunit, wherein the antibody dissociates from human IL-12 with a $k_{off}$ rate constant of about $1\times10^{-4}$ $s^{-1}$ to $1\times10^{-5}$ $s^{-1}$ as determined by surface plasmon resonance, and wherein the antibody, or antigen-binding portion thereof, neutralizes the biological activity of the first heterodimer and the second heterodimer.

7. An isolated human antibody, or antigen-binding portion thereof, which is capable of binding to the p40 subunit of a first heterodimer comprising the p40 subunit of human IL-12 and the p35 subunit of human IL-12, and to the p40 subunit of a second heterodimer comprising the p40 subunit of human IL-12 and a p19 subunit, wherein the antibody, or antigen-binding portion thereof, dissociates from human IL-12 with a $K_d$ of $1.34\times10^{-10}$ M or less or a $k_{off}$ rate constant of about $1\times10^{-4}$ $s^{-1}$ to $1\times10^{-5}s^{-1}$, as determined by surface plasmon resonance, and which neutralizes the biological activity of the first heterodimer and the second heterodimer.

8. The isolated human antibody, or antigen-binding portion thereof, of any of claims 1, 7 or 6, wherein the antibody comprises a heavy chain constant region selected from the group consisting of IgG1, IgG2, IgG3, IgG4, IgM, IgA and IgE constant regions.

9. The isolated human antibody, or antigen-binding portion thereof, of any one of claims 1, 7, or 6, wherein the antibody or antigen-binding portion thereof comprises an IgG1 heavy chain constant region.

10. The isolated human antibody, or antigen-binding portion thereof, of any one of claims 1, 7, or 6, wherein the antibody or antigen-binding portion thereof is a Fab fragment.

11. The isolated human antibody, or antigen-binding portion thereof, of any one of claims 1, 7, or 6, wherein the antibody or antigen-binding portion thereof is a F(ab'$_2$) fragment.

12. The isolated human antibody, or antigen-binding portion thereof, of any of claims 1, 7, or 6, wherein the antibody or antigen-binding portion thereof is a single chain Fv fragment.

13. The isolated human antibody, or antigen-binding portion thereof, of any of claims 1, 7 or 6, wherein the antibody or antigen-binding portion thereof does not neutralize the activity of mouse IL-12.

14. The isolated antibody of any one of claims 1, 7 or 6, or antigen binding portion thereof, which inhibits phytohemagglutinin blast proliferation in an in vitro phytohemagglutinin (PHA) assay with an $IC_{50}$ of $1\times10^{-9}$ M or less.

15. The isolated antibody of any of claims 1, 7 or 6, or antigen binding portion thereof, wherein the antibody inhibits phytohemagglutinin blast proliferation in an in vitro PHA assay with an $IC_{50}$ of $1\times10^{-8}$ M or less.

16. The isolated antibody of any of claims 1, 7 or 6, or antigen binding portion thereof, wherein the antibody inhibits phytohemagglutinin blast proliferation in an in vitro PHA assay with an $IC_{50}$ of $1\times10^{-7}$ M or less.

17. The isolated human antibody, or antigen binding portion thereof, of any of claims 1, 2-4, 7 or 6, wherein the antibody inhibits human interferon γ (IFNγ) production with an $IC_{50}$ of $1.6\times10^{-10}$ M or less.

18. A pharmaceutical composition comprising the antibody or an antigen binding portion thereof, of any one of claims 1, 2-4, 5, 7, and 6 and a pharmaceutically acceptable carrier.

* * * * *